(12) United States Patent
Jiang et al.

(10) Patent No.: US 6,528,054 B1
(45) Date of Patent: Mar. 4, 2003

(54) COMPOSITIONS AND METHODS FOR THE THERAPY AND DIAGNOSIS OF BREAST CANCER

(75) Inventors: Yuqiu Jiang, Kent, WA (US); Davin C. Dillon, Issaquah, WA (US); Jennifer L. Mitcham, Redmond, WA (US); Jiangchun Xu, Bellevue, WA (US); Susan L. Harlocker, Seattle, WA (US); William T. Hepler, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/620,405

(22) Filed: Jul. 20, 2000

Related U.S. Application Data

(63) Continuation-in-part of application No. 09/604,287, filed on Jun. 22, 2000, which is a continuation-in-part of application No. 09/590,751, filed on Jun. 8, 2000, which is a continuation-in-part of application No. 09/551,621, filed on Apr. 17, 2000, which is a continuation-in-part of application No. 09/433,826, filed on Nov. 3, 1999, which is a continuation-in-part of application No. 09/389,681, filed on Sep. 2, 1999, which is a continuation-in-part of application No. 09/339,338, filed on Jun. 23, 1999, which is a continuation-in-part of application No. 09/285,480, filed on Apr. 2, 1999, which is a continuation-in-part of application No. 09/222,575, filed on Dec. 28, 1998.

(51) Int. Cl.$^7$ .................. A61K 39/395; C07K 16/00
(52) U.S. Cl. ................... 424/130.1; 530/387.1
(58) Field of Search ................. 530/387.1, 350; 435/69.1, 325, 6; 536/23.1; 424/130.1

(56) References Cited

U.S. PATENT DOCUMENTS

| | | | |
|---|---|---|---|
| 5,215,926 A | 6/1993 | Etchells, III et al. | |
| 5,240,856 A | 8/1993 | Goffe et al. | |
| 5,668,267 A | 9/1997 | Watson et al. | |
| 5,855,889 A | 1/1999 | Watson et al. | |
| 5,891,857 A | 4/1999 | Holt et al. | |
| 5,922,836 A | 7/1999 | Watson et al. | |
| 5,968,754 A | 10/1999 | Watson et al. | |
| 5,986,170 A | 11/1999 | Subjeck | |
| 6,004,756 A | 12/1999 | Watson et al. | |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/21331 | 5/1998 |
| WO | WO 98/33915 | 8/1998 |
| WO | WO 98/54963 | 12/1998 |
| WO | WO 99/09155 | 2/1999 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |

OTHER PUBLICATIONS

L Anderson et al.,Electrophoresis, "A comparison of selected mRNA and protein abundances in human liver," 1997, 18:pp. 533–537.*
GenBank Accession No. AL157387, Feb. 18, 2000.
GenBank Accession No. AC036170, Apr. 9, 2000.
Jäger, D. et al, "Identification of a Tissue–specific Putative Transcription Factor in Breast Tissue by Serological Screening of a Breast Cancer Library," *Cancer Research* 61(5): 2055–2061, Mar. 1, 2001.
Chang and Shu, "Current status of adoptive immunotherapy of cancer," *Critical Reviews in Oncology/Hematology* 22(3):213–228, Apr. 1996.
Cheever and Chen, "Therapy with cultured T cells: principles revisited," *Immunological Reviews*, 157:177–194, 1997.
Cheever et al., "Potential uses of interleukin 2 in cancer therapy," *Immunobiol*, 172:365–382, 1986.
Chen et al., "T–cells for tumor therapy can be obtained from antigen–loaded sponge implants," *Cancer Research* 54(4):1065–1070, Feb. 15, 1994.
Cole et al., "Characterization of the functional specificity of a cloned T–cell receptor heterodimer recognizing the MART–1 melanoma antigen," *Cancer Research*, 55:748–752, Feb. 15, 1995.
Durrant L., "Cancer vaccines," *Anti–Cancer Drugs*, 8:727–733, 1997.
Eshhar Z., "Tumor–specific T–bodies: toward clinical application," *Cancer Immunol Immnother*, 45:131–136, 1997.
Hwu et al., "In vivo antitumor activity of T cells redirected with chimeric antibody/t–cell receptor genes," *Cancer Research*, 55:3369–3373, Aug. 1, 1995.
Porter–Jordan and Lippman, "Overview of the biologic markers of breast cancer," *Breast Cancer* 8:(1):73–100, Feb. Prilliman et al., "HLA–B15 peptide ligands are preferentially anchored at their c termini," *The Journal of Immunology* 162(12):7277–7284, Jun. 15, 1999.

(List continued on next page.)

Primary Examiner—Sean McGarry
Assistant Examiner—Janet Epps
(74) *Attorney, Agent, or Firm*—Seed Intellectual Property Law Group PLLC

(57) ABSTRACT

Compositions and methods for the therapy and diagnosis of cancer, such as breast cancer, are disclosed. Compositions may comprise one or more breast tumor proteins, immunogenic portions thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

5 Claims, 1 Drawing Sheet 1994.-

OTHER PUBLICATIONS

Figure 1:
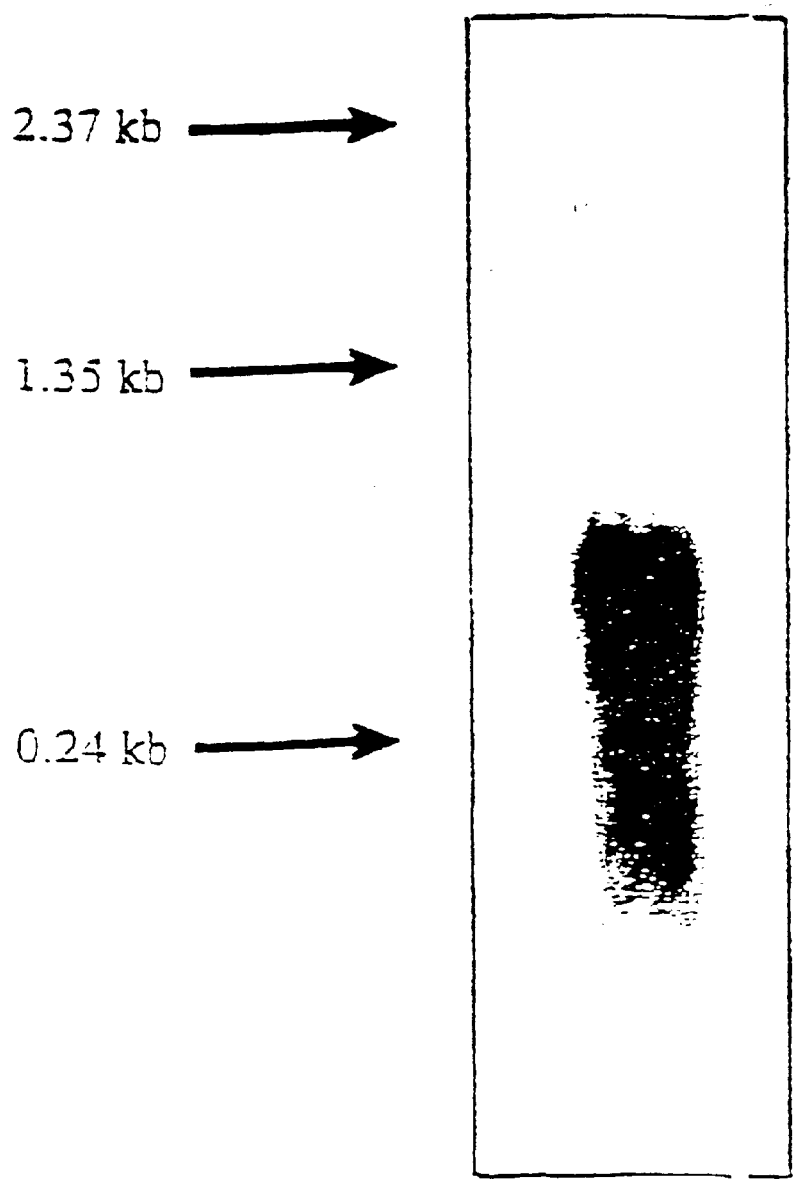

Wei et al., "Protection against mammary tumor growth by vaccination with full–length, modified human ErbB–2 DNA," *Int. J. Cancer*, 81:748–754, 1999.

GenBank Accession No. AA864891, Feb. 20, 1998.

GenBank Accession No. AA398925, Apr. 25, 1997.

Geneseq Accession No. V84525 (Dec. 10, 1998).

Stratagene 1991 product catalog, Prime–It™ Random Labeling Kit, catalog No. 300387, p. 66.

GenBank Accession No. AF269087, Mar. 28, 2001.

GenBank Accession No. AAK27325, Mar. 28, 2001.

GenBank Accession No. AC069200, May 24, 2000.

Sulston et al., "Toward a complete human genome sequence," *Genome Research* 8(11):1097–1108, 1998.

* cited by examiner

SEQUENCE LISTING

<160> NUMBER OF SEQ ID NOS: 495

<210> SEQ ID NO 1
<211> LENGTH: 281
<212> TYPE: DNA
<213> ORGANISM: Homo sapien

<400> SEQUENCE: 1

| | | | | | |
|---|---|---|---|---|---|
| caatgacagt | caatctctat | cgacagcctg | cttcatattt | agctattgtt | cgtattgcct | 60 |
| tctgtcctag | gaacagtcat | atctcaagtt | caaatgccac | aacctgagaa | gcggtgggct | 120 |
| aagataggtc | ctactgcaaa | ccaccCCtCC | atatttccgt | acgcaattac | aattcagttt | 180 |
| ctgtgacatc | tctttacacc | actggaggaa | aaatgagata | ttctctgatt | tattctacta | 240 |
| taacactcta | catagagcta | tggtgagtgc | taaccacatc | g | | 281 |

<210> SEQ ID NO 2
<211> LENGTH: 300
<212> TYPE: DNA
<213> ORGANISM: Homo sapien

<400> SEQUENCE: 2

| | | | | | |
|---|---|---|---|---|---|
| gaggtcctgg | gctaacctaa | tggtttatta | ttggtggaga | gaaagatctg | gaaatacttg | 60 |
| aggttattac | atactagatt | agcttctaat | gtgaaccatt | tttcttttaa | cagtgataaa | 120 |
| ttattatttc | cgaagttaac | tgttcccttg | gtcgtgatac | acactcgatt | aacaaacata | 180 |
| ctgttgtatt | ttttccagtt | ttgtttggct | atgccaccac | agtcatcccc | agggtctata | 240 |
| catactatgt | ctcaactgta | ttatttgcca | tttttggcat | tagaatgctt | cgggaaggct | 300 |

<210> SEQ ID NO 3
<211> LENGTH: 302
<212> TYPE: DNA
<213> ORGANISM: Homo sapien

<400> SEQUENCE: 3

| | | | | | |
|---|---|---|---|---|---|
| ggccgaggta | attggttaag | tctaaagaga | ttattattcc | ttgatgtttg | ctttgtattg | 60 |
| gctacaaatg | tgcagaggta | atacatatgt | gatgtcgatg | tctctgtctt | tttttttgtc | 120 |
| tttaaaaaat | aattggcagc | aactgtattt | gaataaaatg | atttcttagt | atgattgtac | 180 |
| agtaatgaat | gaaagtggaa | catgtttctt | tttgaaaggg | agagaattga | ccatttattg | 240 |
| ttgtgatgtt | taagttataa | cttatcgagc | acttttagta | gtgataactg | tttttaaact | 300 |
| tg | | | | | | 302 |

<210> SEQ ID NO 4
<211> LENGTH: 293
<212> TYPE: DNA
<213> ORGANISM: Homo sapien

<400> SEQUENCE: 4

| | | | | | |
|---|---|---|---|---|---|
| tgtaccaatc | ctttggcaca | agaatatgta | agaactatag | ttgtttttat | tggttttgt | 60 |
| tcttgagatt | gttttcattc | tgttttgac | tgtatctctt | taggaggctg | aggatggcat | 120 |
| tattgcttat | gatgactgtg | gggtgaaact | gactattgct | tttcaagcca | aggatgtgga | 180 |
| aggatctact | tctcctcaaa | tacgagataa | ggcaagataa | ttctgctcat | tcgagagagg | 240 |
| gttaagagtt | gtcatcttaa | tcataaatcc | tgcaggatgg | gttcttcaaa | ttt | 293 |

<210> SEQ ID NO 5
<211> LENGTH: 275
<212> TYPE: DNA
<213> ORGANISM: Homo sapien

<400> SEQUENCE: 5

| | | | | | |
|---|---|---|---|---|---|
| cgaggtttgg | aatcagactt | ctgtgtccag | taaaaaactc | ctgcactgaa | gtcattgtga | 60 |
| cttgagtagt | tacagactga | ttccagtgaa | cttgatctaa | tttcttttga | tctaatgaat | 120 |
| gtgtctgctt | accttgtctc | cttttaattg | ataagctcca | agtagttgct | aattttttga | 180 |
| caactttaaa | tgagtttcat | tcacttcttt | tacttaatgt | tttaagtata | gtaccaataa | 240 |
| tttcattaac | ctgttctcaa | gtggtttagc | tacca | | | 275 |

<210> SEQ ID NO 6
<211> LENGTH: 301
<212> TYPE: DNA
<213> ORGANISM: Homo sapien

<400> SEQUENCE: 6

| | | | | | |
|---|---|---|---|---|---|
| gaggtctggt | ttcctgggta | tgcctggact | gttgcccagt | gtaagatctg | tgcaagccat | 60 |
| attggatgga | agtttacggc | caccaaaaaa | gacatgtcac | ctcaaaaatt | ttggggctta | 120 |
| acgcgatctg | ctctgttgcc | cacgatccca | gacactgaag | atgaaataag | tccagacaaa | 180 |
| gtaatacttt | gcttgtaaac | agatgtgata | gagataaagt | tatctaacaa | attggttata | 240 |
| ttctaagatc | tgctttggaa | attattgcct | ctgatacata | cctaagtaaa | cataacatta | 300 |
| a | | | | | | 301 |

<210> SEQ ID NO 7
<211> LENGTH: 301
<212> TYPE: DNA
<213> ORGANISM: Homo sapien

<400> SEQUENCE: 7

| | | | | | |
|---|---|---|---|---|---|
| gtccagtttg | tacacagtga | ttccttatgc | acgccgaaag | ggtttccgta | aaaatgacat | 60 |
| tatatacaaa | tctgtacacc | catccaccag | agcgattctc | cagctcccag | agggagttat | 120 |
| caacttaaag | caggatacct | gaggtttcat | gtctttagtt | gccttatcat | aatcccaaat | 180 |
| atacatttca | gggtttgttt | tgttttttaa | agacactttc | ctggaatatg | tgcactatgg | 240 |
| ttaaaattaa | aaacaaaagt | aataaaataa | aatgatcgct | ggaaggactg | acctccccac | 300 |
| c | | | | | | 301 |

<210> SEQ ID NO 8
<211> LENGTH: 301
<212> TYPE: DNA
<213> ORGANISM: Homo sapien

<400> SEQUENCE: 8

| | | | | | |
|---|---|---|---|---|---|
| ctgtcctcat | ctctgcaaag | ttcagcttcc | ttccccaggt | ctctgtgcac | tctgtcttgg | 60 |
| atgctctggg | gagctcatgg | gtggaggagt | ctccaccaga | gggaggctca | ggggactggt | 120 |
| tgggccaggg | atgaatattt | gagggataaa | aattgtgtaa | gagccaaaga | attggtagta | 180 |
| gggggagaac | agagaggagc | tgggctatgg | gaaatgattt | gaataatgga | gctgggaata | 240 |
| tggctggata | tctggtacta | aaaaagggtc | tttaagaacc | tacttcctaa | tctcttcccc | 300 |
| a | | | | | | 301 |

<210> SEQ ID NO 9

<211> LENGTH: 301
<212> TYPE: DNA
<213> ORGANISM: Homo sapien

<400> SEQUENCE: 9

| | | | | | | |
|---|---|---|---|---|---|---|
| gaggtctgcc | taagtagagg | acaaagactt | cctcctttca | aaggagaact | gagcccagga | 60 |
| ttggtaagtt | taaggcactt | aaccttgacc | agctctgtag | gtctggagca | ttctggtccc | 120 |
| tggccgcttt | caccaccagg | cccttctcac | ttatccacct | cacatactgc | cccagcattc | 180 |
| ctttggcatt | gcgagctgtg | acttgacaca | ttttaatgac | aagattgaag | tagctacctt | 240 |
| gcaggataga | ttttctgggg | tatagggac | aaaccaacag | tgccatcagg | tgtcttaaca | 300 |
| c | | | | | | 301 |

<210> SEQ ID NO 10
<211> LENGTH: 301
<212> TYPE: DNA
<213> ORGANISM: Homo sapien

<400> SEQUENCE: 10

| | | | | | | |
|---|---|---|---|---|---|---|
| ggcaggtcca | acagttcttc | cagttctggt | cgagctttga | atcgtccctt | gaagtcttct | 60 |
| tcagtgtgct | ccttcactga | cagtctgact | ccttcaggaa | gactgctttg | gattatttcc | 120 |
| aagaaaattt | ctgcaaacgt | agcactcaaa | ccgctgatct | gaaccactcg | ctcatgggtg | 180 |
| gtaagcactg | agtccaggag | cattttgctg | ccttggtcct | gcaactgcaa | cacttctatg | 240 |
| gttttggttg | gcattgcata | actttcctcg | actttaatgg | agagagattg | cagaggttgt | 300 |
| g | | | | | | 301 |

<210> SEQ ID NO 11
<211> LENGTH: 301
<212> TYPE: DNA
<213> ORGANISM: Homo sapien

<400> SEQUENCE: 11

| | | | | | | |
|---|---|---|---|---|---|---|
| aggtctgtga | ctttcaccca | ggacccagga | cgcagccctc | cgtgggcact | gccggcgcct | 60 |
| tgtctgcaca | ctggaggtcc | tccattacag | aggcccagcg | cacatcgctg | gccccacaaa | 120 |
| cgttcagggg | tacagccatg | gcagctcctt | cctctgccgt | gagaaaagtg | cttggagtac | 180 |
| ggtttgccac | acacgtgact | ggacagtgtc | caattcaaat | ctttcagggc | agagtccgag | 240 |
| cagcgcttgg | tgacagcctg | tcctctcctg | ctctccaaag | gccctgctcc | ctgtcctctc | 300 |
| t | | | | | | 301 |

<210> SEQ ID NO 12
<211> LENGTH: 301
<212> TYPE: DNA
<213> ORGANISM: Homo sapien

<400> SEQUENCE: 12

| | | | | | | |
|---|---|---|---|---|---|---|
| gaggtctggg | attacaggca | cgtgccacca | cacctagcta | attttttgagc | atggggctca | 60 |
| aaggaactgc | tctctggggc | atgtcagatt | tcggatttgg | ggctgcacac | tgatactctc | 120 |
| taagtggtgg | aggaacttca | tcccactgaa | attcctttgg | catttggggt | tttgtttttc | 180 |
| ttttttttcct | tcttcatcct | cctccttttt | taaaagtcaa | cgagagcctt | cgctgactcc | 240 |
| accgaagaag | tgcaccactg | ggagccaccc | cagtgccagg | cgcccgtcca | gggacacaca | 300 |
| c | | | | | | 301 |

```
<210> SEQ ID NO 13
<211> LENGTH: 256
<212> TYPE: DNA
<213> ORGANISM: Homo sapien

<400> SEQUENCE: 13 tttttttggca taaaaaacac aatgatttaa tttctaaagc acttatatta ttatggcatg      60
gtttgggaaa caggttatta tattccacat aggtaattat gcagtgcttc tcatggaaaa     120
aatgcttagg tattggcctt ttctctggaa accatatttt ccttttttta ataatcaact     180
aaaatgtata tgttaaaaag cctcatcttt tgattttcaa tatacaaaat gctttcttta     240
aaagaacaag attcaa                                                     256

<210> SEQ ID NO 14
<211> LENGTH: 301
<212> TYPE: DNA
<213> ORGANISM: Homo sapien

<400> SEQUENCE: 14
ggtccttgat agaggaagag gaatatccaa ggcaaagcca ccaccacgtc caacctcctc      60
atcctctacc tttcctgtcc ccagaggtat gagatagacc ccctggcctg gttcctgcac     120
tgtgctaggc ccacagtgga cacttccacc ttaatggaga ataggcccca tggagtggag     180
gtccctcctc catggcctgc aacccaatga ctatggggt gacacaagtg acctctgccc      240
tgtgatggct caacaccatc acacgcaact gtccagacaa gccccctcaa cgggctgctg     300
t                                                                     301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct      60
ctctttctgc ttttctgatc atcctaaagg ctgaatacat cctcctcctg tgtggaggac     120
acgaagcaat actaaaatca atacactcga tcaggtcttc atcagatacc acgtcactgt     180
gggtagagtg ctaattttca acaaatgtgg tgttcttagg gccccacaag gtagtccttt     240
ctcaaggtcg ctgggccac                                                  259

<210> SEQ ID NO 16
<211> LENGTH: 301
<212> TYPE: DNA
<213> ORGANISM: Homo sapien

<400> SEQUENCE: 16
cgaggttgtt cacattttca aataaataat actccccgta agtaataact gcaaccaatc      60
agtgttattc agtgctatgc ctccttgtaa tgggtagtta ttaattattt tcagagcttt     120
ctggaaatac tgtcctaact ggctatgttt aggatctttg ttatctctga agacaaagaa     180
agaactagga ctcttaattt tggggtgctt cttgactctt agttgggaaa ctgaaaatat     240
ttccaacctt ttacccacgt caatggcata ttctgggaat caccaccacc accaccacta     300
c                                                                     301

<210> SEQ ID NO 17
<211> LENGTH: 301
<212> TYPE: DNA
```

<213> ORGANISM: Homo sapien

<400> SEQUENCE: 17

| gcccgggcag | gtctggggcc | tagggtggct | ctttgcaaag | ctgagggca | agctaaggaa | 60 |
| gccaggcagg | tcaggggccc | tttcggcctt | ctcaagcctc | cacctgagtt | ctcgtcaatg | 120 |
| ccagtctccc | tggtatgatt | ggggacatta | tcagagaaac | atctaatagc | gcacatctgg | 180 |
| gcacccacac | tctgcttcag | ttgcatccat | cctcccaccc | caaattcaac | tcctgaccca | 240 |
| atacaaaaga | cttttttaac | caggatttct | tcttgcagga | aagctgactt | ggaaacacgg | 300 |
| g | | | | | | 301 |

<210> SEQ ID NO 18
<211> LENGTH: 301
<212> TYPE: DNA
<213> ORGANISM: Homo sapien

<400> SEQUENCE: 18

| attacaggca | cgtgccacca | cacctagcta | atttttgagc | atggggctca | aaggaactgc | 60 |
| tctctggggc | atgtcagatt | tcggatttgg | ggctgcacac | tgatactctc | taagtggtgg | 120 |
| aggaacttca | tcccactgaa | attcctttgg | catttgggt | tttgttttc | ttttttcct | 180 |
| tcttcatcct | cctccttttt | taaaagtcaa | cgagagcctt | cgctgactcc | accgaagaag | 240 |
| tgcaccactg | ggaccaccc | agtgccaggc | gcccgtccag | ggacacacac | agtcttcact | 300 |
| g | | | | | | 301 |

<210> SEQ ID NO 19
<211> LENGTH: 301
<212> TYPE: DNA
<213> ORGANISM: Homo sapien

<400> SEQUENCE: 19

| agaatctctg | cactgtcatc | aggtacaaca | aaagatcaaa | ccctgtccc | gatgttaact | 60 |
| ttttaactta | aaagaatgcc | agaaaaccca | gatcaacact | ttccagctac | gagccgtcca | 120 |
| caaggccac | ccaaaggcca | gtcagactcg | tgcagatctt | attttttaat | agtagtaacc | 180 |
| acaatacaca | gctcttttaaa | gctgttcata | ttcttccccc | attaaacacc | tgccccgggc | 240 |
| ggccaagggc | gaattctgca | gatatccatc | acactggcgg | ccgctcgagc | atgcatctag | 300 |
| a | | | | | | 301 |

<210> SEQ ID NO 20
<211> LENGTH: 290
<212> TYPE: DNA
<213> ORGANISM: Homo sapien

<400> SEQUENCE: 20

| aggttttttt | tttttttttt | tttttttttt | tttttcccctt | tcaattcatt | taatttcaac | 60 |
| aatctgtcaa | aaaacagcca | ataaacaaat | actgaattac | attctgctgg | gttttttaaa | 120 |
| ggctctaaac | tataaaaaca | tcttgtgtct | cccaccctga | ccaccctgct | acttttccat | 180 |
| ataccacagg | ccacccataa | acacaaagcc | aggggtgaa | gctgacatgg | tctatttgga | 240 |
| gccagtaaac | aggagggcga | taagtcctga | taagcactta | tggacaatat | | 290 |

<210> SEQ ID NO 21
<211> LENGTH: 301
<212> TYPE: DNA
<213> ORGANISM: Homo sapien

<400> SEQUENCE: 21

```
agaaaggtaa ctgccagcca ggcttgcatt gtttagccag aaattgctgc ttggttctag      60
actctttaaa aaaaaaaat acccaggggt tgtcatcatt ttcagaggca gagtgccaaa      120
tatcacccaa agctcttgtg tcttttttt accccttat tttattttta tttattaatt      180
ttttgtgcaa acatcaaatg tcactggtgt tcacagaagg cttttttgac tagccttaaa    240
ttcctgagtc aaaagattaa tcagatttc aggcagtgtt taatcaggtg ctttgtcctg     300
t                                                                      301
```

<210> SEQ ID NO 22
<211> LENGTH: 301
<212> TYPE: DNA
<213> ORGANISM: Homo sapien

<400> SEQUENCE: 22

```
gacgccatgc accctccggt aaccagcagc cgcctgtcca tcccccaaga ccggaaaggc      60
agcagcagcc cccgggagcc cagggctgtc ctcggtgcat ctggctgcag agggaaattg     120
atgaccttac acagcaacta gcggccatgc agtccttcac tgacaagttc caggaccttt    180
gaagttggag ccagcgtccg gagctgcagc caagcgagtt tcctccttat cctccttagc     240
cagggcttt tctcttccgc tgcatttgcc cccttcccaa cgcaattcaa agcagttgtg     300
a                                                                      301
```

<210> SEQ ID NO 23
<211> LENGTH: 381
<212> TYPE: DNA
<213> ORGANISM: Homo sapien

<400> SEQUENCE: 23

```
cgaggtccag acagtggacc aagagatacg ctacataaat tggggtttca caattcttac      60
attatttgtc tgtcacagaa gagagctgct tatgattttg aaggggtcag ggagggtggg    120
agttggtaaa gagtagggta tttctataac agatattatt cagtcttatt tcctaagatt    180
ttgttgtaac ttaaggtatc ttgctacagt agacagaatt ggtaatagca acttttaaaa    240
ttgtcattag ttctgcaata ttagctgaaa tgtagtacag aaaagaatgt acatttagac    300
atttgggttc agttgcttgt agtctgtaaa tttaaaacag cttaatttgg tacaggttac    360
acatatggac ctcccgggcg g                                                381
```

<210> SEQ ID NO 24
<211> LENGTH: 214
<212> TYPE: DNA
<213> ORGANISM: Homo sapien

<400> SEQUENCE: 24

```
aatgatgtaa aaattaatca acagggctgc cacttgcgaa tcccctccaa ggatgctgtg      60
caaagggtct cattggtcct gatgaataat cttgtgactg tacatattcc tgggtgcatg    120
tccacaaata ctgaggtata gcctgcatgc cactaaaaat aacaaaggtt tcaggggtgg    180
aaacattgtc caccacactg tcatgaccat cttt                                  214
```

<210> SEQ ID NO 25
<211> LENGTH: 302
<212> TYPE: DNA
<213> ORGANISM: Homo sapien -continued

<400> SEQUENCE: 25

```
gggggcactg agaactccct ctggaattct tgggggtgt tggggagaga ctgtgggcct      60
ggagataaaa cttgtctcct ctaccaccac cctgtaccct agcctgcacc tgtcctcatc    120
tctgcaaagt tcagcttcct tccccaggtc tctgtgcact ctgtcttgga tgctctgggg   180
agctcatggg tggaggagtc tccaccagag ggaggctcag gggactggtt gggccaggga   240
tgaatatttg agggataaaa attgtgtaag aagccaaaga aattggtagt agggggagaa   300
ac                                                                   302
```

<210> SEQ ID NO 26
<211> LENGTH: 301
<212> TYPE: DNA
<213> ORGANISM: Homo sapien

<400> SEQUENCE: 26

```
ttggagaacg cgctgacata ctgctcggcc acagtcagtg aagctgctgc atctccatta    60
tgttgtgtca gagctgcagc caggattcga atagcttcag cttagccctt ggccttcgcc   120
agaactgcac tggcctctcc tgctgcctga tttatctgtg cagccttttc tgcttcggag   180
gccaggatct gggcctgttt cttcccttct gccacattga tggccgactc tcgggtcccc   240
tcagactcta gaactgtggc ccgtttccgc cgctctgcct ccacctgcat ctgcatagac   300
t                                                                    301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg    60
accattttat tagacaccct ctattagtgt taacagacaa agatgaaggt taagttgaaa   120
tcaaattgaa atcatcttcc ctctgtacag attgcaatat ctgataatac cctcaacttt   180
cttggtgcaa attaattgcc tggtactcac agtccagtgt taacaggcaa taatggtgtg   240
attccagagg agaggactag gtggcaggaa aataaatgag attagcagta tttgacttgg   300
a                                                                    301
```

<210> SEQ ID NO 28
<211> LENGTH: 286
<212> TYPE: DNA
<213> ORGANISM: Homo sapien

<400> SEQUENCE: 28

```
tttttttttg cacaggatgc acttattcta ttcattctcc cccacccttc ccatatttac    60
atccttagag gaagagaggg gtaaggtgat aaagtaactg aaggaccgca agacgggtat   120
gtcccttgtt caccaaatgg tcaaagggtc aaagatcgga ggaggtcagg gggtaacgca   180
ggaacaggtg agggcgtttc gccctctctc cctctcccct tttcaacctc ttaatcactg   240
gctaactcgc gacctcatgg gttaattcgt aagcttacac gcgttg                   286
```

<210> SEQ ID NO 29
<211> LENGTH: 301
<212> TYPE: DNA
<213> ORGANISM: Homo sapien

<400> SEQUENCE: 29

```
gtcatgttct tgctcttcct tctttacaca tttgagttgt gccttctgtt cttaaagaga    60
ttttcctttg ttcaaaggat ttattcctac catttcacaa atccgaaaat aattgaggaa   120
acaggttaca tcattccaat tttgccttgg gtttgaagag tctctcatgg tggcacagtc   180
ctccagggta gctatgttgt tgggctcccc tacatcccag aagctcagag actttgtcaa   240
aggtgtgccg tccacccatt gccactgacc ctcgacaacc tggtctgaca gtccaataaa   300
a                                                                  301
```

<210> SEQ ID NO 30
<211> LENGTH: 332
<212> TYPE: DNA
<213> ORGANISM: Homo sapien

<400> SEQUENCE: 30

```
gagcagaatt gatgcctatg gctccaagtc aaatactgct aatctcattt attttcctgc    60
cacctagtcc tctcctctgg aatcacacca ttattgcctg ttaacactgg actgtgagta   120
ccaggcaatt aatttgcacc aagaaagttg agggtattat cagatattgc aatctgtaca   180
gagggaagat gatttcaatt tgatttcaac ttaaccttca tctttgtctg ttaacactaa   240
tagagggtgt ctaataaaat ggtcaaattt gtgatctcat ttgttataac tagcactctt   300
ttcacagatg tgatgactga tttccagcag ac                                 332
```

<210> SEQ ID NO 31
<211> LENGTH: 141
<212> TYPE: DNA
<213> ORGANISM: Homo sapien

<400> SEQUENCE: 31

```
aaaggctatc aagtactttg aaggacagga aggaatgaac acacccaggt ggacgtttgg    60
tttcatttgc aggggttcag ggagggttgc aggggttcag ggagggctct tgtcccacaa   120 ccggggggaag ggagagggca c                                           141
```

<210> SEQ ID NO 32
<211> LENGTH: 201
<212> TYPE: DNA
<213> ORGANISM: Homo sapien

<400> SEQUENCE: 32

```
gagctgatct cacagcacat acagaatgat gctactatgt agaccctcac tcccttggga    60
aatctgtcat ctaccttaaa gagagaaaaa agatggaaca taggcccacc tagtttcatc   120
catccaccta cataaccaac atagatgtga ggtccactgc actgatagcc agactgcctg   180
gggtaaacct tttcagggag g                                            201
```

<210> SEQ ID NO 33
<211> LENGTH: 181
<212> TYPE: DNA
<213> ORGANISM: Homo sapien

<400> SEQUENCE: 33

```
tttcaaaaca ctcatatgtt gcaaaaaaca catagaaaaa taaagtttgg tggggtgct     60 gactaaactt caagtcacag acttttatgt gacagattgg agcagggttt gttatgcatg   120
tagagaaccc aaactaattt attaaacagg atagaaacag gctgtctggg tgaaatggtt   180
c                                                                  181
```

```
<210> SEQ ID NO 34
<211> LENGTH: 151
<212> TYPE: DNA
<213> ORGANISM: Homo sapien

<400> SEQUENCE: 34
atgtcctgca cagtatagct tggacctctg ggcctgaacc agggtgagca tcaaggcccc      60
catttctcct caccacgggg tcgcttgtca gctccaagaa ccagtctggc cccactgaga     120
acttttcagt cgagggcctg atgaatcttg g                                    151

<210> SEQ ID NO 35
<211> LENGTH: 291
<212> TYPE: DNA
<213> ORGANISM: Homo sapien

<400> SEQUENCE: 35
tctttagggc aaaatcatgt ttctgtgtac ctagcaatgt gttcccattt tattaagaaa      60
agctttaaca cgtgtaatct gcagtcctta acagtggcgt aattgtacgt acctgttgtg     120
tttcagtttg ttttcacct ataatgaatt gtaaaaacaa acatacttgt ggggtctgat     180
agcaaacata gaaatgatgt atattgtttt ttgttatcta tttatttca tcaatacagt     240 attttgatgt attgcaaaaa tagataataa tttatataac aggttttctg t              291

<210> SEQ ID NO 36
<211> LENGTH: 201
<212> TYPE: DNA
<213> ORGANISM: Homo sapien

<400> SEQUENCE: 36
ctgatacaat tataataacg gttccctgaa cctttagag tgcaattaag aacaaaaact      60
aaattttgtt tacatgaata tggaataaat acaataatca aatatgact ctccctaaaa     120 gtgaaacaca caagccaatc cggaactgct gtgcgaaaga taaatcgag aaaggcaagg     180 tttcggtagg aggacgcgat g                                              201

<210> SEQ ID NO 37
<211> LENGTH: 121
<212> TYPE: DNA
<213> ORGANISM: Homo sapien

<400> SEQUENCE: 37
catcacactg gcggccgctc gagcatgcat ctagagggcc caattcgccc tataatgagt      60
cgtattacaa ttcactggcc gtcgttttac aacgtcgtga ctgggaaaac cctggcgtta     120
c                                                                     121

<210> SEQ ID NO 38
<211> LENGTH: 200
<212> TYPE: DNA
<213> ORGANISM: Homo sapien

<400> SEQUENCE: 38
aaacatgtat tactctatat ccccaagtcc tagagcatga cctgcatgtt ggagatgttg      60
tacagcaatg tatttatcca gacatacata tatgatattt agagacacag tgattctttt     120
gataacacca cacatagaac attataatta cacacaaatt tatggtaaaa gaattaatat     180
gctgtctggt gctgctgtta                                                 200
```

<210> SEQ ID NO 39
<211> LENGTH: 760
<212> TYPE: DNA
<213> ORGANISM: Homo sapien

<400> SEQUENCE: 39

| | | | | | |
|---|---|---|---|---|---|
| gcgtggtcgt | cggccgaggt | cctgggctag | acctaatggt | ttattattgg | tggagagaaa | 60 |
| gatctggaaa | tacttgaggt | tattacatac | tagattagct | tctaatgtga | accatttttc | 120 |
| ttttaacagt | gatcaaatta | ttatttcgaa | gttaatcgtt | cccttggtgg | ctgcatacac | 180 |
| atcgcattaa | caaacatact | gttgtatttt | ttcccagttt | tgtttggcta | tgccaccaca | 240 |
| gtcatcccca | gggtctatac | atactatgtt | tcaactgtat | tatttgccat | ttttggcatt | 300 |
| agaatgcttc | gggaaggctt | aaagatgagc | cctgatgagg | tcaagagga | actggaagaa | 360 |
| gttcaagctg | aattaaagaa | gaaagatgaa | gaagtaagcc | atggcactgt | tgatctggac | 420 |
| caaaaggca | ctcaactagg | aataaacact | ctacagaggt | ttctcagtgg | ccccatctgt | 480 |
| gtgatatgcg | ggctacaca | aaaatagctt | cttttgcttt | gttctgttct | tatacctgtc | 540 |
| tgtgatctga | cttggggttg | gtgtgaatgt | agtagagaaa | ggaagctgac | agatgaatac | 600 |
| tgaacacagg | taatcagttt | ccttaattag | gttgattata | agctcctgaa | aagcaggaac | 660 |
| tgtattttat | aattttacct | gtttctcccg | tggtgtctag | gatagtaagt | gagcagagca | 720 |
| gtaaatactg | tttggtttgt | tcagacctgc | ccgggcggcc | | | 760 |

<210> SEQ ID NO 40
<211> LENGTH: 452
<212> TYPE: DNA
<213> ORGANISM: Homo sapien

<400> SEQUENCE: 40

| | | | | | |
|---|---|---|---|---|---|
| aatcactaaa | gatattgact | agagaatgct | gtgtgctatt | tcaattacat | ttgttttct | 60 |
| tttattaaca | ggaattttga | ttcttcaagg | aagtggctca | atttcaattt | caggtgacca | 120 |
| ggtttatcgt | gacttttcct | tcttgtttac | ttttcgctag | gaaggggagt | tgtaggggca | 180 |
| gattcaggta | ttggaatagg | aaaattacgt | ctaaaccatg | gaaatcttgg | aaatggaatt | 240 |
| ggtggaagtg | ggcgaaatgg | atatgggtaa | gggaacacaa | aaaaccctga | agctaattca | 300 |
| tcgctgtcac | tgatacttct | ttttttctcgt | tcctggtctt | gagagactgg | gaaaccaaca | 360 |
| gccactgcca | agatggctgt | gatcaggagg | agaactttct | tcatctcaaa | cgtttcagtc | 420 |
| agttcttcct | ctcacctcgg | ccgcgaccac | gc | | | 452 |

<210> SEQ ID NO 41
<211> LENGTH: 676
<212> TYPE: DNA
<213> ORGANISM: Homo sapien

<400> SEQUENCE: 41

| | | | | | |
|---|---|---|---|---|---|
| aatctttgaa | tgccaagtct | cttctgtact | ttctttttatt | aacatcatag | tctttgcatc | 60 |
| aagatacata | gcaatgatag | caggtttctt | tttaaagctt | agtattaata | ttaaatattt | 120 |
| ttccccattt | aaattttaca | ttacttgcca | agaaaaaaaa | aaaattaaaa | ctcaagttac | 180 |
| ttgaagcctg | gacacacttc | catgattagc | cgggctaggt | aaaagttggt | ggctttattc | 240 |
| ttcctgctct | ataagcagat | ccaggccta | gaaagatggg | accagggtat | ataattgttt | 300 |
| ttgaaaagtg | tgctacaaaa | atggatggcc | tgttataagc | caggatacaa | agttaaggat | 360 |
| gggggtaagg | gagggacatt | ttcttccaga | agaaaagaca | gaatttctga | agagtcccag | 420 |

-continued

```
tccataattt tcccaaaatg gttggaggag agggtaaaat ctcaacatga gtttcaaagt      480
actgtctctg tgaggggccg gtagatgcct tgctgaggag ggatggctaa tttggaccat      540
gccccatccc cagctaggag aatggaaatg gaaactttaa ttgcccagtg ggtgtgaaag      600
tgggctgaag cttggttggt actgaattct ctaagaggtt tcttctagaa acagacaact      660
cagacctgcc cgggcg                                                      676
```

<210> SEQ ID NO 42
<211> LENGTH: 468
<212> TYPE: DNA
<213> ORGANISM: Homo sapien

<400> SEQUENCE: 42

```
agcgtggtcg cggccgaggt ttggccggga gcctgatcac ctgccctgct gagtcccagg       60
ctgagcctca gtctccctcc cttggggcct atgcagaggt ccacaacaca cagatttgag      120
ctcagccctg gtgggcagag aggtagggat ggggctgtgg ggatagtgag gcatcgcaat      180
gtaagactcg ggattagtac acacttgttg attaatggaa atgtttacag atccccaagc      240
ctggcaaggg aatttcttca actccctgcc ccccagccct ccttatcaaa ggacaccatt      300
ttggcaagct ctatgaccaa ggagccaaac atcctacaag acacagtgac catactaatt      360 aaaacccccct gcaaagccca gcttgaaacc ttcacttagg aacgtaatcg tgtccctat     420 cctacttccc cttcctaatt ccacagacct gcccgggcgg ccgctcga                  468
```

<210> SEQ ID NO 43
<211> LENGTH: 408
<212> TYPE: DNA
<213> ORGANISM: Homo sapien

<400> SEQUENCE: 43

```
atcatatcaa aacactatct tcccatctgt ttctcaatgc ctgctacttc ttgtagatat       60
ttcatttcag gagagcagca gttaaacccg tggattttgt agttaggaac ctgggttcaa      120 acctcttttcc actaattggc tatgtctctg gacagttttt tttttttttt tttttttttaa     180 accctttctg aactttcact ttctatggct acctcaaaga attgttgtga ggcttgagat      240
aatgcatttg taagggtct gccagatagg aagatgctag ttatggattt acaaggttgt      300
taaggctgta agagtctaaa acctacagtg aatcacaatg catttacccc cactgacttg      360
gacataagtg aaaactagcc cgaagtctct ttttcaaatt acttacag                   408
```

<210> SEQ ID NO 44
<211> LENGTH: 160
<212> TYPE: DNA
<213> ORGANISM: Homo sapien

<400> SEQUENCE: 44

```
tggtcgcggc cgaggtcttg tgtgccctgt ggtccagggg accaagaaca acaagatcca       60
ctctctgtgc tacaatgatt gcaccttctc acgcaacact ccaaccagga ctttcaacta      120
caacttctcc gctttggcaa acaccgtcac tcttgctgga                            160
```

<210> SEQ ID NO 45
<211> LENGTH: 231
<212> TYPE: DNA
<213> ORGANISM: Homo sapien

<400> SEQUENCE: 45

```
cgagcggccg cccgggcagg tctggggagg tgattccatc cagagtcata tctgttgtca       60
```

| | |
|---|---|
| ccccaataag tcgatcagca aggctgacag gctgtgagga aacccggcc ttgtagcctg | 120 |
| tcacctctgg ggggatgatg actgcctggc agacgtaggc tgtgatagat ttgggagaaa | 180 |
| acctgactca ccctcaggaa tccggaggtc ggtgacattg tcggtgcaca c | 231 |

<210> SEQ ID NO 46
<211> LENGTH: 371
<212> TYPE: DNA
<213> ORGANISM: Homo sapien

<400> SEQUENCE: 46

| | |
|---|---|
| cccgggcagg tctgtgtaac atgccaaggc tttgcacttt ctgcagagca gttttttatt | 60 |
| ttccttatca ggtacaggtt ttggttttc ttgactatct ctgatgaatt tttcatgagt | 120 |
| ctgtatatgc agaatctttt ccctaaatac tgcttcgtcc catgtctgaa ggcgtaaaat | 180 |
| aaagtcattc atcattttttt ctttgtacat gtttatttgt tctttttcaa ttacaccaag | 240 |
| cattactagt cagaaggaag cacttgctac ctcttgctct tcctctgcct ctggtttgga | 300 |
| tcattttgat gacattgccc acattactca tgaaggatga caagattgca ctgtgcaatg | 360 |
| tcaattgcct t | 371 |

<210> SEQ ID NO 47
<211> LENGTH: 261
<212> TYPE: DNA
<213> ORGANISM: Homo sapien

<400> SEQUENCE: 47

| | |
|---|---|
| gccctgtttt tatacacttc acatttgcag aaatataatg atgccctcat tatcagtgag | 60 |
| catgcacgaa tgaaagatgc tctggattac ttgaaagact tcttcagcaa tgtccgagca | 120 |
| gcaggattcg atgagattga gcaagatctt actcagagat ttgaagaaaa gctgcaggaa | 180 |
| ctagaaagtg tttccaggga tcccagcaat gagaatccta aacttgaaga cctctgcttc | 240 |
| atcttacaag aagagtacca c | 261 |

<210> SEQ ID NO 48
<211> LENGTH: 701
<212> TYPE: DNA
<213> ORGANISM: Homo sapien

<400> SEQUENCE: 48

| | |
|---|---|
| cgagcggccc ccgggcaggt ccaattagta caagtctcat gatataatca ctgcctgcat | 60 |
| acatatgcac agatccagtt agtgagtttg tcaagcttaa tctaattggt taagtctcaa | 120 |
| agagattatt attcttgatg tttgcttgt attggctaac aaatgtgcag aggtaataca | 180 |
| tatgtgatgt ccgatgtctc tgtctttttt tttgtcttta aaaataatt ggcagcaact | 240 |
| gtatttgaat aaaatgattt cttagtatga ttgtaccgta atgaatgaaa gtggaacatg | 300 |
| tttcttttg aaagggagag aattgaccat ttattattgt gatgtttaag ttataactta | 360 |
| ttgagcactt ttagtagtga taactgtttt taaacttgcc taatacccttt cttgggtatt | 420 |
| gtttgtaatg tgacttattt aaccccttt tttgtttgtt taagttgctg ctttaggtta | 480 |
| acagcgtgtt ttagaagatt taaatttttt tcctgtctgc acaattagtt attcagagca | 540 |
| agagggcctg attttataga agccccttga aaagaggtcc agatgagagc agagatacag | 600 |
| tgagaaatta tgtgatctgt gtgttgtggg agagaatttt tcaatatgta actacggagc | 660 |
| tgtagtgcca ttagaaactg tgaatttcca aataaatttg a | 701 |

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat      60
tttatgggcg ggtgccaaat actgctgtga atctatttgt atagtatcca tgaatgaatt     120
tatgaaaata gatatttgtg cagctcaatt tatgcagaga ttaaatgaca tcataatact     180
ggatgaaaac ttgcatagaa ttctgattaa atagtgggtc tgtttcacat gtgcagtttg     240
aagtatttaa attaaccact cctttcacag                                      270
```

<210> SEQ ID NO 50
<211> LENGTH: 271
<212> TYPE: DNA
<213> ORGANISM: Homo sapien

<400> SEQUENCE: 50

```
atgcatttat ccatatgaac ttgattattc tgaattactg actataaaaa ggctattgtg      60
aaagatatca cactttgaaa cagcaaatga attttcaatt ttacatttaa ttataagacc     120
acaataaaaa gttgaacatg cgcatatcta tgcatttcac agaagattag taaaactgat     180
ggcaacttca gaattatttc atgaagggta caaacagtct ttaccacaat tttcccatgg     240
tcttatcctt caaaataaaa ttccacacac t                                    271
```

<210> SEQ ID NO 51
<211> LENGTH: 241
<212> TYPE: DNA
<213> ORGANISM: Homo sapien

<400> SEQUENCE: 51

```
tggtcgcggc cgaggtgtga ggagatgaac tttgtgttaa tgggggggcac tttaaatcga      60
aatggcttat ccccaccgcc atgtaagtta ccatgcctgt ctcctccctc ctacacattt     120
ccagctcctg ctgcagttat tcctacagaa gctgccattt accagccctc tgtgattttg     180
aatccacgag cactgcaggc cctccacagc gttactaccc agcaggcact cagctcttca     240
t                                                                     241
```

<210> SEQ ID NO 52
<211> LENGTH: 271
<212> TYPE: DNA
<213> ORGANISM: Homo sapien

<400> SEQUENCE: 52

```
tccaagactt aaaacttagg aaacacctat gatgccactt taactggaag taatggagac      60
atctgattcc aaattcacat tttaaatgcc tatttgcaat cagcaaagag ccaggtatgc     120
tgcatgctgc ttgctgtaag ttacgatttg gcttcactag ctcaaatttt ttcactccac     180
caaaagataa ggcacaggcc cgtttgtcca atcaagtttg ctgaaaatac tgcagcctga     240
gtgtagacaa acttcccctg aatttgctag a                                    271
```

<210> SEQ ID NO 53
<211> LENGTH: 493
<212> TYPE: DNA
<213> ORGANISM: Homo sapien

<400> SEQUENCE: 53

```
ttagcgtggt cgcggtccga ggtctggcct gactagctca ctctgaagag tgtctttcac        60
atggattaac caaaaaatgc attactgcct tggcacact gtcttgaata ttctttctga        120
caatgagaaa atatgattta atggagtcgt tcaataacct cacaatctcg ctgttccgag       180
cagatagttt tcgtgccaac aggaactgga acatctagca ggttcacggc atgaccttt        240 tgtggactgg ctggcataat tggaatgggt tttgattttt cttctgctaa taactcttca      300
agcttttgaa gttttcaagc attcctctcc agttgcctgt ggttggttct tgaacaccat      360
ctccaacccc accacctcca gatgcaacct tgtctcgtga tacagacctg cccgggcggc      420
cctcaagggc gaattctgca gatatccatc acactggcgg ccgctcgagc atgcatctag      480
agggcccaat tcg                                                          493

<210> SEQ ID NO 54
<211> LENGTH: 321
<212> TYPE: DNA
<213> ORGANISM: Homo sapien

<400> SEQUENCE: 54
cgtggtcgcg gccgaggtct gtttgcttgt tggtgtgagt ttttcttctg gagactttgt       60
actgaatgtc aataaactct gtgattttgt taggaagtaa aactgggatc tatttagcca      120
ctggtaagct tctgaggtga aggattcagg acatctcgt ggaacaaaca ctccccactg      180
gactttctct ctggagatac ccttttgaat atacaatggc cttggctcac taggtttaaa     240
tacaaacaag tctgaaaccc actgaagact gagagattgc agcaatattc tctgaattag    300
gatcgggttc cataactcta a                                                 321

<210> SEQ ID NO 55
<211> LENGTH: 281
<212> TYPE: DNA
<213> ORGANISM: Homo sapien

<400> SEQUENCE: 55
ttgcaaatga aactgtggat gtataataag aaaacacaag ggtttattct taacactaaa      60
attaacatgc cacacgaaga ctgcattaca gctctctgtt tctgtaatgc agaaaaatct    120
gaacagccca ccttggttac agctagcaaa gatggttact tcaaagtatg gatattaaca   180
gatgactctg acatatacaa aaaagctgtt ggctggacct gtgactttgt tggtagttat   240
cacaagtatc aagcaactaa ctgttgtttc tccgaagatg g                          281

<210> SEQ ID NO 56
<211> LENGTH: 612
<212> TYPE: DNA
<213> ORGANISM: Homo sapien

<400> SEQUENCE: 56
gcgtggtcgc ggccgaggtc ctgtccgggg gcactgagaa ctccctctgg aattcttggg      60
gggtgttggg gagagactgt gggcctggag ataaaacttg tctcctctac caccaccctg    120
taccctagcc tgcacctgtc ctcatctctg caaagttcag cttccttccc caggtctctg   180
tgccactctg tcttggatgc tctggggagc tcatgggtgg aggagtctcc accagaggga   240
ggctcagggg actggttggg ccagggatga atatttgagg gataaaaatt gtgtaagagc   300
caaagaattg gtagtagggg gagaacagag aggagctggg ctatgggaaa tgatttgaat   360
aatggagctg ggaatatggc tggatatctg gtactaaaaa aggtctttta agaacctact   420
```

| | |
|---|---|
| tcctaatctc ttccccaatc caaaccatag ctgtctgtcc agtgctctct tcctgcctcc | 480 |
| agctctgccc caggctcctc ctagactctg tccctgggct agggcagggg aggagggaga | 540 |
| gcagggttgg gggagaggct gaggagagtg tgacatgtgg ggagaggacc agacctgccc | 600 |
| gggcggccgt cg | 612 |

<210> SEQ ID NO 57
<211> LENGTH: 363
<212> TYPE: DNA
<213> ORGANISM: Homo sapien

<400> SEQUENCE: 57

| | |
|---|---|
| gtcgcggccg aggtcctgag cgtcaccta gttctgcccc tttttagctg tgtagacttg | 60 |
| gacaagacat ttgacttccc tttctccttg tctataaaat gtggacagtg gacgtctgtc | 120 |
| acccaagaga gttgtgggag acaagatcac agctatgagc acctcgcacg gtgtccagga | 180 |
| tgcacagcac aatccatgat gcgttttctc cccttacgca ctttgaaacc catgctagaa | 240 |
| aagtgaatac atctgactgt gctccactcc aacctccagc gtggatgtcc ctgtctgggc | 300 |
| ccttttctg tttttttattc tatgttcagc accactggca ccaaatacat tttaattcac | 360 |
| cga | 363 |

<210> SEQ ID NO 58
<211> LENGTH: 750
<212> TYPE: DNA
<213> ORGANISM: Homo sapien

<400> SEQUENCE: 58

| | |
|---|---|
| cgtggtcgcg gccgaggtct aattccacct gactggcaga acctgcgccc ctcgcctaac | 60 |
| ctgcgccctt ctcccaactc gcgtgcctca cagaacccag gtgctgcaca gccccgagat | 120 |
| gtggcccttc ttcaggaaag agcaaataag ttggtccaag tacttgatgc ttaaggaata | 180 |
| cacaaaggtg cccatcaagc gctcagaaat gctgagagat atcatccgtg aatacactga | 240 |
| tgtttatcca gaaatcattg aacgtgcatg ctttgtccta gagaagaaat ttgggattca | 300 |
| actgaaagaa attgacaaag aagaacacct gtatattctc atcagtaccc ccgagtccct | 360 |
| ggctggcata ctgggaacga ccaaagacac acccaagctc ggtctcttct tggtgattct | 420 |
| gggtgtcatc ttcatgaatg gcaaccgtgc cagtgaggct gtcttttggg aggcactacg | 480 |
| caagatggga ctgcgtcctg gggtgagaca tcccctccct tggagatcta aggaaacttc | 540 |
| tcacctatga gtttgtaaag cagaaatacc tggactacag acgagtgccc aacagcaacc | 600 |
| ccccggagta tgagttcctc tggggcctcc gtccctacca tgagactagc aagatgaaaa | 660 |
| tgctgagatt cattgcagag gttcagaaaa gagaccctcg tgactggact gcacagttca | 720 |
| tggaggctgc agatgaggac ctgcccgggc | 750 |

<210> SEQ ID NO 59
<211> LENGTH: 505
<212> TYPE: DNA
<213> ORGANISM: Homo sapien

<400> SEQUENCE: 59

| | |
|---|---|
| tggccgcccg ggcaggtcca gtctacaagc agagcactct catggggagc accagatgag | 60 |
| ttccagccgc agttcttta taagctttaa gtgcctcatg aagacgcgag gatctcttcc | 120 |
| aagtgcaacc tggtcacatc agggcacatt cagcagcaga agtctgtttc cagtatagtc | 180 |
| cttggtatgg ctaaattcca ctgtcccttt ctcagcagtc aataatccat gataaattct | 240 |

```
gtacaacact gtagtcaata acagcagcac cagacagcat attaattctt ttaccataaa      300
tttgtgtgta attataatgt tctatgtgtg gtgttatcaa aagaatcact gtgtctctaa      360
atatcatata tgtatgtctg gataaataca ttgctgtaca acatctccaa catgcaggtc      420
atgctctaag acttggggat atagagtaat acatgtttcg tggacctcgg ccgcgaccac      480
gctaagggcg aattctgcag atatc                                            505

<210> SEQ ID NO 60
<211> LENGTH: 520
<212> TYPE: DNA
<213> ORGANISM: Homo sapien

<400> SEQUENCE: 60
cgtggtcgcg gccgaggtcc tcaggacaag gaaacaggta tcagcatgat ggtagcagaa       60
accttatcac caaggtgcag gagctgactt cttccaaaga gttgtggttc cgggcagcgg      120
tcattgcctg cccttgctgg agggctgatt ttagtgttgc ttattatgtt ggccctgagg      180
atgcttcgaa gtgaaaataa gaggctgcag gatcagcggc aacagatgct ctcccgtttg      240
cactacagct ttcacggaca ccattccaaa aaggggcagg ttgcaaagtt agacttggaa      300
tgcatggtgc cggtcagtgg gcacgagaac tgctgtctga cctgtgataa aatgagacaa      360
gcagacctca gcaacgataa gatcctctcg cttgttcact ggggcatgta cagtgggcac      420
gggaagctgg aattcgtatg acggagtctt atctgaacta cacttactga acagcttgaa      480
ggacctgccc gggcggccgc tcgaaagggg cgaattctgc                            520

<210> SEQ ID NO 61
<211> LENGTH: 447
<212> TYPE: DNA
<213> ORGANISM: Homo sapien

<400> SEQUENCE: 61
agagaggtgt ttttattctt tggggacaaa gccgggttct gtgggtgtag gattctccag       60
gttctccagg ctgtagggcc cagaggctta atcagaattt tcagacaaaa ctggaacctt      120
tcttttttcc cgttggttta tttgtagtcc ttgggcaaac caatgtcttt gttcgaaaga      180
gggaaaataa tccaaacgtt tttcttttaa cttttttttt aggttcaggg gcacatgtgt      240
aggcttgcta tataggtaaa ttgcatgtca ccagggtttg ttgtacagat tatttcatca      300
tccagataaa aagcatagta ccagataggt agttttttga tcctcaccct ccttccatgc      360
tccgacctca ggtaggcccc agtgtctgac ctgcccggcg gcccgctcga aagggccaat      420
tctgcagata tccatcacac tggccgg                                          447

<210> SEQ ID NO 62
<211> LENGTH: 83
<212> TYPE: PRT
<213> ORGANISM: Homo sapien

<400> SEQUENCE: 62

Lys Lys Val Leu Leu Leu Ile Thr Ala Ile Leu Ala Val Ala Val Gly
  1               5                  10                  15

Phe Pro Val Ser Gln Asp Gln Glu Arg Glu Lys Arg Ser Ile Ser Asp
                 20                  25                  30

Ser Asp Glu Leu Ala Ser Gly Phe Phe Val Phe Pro Tyr Pro Tyr Pro
             35                  40                  45

Phe Arg Pro Leu Pro Pro Ile Pro Phe Pro Arg Phe Pro Trp Phe Arg
```

Arg Asn Phe Pro Ile Pro Ile Pro Ser Ala Pro Thr Thr Pro Leu Pro
65                  70                  75                  80

Ser Glu Lys

<210> SEQ ID NO 63
<211> LENGTH: 683
<212> TYPE: DNA
<213> ORGANISM: Homo sapien

<400> SEQUENCE: 63

| | | | | | |
|---|---|---|---|---|---|
| acaaagattg | gtagctttta | tattttttta | aaaatgctat | actaagagaa | aaaacaaaag | 60 |
| accacaacaa | tattccaaat | tataggttga | gagaatgtga | ctatgaagaa | agtattctaa | 120 |
| ccaactaaaa | aaaatattga | aaccactttt | gattgaagca | aaatgaataa | tgctagattt | 180 |
| aaaaacagtg | tgaaatcaca | ctttggtctg | taaacatatt | tagctttgct | tttcattcag | 240 |
| atgtatacat | aaacttattt | aaaatgtcat | ttaagtgaac | cattccaagg | cataataaaa | 300 |
| aaagwggtag | caaatgaaaa | ttaaagcatt | tattttggta | gttcttcaat | aatgatrcga | 360 |
| gaaactgaat | tccatccagt | agaagcatct | ccttttgggt | aatctgaaca | agtrccaacc | 420 |
| cagatagcaa | catccactaa | tccagcacca | attccttcac | aaagtccttc | cacagaagaa | 480 |
| gtgcgatgaa | tattaattgt | tgaattcatt | tcagggcttc | cttggtccaa | ataaattata | 540 |
| gcttcaatgg | gaagaggtcc | tgaacattca | gctccattga | atgtgaaata | ccaacgctga | 600 |
| cagcatgcat | ttctgcattt | tagccgaagt | gagccactga | acaaaactct | tagagcacta | 660 |
| tttgaacgca | tctttgtaaa | tgt | | | | 683 |

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64

| | | | | | |
|---|---|---|---|---|---|
| ctgttcattt | gtccgccagc | tcctggactg | gatgtgtgaa | aggcatcaca | tttccatttt | 60 |
| cctccgtgta | aatgttttat | gtgttcgcct | actgatccca | ttcgttgctt | ctattgtaaa | 120 |
| tatttgtcat | ttgtatttat | tatctctgtg | tttttccccct | aaggcataaa | atggtttact | 180 |
| gtgttcattt | gaacccattt | actgatctct | gttgtatatt | tttcatgcca | ctgctttgtt | 240 |
| ttctcctcag | aagtcgggta | gatagcattt | ctatcccatc | cctcacgtta | ttggaagcat | 300 |
| gcaacagtat | ttattgctca | gggtcttctg | cttaaaactg | aggaaggtcc | acattcctgc | 360 |
| aagcattgat | tgagacattt | gcacaatcta | aaatgtaagc | aaagtaagtc | attaaaaata | 420 |
| caccctctac | ttgggctttta | tactgcatac | aaatttactc | atgagccttc | ctttgaggaa | 480 |
| ggatgtggat | ctcaaaataa | agattagtg | tttattttga | gctctgcatc | ttancaagat | 540 |
| gatctgaaca | cctctccttt | gtatcaataa | atagccctgt | tattctgaag | tgagaggacc | 600 |
| aagtatagta | aaatgctgac | atctaaaact | aaataaatag | aaaacaccag | gccagaacta | 660 |
| tagtcatact | cacacaaagg | gagaaattta | aactcgaacc | aagcaaaagg | cttcacggaa | 720 |
| atagcatgga | aaaacaatgc | ttccagtgg | | | | 749 |

<210> SEQ ID NO 65

<211> LENGTH: 612
<212> TYPE: DNA
<213> ORGANISM: Homo sapien

<400> SEQUENCE: 65

| acagcagcag | tagatggctg | caacaacctt | cctcctaccc | cagcccagaa | aatatttctg | 60 |
| cccaccccca | ggatccggga | ccaaaataaa | gagcaagcag | gccccccttca | ctgaggtgct | 120 |
| gggtagggct | cagtgccaca | ttactgtgct | ttgagaaaga | ggaaggggat | ttgtttggca | 180 |
| ctttaaaaat | agaggagtaa | gcaggactgg | agaggccaga | gaagatacca | aaattggcag | 240 |
| ggagagacca | tttggcgcca | gtcccctagg | agatgggagg | agggagatag | gtatgagggt | 300 |
| aggcgctaag | aagagtagga | ggggtccact | ccaagtggca | gggtgctgaa | atgggctagg | 360 |
| accaacagga | cactgactct | aggtttatga | cctgtccata | cccgttccac | agcagctggg | 420 |
| tgggagaaat | caccattttg | tgacttctaa | taaaataatg | ggtctaggca | acagttttca | 480 |
| atggatgcta | aaacgattag | gtgaaaagtt | gatggagaat | tttaattcag | gggaattagg | 540 |
| ctgataccat | ctgaaaccat | ttggcatcat | taaaaatgtg | acaacctggt | ggctgccagg | 600 |
| gaggaagggg | ag | | | | | 612 |

<210> SEQ ID NO 66
<211> LENGTH: 703
<212> TYPE: DNA
<213> ORGANISM: Homo sapien

<400> SEQUENCE: 66

| tagcgtggtc | gcggccgagg | tacattgatg | ggctggagag | cagggttggc | agcctgttct | 60 |
| gcacagaacc | aagaattaca | gaaaaaagtc | caggagctgg | agaggcacaa | catctccttg | 120 |
| gtagctcagc | tccgccagct | gcagacgcta | attgctcaaa | cttccaacaa | agctgcccag | 180 |
| accagcactt | gtgttttgat | tcttcttttt | tccctggctc | tcatcatcct | gcccagcttc | 240 |
| agtccattcc | agagtcgacc | agaagctggg | tctgaggatt | accagcctca | cggagtgact | 300 |
| tccagaaata | tcctgaccca | caaggacgta | acagaaaatc | tggagaccca | agtggtagag | 360 |
| tccagactga | gggagccacc | tggagccaag | gatgcaaatg | gctcaacaag | gacactgctt | 420 |
| gagaagatgg | gagggaagcc | aagacccagt | gggcgcatcc | ggtccgtgct | gcatgcagat | 480 |
| gagatgtgag | ctgaacagaa | ccttcctggc | ccacttcctg | atcacaagga | atcctgggct | 540 |
| tccttatggc | tttgcttccc | actgggattc | ctacttaggt | gtctgccctc | aggggtccaa | 600 |
| atcacttcag | gacaccccaa | gagatgtcct | ttagtctctg | cctgaggcct | agtctgcatt | 660 |
| tgtttgcata | tatgagaggg | tacctgcccg | ggcggccgct | cga | | 703 |

<210> SEQ ID NO 67
<211> LENGTH: 1022
<212> TYPE: DNA
<213> ORGANISM: Homo sapien

<400> SEQUENCE: 67

| cttgagaaag | caggattgtt | ttaagttcca | agatttaaca | aacttactgt | tcagcatcat | 60 |
| attcaagcct | aaaaggaaga | taggatttttc | aagatatatt | tccaacttct | ttaacatggc | 120 |
| accatggatg | aactgtttct | cagcactgtg | ctgcttcact | tggaattaag | gatgaattgg | 180 |
| gaggagacag | tatgacatag | gtgggtaggt | tgggtggtga | ggggaaccag | ttctaatagt | 240 |
| cctcaactcc | actccagctg | ttcctgttcc | acacggtcca | ctgagctggc | ccagtccctt | 300 |
| tcactcagtg | tgtcaccaaa | ggcagcttca | aggctcaatg | gcaagagacc | acctataacc | 360 |

```
tcttcacctt ctgctgcctc tttctgctgc cactgactgc catggccatc tgctatagcc      420
gcattgtcct cagtgtgtcc aggccccaga caaggaaggg gagccatggt gagactccaa      480
ttcccaggcc ttaatcctta accctagacc tgttgcctct agcatcattt atttatctac      540
ctacctaata gctatctacc agtcattaaa ccatggtgag attctaacca tgtctagcac      600
ctgatgctag agataatttt gttgaatccc ttcaattata aacagctgag ttagctggac      660
aaggactagg gaggcaatca gtattattta ttcttgaaca ccatcaagtc tagacttggt      720
ggcttcatat ttctatcata atccctgggg gtaagaaatc atatagcccc aggttgggaa      780
ggggaaaacg gtttgcaaca ttctcctcct tgtaggaggc gagctctgtc tcactagcta      840
tgcccctcca tcaattcacc ctatactcag atcagaagct gagtgtctga attacagtat      900
attttctaaa ttcctagccc ctgctggtga atttgccctc cccgctcct ttgacaattg       960 tccccgtgtt cgtctccggg ccctgagact ggccctgctt atcttgctga ccttcatcct     1020
ct                                                                    1022

<210> SEQ ID NO 68
<211> LENGTH: 449
<212> TYPE: DNA
<213> ORGANISM: Homo sapien

<400> SEQUENCE: 68
ccagatccat tttcagtggt ctggatttct ttttattttc ttttcaactt gaaagaaact       60
ggacattagg ccactatgtg ttgttactgc cactagtgtt caagtgcctc ttgttttccc      120
agagatttcc tgggtctgcc agaggcccag acaggctcac tcaagctctt taactgaaaa      180
gcaacaagcc actccaggac aaggttcaaa atggttacaa cagcctctac ctgtcgcccc      240
agggagaaag gggtagtgat acaagtctca tagccagaga tggttttcca ctccttctag      300
atattcccaa aaagaggctg agacaggagg ttatttcaa ttttattttg gaattaaata       360
cttttttccc tttattactg ttgtagtccc tcacttggat atacctctgt tttcacgata      420
gaaataaggg aggtctagag cttctattc                                        449

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69
gcccttagcg tgggtcgcgg cncgangtct ggagcntatg tgatncctat ggtncncagg       60
cnnatactgc tantctcatt tattctcctg cnacctantc ctctnctctg gaatcacacc      120
attattgcct gttaacactg gactgtgagt accangcaat taatttgcac caanaaagtt      180
gagggtatta tcanatattg caatctgtac agagggaaga tgatttcaat ttgatttcaa      240
cttaaccttc atctttgtct gttaacacta atagagggtg tctaataaaa tggcaaattt      300
gngatctcat tnggtataac tacactcttt ttcacagatg tgatgactga atttccanca      360
acctgcccgg gcggncgntc naagggc                                          387

<210> SEQ ID NO 70
<211> LENGTH: 836
<212> TYPE: DNA
```

<213> ORGANISM: Homo sapien

<400> SEQUENCE: 70

```
tattccattt acaaataaa ttcagccctg cactttcttt agatgccttg atttccagaa     60
tggagcttag tgctactgaa taccctggcc acagagccac ctcaggatat tcttttctcc    120
accctagttt atttatttat agatatctgt ttacaaagtc tgtagtaaat cctgatgctg    180
accatctgaa atgtactttt tttctgaatg ctgtttcaat ctaaatagc agcttttgag     240
aaaacaatga tgtaaattcc ttatgataaa aggatgattc tatatattct ttaatgatat    300
taaatatgcc gaagccaagc acacagtctt tctaaagtgt gtgtatgttt gtgtgaatgt    360
gaatgatact gatcttatat ctgttaaaag ttgttttaaa aagctgtggc atcccattgt    420
tcatatttgc caagtcttct gtaaagatgt ctaggacgaa atattttatg tgctaatgca    480
tgtatttgta aaccagattt gtttaccact caaaattaac ttgttttctt catccaaaaa    540
agtttatttc ttccacgtac ttaaattttc tgtgtgggta aatatagct ttctaatttt     600
tttctttcac aaaggcaggt tcaaaattct gttgaaagaa aaatgctttc tgaaactgag    660
gtataacacc agagcttgct gtttaaagga ttatatgatg tacatcagtt ctataaatgt    720
gctcagcagt ttaacatgtg aatcctgttt taaagtgctc agatttcaac tgtgtaagcc    780
attgatataa cgctgtaatt aaaaatgttt atatgaaaaa aaaaaaaaa aaaaaa         836
```

<210> SEQ ID NO 71
<211> LENGTH: 618
<212> TYPE: DNA
<213> ORGANISM: Homo sapien

<400> SEQUENCE: 71

```
gttgcagtga gctcaagtgt tgggtgtatc agctcaaaac accatgtgat gccaatcatc     60
tccacaggag caatttgttt accttttttt tctgatgctt tactaacttc atcttttaga    120
tttaaatcat tagtagatcc tagaggagcc agtttcagaa aatatagatt ctagttcagc    180
accaccgta gttgtgcatt gaataatta tcattatgat tatgtatcag agcttctggt      240
tttctcattc tttattcatt tattcaacaa ccacgtgaca aacactggaa ttacaggatg    300
aagatgagat aatccgctcc ttggcagtgt tatactatta tataacctga aaaacaaac    360
aggtaatttt cacacaaagt aatagatatc atgacacatt taaataggg cactactgga    420
acacacagat aggacatcca ggttttgggt caatattgta gacttttgg tggatgagat    480
atgcaggttg atrccagaag gacaacaaaa acatatgtca gatagaaggg aggagcaaat   540
gccaagagct ggagctgagg aagatcactg tgaaattcta tgtagtctag ttggctggat    600
gctagagcaa agaggtgg                                                   618
```

<210> SEQ ID NO 72
<211> LENGTH: 806
<212> TYPE: DNA
<213> ORGANISM: Homo sapien

<400> SEQUENCE: 72

```
tctacgatgg ccatttgctc attgtctttc ctctgtgtgt agtgagtgac cctggcagtg     60
tttgcctgct cagagtggcc cctcagaaca acagggctgg ccttggaaaa accccaaaac    120
aggactgtgg tgacaactct ggtcaggtgt gatttgacat gagggccgga ggcggttgct    180
gacggcagga ctggagaggc tgcgtgcccg gcactggcag cgaggctcgt gtgtccccca    240
ggcagatctg ggcacttcc caacccaggt ttatgccgtc tccagggaag cctcggtgcc     300
```

```
agagtggtgg gcagatctga ccatccccac agaccagaaa caaggaattt ctgggattac    360
ccagtccccc ttcaacccag ttgatgtaac cacctcattt tttacaaata cagaatctat    420
tctactcagg ctatgggcct cgtcctcact cagttattgc gagtgttgct gtccgcatgc    480
tccgggcccc acgtggctcc tgtgctctag atcatggtga ctcccccgcc ctgtggttgg    540
aatcgatgcc acgattgca ggccaaattt cagatcgtgt ttccaaacac ccttgctgtg     600 cccttttaatg ggattgaaag cacttttacc acatggagaa atatatttt aatttgtgat    660 gcttttctac aaggtccact atttctgagt ttaatgtgtt tccaacactt aaggagactc    720
taatgaaagc tgatgaattt tcttttctgt ccaaacaagt aaaataaaaa taaaagtcta    780
tttagatgtt gaaaaaaaaa aaaaaa                                         806

<210> SEQ ID NO 73
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 73
actctggtaa gcttgttgtt gtccaagtga agctccctca gatgaggcgt gttggccana    60
gagccattgt caacagcaga gatgctgttg aaactcaatc ccaacttagc caaattattc    120
agtcctttca ggctagctgc atcaactctg ctgattttgt tgccatcaag atgtaattcc    180
gtaagggaag gaggaagacc ttgaggaatg ctggygatat tggyatcagc aatgcggatg    240
tasgaagagc ttcttcmttc cctggaaagc cccattttca atyccttgag ctcttcakcg    300
g                                                                    301

<210> SEQ ID NO 74
<211> LENGTH: 401
<212> TYPE: DNA
<213> ORGANISM: Homo sapien

<400> SEQUENCE: 74
agtttacatg atccctgtaa cagccatggt ctcaaactca gatgcttcct ccatctgcca    60
agtgtgttct ggatacagag cacatcgtgg cttctggggt cacactcagc ttaggctgtg    120
ggtccacaga gcactcatct ggctgggcta tggtggtggt ggctctactc aagaagcaaa    180
gcagttacca gcacattcaa acagtgtatt gaacatcttt taaatatcaa agtgagaaac    240
aagaaggcaa cataataatg ttatcagaaa gatgttagga agtaaggaca gctgtgtaaa    300
gcttgaggct gaaagtagc ttgccagctt catttctttg gtttcttggg tagtgggccg     360
ccggaacagc aagatgtgag gttctggttc atggatcata t                        401

<210> SEQ ID NO 75
<211> LENGTH: 612
<212> TYPE: DNA
<213> ORGANISM: Homo sapien

<400> SEQUENCE: 75
ttatttttca attttatttt tggttttctt acaaaggttg acatttttcca taacaggtgt    60 aagagtgttg aaaaaaaaat tcaaatttt ggggagcgag ggaaggagtt aatgaaactg     120
tattgcacaa tgctctgatc aatccttctt tttctctttt gcccacaatt taagcaagta    180
```

```
gatgtgcaga agaaatggaa ggattcagct ttcagttaaa aaagaagaag aagaaatggc       240
aaagagaaag ttttttcaaa tttctttctt ttttaattta gattgagttc atttatttga       300
aacagactgg gccaatgtcc acaaagaatt cctggtcagc accaccgatg tccaaaggtg       360
caatatcaag gaagggcagg cgtgatggct tatttgtttt gtattcaatg attgtctttc       420
cccattcatt tgtcttttta gagcagccat ctacaagaac agtgtaagtg aacctgctgt       480
tgccctcagc aacaagttca acatcattag agccctgtag aatgacagcc ttttcaggt        540 tgccagtctc ctcatccatg tatgcaatgc tgttcttgca gtggtaggtg atgttctgag       600
aggcatagtt gg                                                           612

<210> SEQ ID NO 76
<211> LENGTH: 844
<212> TYPE: DNA
<213> ORGANISM: Homo sapien

<400> SEQUENCE: 76
ggctttcgag cggccgcccg ggcaggtctg atggttctcg taaaaacccc gctagaaact        60
gcagagacct gaaattctgc catcctgaac tcaagagtgg agaatactgg gttgaccta       120 accaaggatg caaattggat gctatcaagg tattctgtaa tatggaaact ggggaaacat       180
gcataagtgc caatcctttg aatgttccac ggaaacactg gtggacagat tctagtgctg       240
agaagaaaca cgtttggttt ggagagtcca tggatggtgg ttttcagttt agctacggca       300
atcctgaact tcctgaagat gtccttgatg tgcagcykgc attccttcga cttctctcca       360
gccgagcttc ccagaacatc acatatcact gcaaaaatag cattgcatac atggatcagg       420
ccagtggaaa tgtaaagaag gccctgaagc tgatggggtc aaatgaaggt gaattcaagg       480
ctgaaggaaa tagcaaattc acctacacag ttctggagga tggttgcacg aaacacactg       540
gggaatggag caaaacagtc tttgaatatc gaacacgcaa tgctgttcct tgacattgca       600
ccaccaatgt ccagaggtgc aatgtcaagg aacggcaggc gagatggctt atttgttttg       660
tattcaatga ttgtcttgcc ccattcattt gtcttttgg agcagccatc gactaggaca       720
gagtaggtga acctgctgtt gccctcagca acaagttcca catcgttgga accctgcaga       780
agcacagcct tgttcaarct gcccgtctcc tcatccagat acctcggccg cgaccacgct       840
aatc                                                                   844

<210> SEQ ID NO 77
<211> LENGTH: 314
<212> TYPE: DNA
<213> ORGANISM: Homo sapien

<400> SEQUENCE: 77
ccagtcctcc acttggcctg atgagagtgg ggagtggcaa gggacgtttc tcctgcaata        60
gacacttaga tttctctctt gtgggaagaa accacctgtc catccactga ctcttctaca       120
ttgatgtgga aattgctgct gctaccacca cctcctgaag aggcttccct gatgccaatg       180
ccagccatcc tggcatcctg gccctcgagc aggctgcggt aagtagcgat ctcctgctcc       240
agccgtgtct ttatgtcaag cagcatcttg tactcctggt tctgagcctc catctcgcat       300
cggagctcac tcag                                                         314

<210> SEQ ID NO 78
<211> LENGTH: 548
<212> TYPE: DNA
<213> ORGANISM: Homo sapien
```

<400> SEQUENCE: 78

```
accaagagcc aagtgttaca caggatattt taaaaataaa atgttttgg aatcctcacc      60
tcccatgcta tcttctaaga taactacaaa tattcttcaa agatttaact gagttctgcc    120
aaggacctcc caggactcta tccagaatga ttattgtaaa gctttacaaa tcccaccttg    180
gccctagcga taattaggaa atcacaggca aacctcctct ctcggagacc aatgaccagg    240
ccaatcagtc tgcacattgg ttttgttaga tactttgtgg agaaaaacaa aggctcgtga    300
tagtgcagct ctgtgcctac agagagcctc cctttggtt ctgaaattgc tgatgtgaca    360
gagacaaagc tgctatgggt ctaaaacctt caataaagta actaatgaca ctcaaggtcc    420
tgggactctg agacagacgg tggtaaaacc cacagctgcg attcacattt ccaatttatt    480
ttgagctctt tctgaagctg ttgcttccta cctgagaatt cccatttaga gagctgcaca    540
gcacagtc                                                             548
```

<210> SEQ ID NO 79
<211> LENGTH: 646
<212> TYPE: DNA
<213> ORGANISM: Homo sapien

<400> SEQUENCE: 79

```
accccgtcac tatgtgaata aaggcagcta gaaaatggac tcaattctgc aagccttcat     60
ggcaacagcc catattaaga cttctagaac aagttaaaaa aaatcttcca tttccatcca   120
tgcatgggaa aagggctta gtatagttta ggatggatgt gtgtataata ataaaatgat    180
aagatatgca tagtggggga ataaagcctc agagtccttc cagtatgggg aatccattgt    240
atcttagaac cgagggattt gtttagattg ttgatctact aattttttc ttcacttata    300
tttgaatttt caatgatagg acttattgga aattggggat aattctgttg tggtattaaa    360
taatattcat tttttaaaaa ctcatcttgg tattgagtta gtgcattgac ttccaatgaa    420
ttgacataag cccatatttc attttaacca gaaacaaaaa ctagaaaatg ttactcccta    480
aataggcaac aatgtatttt ataagcactg cagagattta gtaaaaaaca tgtatagtta    540
ctttagaaac aacttctgac acttgagggt tacccaatgg tctccttccc attctttata    600
tgaggtaaat gcaaaccagg gagccaccga ataaacagcc ctgagt                  646
```

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80

```
gtctgaatga gcttcnctgc gagatgggan ancataaccc agaantccaa aancntanng     60
aacgnnaaaa cccgntngaa caagnaaacn gcaactnacg gccgcctgnt gnagggcgag   120
gacgcccacc tctcctcctc ccagttctcc tctggatcgc agncatccan agatgtgacc    180
tcttccagcc gccaaatccg caccaaggtc atggatgtgc acgatggcaa ggtgggtgtc   240
cacccacgaa caggtccttc gcaccaagaa ctgagg                              276
```

<210> SEQ ID NO 81
<211> LENGTH: 647
<212> TYPE: DNA

<213> ORGANISM: Homo sapien

<400> SEQUENCE: 81

```
gtcctgcctt tcatcttttc tttaaaaaaa ataaatgttt acaaaacatt tccctcagat      60
tttaaaattc atggaagtaa taaacagtaa taaaatatgg atactatgaa aactgacaca     120
cagaaaaaca taaccataaa atattgttcc aggatacaga tattaattaa gagtgacttc     180
gttagcaaca cgtagacatt catacatatc cggtggaaga ctggtttctg agatgcgatt     240
gccatccaaa cgcaaatgct tgatcttgga gtaggrtaat ggccccagga tcttgcagaa     300
gctctttatg tcaaacttct caagttgatt gacctccagg taatagtttt caaggttttc     360
attgacagtt ggtatgtttt taagcttgtt ataggacaga tccagctcaa ccagggatga     420
cacattgaaa gaatttccag gtattccact atcagccagt tcgttgtgag ataaacgcag     480
atactgcaat gcattaaaac gcttgaaata ctcatcaggg atgttgctga tcttattgtt     540
gtctaagtag agagttagaa gagagacagg gagaccagaa ggcagtctgg ctatctgatt     600
gaagctcaag tcaaggtatt cgagtgattt aagaccttta aaagcag                  647
```

<210> SEQ ID NO 82
<211> LENGTH: 878
<212> TYPE: DNA
<213> ORGANISM: Homo sapien

<400> SEQUENCE: 82

```
ccttctttcc ccactcaatt cttcctgccc tgttattaat taagatatct tcagcttgta      60
gtcagacaca atcagaatya cagaaaaatc ctgcctaagg caaagaaata taagacaaga     120
ctatgatatc aatgaatgtg ggttaagtaa tagatttcca gctaaattgg tctaaaaaag     180
aatattaagt gtggacagac ctatttcaaa ggagcttaat tgatctcact tgttttagtt     240
ctgatccagg gagatcaccc ctctaattat ttctgaactt ggttaataaa agtttataag     300
atttttatga agcagccact gtatgatatt ttaagcaaat atgttattta aaatattgat     360
ccttcccttg gaccaccttc atgttagttg gtattataa ataagagata caaccatgaa     420
tatattatgt ttatacaaaa tcaatctgaa cacaattcat aaagatttct cttttatacc     480
ttcctcactg gccccctcca cctgcccata gtcaccaaat tctgttttaa atcaatgacc     540
taagatcaac aatgaagtat tttataaatg tatttatgct gctagactgt gggtcaaatg     600
tttccatttt caaattattt agaattctta tgagtttaaa atttgtaaat ttctaaatcc     660
aatcatgtaa aatgaaactg ttgctccatt ggagtagtct cccacctaaa tatcaagatg     720
gctatatgct aaaagagaa aatatggtca agtctaaaat ggctaattgt cctatgatgc     780
tattatcata gactaatgac atttatcttc aaaacaccaa attgtcttta gaaaaattaa     840
tgtgattaca ggtagagaac ctcggccgcg accacgct                             878
```

<210> SEQ ID NO 83
<211> LENGTH: 645
<212> TYPE: DNA
<213> ORGANISM: Homo sapien

<400> SEQUENCE: 83

```
acaaacattt tacaaaaaag aacattacca atatcagtgg cagtaagggc aagctgaaga      60
ataaatagac tgagtttccg ggcaatgtct gtcctcaaag acatccaaac tgcgttcagg     120
cagctgaaac aggcttcttt cccagtgaca agcatatgtg gtcagtaata caaacgatgg     180
taaatgaggc tactacatag gcccagttaa caaactcctc ttctcctcgg gtaggccatg     240
```

```
atacaagtgg aactcatcaa ataatttaaa cccaaggcga taacaacgct atttcccatc    300
taaactcatt taagccttca caatgtcgca atggattcag ttacttgcaa acgatcccgg    360
gttgtcatac agatacttgt ttttacacat aacgctgtgc catcccttcc ttcactgccc    420
cagtcaggtt tcctgttgtt ggaccgaaag gggatacatt ttagaaatgc ttccctcaag    480
acagaagtga gaaagaaagg agaccctgag gccaggatct attaaacctg gtgtgtgcgc    540
aaaagggagg gggaaggcag gaatttgaaa ggataaacgt ctcctttgcg ccgaggaatc    600
aggaagcgtg actcacttgg gtctgggacg ataccgaaat ccggt                   645
```

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84

```
tctgatgtca atcacaactt gaaggatgcc aatgatgtac caatccaatg tgaaatctct    60
cctcttatct cctatgctgg agaaggatta gaaggttatg tggcagataa agaattccat    120
gcacctctaa tcatcgatga gaatggagtt catgggctgg tgaaaaatgg tatttgaacc    180
agataccaag ttttgtttgc cacgatagga atagctttta tttttgatag accaactgtg    240
aacctacaag acgtcttgga caactgaagn ttaaatatcc acangggttt attttgcttg    300
g                                                                    301
```

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

```
agcgtgggtc gcggcncgan gtagagaacc gactgaaacg tttgagatga agaaagttct    60
cctcctgatc acagccatct tggcagtggc tgttggtttc ccagtctctc aagaccagga    120
acgagaaaaa agaagtatca gtgacagcga tgaattagct tcagggtttt ttgtgttccc    180
ttacccatat ccatttcgcc cacttccacc aattccattt ccaagatttc catggtttan    240 acgtaattt cctattccaa tacctgaatc tgcccctaca actccccttc ctagcg        296
```

<210> SEQ ID NO 86
<211> LENGTH: 806
<212> TYPE: DNA
<213> ORGANISM: Homo sapien

<400> SEQUENCE: 86

```
tctacgatgg ccatttgctc attgtctttc ctctgtgtgt agtgagtgac cctggcagtg    60
tttgcctgct cagagtggcc cctcagaaca acagggctgg ccttggaaaa accccaaaac   120
aggactgtgg tgacaactct ggtcaggtgt gatttgacat gagggccgga ggcggttgct   180
gacggcagga ctggagaggc tgcgtgcccg gcactgcag cgaggctcgt gtgtccccca    240
ggcagatctg ggcactttcc caacccaggt ttatgccgtc tccagggaag cctcggtgcc   300
```

-continued

| | |
|---|---|
| agagtggtgg gcagatctga ccatccccac agaccagaaa caaggaattt ctgggattac | 360 |
| ccagtccccc ttcaacccag ttgatgtaac cacctcattt tttacaaata cagaatctat | 420 |
| tctactcagg ctatgggcct cgtcctcact cagttattgc gagtgttgct gtccgcatgc | 480 |
| tccgggcccc acgtggctcc tgtgctctag atcatggtga ctccccgcc ctgtggttgg | 540 |
| aatcgatgcc acggattgca ggccaaattt cagatcgtgt ttccaaacac ccttgctgtg | 600 |
| cccttaatg ggattgaaag cacttttacc acatggagaa atatatttt aatttgtgat | 660 |
| gcttttctac aaggtccact atttctgagt ttaatgtgtt ccaacactt aaggagactc | 720 |
| taatgaaagc tgatgaattt tcttttctgt ccaaacaagt aaaataaaaa taaagtcta | 780 |
| tttagatgtt gaaaaaaaaa aaaaaa | 806 |

<210> SEQ ID NO 87
<211> LENGTH: 620
<212> TYPE: DNA
<213> ORGANISM: Homo sapien

<400> SEQUENCE: 87

| | |
|---|---|
| tttttgcatc agatctgaaa tgtctgagag taatagtttc tgttgaattt tttttgttc | 60 |
| attttctgc acagtccatt ctgtttttat tactatctag cttgaaaata tagtttga | 120 |
| aattatgaca tccttcctct ttgttatttt cctcatgatt gctttggcta ttcaaagttt | 180 |
| attttagttt catgtaaatt tttgaattgt attttccatt attgtgaaaa tagtaccact | 240 |
| gcaatttaa taggaagttt attgaatcta tagattactt tggataatat ggcacttcaa | 300 |
| taatattcat gttttcaatt catagacaaa atatttaaa attatttgt atcttttcta | 360 |
| attttttcctt tttttattgt aaagattac ctccttggtt aatatttcc tcagaaattt | 420 |
| attatttaag gtatagtcaa taaaatttc ttcctctatt ttgtcagata gtttaagtgt | 480 |
| atgaaaccat agatatactt gtatgttaat tttatatttt gctaatttac tgagtgtatt | 540 |
| tattagttta gagaggtttt aatgtactgt ttatggtttt taaatataa gattacttat | 600 |
| tttttaaaaa aaaaaaaaaa | 620 |

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88

| | |
|---|---|
| tagctgtgnt cagcaggccg aggtttttt tttttttgag atggagtctc gccctgtcac | 60 |
| ccaggctgga gtgcagtggc ctgatctcag ctcactgcaa gctccacctc ctggattcac | 120 |
| gctattctcc tgcctcagcc tcccaagtag ctgggactac aggcgcccgc caccacgccc | 180 |
| agctaattnt ttgnattttt agtacnagat gcggtttcat cgtgttagcc agcatggnct | 240 |
| cgatctcctg acctcgtgaa ctgcccgcct cggcctccca agacctgcc cgggcnggcc | 300 |
| gctcgaaa | 308 |

<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89

```
agcggccgcc cgggcaggtc tgttaagtaa catacatatc accttaataa aaatcaagat      60
gaaatgtttt agaaactatt ttatcaaaag tggctctgat acaaagactt gtacatgatt     120
gttcacagca gcactattaa tgccaaaaag tagacaaaac ctaaatgtcc attaactgat     180
aagcaaaatg tggtatatcc atacaatgga atattatgta gcccacaaca tggcatggag     240
tactacaaca tggatgagcc tcaaaaacgt tatgctaaat gaaaaaagtc agatatagga     300
aaccacatgt catatgatcc catttatatg aaatagccag aaaaggcaag tcatagaaac     360
aagatagatc ggaaaatggg ttggaggact acaaatggca ccaggatct ttgaagttga      420
tggaaatggt ctaaaatcag actgtggntg tggttgaaca agtctgtaaa tttaccaaaa     480
tgcgttaata ca                                                        492
```

<210> SEQ ID NO 90
<211> LENGTH: 390
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90

```
tcgagcggcc gcccgggcag gtacaagctt ttttttttttt tttttttttt ttttctaaca    60
gttctctgtt ttattgcaat acagcaaagt ctggttaata ttaagngata tcaacataaa    120
gtattggtga ggagtctttt gtgacatttt ttaccatccc accttaaata tttctgtgca    180
aaanaatcca catcattgtt tggtancana ggatctctta aaaagttccc taanacactg    240
agggcataaa accaaacaaa ataaaataag gagtgatagg ctaaagcagt atcttcccct    300
ccatccacat ttgncaagca ttatattcta accaaaaaat gatcacacca ggccatgcaa    360
aactgtccaa tattaccgag aaaaaaccct                                     390
```

<210> SEQ ID NO 91
<211> LENGTH: 192
<212> TYPE: DNA
<213> ORGANISM: Homo sapien

<400> SEQUENCE: 91

```
agcgtggtcg cggccgaggt ctgtcaatta atgctagtcc tcaggattta aaaaataatc     60
ttaactcaaa gtccaatgca aaacattaa gttggtaatt actcttgatc ttgaattact     120
tccgttacga aagtccttca cattttcaa actaagctac tatatttaag gcctgcccgg     180
gcggccgctc ga                                                        192
```

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92

```
agcgtggtcg cggccgaggt ctgacaacta acaaagaagc aaaaactggc atcttggaca     60
```

```
tcctagtatt acacttgcaa gcaattagaa cacaaggagg gccaaggaaa aagtttagct      120
ttgaatcact tccaaatcta ctgattttga ggttccgcag tagttctaac aaaacttttc      180
agacaatgtt aactttcgat taagaaagaa aaaaaccccca aacatcttca ggaattccat     240
gccaggttca gtctcttcca gtgagcccgc ttgctaaaag tccacgtgca ccattaatta      300
gctgggctgg cagcaccatg taaaaagaag cctattcacc accaaccaca cagactagac      360
atgtaaagta ggatcaagta atggatgaca accatggtcg tggaatatgg tcaatgagag      420
tcagaaaagt acaggcacca gtacaagcag cagataacaa aattgacggg ccaaaggata      480
aaaataggct tatttaaata ggatgctaca gaacacatnc acttctaatt ggaagctgct      540
ttacactggg tggcattgna ccatatgcat                                       570
```

<210> SEQ ID NO 93
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 93

```
tcgagcggcc gcccgggcag gtccaggttt ttatttagtt gtgtaatctt ggacaagtta       60
cctaactttt ttgagtctga atatatttaa tctgcaaaat gagaatcatg ataatacgtc      120
ataggcttaa ttaggaggat taaatgaaat aatttatagg tggtgccatg gttacataca      180
agtattagta gttaattctt ttcctttgtt tactttttata gtataggttg gatgaaggtt     240
ccagtatagg caaaaatact acttgggggt aaagtagagt gtgatacttt atttgaaatg      300
ttccctgaat ctgatcttta cttttttgnta ctgctgcact acccaaatcc aaattttcat     360
cccaacattc ttggatttgt gggacagcng tagcagcttt tccaatataa tctatactac      420
atcttttctt actttggtgc tttttg                                           446
```

<210> SEQ ID NO 94
<211> LENGTH: 409
<212> TYPE: DNA
<213> ORGANISM: Homo sapien

<400> SEQUENCE: 94

```
cgagcggccg cccgggcagg tccatcagct cttctgctta gaatacgagg cagacagtgg       60
agaggtcaca tcagttatcg tctatcaggg tgatgaccca agaaaggtga gtgagaaggt      120
gtcggcacac acgcctctgg atccacccat gcgagaagcc ctcaagttgc gtatccagga      180
ggagattgca aagcgccaga gccaacactg accatgttga aggcgttctc tccaggctgg      240
attcactgca ctcggaagaa ttctgcccag ggaatttagt gtgggggtac caggaccagt      300
ttgtcttgat cttgagaccc ccagagctgc tgcatccata gggtgttgca ggactacacc      360
tggcctgcct tgcagtcatt ctttcttata tgttgaccca tttgcccaa                  409
```

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95

```
tcgagcggcc gcccgggcag gtcctacttg tttgcagctt ccacacactg cacctaccta    60
ctacctctct tccatgctta actgggttta gaaaggtgag ctatgcgtag aagaactact   120
tgggatattc aagtgctgta tttgaacgat aagcctatag ataacagtct gaagctgcaa   180
gggagacttt gttagtacac tactataaac aggtaaacta cctgtttgta cttgatatag   240
tgcatatgaa atgactgatt taatacaaaa ctacagaaca tgcaaaattt tttctgagat   300
gttaagtatt acttcagtgg agaacaaaac ttacttaacc tttcgctaat gcatgtagta   360
ccagaaagca aacatggttt tagcttcctt tactcaaaat atgaacatta agtggttgtg   420
aattttgtct gccaagtggt tcagaaaata cattataaat aacctaagtt aaaaaaaga   480 aactgngaac                                                           490

<210> SEQ ID NO 96
<211> LENGTH: 223
<212> TYPE: DNA
<213> ORGANISM: Homo sapien

<400> SEQUENCE: 96
agcgtggtcg cggccgaggt ctggaagccc acctaggac ttgaatggca ccttgtcctt    60
tctctgccag taatgcaatc caacacaata tgctacaggg aaaacagaat ttccacggtg   120
ccgccctctg gtacaaggga acagcacgc aaagcaaaag gccacagagg gctccctgag    180
aatccagtac aactaagcga ggacctgccc gggcggccgc tcg                     223

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97
tcgagcggcc gcccgggcag gtctgtgcag gagacactga agtgggtagt gtccataatc    60
tttttagcct gttgctgaaa ttccagttgt actccttcaa accaaaatgc ttacaggatc   120
atgggaaagc ctcggttgca gaaatcaaga caggcaagtg ggaagataac tcggctttga   180
ggttaaacag atctgggttc aaagcatagt ttcactctct gtcttgtgaa gtgtcctggg   240
tgaagtcatt tcctctcttg aatttcagag aggatgaaaa tataaaaagt ataataacta   300
tcttcataat ctttgtgagg attaaagaag acgaagtgtg tgaaaagcta agcacagagc   360
aggcattcta caataagtag ttattatttt tggaaccatc ccgncctag ccccagccca   420 attaccttct cttagnctct tcatatcgaa ngccgtaatc ttgaccttct cttgcnactg    480
gattggtgct ggttgatgcc caaacttccc gagatgctgt ctgggaa                 527

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98
tcgagcggcc gcccgggcag gtctggctcc catggccctt ggggtggcct gactctgtca    60
```

```
ctattcctaa aaccttctag gacatctgct ccaggaagaa ctttcaacac caaaattcat      120 ctcaattta cagatgggaa aagtgattct gagaccagac cagggtcagg ccaaggtcat      180
ccagcatcag tggctgggct gagactgggc cagggaacc ctgtctgctc ctcttttcc      240 cagagctgtg agttctctag ccaaggctgc actcttgagg gagagccagg aagcatagct     300
gaggccatga caacctcact cttcacctga aatttaacc cgtggcagag gatccaggca     360
catataggct tcggagccaa acaggacctc ggccgcgacc acgctaagcc gaattccagc    420
acactggcgg ccgttactag tggatcccga gcttnggtac caagcttggc gtaatcatgg    480
gcatagctgg ttcctggggt gaaaatggta tccg                                 514
```

```
<210> SEQ ID NO 99
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 99
```

```
tcgagcggcc gcccgggcag gtctgaagaa acaggtataa atttggcagc cagtaatttt    60
gacagggaag ttacagcttg catgacttta aatatgtaaa tttgaaaata ctgaatttcg   120
agtaatcatt gtgctttgtg ttgatctgaa aaatataaca ctggctgtcg aagaagcatg   180
ttcaaaaata tttaattcac ttcaaaatgt catacaaatt atggtggttt ctatgcaccc   240
ctaaagcttc aagtcattta gctcaggtac atactaaagt aatatattaa ttcttccagt   300
acagtggtgt ttcataccat tgacatttgc atacccctaga ataatttaag aaagacatgt   360
gtaatattca caatgttcag aaaagcaagc aaaaggtcaa ggaacctgct ttggttcttc    420
tggagatggn ctcatatcag cttcataaac attcattcta caaaatagta agctaaccat    480
ttgaacccca atttccagat taagcatatt ttctcataaa tnatgaagcc                530
```

```
<210> SEQ ID NO 100
<211> LENGTH: 529
<212> TYPE: DNA
<213> ORGANISM: Homo sapien

<400> SEQUENCE: 100
```

```
agcgtggtcg cggccgaggt ccaggcacgg tggcttatgt gtgtaatccc agcacttggg    60
gaggctgagg gaggtggatc acttgagtcc aggagtttga gaccagtctg ggcaacatgg   120
cgaaacttca tcactaccaa agaagaaaaa aattagccag gtgtggtggt gtatgcctgt   180
agtcccagat actctggtgg ctgaggtgag aggatagctt gagcccagga aattgaggct    240
gcagtgaact atgattgcac tactgtgctc cagcttgggc aacagagtga atcttgtct    300 ccaaaagtcc ttgaaggatt ttaggaagtt gttaaaagtc ttgaaacgat gtttggggc    360 atgttagggt tcttgaatgt ttaattcctc taataactgc ttattcaaga gaagcatttc    420
tgactgggtg cggggcagtg gcttcatgcc ccataatccc agtactttgg gaggctgaag    480
caggaacatt gcttgagccc aggacttcaa gaacagcctg ggtaacata                529
```

```
<210> SEQ ID NO 101
<211> LENGTH: 277
<212> TYPE: DNA
<213> ORGANISM: Homo sapien

<400> SEQUENCE: 101
```

```
tcgagcggcc gcccgggcag gtcgcaggaa gaggatggaa actgaggagt ccaggaagaa    60
gagggaacga gatcttgagc tggaaatggg agatgattat attttggatc ttcagaagta   120
ctgggattta atgaatttgt ctgaaaaaca tgataagata ccagaaatct gggaaggcca   180
taatatagct gattatattg atccagccat catgaagaaa ttggaagaat tagaaaaaga   240
agaagagctg agaacagacc tcggccgcga ccacgct                           277

<210> SEQ ID NO 102
<211> LENGTH: 490
<212> TYPE: DNA
<213> ORGANISM: Homo sapien

<400> SEQUENCE: 102
gcgtggtcgc ggccgaggtc tgacggcttt gctgtcccag agccgcctaa acgcaagaaa    60
agtcgatggg acagttagag gggatgtgct aaagcgtgaa atcagttgtc cttaattttt   120
agaaagattt tggtaactag gtgtctcagg gctgggttgg ggtccaaagt gtaaggaccc   180
cctgccctta gtggagagct ggagcttgga gacattaccc cttcatcaga aggaattttc   240
ggatgttttc ttgggaagct gttttggtcc ttggaagcag tgagagctgg gaagcttctt   300
ttggctctag gtgagttgtc atgtgggtaa gttgaggtta tcttgggata aagggtcttc   360
tagggcacaa aactcactct aggtttatat tgtatgtagc ttatattttt tactaaggtg   420
tcaccttata agcatctata aattgacttc ttttcttag ttgtatgacc tgccccgggc   480
ggccgctcga                                                         490

<210> SEQ ID NO 103
<211> LENGTH: 490
<212> TYPE: DNA
<213> ORGANISM: Homo sapien

<400> SEQUENCE: 103
gagcggccgc ccgggcaggt ccaaaccagc ttgctcataa gtcattaacc aaatccatta    60
taggtaattt gttcagttca atgtttacaa ttcttatgga aaaaattagc aacacacaca   120
tttaaaacgt gtgcatttac ctttgcgtga gtgcttaaaa tacatatttc tatttcaaga   180
tgacatttaa aaattattct aatatatcag cagcaaaaat ataatttgca attacaaaaa   240
actaaactag aatccttaag ttattctcat gtttacagtt gtgattcttt aataaatact   300
attatgcagc tctattgttt aagctttctg gatttggttt aaacacatgc atatatattg   360
tcaattgtgg gaagctttac aagttatatt ccatgcactt tttggacaga gttctaacag   420
agccagccag tccacaaaac aggcaagaca aaagttgaat taactgggc aaaataggac   480 tcttatgcaa                                                         490

<210> SEQ ID NO 104
<211> LENGTH: 489
<212> TYPE: DNA
<213> ORGANISM: Homo sapien

<400> SEQUENCE: 104
cgtggtcgcg gccgaggtcc aggctggtct cgaactcctg accttgtgat ctgcccgcct    60
cggcctccca agtgttggga ttacaggca tgagccactg cgcccgaccg agttgaacat   120
ttaatgtcag actaggccag agtttctcaa tctttttatt ctcacttccc aaaggagccg   180
ttggagattt tcccctcaat ctctctcctt catgaaattt cataccacaa atatagtatg   240
```

-continued

| | | |
|---|---|---|
| ttttatttat gtactgtgac cctttgaagg atcacaaacc aatataatag tttttctttt | 300 | |
| taacccgtca aggaccaagt ttttgcccct gttggaaatg cataaactgg actgatgaat | 360 | |
| tggtatagat ggcttttatc atgaggatca gaaaaacttg aaattccttg ctacgacac | 420 | |
| tccatattta tcaccgtata gggaggacct tggtatgggg aagtagaaac acttctacac | 480 | |
| tttacagca | 489 | |

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105

| | | |
|---|---|---|
| gcgtggtcgc ggccgaggtc tgactggctt cagccccaga agttgagctg gcctttagac | 60 | |
| aaaataattg cacctccctc tgctgcttat tcccttccgt ttttcatttg agtgtgaaca | 120 | |
| gttagataaa atctgtggct gnctcttcca ccttgctcta gtttccattg ctgtgagcag | 180 | |
| gccctcctat gccccgcatt tagctacaat gctgtggact cacttgattc tttttctccg | 240 | |
| agctttgtct agaaatatgt gaaggtgagg ttaagtgctt ctctgtgtag atccacttag | 300 | |
| ccctgtctgc tgtctcgatg ggcgttgctt cgtctctcct ctcttccatc ctttccattt | 360 | |
| gcttctcacc accttctggc ttcttttctt aatgcaataa aggcagtttc taacaaagaa | 420 | |
| agaatgtggg ctttggagtt agacagacct ggntttaaat tctgcttctg gctctccaa | 479 | |

<210> SEQ ID NO 106
<211> LENGTH: 511
<212> TYPE: DNA
<213> ORGANISM: Homo sapien

<400> SEQUENCE: 106

| | | |
|---|---|---|
| tcgcggccga ggtccaaaac gtggattcca atgacctgcc ttgagcccgc ggttgccagg | 60 | |
| agttggacct gcagtagtat gggaagctca cggcctaaat accgactgcc ctctgacccc | 120 | |
| accgtccagc gattctagaa catttctagt aggaaagaca tagcaaggga ttttcatgat | 180 | |
| tgggaaatac tgggagacaa gctgaagatt tgttaagggc tatgcttctg tcatctttta | 240 | |
| ggtatttaag gctactcctt tagctagcta ctttgagctg tttaaagtga ctatctccct | 300 | |
| acacagagtt acacaatgag catctctgaa agagaatatt accctggatt tccaaagatg | 360 | |
| tactctaaca ggatgaccag gcaaaaggtg acccggggga ggagtctgtt ataacactcg | 420 | |
| gacccacatg ttctcaaggc acttcagaac tttgggaaat cattttgtac cggatcctca | 480 | |
| gaaagcattt atggaaatac acatccttta g | 511 | |

<210> SEQ ID NO 107
<211> LENGTH: 451
<212> TYPE: DNA
<213> ORGANISM: Homo sapien

<400> SEQUENCE: 107

| | | |
|---|---|---|
| ggccgcccgg gcaggtccag aatatcaaat caaaggtca caaatgttca cttcctcctc | 60 | |
| caccctctta catattggat cttcaattgc aatagggagt gtaagatggg cattttagag | 120 | |
| acgtagttgc atcagcagaa gcaaacccat cttatacaaa tgggttttgg ggataggaaa | 180 | |
| aggctgctaa aaattcacaa gtcaccattc cccagaagca atgaatagcc gtagaagacc | 240 | |

```
aaggaagatc aacaagtttc caaagtgcta aagccagaga tttggcccttt ccaaaatacc    300 accaggacgc ctggacccgt gggctctccg catgtcacca ctgactgcca ggatgctgct    360
gcacctccct tccttgagac acaacagaga gacagtgaag tcacccaaga ctgggatcat    420
cagaggctcc tcatgcttgc tacagagaag c                                   451
```

<210> SEQ ID NO 108
<211> LENGTH: 461
<212> TYPE: DNA
<213> ORGANISM: Homo sapien

<400> SEQUENCE: 108

```
ccgcccgggc aggtcctgaa acattcaga ctaatcaaaa tggtactact gtaacttctt    60
ataatacata atataaaagt ttttgaaaga tatagacaca attaacccct aaacaacaca   120
ctatctgatt ctcaaaagca atggctattt aacaagatgt aaaaggacaa taacatatca   180
aagaactttc acacacctaa agatagcatt tagcagcaag ttagtcagac aaaacaaaca   240
caaatatttt cacatttcct atgtttgttt ttaactttac ttcataaagc cactgataat   300
tgaggtttct ttcaagtata agatttctaa aattaaaaac tgttttttgac atattttat    360 aaagaaataa aaagcaaaac gcaatccaac tatttatatg agtccctctt ctccaacagc   420
tttagatggt tttctgagta ctttttttaca cagaatattt t                      461
```

<210> SEQ ID NO 109
<211> LENGTH: 441
<212> TYPE: DNA
<213> ORGANISM: Homo sapien

<400> SEQUENCE: 109

```
ggccgcccgg gcaggtctga ttataagaga agaaatcca gtgacacgag ggcaggcagg     60
ccccgctctg ctctgatcga gaaaagcttc ctgatgtcag ggagatggaa ctgccaccat   120
cagaaccatg gcactttggg tgaaggtgtg tcagcgacca aggggggcagg aaatgggcag  180 tgactaaggg ggcaggaaac aggcaggcac atggcaaggt tctcccagcc catcagccca  240
gtgatggcct cgatttttgaa gctgcactac tgtctgaaaa gcacaattac tggtgactct  300
taacaaactt cagcatactg gggaaggaga ctgtcaagta actgaattgg aaagatgaaa  360 agaaccatc tctaaaagtt gatgcttgtc agaagaataa cctcctttgt gcaagtcttg   420
caacatcttc attcaaccac a                                            441
```

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110

```
ggtcgcggcc gaggtctggg gaagggggtga gaatccctgg gccttgccca gtcctgagct    60
ctgggtgtct gcagggaagc acagtggtga gttagtgtta aagaaagcat ccagagaggt   120
aagaggggct tgggtagcac cctttgcctc tgtcacttcc gcaaaaactt cttgttgagg   180
aggaagatga gaaggttgac attgactttg gccttgttga agagtttcat gacagccaca   240
ccctcatact ggagctgcan gagatcctga tagtgaagct tgaaatcgct ccatgtccac   300
```

```
acccaggaac ttggcattta cttcaaactt tcctgcctca tctcccggcg tgatgtcaaa        360
natgacgttt cttgaagtga gaggcgggaa agatcttcaa tttccaccaa agacaccctt        420
tttccaggaa gcttgagcaa caagtgtaat g                                       451
```

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111

```
ggccgacgtt cgacctgact tctttngagc agntgncact acccgtcttg aggaatgccg         60
actgcagaca gtggcccang gcaaagagtg tgcgtcatcg atganattgg naagatggag        120
ctcttcagtc agnttttcat tcaagctgnt cgtcagacgc tgtctacccc agggactata        180
atcctnggca caatcccagt tcctanagga aagccactgn ctcttgtaga agaaatcana        240
cacanaaagg atgtgaacng tgtttaatgt caccaaggga aaacatgaaa ccaccttctg        300
ccagatatcg ggacgttgcg tgcagatcaa gcacgnaagt gaagacgcgt gcattccttg        360
ccttccgtga acgantgccc agntcaagaa gancctgatg gaaccct                      407
```

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

```
tcgcggccga ggtcggccga ggtctgacat ctgttgtctg tgataaccac ttctgtattg         60
cgtcttaacc acttctgtat tgtgtggttt taactgccta aggcggcaat gggcagtggg        120
cccctttccc ttaggatggg tatcaattca acaatattta taaggcattt actgtgtgct        180
aagcatttgg aagacccagg ctacaaaata agacatagtt cctgccctcc aggccagcag        240
agggaggcac aaatacccag gaatctctga tgggtgtgaa gtgcggtcgt gggccacaga        300
aaatgaccgt catggagacc ctgctaaagg tcggaccctg agcccaaagg ggtattcaga        360
agnggagatg attttggccc cactcataga tgggtggcaa a                            401
```

<210> SEQ ID NO 113
<211> LENGTH: 451
<212> TYPE: DNA
<213> ORGANISM: Homo sapien

<400> SEQUENCE: 113

```
gtcgcggccg aggtccatat taaaaagtcc atcataaaca aagactcctc ctcatggtat         60
gaatatgctc catatgccca taatggtgca taacggactt agaaattcca atgagtctta        120
gggttgaaat ttccaatgac ctgagcaagg cagctcccta tagcttctgg ataacatttt        180
acacccagag ttcaggctta aacagaccta tcaacacaat tattttcgga ttgtctgtct        240
agaaaacggc aatgctcaaa ggaatataaa taagggtggg gggacatatg cttccagcct        300
ggcctttctc catgtggtaa aaaacaatgg aatggctgtg ttaatttttt tttaatcttt        360
tctgaccttt actatgtttg gtaatggaaa taagtcaggg aaaacaaaat gaacaggtct        420
```
catcacttaa ttaatactgg gttttcttct t                                    451

<210> SEQ ID NO 114
<211> LENGTH: 441
<212> TYPE: DNA
<213> ORGANISM: Homo sapien

<400> SEQUENCE: 114
ggccgcccgg gcaggtccat cctgtcagag atgggagaag tcacagacgg aatgatggat       60
acaaagatgg ttcactttct tacacactat gctgacaaga ttgaatctgt tcatttttca      120
gaccagttct ctggtccaaa aattatgcaa gaggaaggtc agcctttaaa gctacctgac      180
actaagagga cactgttgtt tacatttaat gtgcctggct caggtaacac ttacccaaag      240
gatatggagg cactgctacc cctgatgaac atggtgattt attctattga taaagccaaa      300
aagttccgac tcaacagaga aggcaaacaa aaagcagata agaaccgtgc ccgagtagaa      360
gagaacttct tgaaacttga cacatgtgca aagacaggaa gcagcacagt ctcggcggga      420
ggaagaaaaa aagaacagag a                                                441

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115
gccgcccggg caggtccatt ggcggtgaca aaggaaaag aagcaaagag actcagtcca        60
taatgctgat tagttagaag aaagggctag gattgagaaa gtaccaggaa cttttaatta      120
tttaaaagag aatgctgact gttaatgttt taaatcttac tgttcaaatg tactaatatg      180
aatttttacc ctttgtgcat gaatattcta acaactaga agacctccac aatttagcag       240
ttatgaaagt taaacttttt attataaaaa ttctaaacct tactgctcct ttaccaggaa      300
catgacacac tatttancat cagttgcata cctcgccaat agtataattc aactgtcttg      360
cccgaacaat catctccatc tggaagacgt aagcctttag aaacacattt ttctattaat      420
ttctctagaa c                                                           431

<210> SEQ ID NO 116
<211> LENGTH: 421
<212> TYPE: DNA
<213> ORGANISM: Homo sapien

<400> SEQUENCE: 116
gtcgcggccg aggtccagaa atgaagaaga agtttgcaga tgtatttgca aagaagacga       60
aggcagagtg gtgtcaaatc tttgacggca cagatgcctg tgtgactccg gttctgactt      120
ttgaggaggt tgttcatcat gatcacaaca aggaaccggg gctcgtttat caccagtgag      180
gagcaggacg tgagcccccg ccctgcacct ctgctgttaa acaccccagc catcccttct      240
ttcaaaaggg atcctttcat aggagaacac actgaggaga tacttgaaga atttggattc      300
agcccgcgaa gagatttatc aagcttaact cagataaaat cattgaaagt aataaggtaa      360
aagctaagtc tctaacttcc aggcccacgg ctcaagtgaa tttcgaatac tgcatttaca      420
g                                                                      421

<210> SEQ ID NO 117
<211> LENGTH: 489
<212> TYPE: DNA
<213> ORGANISM: Homo sapien

<400> SEQUENCE: 117

| | | | | | |
|---|---|---|---|---|---|
| agcgtggtcg | cggccgaggt | aaggctgcga | ggttgtggtg | tctgggaaac | tccgaggaca | 60 |
| gagggctaaa | tccatgaagt | ttgtggatgg | cctgatgatc | cacagcggag | accctgttaa | 120 |
| ctactacgtt | gacactgctg | tgcgccacgt | gttgctcaga | cagggtgtgc | tgggcatcaa | 180 |
| ggtgaagatc | atgctgccct | gggacccaac | tggtaagatt | ggccctaaga | agcccctgcc | 240 |
| tgaccacgtg | agcattgtgg | aacccaaaga | tgagatactg | cccaccaccc | ccatctcaga | 300 |
| acagaagggt | gggaagccag | agccgcctgc | catgccccag | ccagtcccca | cagcataaca | 360 |
| gggtctcctt | ggcagacctg | cccggggcggc | cgctcgaaag | cccgaattcc | agcacactgg | 420 |
| cggccgttac | tagtggatcc | cagctcggta | ccaagcttgg | cgtaatcatg | gtcatagctg | 480 |
| gtttcctgt | | | | | | 489 |

<210> SEQ ID NO 118
<211> LENGTH: 489
<212> TYPE: DNA
<213> ORGANISM: Homo sapien

<400> SEQUENCE: 118

| | | | | | |
|---|---|---|---|---|---|
| tcgagcggcc | gcccgggcag | gtattgaata | cagcaaaatt | ctatatacaa | agtgacctgg | 60 |
| acctgctgct | tcaaaacatg | atcctttctt | actaatatct | tgatagtcgg | tccatagagc | 120 |
| attagaaagc | aattgactct | taaataaaca | gaaaagtgcc | taatgcacat | taaatgaatg | 180 |
| gcctaactac | tggaacttta | gtagttctat | aaggtgatta | acataggtag | gatccagttc | 240 |
| ctatgacagg | ctgctgaaga | acagatatga | gcatcaagag | gccatttgt | gcactgccac | 300 |
| cgtgatgcca | tcgtgtttct | ggatcataat | gttcccatta | tctgattcta | gacacaccac | 360 |
| aggaatatca | gtggggtcag | aggttagctt | agctgcttgc | tgggctagaa | cagatatcac | 420 |
| tccagcatgc | tcatctgaca | gggtcccgcg | gcaacccaga | ttaagtcctt | gtgaatctgt | 480 |
| gcacaggga | | | | | | 489 |

<210> SEQ ID NO 119
<211> LENGTH: 181
<212> TYPE: DNA
<213> ORGANISM: Homo sapien

<400> SEQUENCE: 119

| | | | | | |
|---|---|---|---|---|---|
| taggttccag | agactttttgg | cccaggagga | atatttactt | ttagctctgg | acatcattac | 60 |
| aaaaaggaat | atttcccaaa | cctcttcaga | ccgagaatac | atgggtaaaa | ttattaaata | 120 |
| gttgtataat | aaaaataatt | ttttccttaa | aaaaaaaaaa | aacctcggcc | gcgaccacgc | 180 |
| t | | | | | | 181 |

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120

```
gcgtggtcgc ggccgaggtc catttaaaac aaagaaaaat actaaagcca ctagtaaaca      60
tctgatgtgc aaaatacaac atcctctagt tggctttatg ccattattac ataagctcca     120
aatagctcat cttaaattaa aaagaaaaag tggctgtccc atctctgctg cataaatcag     180 atttttttt aaaggtttag agtactttaa ggaagggaag ttcaaaactg ccagtgaaat      240
tcacagagaa tacaaattta gcaatttaat ttcccaaagc tctttgaaga agcaagagag     300
tctctcttct taatgcagtg ttctcccaag aggaactgta attttgcttg gtacttatgc     360
tgggagatat gcaaaatgtg tttttcaatg tttgctagaa tataatggtt cctcttcagt     420
gnctggttca tcctggaact catgggttaa gaaggacttc ttggagccga actgcccggg     480 cgggccntt                                                             489
```

<210> SEQ ID NO 121
<211> LENGTH: 531
<212> TYPE: DNA
<213> ORGANISM: Homo sapien

<400> SEQUENCE: 121

```
cgagcggccg cccgggcagg tggccagcgc tggtcccgca gacgccgaga tggaggaaat      60
atttgatgat gcgtcacctg gaaagcaaaa ggaaatccaa gaaccagatc ctacctatga     120
agaaaaaatg caaactgacc gggcaaatag attcgagtat ttattaaagc agacagaact     180
ttttgcacat tcattcaac ctgctgctca gaagactcca acttcacctt tgaagatgaa      240
accagggcgc ccacgaataa aaaagatga gaagcagaac ttactatccg ttggcgatta     300
ccgacaccgt agaacagagc aagaggagga tgaagagcta ttaacagaaa gctccaaagc     360
aaccaatgtt tgcactcgat ttgaagactc tccatcgtat gtaaaatggg gtaaactgag     420
agattatcag gtcccgagga ttaaactggc tcatttcttt gtatgagaat ggcatcaatg     480
gtatccttgc agatgaaatg ggcctaggaa agactcttca acaatttctc t              531
```

<210> SEQ ID NO 122
<211> LENGTH: 174
<212> TYPE: DNA
<213> ORGANISM: Homo sapien

<400> SEQUENCE: 122

```
tcgagcggcc gcccgggcag gtctgccaac agcagaggcg gggcctccgg catcttcaaa      60
gcacctctga gcaggctcca gccctctggc tgcgggaggg gtctgggggtc tcctctgagc    120 tcggcagcaa agcagatgtt atttctctcc cgcgacctcg ccgcgacca cgct            174
```

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123

```
agcgtggtcg cggccgaggt cctcaaccaa gagggttgat ggcctccagt caagaaactg      60
tggctcatgc cagcagagct ctctcctcgt ccagcaggcg ccatgcaagg gcaggctaaa     120
agacctccag tgcatcaaca tccatctagc anagagaaaa ggggcactga agcagctatg    180
tctgccaggg gctaggggct cccttgcaga cagcaatgct acaataaagg acacagaaat    240
```

```
gggggaggtg ggggaagccc tattttata acaaagtcaa acagatctgt gccgttcatt      300
cccccagaca cacaagtaga aaaaaaccaa tgcttgtggt ttctgccaag atggaatatt      360
cctccttcct aanttccaca catggccgtt tgcaatgctc gacagcattg cactgggctg      420
cttgtctctg tggtctgggc accagtagct tgggccccat atacacttct cagttcccac      480
anggcttatg gccnangggc angctccaat tttcaagcac cacgaaggaa g               531
```

<210> SEQ ID NO 124
<211> LENGTH: 416
<212> TYPE: DNA
<213> ORGANISM: Homo sapien

<400> SEQUENCE: 124

```
tcgagcggcc gcccgggcag gtccatctat actttctaga gcagtaaatc tcataaattc       60
acttaccaag cccaggaata atgactttta aagccttgaa tatcaactaa gacaaattat      120
gccaattctg atttctcaca tatacttaga ttacacaaag ataaagcttt agatgtgatc      180
attgtttaat gtagacttat ctttaaagtt tttaattaaa aactacagaa gggagtaaac      240
agcaagccaa atgatttaac caaatgattt aagagtaaaa ctcactcaga aagcattata      300
cgtaactaaa tatacatgag catgattata tacatacatg aaactgcaat tttatggcat      360
tctaagtaac tcatttaagt acattttggg catttaaaca aagatcaaat caagct         416
```

<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

```
agcgtggtcg cggccgaggt gcttttttt ttttttttt ttttttttt gctattctaa       60 aggggaaggc ccctttttat taaacttgta cattttactt tccttctttc anaatgctaa     120
taaaaaactt tgtttatac ttaaaaaaac cataaatcan acaaacaaaa gaaacgattc     180
caacatcact tctgngatg                                                  199
```

<210> SEQ ID NO 126
<211> LENGTH: 490
<212> TYPE: DNA
<213> ORGANISM: Homo sapien

<400> SEQUENCE: 126

```
cgtggtcgcg gccgaggtcc agttgctcta agtggattgg atatggttgg agtggcacag       60
actggatctg ggaaaacatt gtcttatttg cttcctgcca ttgtccacat caatcatcag      120
ccattcctag agagaggcga tgggcctatt tgtttggtgc tggcaccaac tcgggaactg      180
gcccaacagg tgcagcaagt agctgctgaa tattgtagag catgtcgctt gaagtctact      240
tgtatctacg gtggtgctcc taagggacca caaatacgtg atttggagag aggtgtggaa      300
atctgtattg caacacctgg aagactgatt gacttttag agtgtggaaa aaccaatctg      360
agaagaacaa cctaccttgt ccttgatgaa gcagatagaa tgcttgatat gggctttgaa      420
ccccaaataa ggaagattgt ggatcaaata agacctgata ggcaaactct aatgtggagt      480
gcgacttggc                                                             490
```

<210> SEQ ID NO 127
<211> LENGTH: 490
<212> TYPE: DNA
<213> ORGANISM: Homo sapien

<400> SEQUENCE: 127

```
cgtggtcgcg gccgaggtcg gccgaggtct ggagatctga gaacgggcag actgcctcct      60
caagtgggtc cctgacccct gaccccgag cagcctaact gggaggcacc ccccagcagg     120
ggcacactga cacctcacac ggcagggtat tccaacagac ctgaagctga gggtcctgtc     180
tgttagaagg aaaactaaca agcagaaagg acagccacat caaaacccca tctgtacatc     240
accatcatca aagaccaaaa gtaaataaaa ccacaaagat gggaaaaaaa cagaacagaa     300
aaactggaaa ctctaaaaag cagagcacct ctcctcttcc aaaggaacgc agttcctcac     360
cagcaatgga acaaagctgg atggagaatg actttgacga gctgagaaaa gaacgcttca     420
gacgatcaaa ttactctgag ctacgggagg acattcaaac caaaggcaaa gaagttgaaa     480
actttgaaaa                                                            490
```

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128

```
cgtggtcgcg gccgaggtgc tttttttttt tttttttttt tttttttttt tgctgattta      60
ttttttctnt ttattgttac atacaatgta taaacacata aaacanaaaa cagtagggat     120
cctctaggat ctctagggan acagtaaagt anaaagaggt ctcanaaaca ttttttttaaa    180
gtacaagaca ttcagngctc ggcccaaagg cgtaaaaggt ttanagccag canatagctg     240
nactaaaggc tccgtctntn tccccanagc caggacaacc ccaggagct ntccattagc      300
agccagtcca cgcaggcagg atgctgcgga aaaagctcta tgctganaac attccccttg     360
atggaaagaa gggcaacaca aaaggggtaa ctaanagctc cttcctctcg tgagggcgac     420
aactgaggaa cagaaaagga gtgtcccatg tcacttttga ccccctccc                 469
```

<210> SEQ ID NO 129
<211> LENGTH: 419
<212> TYPE: DNA
<213> ORGANISM: Homo sapien

<400> SEQUENCE: 129

```
gcgtggtcgc ggccgaggtc tgattttcat ttaaatattt cagagctata gcatttgcct      60
ccatgctcaa atccacacca ttggggctta agccgctcat gccaacatta gcaaatgaca     120
tgcagtttaa tccagagatc actgcttctg ggctgatgca tgccaacaca ctggcgtgat     180
ccacgttatg tgcattttc ttcactttag tgggagaatc aatttttact ccaaggcttc      240
ttagttgctt aagagttgca ttaaggacac aatctttgtc caccagtctt gaatgatgtg     300
ttttttttctt tgtatggtaa acgttttggg ttctggtgca ttcatgactg ataattactg    360
ctttggtaga cggctgctca agtttccttg gaggaactat ttaataggtg ggttacttg     419
```

<210> SEQ ID NO 130
<211> LENGTH: 354
<212> TYPE: DNA

<213> ORGANISM: Homo sapien

<400> SEQUENCE: 130

| | | | | | |
|---|---|---|---|---|---|
| agcgtggtcg | cggccgaggt | ccatctgagg | agataaccac | atcactaaca | aagtgggagt | 60 |
| gaccccgcag | agcacgctgt | ggaattccat | agttggtctc | atccctggtc | agtttccaca | 120 |
| tgatgatggt | cttatctcga | gaggcggaga | ggatcatgtc | cgggaactgc | ggggtagtag | 180 |
| cgatctgggt | tacccagccg | ttgtggccct | tgagggtgcc | acgaagggtc | atctgctcag | 240 |
| tcatggcggc | ggcgagagcg | tgtgtcgctg | cagcgacgag | gatggcactg | gatggcttag | 300 |
| agaaactagc | accacaacct | ctcctgccgc | acctgcccgg | gcggcccgct | cgaa | 354 |

<210> SEQ ID NO 131
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 131

| | | | | | |
|---|---|---|---|---|---|
| cgagcggccg | cccgggcagg | tctggcagca | gcttcctctg | gaataattga | cagctttgtg | 60 |
| ctgcctgact | aaaatttgaa | atgacaaccg | ctgaatgtaa | aatgatgtac | ctacaatgag | 120 |
| agagatttag | gaatactatc | tgtcaatcca | tagatgtaga | aacaaaacaa | actacagaat | 180 |
| gaaaacaaac | ttattttaaa | ccaaagaaac | aaatgtatcc | aaaatatagt | ccatgatata | 240 |
| tttgattact | agtataacca | cagttgaaaa | cttaaaaaaa | aaaattgaca | ttttttgtaa | 300 |
| tgggtactaa | tggatttata | aaaggtttct | gtttccaaag | atgttattgg | ggtccacata | 360 |
| ttccttgaag | acttcagcat | cccaaagccc | gacatcagag | atactttcct | ttagccattg | 420 |
| nttcccgtaa | cttgcccact | ccatggtgat | gtgacaggct | tcccttcatt | agca | 474 |

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132

| | | | | | |
|---|---|---|---|---|---|
| ggccgaggtg | gggaattcat | gtggaggtca | gagtggaagc | aggtgtgaga | gggtccagca | 60 |
| gaaggaaaca | tggctgccaa | agtgtttgag | tccattggca | agtttggcct | ggccttagct | 120 |
| gttgcaggag | gcgtggtgaa | ctctgcctta | tataatgtgg | atgctgggca | cagagctgtc | 180 |
| atctttgacc | gattccgtgg | agtgcaggac | attgtggtag | gggaagggac | tcattttctc | 240 |
| atcccgtggg | tacagaaacc | aattatcttt | gactgccgtt | ctcgaccacg | taatgtgcca | 300 |
| gtcatcactg | gtagcaaaga | tttacagaat | gtcaacatca | cactgcgcat | cctcttccgg | 360 |
| cctgtcgcca | gccagcttcc | tcgcatcttc | accagcatcg | ganaggacta | tgatgaaccg | 420 |
| tgtgctgccg | tccatcacaa | ctgagatcct | caagtcagtg | gtggctcgct | ttga | 474 |

<210> SEQ ID NO 133
<211> LENGTH: 387
<212> TYPE: DNA
<213> ORGANISM: Homo sapien

<400> SEQUENCE: 133

```
tgctcgagcg gccgccagtg tgatggatat ctgcagaatt cggcttagcg tggtcgcggc    60
cgaggtctgc gggccccttta gcctgccctg cttccaagcg acggccatcc cagtaggga    120 ctttcccaca ctgtgccttt acgatcagcg tgacagagta aagctggag tgcctcacca    180 cacggcccgg aaacagcggg aagtaactgg aaagagcttt aggacagctt agatgccgag    240
tgggcgaatg ccagaccaat gatacccaga gctacctgcc gccaacttgt tgagatgtgt    300
gtttgactgt gagagagtgt gtgtttgtgt gtgtgttttg ccatgaactg tggccccagt    360
gtatagtgtt tcagtggggg agaactg                                        387

<210> SEQ ID NO 134
<211> LENGTH: 401
<212> TYPE: DNA
<213> ORGANISM: Homo sapien

<400> SEQUENCE: 134
ggccgcccgg gcaggtctga tgaagaacac gggtgtgatc cttgccaatg acgccaatgc    60
tgagcggctc aagagtgttg tgggcaactt gcatcggctg ggagtcacca acaccattat    120
cagccactat gatgggcgcc agttccccaa ggtggtgggg ggctttgacc gagtactgct    180
ggatgctccc tgcagtggca ctggggtcat ctccaaggat ccagccgtga agactaacaa    240
ggatgagaag gacatcctgc gcttgtgctc acctccagaa ggaagttgct cctgagtgct    300
attgactctt gtcaatgcga ccttcaagac aggaggctac ctggtttact gcacctgttc    360
tatcacagtg agacctctgc catggcagaa caggggaagc t                        401

<210> SEQ ID NO 135
<211> LENGTH: 451
<212> TYPE: DNA
<213> ORGANISM: Homo sapien

<400> SEQUENCE: 135
ggtcgcggcc gaggtctgtt cctgagaaca gcctgcattg gaatctacag agaggacaac    60
taatgtgagt gaggaagtga ctgtatgtgg actgtggaga aagtaagtca cgtgggccct    120
tgaggacctg gactgggtta ggaacagttg tactttcaga ggtgaggtgt cgagaaggga    180
aagtgaatgt ggtctggagt gtgtccttgg ccttggctcc acagggtgtg ctttcctctg    240
gggccgtcag ggagctcatc ccttgtgttc tgccagggtg gggtaccggg gtttgacact    300
gaggagggta acctgctggc tggagcggca gaacagtggc cttgatttgt cttttggaag    360 atttttaaaaa ccaaaaagca taaacattct ggtccttcac aatgctttct ctgaagaaat    420
acttaacgga aggacttctc cattcaccat t                                   451

<210> SEQ ID NO 136
<211> LENGTH: 411
<212> TYPE: DNA
<213> ORGANISM: Homo sapien

<400> SEQUENCE: 136
ggccgcccgg gcaggtctga atcacgtaga atttgaagat caagatgatg aagccagagt    60
tcagtatgag ggttttcgac ctgggatgta tgtccgcgtt gagattgaaa atgttccctg    120
tgaatttgtg cagaactttg accccctta ccccattatc ctgggtggct gggcaacag     180 tgagggaaat gttggacatg tgcaggtggg tcccttttgct gcgtatttgg tgcctgaggc    240
tctgtggatt tcccctccat caatcatctt accctctcat ccccctcaga tgcgtctgaa    300
```

| | |
|---|---:|
| gaaacatctc tggtataaga aaatcctcaa gtcccaagat ccaatcatat tttctgtagg | 360 |
| gtggaggaag tttcagacca tcctgctcta ttatatccga agaccacaat g | 411 |

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137

| | |
|---|---:|
| cggccgcccg ggcaggtcgg ttggtgcggc ctccattgtt cgtgttttaa ggcgccatga | 60 |
| ggggtgacag aggccgtggt cgtggtgggc gctttggttc cagaggaggc ccaggaggag | 120 |
| ggttcaggcc ctttgcacca catatcccat ttgacttcta tttgtgtgaa atggcctttc | 180 |
| cccggntcaa gccagcacct cgatgaaact t | 211 |

<210> SEQ ID NO 138
<211> LENGTH: 471
<212> TYPE: DNA
<213> ORGANISM: Homo sapien

<400> SEQUENCE: 138

| | |
|---|---:|
| gccgcccggg caggtctggg ctggcgactg gcatccaggc cgtaactgca aatctatgct | 60 |
| aggcggggtc tcccttctgt gtgttcaagt gttctcgact tggattctta actatttaa | 120 |
| aaaatgcact gagtttgggt taaaaaccaa ccaccaaaat ggatttcaac acagctctaa | 180 |
| agccaagggc gtggccggct ctcccaacac agcgactcct ggaggccagg tgcccatggg | 240 |
| cctacatccc ctctcagcac tgaacagtga gttgattttt ctttttacaa taaaaaaagc | 300 |
| tgagtaatat tgcataggag taccaagaaa ctgcctcatt ggaaacaaaa actatttaca | 360 |
| ttaaataaaa agcctggccg caggctgcgt ctgccacatt tacagcacgg tgcgatgcac | 420 |
| acggtgacca aaccacggag gcaagcttct ggcactcaca ccacgacccg c | 471 |

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139

| | |
|---|---:|
| gtcgcggccg aggtctgttc tttagctcag atttaaacct gctgtctctt ctttatttgc | 60 |
| agaatgaatt cccagttcct gagcagttca agaccctatg gaacgggcag aagttggtca | 120 |
| ccacagtgac agaaattgct ggataagcga agtgccactg ggttctttgc cctcccttca | 180 |
| caccatggga taaatctgta tcaagacggt tcttttctag atttcctcta cctttttgct | 240 |
| cttaaaactg cttctctgct ctgagaagca cagctacctg ccttcactga aatataccctc | 300 |
| aggctgaaat ttggggtggg atagcaggtc agttgatctt ctgcaggaag gtgcagcttt | 360 |
| tccatatcag ctcaaccacg ccgncagtcc attcttaagg aactgccgac taggactgat | 420 |
| gatgcatttt agcttttgag cttttggggg gtattctacc aaccaacagt ccatttggaa | 480 |
| a | 481 |

<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140

```
gtcgcggccg aggtttccca tttaagaaaa atagatcttg agattctgat tcttttccaa      60
acagtcccct gctttcatgt acagcttttt ctttaccttg cccaaaattc tggccttgaa     120
gcagttttcc tctatggctt tgcctttctg attttctcag aggctcgagt ctttaatata     180
accccaaatg aaagaaccaa ggggagggt gggatggcac ttttttttgt tggtcttgtt      240
ttgttttgtt ttttggttgg ttgggttccg ttatttttta agattagcca ttctctgctg     300
ctatttccct acataatgtc aattttaac cataattttg acatgattga gatgtacttg      360
aggctttttt gntttaattg agaaaagact ttgcaatttt tttttagga tgagcctctc      420
c                                                                    421
```

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141

```
cgantngccc gcccgggcan gtctgtctaa ntttntcang gaccacgaac agaaactcgt      60
gcttcaccga anacaatat cttaaacatc gaanaattta atattatga aaaaaaacat      120
tgcaaaatat aaaataaata nnaaaggaa aggaaacttt gaaccttatg taccgagcaa     180
atccaggtct agcaaacagt gctagtccta nattacttga tntacaacaa cacatgaata     240
ca                                                                   242
```

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142

```
agcgtggtcg cggcncgang tccacagggc anatattctt ttagtgtctg gaattaaaat     60
gtttgaggtt tangtttgcc attgtctttc caaaaggcca ataattcan atgtaaccac     120
accaagtgca aacctgtgct ttctatttca cgtactgttg tccatacagt tctaaataca    180
tgtgcagggg attgtagcta atgcattaca cagtcgttca gtcttctctg cagacacact    240
aagtgatcat accaacgtgt tatacactca actagaanat aataagcttt aatctgaggg    300
caagtacagt cctgacaaaa gggcaagttt gcataataga tcttcgatca attctctctc    360
caagggccc gcaactaggc tattattcat aaaacacaac tgaanagggg attggtttta     420
ctggtaaatc atgtgntgct aaatcatttt ctgaacagtg gggtctaaat cantcattga    480
tttagtggca gccacctgcc cggcggccgn tcgaagccca attctgcaga tatccatcac    540
```

```
actggcggcc g                                                      551
```

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143

```
cgagnggccc gcccgggcag gtatcttcac aaactcaaca aaggcactac atgagacttc   60
acattcccct agtccaatag ctgacaaatt tttgcaacgt tctgcaatgc gaattaactc  120
ttcatcaagt ggccgtaatc catttgcaca cactactagt tcaaccagtc tagggcatgt  180
cattcccaca cggccaagca catctttgct tactgatctc ccaaagtaca gatgggtggc  240
aggtatttca tagcgaaaga agggtcaaa ttcttcttca tataanaaaa aatacatcac  300
taagttcact ttgggtgaat gtctgatgaa agcatcccag ctactcttct gaatagtatg  360
gaagtgtgtc tgtccaggat tctcactgac tacatcaatg cgcaaatgtt ctaatcgaac  420
atgtttttca gaagacaatg caagtaacaa ctcatcactc aataagtggt aagttcaggg  480
ctagttctct taagccgnga cactgatcag cacac                             515
```

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144

```
tgcattctct ntggatgcan acctgcccgt tggtagggac tntgctcaca cggaacatgg   60
acggttacac ctgtgccgtg ggtgacgtcc accagcttct ggatcatctc ggcgngggtg  120
ttgtggaagg gcagactatc cacctccatg cncacgatgc ccganacgcc actccggact  180
ntgtgctgca ccaanatgcc cagcattnta tcttcaagca nagcacttat cagggtcctt  240
ggcacac                                                           247
```

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145

```
cgtgggtcgc ggcccgangt ctgctgtaac aaaacaccat agtctgggca gctcatagac   60
aatggaattt tatttctcac gcttctggag gctggattcc aagatcaagg ttccaggaga  120
ctcagtgtct gcaaggtct cggtttctgc ctcanagatg gtgccatctg gctgtgtcct  180
cacaagtagg aaggtgcaag aagctcccct caggctctgt ctgtaagaca ctgatcccat  240
tcatgangg gaaacgtaat gacctaatca gccccagag accccacttc taacaccatc  300
accttgggg                                                         309
```

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146

| | | | | | |
|---|---|---|---|---|---|
| agcgtgggtc | gcggcncgac | gtcctgtcca | tatttcacag | cccgagaact | aatacaagat | 60 |
| gctgacatca | tattttgtcc | ctacaactat | cttctanatg | cacaaataag | ggaaagtatg | 120 |
| gatttaaatc | tgaaagaaca | ggttgtcatt | ttanatgaag | ctcataacat | cgaggactgt | 180 |
| gctcgggaat | cagcaagtta | cagtgtaaca | gaagttcagc | ttcggtttgc | tcgggatgaa | 240 |
| ctanatagta | tggtcaacaa | taatataagg | aaganagatc | atgaacccct | acgagctgtg | 300 |
| tgctgtagcc | tcattaattg | gntagaagca | aacgctgaat | atcttgnana | angagantat | 360 |
| gaatcagctt | gtaaaatatg | gagtggaaat | gaaatgctct | taactttaca | caaaatgggt | 420 |
| atcaccactg | ctacttttcc | catttttgcng | gtaagatatn | ttttctacct | gngaaacgta | 480 |
| tttaag | | | | | | 486 |

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147

| | | | | | |
|---|---|---|---|---|---|
| gccgcccggg | cangttcgac | attacntnga | gttccatgat | gtacaattct | ttcacgaaaa | 60 |
| acaatgaatg | caagaatttg | aggatctcct | tactcctccc | ttttacagat | ggtctctcaa | 120 |
| tcccttcttc | ttcctcttca | tcttcatctt | cttctgaacg | cgctgccggg | taccacggct | 180 |
| ttctttgtct | ttatcgtgag | atgaaggtga | tgcttctgtt | tcttctacca | taactgaaga | 240 |
| aatttcgctg | caagtctctt | gactggctgt | ttctccgact | tcgcctttnt | gtcaaacgng | 300 |
| agtcttttta | cctcatgccc | ctcagcttca | cagcatcttc | atctggatgt | tnatttctca | 360 |
| aagggctcac | tgaggaaact | tctgattcan | atgtcgaana | gcactgtgaa | gttttctctt | 420 |
| cattttgctg | | | | | | 430 |

<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148

| | | | | | |
|---|---|---|---|---|---|
| cccgggcagg | tctgtgttgn | tttncaaccg | gtgtcctccc | cagcgtccag | aanangggaaa | 60 |
| tgtggagcgg | gtgatgatga | cccctcgctg | tcctgtcacc | tcctgcacag | cttcgtatgt | 120 |
| gggtctggtc | tgggaccacc | cgtacaggtt | gtgcacgttg | tagtgctcca | cggggagct | 180 |
| gtccggcagg | atctgctgac | tctccatgca | cagagtcttg | ctgctcaggc | ccttgtccct | 240 |
| agattccaaa | tatggcatat | agggtgggt | tatttagcat | tcattgctg | cagcccctga | 300 |

| | |
|---|---|
| cagatccatc cacaaaattt gatggctcat tcatatcaat ccacaatcca tcaaacttca | 360 |
| agctcttctc tggntctcga nggtttgcat agaactcttc tatctctttc ttccaccacg | 420 |
| canacctcgg ncgcgaccac gctaagccga attctgcana tatccatcac actggcggcc | 480 |
| gct | 483 |

<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149

| | |
|---|---|
| ctttcacgaa nacaatgaat gcaagaattt gaggatctcc ttactcctcc cttttacaga | 60 |
| tggtctctca atcccttctt cttcctcttc atcttcatct tcttctgaac gcgctgccgg | 120 |
| gtaccacggc tttctttgtc tttatcgtga gatgaaggtg atgcttctgt ttcttctacc | 180 |
| ataactgaag aaatttcgct gcaagtctct tgactggctg tttctccgac ttcgccttttt | 240 |
| tgcaaacgtg agtctttta cctcatgccc ctcagcttcc acagcatctt catctggatg | 300 |
| ttcatttctc aaagggctca ctgaggaaac ttctgactca catgtcgaag aagcactgng | 360 |
| agtttctctt catttgctgc aaanttgctc tttgctggct gngctctcag accacccatt | 420 |
| tggctgcatg ggggctgac | 439 |

<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

| | |
|---|---|
| ggcncgcccg ggcangtcca ctccactttt gagctctgag ggaataccttt caggagggac | 60 |
| agggtcaggg agtcctggca gctccgcagc agagattcac attcattcag agacttgttg | 120 |
| tccagtgcaa tgccattgat cgcaacgatc ctgtctccca cagcaaggga cccttcttta | 180 |
| gcggcagggc ttccaggcag cacagcggca gcatacactc cattctccag actgatgcca | 240 |
| ctgtctttct gtccactgan gttgatgtgc agcggcgtga ccacttccc acccagggac | 300 |
| ttcctccgcc gcacgaccat gttgatgggc cccctnccca ttgaggagcg ccttgatggc | 360 |
| ctgcttcttg nccttggtga tgaagtccac atcggtgatt ctcacagcca gtcattgacc | 420 |
| cttaagcggn catcagcaat gcttcctttg gccactttag ngacaaatat gccacagtcc | 480 |
| ccgggaaaca agggtcattc acaccttctg gcatatcaaa cacctcggcc gggancacta | 540 |
| agccgaattc tgcagatatc catcacactg gngggccg | 578 |

<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151

```
cgagcggccc gcccgggcag gtctgggaga tcagcgactg ctgccacgtg cccagaaatg      60
gctcgtcctt tcactacagc ggaatgcaat gagggtgggt gagaagatga tgggtcggtt     120
atttcattcc ttttctttt acaacttcac tttcagagac ttcagcgttc catgtctgct     180
gtgctgtgga acccagagtg ctcttgcctg gatggctgag aatcccttgg accctggaag    240
cacctactcc atgatggccc ggtatagtgc aggctcaata taatcttccc ggtatcttga    300
gttgataact cgttgccgtt tcttttcttg cttaacctct ttctctgtga aatctcatt     360 gaagcgcatg tctgaagcta ctgacagtct anatttgact ctcttgggaa gctcttcatc    420
cagtgtgtat acatcatctc tcttaaccac aagttggagc catncttaaa cttcacctgg    480
tacatttgga tagggtggga ggc                                            503

<210> SEQ ID NO 152
<211> LENGTH: 553
<212> TYPE: DNA
<213> ORGANISM: Homo sapien
<220> FEATURE:
<221> NAME/KEY: misc_feature
<222> LOCATION: (1)...(553)
<223> OTHER INFORMATION: n = A,T,C or G

<400> SEQUENCE: 152
agcgtggtcg cggcccgagg tccactgagc tccgccttcc ccgggctccc tgaggaagca     60
gagtcctgac ttccaggaag gacaggcaca agaggcaaga actcagcctg tgaggctctg    120
ggtggctcct gaggccagag gacgccttcc gcgatccatg gctcagcatc gtccttctgg    180
cttcccagcc ccgggccgaa cgttcgggtt aataagcaga gcagttattc ggctcctggc    240
aggagctccc ccgttagttt ccacgttgtg agcacattca tacttaagac tgnttctctt    300
tgtgttttaa gcgtctgtct ctgtagtaaa ctgaaatgtt aacagaaatg cagacctgcc    360
cgggcggccg ctcgaaagcc gaattctgca gatatccatc acactggcgg ccgctcgagc    420
atgcatctag anggcccaat cgccctata gtgagtcgna ttacaattca ctgggccgcg    480
ntttacaacg tcgtgactgg gaaaaccctg cggtacccac ttaatcgcct tgcagnacat    540 cccccttttcg cca                                                      553

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153
tcgagcggct cgcccgggca ggtccaccta gcatggctcc tctaaacacg caactcagcg      60
aggggacccc cttcacctct ggcaagagag ctgggtagat cagaaacttg gtgacacctg    120
gctagcacag agcaggctca cttgtcttgg tcccactacc cagattcctg cagacattgc    180
aaaccaaatg aaggttgntg aatgacccct gtccccagcc acttgttttg gtatcatctg    240
ctctgcagtg gaatgcctgt gtgtttgagt tcactctgca tctgtatatt tgagtataga    300
aaccgantca agtgatctgt gcatncagac acactggggc acctgancac agaacaaatc    360
accttaacga tctggaatga aactgngananc antgcccgcc tgggtgggtc tgganaaact    420
gccgncttct tgttggacct tggccgcacc acct                                 454
```

```
<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154
agcgtggtcg cggcccgang gcggcctcct gantganggg aagggacgtg ggggcggcca      60
cggcaggatt aacctccatt tcagctaatc atgggagaga ttaaagtctc tcctgattat     120
aactggttta naggtacagt tccccttaaa aagattattg tggatgatga tgacagtaag    180
atatggtcgc tctatgacgc gggcccccga agtatcaggt gtcctctcat attcctgccc    240
cctgtcagtg gaactgcaga tgtctttttc cggcagattt tggctctgac tggatggggt    300
taccgggtta tcgctttgca gtatccagtt tattgggacc atctcgagtt cttgtgatgg    360
attcacaaaa cttttanacc atttacaatt ggataaagtt catcttttg gcgcttcttt     420 gggangcttt ttggcccana aatttgctga atacactcac aaatctccta gaagccattc    480
cctaatcctc tgcaattcct tcagngacac ctctatcttc aaccaacttg gactggaaac    540
agctttggct gatgcctgca tttatgctca aaaaatagtt cttggaaatt ttcatc        596

<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155
ctcganttgg cncgcccggg cangtctgcc tggttttga ccgngcgagc tatttagnct       60
ctggctctgt ttccggagct caaggnaaaa atcttgaana actcgagcag cttctgtgga    120
tagccttggg tacacatact gccgagcata gccaatgtac tttctcaata gctggtgggg    180
aatgggatct attgttctc caggaaccac ctttagtctt tctgataatg gcttctcaga     240
aactacttca agtacggaag tatttgaatc ttgactatnc atacgagcta ctgtggcact    300
gctaatgggn tctctgctnt ccagctctta ttgcaatcac atg                      343

<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156
tcgagcggcc cgcccgggca ggtctggcac cacncagatc gattaactgg ctcatctgat     60
ctcgtggccc ccaccctgga actgacttag cacaaaagga cacctcaatt ccttatgatt    120
tcatctccga cccaaccaat caacacccct gactcactgg ccttcccct cccaccaaat     180 tatccttaaa aactctgatc cccgaatgct caggagatc gatttgagta ctaataagac     240
tccagtctcc tgcacaagca gctctgtgta ctcttcctct attgcaattc ctgtcttgat    300
aaatcggctc tgtgtaggcg gcggaagaag tgaacctgtt gggcggttac cacctctgtc    360
```

```
gtgtgtgaca gttgntttga atctctaatt gctcagtaca gatccacatg caggttaagt    420
aagaagcttt tgaagaaaat ggaaagtctt aagtgatggc ttccaagaaa tcaaacctac    480
attaattagg gaacaacgga ctttacgtat cacaaatgaa gagactgacn aagtaaatca    540
acttggcctt ttctta                                                   556
```

```
<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157
ggtccacaaa aatatatnaa ataagctgga tatataaaan caaacactta acatngncan     60
cattccttca gttattcaaa ctcactgata nctaacnggg agnagttggn attctggaag    120
acttcctaag ctaaaagtat atttacatat ttacaacaca ngtaaatata acngaagaac    180
tacttcaaat aangnngaaa ttccagaatt ctanagattt atagctatag ntnacaanta    240
tcaccaattg gtttgcaatc aanngnccag cactacttat gannaangtt taactannaa    300
accaaaaggg gagaaaacct ggnagggaaa nat                                 333
```

```
<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158
tcgagcggcc gcccgggcag gtctggtaca tttgtgcgag gtccggcact ctgttctcat     60
ccagtaagtg gtcgagccct tctgcagaa ttgctgttaa atgttctcct aatagctgtt    120
tctccacaca agcaatcagt ggtttctgtg tgctgtggtc caagtaagtg attactctgt    180
ctccctcttc ttctaagcgt ttacttacat ggttaagata ttctggaacc tctctttcct    240
gcattaacct ttggccttcg gcagcatata agcaattagt ctcttccaaa aatttcagtt    300
caaatgaatc tttatacacc tgcaggtcag acagcatgcc caggnaggct ccgcaacagg    360
ctccggtcca cggcctcgcc gctcctctcg cgctcgatca gcagtaggat tccatcaatg    420
gttttactct gaaccatttt atcactaata atatgggttc taaacagttc taatcccata    480
tcccagatgg agggcagcgt ggagttctgc agcacatagg tgcggtccaa gaacaggaag    540
atgcttctga tcatgaatca tttgnctggc aatggtcctg ccagcacgtg gtaatctttc    600 tttttaaaaat aaacccttat ctaaacgtc                                     629
```

```
<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159
```

```
tcgagcggcc gcccgggcag gttctagagg ganaatctgg ctgatttggg aataaaatat    60
aatcgaatat tcaacaccat gaagataaat cttattttgg aaatctactg accttaatac   120
cccaagcttg ccctgaatac tttgattgga attggaatat atcaaaaaag gttagtattt   180
ttgttgtagt taggatacta aaaggatatt agttacccaa gagatccaat ttgttttttct  240 gatgaatagt gttcagtaaa atgaagcagt cttaagagtg actaataatt tcaaagtgat   300
ttttcgtcta ttcttaatat tttttaatta tttattttta agagttttat accttgagca   360
gatacaatga tccgctttag tgagaggaca atttctgatt gattgttttc tcttcaggcc   420
atctcacctc ttcattctct tgttacattt gaagcagttg atataatggg tttatacttt   480
aaaagataga catggtgcca tgaagtttgg ggaagttggg tgaattatcc cattctagtt   540
acagangagc tttccttaaa tgccctttac ttctangttt ggtcaagaag tcattttctg   600
agtaaaagtt attttcatat atgttgggg                                     629
```

<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160

```
tcgagcggcg cgcccgggca ggtctgctgg gattaatgcc aagttnttca gccataaggt    60
agcgaaatct agcagaatcc agattacatc cacttccaat cacgcggtgt ttgggtaatc   120
cacttagttt ccagataaca tacgtaagaa tgtccactgg gttggaaacc acaattatga   180
tgcaatcagg actgtacttg acgatctgag gaataatgaa tttgaagaca ttaacatttc   240
tctgcaccag attgagccga ctctcccctt cttgctgacg gactcctgca gttaccacta   300
caatcttana attgggcggg tcacagaata atctttatct gccacaattt taggtgctga   360
agaaataagc tccatgctg cagatccatc atttctnctt taagcttatc ttccaaaaca    420
tccacaagan caangttcat cagccagaga cttttcccaga atgctgatag nacacgccat   480
accaacttgt ccaacancca ctacagcgat cttattggt                          519
```

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161

```
cgagnggccc gcccgggcag gtccagtaag cntttnacga tgatgggaaa ggttatgcaa    60
ggtcccagcg gtacaacgag ctgtttctac atcatttgta ttctgcatgg tacgtacaat   120
agcagacacc atctgaggag aacgcatgat agcgtgtctg gaagcttcct ttttagaaag   180
ctgatggacc ataactgcag ccttattaac caccacctgg tcctcgtcat ttagcagttt   240
tgtcagttca gggattgcac gtgtggcang ttctgcatca tcttgatagt taatcaagtt   300
tacaactggc atgtttcagc atctgcgatg ggctcagcaa acgctggaca ttantgggat   360
gagcagcatc aaactgtgta natgggatct gcatgccctc atctaatgtc tcagggaaca   420
tagcagctcg taccctctga gctcga                                        446
```

<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162

| | | | | | |
|---|---|---|---|---|---|
| agcgtngtcg | cggcccgang | tcctgggaag | cctttnttgc | tgagcctcac | agcctctgtc | 60
| aggcggctgc | ggatccagcg | gtccaccagg | ctctcatggc | ctccgggctg | ggaggngggt | 120
| gagggcacaa | aacccttccc | aaggccacga | anggcaaact | tggtggcatt | ccanagcttg | 180
| ttgcanaagt | ggcggnaacc | cagtatccgg | ttcacatcca | ggntgatgtc | acgaccctgg | 240
| gacatgtang | cacataatcc | aaaccggaga | gcatcggtgc | cacattcacg | aatcccgct | 300
| gggaagtcag | ctttctgccc | ttctttggcc | ttctccacct | cgctgggatc | cagg | 354

<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163

| | | | | | |
|---|---|---|---|---|---|
| tttttcncca | agtcctcttg | ccgngggatc | tngactgcaa | tttaagacac | ttctaattag | 60
| ttatacccag | gccctgcaaa | attgctgggt | ttatataata | tattcttgct | gcacgaagat | 120
| ttattattct | gttggatgat | tctatttaa | ttntatttat | tctggccaaa | aaagaacctt | 180
| ctccgctcgt | caagagangc | caatngtct | tgaaggacaa | gagaaagatg | ctaacacaca | 240
| ctttcttctt | cttgagga | | | | | 258

<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164

| | | | | | |
|---|---|---|---|---|---|
| ggaacatatt | acttttaaat | tacttgggtc | aatgaaacat | ttaataaaaa | catttgcttc | 60
| tctatataat | acgtatgtat | aaaataagcc | ttttcanaaa | ctctggttct | cataatcctc | 120
| tataaatcan | atgatctgac | ttctaagagg | aacaaattac | agnaagggt | atacattnat | 180
| gaatactggt | agtactagag | ganngacgct | aaaccactct | actaccactt | gcggaactct | 240
| cacagggtaa | atgacaaagc | caatgactga | ctctaaaaac | aa | | 282

<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165

```
gcccgggcan gtcctgtaat cccagctact cangangctg agtcatgana atcgcctgaa      60
tccgggaggt agaggccgca gcgagcaaag attaagccac tgcactccag tctgggtgac     120
agagtgagaa tctgtctgtt gctcctctgg cattggtctg aaatgggttt gtagaacatg     180
ccacagaagg accagcanca gcaacaaatg gatttgtgga angcgtagct ccaaatggag     240
cangcacact tgatgaagca cgctgtgtct gtgcagangc aaccactggc actgttccaa     300
aaacattgct gctagcatta cttgtggaag tatacgcatt actggaggtg gctgcanaac     360
tgaaaacgct gtctagttct gccanagctg catacttgnc tgaanatgca cttgactgac     420
tgggaactga accacanaac caacaggacc tttacctgtg ga                        462
```

<210> SEQ ID NO 166
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 166

```
cgtgggtcgc ggcncgangt ctgaaaccaa tccagaacta acatcagca cacaaaaaat      60
accaggatag atgaatcaa aagactctga agccaaaagg aggctaggga gagcaactga     120
acttagcaag ctgaggactt cagtgtccat catccgatcc tgccctgtaa caacaggtct     180
atatgataga gatattccat ctgagctgga ggccattatc cttagcaaac taacacagaa     240
cagaaaacca aatacatgtt ctcatttaga agtaggagct aaatgatgag aactcaagga     300
cacaaagaaa ggaacaacag acactggggc ctacttgagg gtggagggtg ggaggaggga     360
gaaga                                                                365
```

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167

```
agcgtggtcg cggcgcgang tccagcccta gcttgcctgt gactccgcct tcactgggtg      60
ctctctctaa aagttgctga ctctttactg tatctcccaa ttcccactcc attggttcca     120
taagggagg ggtgtctcac tcaacatggt gttcctggta ccaagaactg gctgacgaag     180
ctgggtgccg tggctcatgc ctgtaatccc agcacttttg ggaggccaag aagggcggat     240
cacctgaggt ctggagttca agatcagcct gaccaacatg atgaaaccaa gtctccacta     300
aaaatataaa acaattagcc aggcatggtg gtgggtgcct gnaatcccag ctactgggga     360
ngct                                                                 364
```

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168

```
cccgggcagg tcaaaaccca aaacctttca ttttagccca aaccagctca tgattaggta      60
tacaaggata acagaaccag ttgtcaggac gagcatttga caagtaaaag caattcttgc     120
aaagctgcag ttcatccagc tcatggcatg tgtctttata tagcatcctc gcaatgtcag     180
cttgctcact gtctgctcca tagaaaatca cggtattgtg gagaagcaat tgggcatcag     240
ctttgaactc ttcataactt cggtatttcc cttcattcac tttctcttga atggtgggaa     300
cgtccacaga cctcggccgc gaccacgcta agcccgaatt ctgcagatat ccatcacact     360
ggcggccgtt cgagcatggc atctagaagg cccaattcgc ctatagngag tcgnattacc     420
aattcactgg ccgtcgnttt acaacgc                                         447
```

<210> SEQ ID NO 169
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 169

```
cgantngcgc gcccgggcag gtctgagcag cctttctgnn tgctggacta ttgggattgg      60
gttcatccaa cagagactgt atggatgtta gaatggaaga cacatcatag gttggactcc     120
aacggttctg aagtatgtcc agacatatac taccatctgc atagactaag aacaaagaag     180
taggtacatt aaacgtaaca agaccactaa ggttttaaca ttatagacaa aacanaaata     240
gtcaagnata ctttgctttt gaagtttaaa gattcctatg ttgcttccca gttaactgcc     300
taaaaagata agncataacc accactagtg aaataatcan gatgatcaga gaatgtcana     360
tgtgatcagt ataaaactgg angatattna gtgtcatcct ttggaaaagg ctgccctatn     420
atccaggaaa tcanaaacat tnttgaacag ggncecctagc tatccacaga catgtgggaa     480
attcattccc caaatngtag gctggatccc ctatctgaaa taac                     524
```

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

```
tcgancggcn cgcccgggca ggtgacaaac ctgttattga agatgttggt tctgatgagg      60
aanaanatca gaagggatgg tgacaagaan aanaanaaga agattaagga aaagtacatc     120
gatcaagaag agctcaacaa aacaaagccc atctggacca gaaatcccga cgatattact     180
aatgangagt acggagaatt ctataanagc ttgaccaatg actgggaaga tcacttggca     240
gtgaagcatt tttcagttga nggacagttg gaattcagag cccttctatn tgtcccacga     300
cgtgctcctt ttgatctgtt tganancaga aa                                   332
```

<210> SEQ ID NO 171
<211> LENGTH: 334
<212> TYPE: DNA
<213> ORGANISM: Homo sapien
<220> FEATURE:

<221> NAME/KEY: misc_feature
<222> LOCATION: (1)...(334)
<223> OTHER INFORMATION: n = A,T,C or G

<400> SEQUENCE: 171

| | | | | | |
|---|---|---|---|---|---|
| cgagnggcnc | gcccgggcag | gtctgttgat | agcgacttaa | cagaaaagtc | tagacaaaca | 60 |
| taagcataaa | aaattacagt | ctttctaccc | ttgggaatgg | ggagaaaaag | gaatctctac | 120 |
| cccaagacca | gaaataataa | gtcctgtttc | tggtcctgaa | catccagaat | tatggaggct | 180 |
| ttggcctgac | accacattan | aatttggtct | ggaaatcaaa | ctttaganac | angagatcgt | 240 |
| aagccatttt | atactatcga | cctaaattcc | agtctaacgg | ttcctttaca | aagttgcgga | 300 |
| aagccctctt | atatgctagc | tgtaggaaat | atag | | | 334 |

<210> SEQ ID NO 172
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172

| | | | | | |
|---|---|---|---|---|---|
| agcgtggtcg | cggcccgang | tctgcctata | aaactagact | tctgacgctg | ggctccagct | 60 |
| tcattctcac | aggtcatcat | cctcatccgg | gagagcagtt | gtctgagcaa | cctctaagtc | 120 |
| gtgctcatac | tgtgctgcca | aagctgggtc | catgacaact | tctggtgggg | cgagagcagg | 180 |
| catggcaaca | aattccaagt | tagggtctcc | aatgagcttc | ctagcaagcc | agaggaaggg | 240 |
| cttttcaaag | ttgtagttac | ttttggcaga | aatgtcgtag | tactgaagat | tcttctttcg | 300 |
| gtggaagaca | atggatttcg | ccttcacttt | ctgccttaat | atccactttg | gtgccacaca | 360 |
| acacaatggg | gatgntttca | cacacttngn | accanatctc | tatgccagnt | aggccatttt | 420 |
| ggaagnactt | cganggtac | | | | | 439 |

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173

| | | | | | |
|---|---|---|---|---|---|
| cgatnggccg | cccgggcagg | tcctgtaaaa | naggaaattc | agacatcgta | cgactcgtaa | 60 |
| ttgaatgtgg | agctgactgc | aatattttgt | caaagcacca | gaatagtgcc | ctgcactttg | 120 |
| cgaagcagtc | taacaatgtg | cttgtgtacg | acttgctgaa | gaaccattta | gagacactttt | 180 |
| caagagtagc | agaagagaca | ataaaggatt | actttgaagc | tcgccttgct | ctgctagaac | 240 |
| cagttttttcc | aatcgcatgt | catcgactct | gtgagggtcc | agattttttca | acagatttca | 300 |
| attaccaacc | cccacagaac | ataccagaag | gctctggcat | cctgctgttt | atcttccatg | 360 |
| caaactttttt | gggtaaagaa | gttattgctc | ggctctgtgg | accgtgtagt | gtacaagctg | 420 |
| tagttctgaa | tgataaattt | cagcttcctg | tttttctggg | tctcgctctg | ttgtccaggc | 480 |
| tggagtgcag | tggcgcggat | tacagctcac | tggagtcttg | acttcccagg | cacaagcaat | 540 |
| cctcccacct | cagcctccta | actacctggg | actaaaaatg | caccgccacc | acattccgg | 599 |

```
<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174
tcgatttggc cgcccgggca ggtccatgcn gnttntgccc attcccatgg ngcccgacaa      60
ncccatcccc gaggccgaca tccccatgtt catgttcatg cccaccatgc cctggctcat    120
ccctgcgctg ttccccagag gggccattcc catggtgccc gtcattacac cgggcatgtt    180
cataggcatg ggtcccccca ggagagggtt agnttgaggc cggacaggaa gcatgtttga    240
tggagaactg aggttcacag nctccaaaac tttgagtcat cacattcata ggctgctgca    300
tattctgtct gctgaatcca ttgtatncag tgatggcctg ctggggnttt ggaaggctng    360
cataccaggt agtaagntcg tctaggctga tgtttacacc tggggtcaga ccaagtanga    420
gggcaaggtt ttgctgactg attttctgga cccatatc                            458

<210> SEQ ID NO 175
<211> LENGTH: 1206
<212> TYPE: DNA
<213> ORGANISM: Homo sapien

<400> SEQUENCE: 175
ggcacgagga agttttgtgt actgaaaaag aaactgtcag aagcaaaaga aataaaatca      60
cagttagaga accaaaaagt taaatgggaa caagagctct gcagtgtgag gtttctcaca    120
ctcatgaaaa tgaaaattat ctcttacatg aaaattgcat gttgaaaaag gaaattgcca    180
tgctaaaact ggaaatagcc acactgaaac accaatacca ggaaaaggaa ataaatact     240
ttgaggacat taagatttta aagaaaaga atgctgaact tcagatgacc ctaaaactga    300
aagaggaatc attaactaaa agggcatctc aatatagtgg gcagcttaaa gttctgatag    360
ctgagaacac aatgctcact tctaaattga aggaaaaaca agacaaagaa atactagagg    420
cagaaattga atcacaccat cctagactgg cttctgctgt acaagaccat gatcaaattg    480
tgacatcaag aaaaagtcaa gaacctgctt tccacattgc aggagatgct tgtttgcaaa    540
gaaaaatgaa tgttgatgtg agtagtacga tatataacaa tgaggtgctc catcaaccac    600
tttctgaagc tcaaaggaaa tccaaaagcc taaaaattaa tctcaattat gccggagatg    660
ctctaagaga aaatacattg gtttcagaac atgcacaaag agaccaacgt gaaacacagt    720
gtcaaatgaa ggaagctgaa cacatgtatc aaaacgaaca agataatgtg aacaaacaca    780
ctgaacagca ggagtctcta gatcagaaat tatttcaact acaaagcaaa aatatgtggc    840
ttcaacagca attagttcat gcacataaga agctgacaa caaaagcaag ataacaattg    900
atattcattt tcttgagagg aaaatgcaac atcatctcct aaaagagaaa aatgaggaga    960
tatttaatta caataaccat ttaaaaaacc gtatatatca atatgaaaaa gagaaagcag    1020
aaacagaagt tatataatag tataacactg ccaaggagcg gattatctca tcttcatcct    1080
gtaattccag tgtttgtcac gtggttgttg aataaatgaa taaagaatga gaaaccaga    1140
agctctgata cataatcata atgataatta tttcaatgca caactacggg tggtgctgct    1200
cgtgcc                                                              1206

<210> SEQ ID NO 176
```

<211> LENGTH: 317
<212> TYPE: PRT
<213> ORGANISM: Homo sapien

<400> SEQUENCE: 176

Met Gly Thr Arg Ala Leu Gln Cys Glu Val Ser His Thr His Glu Asn
1               5                   10                  15

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile
305                 310                 315

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177
ccaatcatct ccacaggagc                                         20

<210> SEQ ID NO 178
<211> LENGTH: 1665
<212> TYPE: DNA
<213> ORGANISM: Homo sapien

<400> SEQUENCE: 178

| | | | | | |
|---|---|---|---|---|---|
| gcaaactttc | aagcagagcc | tcccgagaag | ccatctgcct | tcgagcctgc | cattgaaatg | 60 |
| caaaagtctg | ttccaaataa | agccttggaa | ttgaagaatg | aacaaacatt | gagagcagat | 120 |
| cagatgttcc | cttcagaatc | aaaacaaaag | aaggttgaag | aaaattcttg | ggattctgag | 180 |
| agtctccgtg | agactgtttc | acagaaggat | gtgtgtgtac | ccaaggctac | acatcaaaaa | 240 |
| gaaatggata | aaataagtgg | aaaattagaa | gattcaacta | gcctatcaaa | aatcttggat | 300 |
| acagttcatt | cttgtgaaag | agcaaggaa | cttcaaaaaa | atcactgtga | acaacgtaca | 360 |
| ggaaaaatgg | aacaaatgaa | aagaagttt | tgtgtactga | aaagaaaact | gtcagaagca | 420 |
| aaagaaataa | aatcacagtt | agagaaccaa | aaagttaaat | gggaacaaga | gctctgcagt | 480 |
| gtgaggtttc | tcacactcat | gaaaatgaaa | attatctctt | acatgaaaat | tgcatgttga | 540 |
| aaaggaaat | tgccatgcta | aaactggaaa | tagccacact | gaaacaccaa | taccaggaaa | 600 |
| aggaaaataa | atactttgag | gacattaaga | ttttaaaaga | aagaatgct | gaacttcaga | 660 |
| tgaccctaaa | actgaaagag | gaatcattaa | ctaaaagggc | atctcaatat | agtgggcagc | 720 |
| ttaaagttct | gatagctgag | aacacaatgc | tcacttctaa | attgaaggaa | aaacaagaca | 780 |
| aagaaatact | agaggcagaa | attgaatcac | catcctag | actggcttct | gctgtacaag | 840 |
| accatgatca | aattgtgaca | tcaagaaaaa | gtcaagaacc | tgctttccac | attgcaggag | 900 |
| atgcttgttt | gcaaagaaaa | atgaatgttg | atgtgagtag | tacgatatat | aacaatgagg | 960 |
| tgctccatca | accactttct | gaagctcaaa | ggaaatccaa | aagcctaaaa | attaatctca | 1020 |
| attatgccgg | agatgctcta | agagaaaata | cattggtttc | agaacatgca | caaagagacc | 1080 |
| aacgtgaaac | acagtgtcaa | atgaaggaag | ctgaacacat | gtatcaaaac | gaacaagata | 1140 |
| atgtgaacaa | acacactgaa | cagcaggagt | ctctagatca | gaaattattt | caactacaaa | 1200 |
| gcaaaaatat | gtggcttcaa | cagcaattag | ttcatgcaca | taagaaagct | gacaacaaaa | 1260 |
| gcaagataac | aattgatatt | cattttcttg | agaggaaaat | gcaacatcat | ctcctaaaag | 1320 |
| agaaaaatga | ggagatattt | aattacaata | accatttaaa | aaaccgtata | tatcaatatg | 1380 |
| aaaaagagaa | agcagaaaca | gaaaactcat | gagagacaag | cagtaagaaa | cttcttttgg | 1440 |
| agaaacaaca | gaccagatct | ttactcacaa | ctcatgctag | gaggccagtc | ctagcattac | 1500 |
| cttatgttga | aaatcttacc | aatagtctgt | gtcaacagaa | tacttatttt | agaagaaaaa | 1560 |
| ttcatgattt | cttcctgaag | cctgggcgac | agagcgagac | tctgtctcaa | aaaaaaaaa | 1620 |
| aaaaaagaa | agaaagaaat | gcctgtgctt | acttcgcttc | ccagg | | 1665 |

<210> SEQ ID NO 179
<211> LENGTH: 179
<212> TYPE: PRT
<213> ORGANISM: Homo sapien

<400> SEQUENCE: 179

Ala Asn Phe Gln Ala Glu Pro Pro Glu Lys Pro Ser Ala Phe Glu Pro
1               5                   10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

```
Gln Lys Lys Val Glu Glu Asn Ser Trp Asp Ser Glu Ser Leu Arg Glu
     50                  55                  60
Thr Val Ser Gln Lys Asp Val Cys Val Pro Lys Ala Thr His Gln Lys
65                  70                  75                  80
Glu Met Asp Lys Ile Ser Gly Lys Leu Glu Asp Ser Thr Ser Leu Ser
                85                  90                  95
Lys Ile Leu Asp Thr Val His Ser Cys Glu Arg Ala Arg Glu Leu Gln
            100                 105                 110
Lys Asp His Cys Glu Gln Arg Thr Gly Lys Met Glu Gln Met Lys Lys
        115                 120                 125
Lys Phe Cys Val Leu Lys Lys Lys Leu Ser Glu Ala Lys Glu Ile Lys
    130                 135                 140
Ser Gln Leu Glu Asn Gln Lys Val Lys Trp Glu Gln Glu Leu Cys Ser
145                 150                 155                 160
Val Arg Phe Leu Thr Leu Met Lys Met Lys Ile Ile Ser Tyr Met Lys
                165                 170                 175
Ile Ala Cys

<210> SEQ ID NO 180
<211> LENGTH: 1681
<212> TYPE: DNA
<213> ORGANISM: Homo sapien

<400> SEQUENCE: 180
gatacagtca ttcttgtgaa agagcaaggg aacttcaaaa agatcactgt gaacaacgta      60
caggaaaaat ggaacaaatg aaaaagaagt tttgtgtact gaaaaagaaa ctgtcagaag     120
caaaagaaat aaaatcacag ttagagaacc aaaaagttaa atgggaacaa gagctctgca     180
gtgtgagatt gactttaaac caagaagaag agaagagaag aatgccgat atattaaatg      240 aaaaaattag ggaagaatta ggaagaatcg aagagcagca taggaaagag ttagaagtga     300
aacaacaact tgaacaggct ctcagaatac aagtatataga attgaagagt gtagaaagta    360
atttgaatca ggtttctcac actcatgaaa atgaaaatta tctcttacat gaaaattgca     420
tgttgaaaaa ggaaattgcc atgctaaaac tggaaatagc cacactgaaa caccaatacc     480
aggaaaagga aaataaatac tttgaggaca ttaagatttt aaaagaaaag aatgctgaac     540
ttcagatgac cctaaaactg aaagaggaat cattaactaa aagggcatct caatatagtg     600
ggcagcttaa agttctgata gctgagaaca caatgctcac ttctaaattg aaggaaaaac     660
aagacaaaga aatactagag gcagaaattg aatcacacca tcctagactg gcttctgctg     720
tacaagacca tgatcaaatt gtgacatcaa gaaaagtca agaacctgct ttccacattg      780
caggagatgc ttgtttgcaa agaaaaatga atgttgatgt gagtagtacg atatataaca     840
atgaggtgct ccatcaacca ctttctgaag ctcaaaggaa atccaaaagc ctaaaaatta     900
atctcaatta tgccggagat gctctaagag aaaatacatt ggtttcagaa catgcacaaa     960
gagaccaacg tgaaacacag tgtcaaatga aggaagctga acacatgtat caaaacgaac    1020
aagataatgt gaacaaacac actgaacagc aggagtctct agatcagaaa ttatttcaac    1080
tacaaagcaa aaatatgtgg cttcaacagc aattagttca tgcacataag aaagctgaca    1140
acaaaagcaa gataacaatt gatattcatt ttcttgagag gaaatgcaa catcatctcc     1200 taaaagagaa aaatgaggag atatttaatt acaataacca tttaaaaaac cgtatatatc    1260
aatatgaaaa agagaaagca gaaacagaaa actcatgaga gacaagcagt aagaaacttc    1320
```

-continued

```
ttttggagaa acaacagacc agatctttac tcacaactca tgctaggagg ccagtcctag    1380
cattacctta tgttgaaaaa tcttaccaat agtctgtgtc aacagaatac ttattttaga    1440
agaaaaattc atgatttctt cctgaagcct acagacataa aataacagtg tgaagaatta    1500
cttgttcacg aattgcataa aagctgccca ggatttccat ctaccctgga tgatgccgga    1560
gacatcattc aatccaacca gaatctcgct ctgtcactca ggctggagtg cagtgggcgc    1620
aatctcggct cactgcaact ctgcctccca ggttcacgcc attctctggc acagcctccc    1680
g                                                                    1681
```

<210> SEQ ID NO 181
<211> LENGTH: 432
<212> TYPE: PRT
<213> ORGANISM: Homo sapien

<400> SEQUENCE: 181

```
Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Phe Cys
                20                  25                  30

Val Leu Lys Lys Lys Leu Ser Glu Ala Lys Glu Ile Lys Ser Gln Leu
             35                  40                  45

Glu Asn Gln Lys Val Lys Trp Glu Gln Glu Leu Cys Ser Val Arg Leu
         50                  55                  60

Thr Leu Asn Gln Glu Glu Lys Arg Arg Asn Ala Asp Ile Leu Asn
 65                  70                  75                  80

Glu Lys Ile Arg Glu Glu Leu Gly Arg Ile Glu Glu Gln His Arg Lys
                 85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
         115                 120                 125

His Glu Asn Glu Asn Tyr Leu Leu His Glu Asn Cys Met Leu Lys Lys
     130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Ser Leu Lys Ile Asn Leu Asn Tyr
    290                 295                 300
```

```
Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
            325                 330                 335

Tyr Gln Asn Glu Gln Asp Asn Val Asn Lys His Thr Glu Gln Gln Glu
                340                 345                 350

Ser Leu Asp Gln Lys Leu Phe Gln Leu Gln Ser Lys Asn Met Trp Leu
            355                 360                 365

Gln Gln Gln Leu Val His Ala His Lys Lys Ala Asp Asn Lys Ser Lys
        370                 375                 380

Ile Thr Ile Asp Ile His Phe Leu Glu Arg Lys Met Gln His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
            420                 425                 430

<210> SEQ ID NO 182
<211> LENGTH: 511
<212> TYPE: DNA
<213> ORGANISM: Homo sapiens

<400> SEQUENCE: 182
gaagtttcat gaggtttagc ttttctgggc tggggagtgg agagaaagaa gttgcagggc      60
ttacaggaaa tcccagagcc tgaggttttc tcccagattt gagaactcta gattctgcat     120
cattatcttt gagtctatat tctcttgggc tgtaagaaga tgaggaatgt aataggtctg     180
ccccaagcct tcatgccttt ctgtaccaag cttgtttcct tgtgcatcct tcccaggctc     240
tggctgcccc ttattggaga atgtgatttc caagacaatc aatccacaag tgtctaagac     300
tgaatacaaa gaacttcttc aagagttcat agacgacaat gccactacaa atgccataga     360
tgaattgaag gaatgttttc ttaaccaaac ggatgaaact ctgagcaatg ttgaggtgtt     420
tatgcaatta atatatgaca gcagtctttg tgatttattt taactttctg caagaccttt     480
ggctcacaga actgcagggt atggtgagaa a                                     511

<210> SEQ ID NO 183
<211> LENGTH: 260
<212> TYPE: DNA
<213> ORGANISM: Homo sapiens

<400> SEQUENCE: 183
cacctcgcgg ttcagctcct ctgtcttggt gaagaaccat tcctcggcat ccttgcggtt      60
cttctctgcc atcttctcat actggtcacg catctcgttc agaatgcggc tcaggtccac     120
gccaggtgca gcgtccatct ccacattgac atctccaccc acctggcctc tcagggcatt     180
catctcctcc tcgtggttct tcttcaggta ggccagctcc tccttcaggc tctcaatctg     240
catctccagg tcagctctgg                                                  260

<210> SEQ ID NO 184
<211> LENGTH: 461
<212> TYPE: DNA
<213> ORGANISM: Homo sapiens

<400> SEQUENCE: 184
gtctgatggg agaccaaaga atttgcaagt ggatggtttg gtatcactgt aaataaaaag      60
agggcctttt ctagctgtat gactgttact tgaccttctt tgaaaagcat tcccaaaatg     120
```

```
ctctatttta gatagattaa cattaaccaa cataattttt tttagatcga gtcagcataa      180
atttctaagt cagcctctag tcgtggttca tctctttcac ctgcatttta tttggtgttt      240
gtctgaagaa aggaaagagg aaagcaaata cgaattgtac tatttgtacc aaatctttgg      300
gattcattgg caaataattt cagtgtggtg tattattaaa tagaaaaaaa aaattttgtt      360
tcctaggttg aaggtctaat tgataccgtt tgacttatga tgaccattta tgcactttca      420
aatgaatttg ctttcaaaat aaatgaagag cagacctcgg c                         461
```

<210> SEQ ID NO 185
<211> LENGTH: 531
<212> TYPE: DNA
<213> ORGANISM: Homo sapiens

<400> SEQUENCE: 185

```
tctgatttta tttccttctc aaaaaaagtt atttacagaa ggtatatatc aacaatctga       60
caggcagtga acttgacatg attagctggc atgattttt cttttttttc ccccaaacat      120
tgtttttgtg gccttgaatt ttaagacaaa tattctacac ggcatattgc acaggatgga      180
tggcaaaaaa aagtttaaaa acaaaaaccc ttaacggaac tgccttaaaa aggcagacgt      240
cctagtgcct gtcatgttat attaaacata catacacaca atcttttttgc ttattataat      300 acagacttaa atgtacaaag atgttttcca cttttttcaa tttttaaaca caacagctat      360
aaacctgaac acatatgcta tcatcatgcc ataagactaa acaattata tttagcgaca       420 agtagaaagg attaaatagt caaatacaag aatgaaaaac gcagtacata gtgtcgcgaa      480
ctcaaatcgg catttagata gatccagtgg tttaaacggc acgttttgc t                531
```

<210> SEQ ID NO 186
<211> LENGTH: 441
<212> TYPE: DNA
<213> ORGANISM: Homo sapiens

<400> SEQUENCE: 186

```
cattcctttc ctcgcgttgg ggtttctctg tgtcagcgag cctcggtaca ctgatttccg       60
atcaaaagaa tcatcatctt taccttgact tttcagggaa ttactgaact ttcttctcag      120
aagatagggc acagccattg ccttggcctc acttgaaggg tctgcatttg ggtcctctgg      180
tctcttgcca agtttcccaa ccactcgagg gagaaatatc gggaggtttg acttcctccg      240
gggctttccc gagggcttca ccgtgagccc tgcggccctc agggctgcaa tcctggattc      300
aatgtctgaa acctcgctct ctgcctgctg gacttctgag gccgtcactg ccactctgtc      360
ctccagctct gacagctcct catctgtggt cctgttgtac tggacggggt ccccagggtc      420 ctggggggctt ttttcctgtc t                                               441
```

<210> SEQ ID NO 187
<211> LENGTH: 371
<212> TYPE: DNA
<213> ORGANISM: Homo sapiens

<400> SEQUENCE: 187

```
aaaagtgaat gagtaactat tatattgttg gcaataataa gttgcaaaat catcaggctg       60
caggctgctg atggtgagag tgaactctgt cccagatcca ctgccgctga accttgatgg      120
gaccccagat tctaaactag acgccttatg gatcaggagc tttggggctt tccctggttt      180
ctgttgatac caggccaacc aactactaac actctgactg gcccggcaag tgatggtgac      240
```

-continued

| | |
|---|---|
| tctgtctcct acagttgcag acagggtgga aggagactgg gtcatctgga tgtcacattt | 300 |
| ggcacctggg agccagagca gcaggagccc caggagctga gcggggaccc tcatgtccat | 360 |
| gctgagtcct g | 371 |

<210> SEQ ID NO 188
<211> LENGTH: 226
<212> TYPE: DNA
<213> ORGANISM: Homo sapiens

<400> SEQUENCE: 188

| | |
|---|---|
| ggtatataaa ttgagatgcc cccccaggcc agcaaatgtt ccttttttgtt caaagtctat | 60 |
| ttttattcct tgatattttt cttttttttt tttttgtgga tggggacttg tgaattttttc | 120 |
| taaaggtgct atttaacatg ggaggagagc gtgtgcggct ccagcccagc ccgctgctca | 180 |
| ctttccaccc tctctccacc tgcctctggc ttctcaggac ctgccc | 226 |

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n=A,T,C or G

<400> SEQUENCE: 189

| | |
|---|---|
| tgggtgaagt ttattctgtt ttcacatcta ggttgttggg ganagtgata gacaaagttc | 60 |
| tggattctgg gcatcgtcgg cgcatgcttg taatcctact tgggaggttg anacaggaga | 120 |
| cctcggccgc naccacgcta agggcgaatt ctgcanatat ccatcacact ggcggccgct | 180 |
| cgagcatgca tctanagggc ccaattcncc ctatagtgag ncgtattaca attcactggc | 240 |
| cgtcgtttta caacgtcgtg actgggaaaa ccctggcgtt acccaactta atcgccttgc | 300 |
| agcacatccc cctttcncca gctggcttaa tancgaagag gcccgcaccg atcgcccttc | 360 |
| ccaacanttg cgcagcctga atggcgaatg g | 391 |

<210> SEQ ID NO 190
<211> LENGTH: 501
<212> TYPE: DNA
<213> ORGANISM: Homo sapiens

<400> SEQUENCE: 190

| | |
|---|---|
| catcttggcc tttttgagct gtttccgctt cttctcatcc cggtcactgt caccctcatt | 60 |
| actggaggag ctggcagagg cgttgctgtc aaactcctct gccacatctt cctcctcttc | 120 |
| acctgggttg aatgactcat cggtttcttc tcctgagtca tcgctgctgt cattggcatt | 180 |
| ctcctcccgg atcttgcctt cctccttcat cctctccaag taggcatcat gctggtcctc | 240 |
| atcagagtca gcatattcat cgtagcttgg gttcatgccc tctttcaatc ctcggttttt | 300 |
| gatgttgagc ttttttcgcgt tgacaaaatc aaacagtttc ccgtactcct ccctctcaat | 360 |
| gctgctgaag gtatactgag tgccctgctt ggtctcaatt tcaaagtcaa aggaacgagt | 420 |
| agtagtggta ccacgagcaa agttgacaaa ggagatctca tcgaagcgga tgtgcacagg | 480 |
| tggcttgtgg acgtagatga a | 501 |

<210> SEQ ID NO 191
<211> LENGTH: 241
<212> TYPE: DNA
<213> ORGANISM: Homo sapiens

```
<220> FEATURE:
<221> NAME/KEY: misc_feature
<222> LOCATION: (49)
<223> OTHER INFORMATION: n=A,T,C or G

<400> SEQUENCE: 191
ggaaaaactg tgaaaaatat atctgaattt attaagtaca gtataaaana gggttgtggc    60
aacagaaagt aaaaactaac atggattgct ataaatatgc tgaagcctag ttgttcaaat   120
gatacaattc tctcatgcta ctctaaagtt tataaagaaa aaggatttac actttacaca   180
ctgtacacaa aaggaatacc ttctgagagc cagggagtgg ggaaagggga aggagacttg   240
a                                                                  241

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n=A,T,C or G

<400> SEQUENCE: 192
tggtcntgga ttcacanata aantanatcg actaaaactg gcagaaattg tgaagcaggt    60
gatagaagan caaaccacgt cccacgaatc ccaataatga cagcttcaga ctttgctttt   120
ttaacaattt gaaaaattat tctttaatgt ataaagtaat tttatgtaaa ttaataaatc   180
ataatttcat ttccacattg attaaagctg ctgtatagat ttagggngca ggacttaata   240
atagnggaaa tgaaattatg atttattaat c                                 271

<210> SEQ ID NO 193
<211> LENGTH: 351
<212> TYPE: DNA
<213> ORGANISM: Homo sapiens

<400> SEQUENCE: 193
agtcgaggcg ctgatcccta aaatggcgaa catgtgtttt catcatttca gccaaagtcc    60
taacttcctg tgcctttcct atcacctcga gaagtaatta tcagttggtt tggattttg    120 gaccaccgtt cagtcatttt gggttgccgt gctcccaaaa cattttaaat gaaagtattg   180
gcattcaaaa agacagcaga caaaatgaaa gaaaatgaga gcagaaagta agcatttcca   240
gcctatctaa tttctttagt tttctatttg cctccagtgc agtccatttc ctaatgtata   300
ccagcctact gtactattta aaatgctcaa tttcagcacc gatggacctg c            351

<210> SEQ ID NO 194
<211> LENGTH: 311
<212> TYPE: DNA
<213> ORGANISM: Homo sapiens

<400> SEQUENCE: 194
ctgagacaca gaggcccact gcgaggggga cagtggcggt gggactgacc tgctgacagt    60
caccctccct ctgctgggat gaggtccagg agccaactaa acaatggca gaggagacat    120 ctctggtgtt cccaccaccc tagatgaaaa tccacagcac agacctctac cgtgtttctc   180
ttccatccct aaaccacttc cttaaaatgt ttggatttgc aaagccaatt tggggcctgt   240
ggagcctggg gttggatagg gccatggctg gtcccccacc atacctcccc tccacatcac   300
tgacacagac c                                                       311
```

<210> SEQ ID NO 195
<211> LENGTH: 381
<212> TYPE: DNA
<213> ORGANISM: Homo sapiens

<400> SEQUENCE: 195

```
tgtcagagtg gcactggtag aagttccagg aaccctgaac tgtaagggtt cttcatcagt      60
gccaacagga tgacatgaaa tgatgtactc agaagtgtcc tggaatgggg cccatgagat     120
ggttgtctga gagagagctt cttgtcctgt cttttccctt ccaatcaggg gctcgctctt     180
ctgattattc ttcagggcaa tgacataaat tgtatattcg gttcccggtt ccaggccagt     240
aatagtagcc tctgtgacac cagggcgggg ccgagggacc acttctctgg gaggagaccc     300
aggcttctca tacttgatga tgtagccggt aatcctggca cgtggcggct gccatgatac     360
cagcagggaa ttgggtgtgg t                                                381
```

<210> SEQ ID NO 196
<211> LENGTH: 401
<212> TYPE: DNA
<213> ORGANISM: Homo sapiens

<400> SEQUENCE: 196

```
cacaaacaag aggagcacca gacctcctct tggcttcgag atggcttcgc cacaccaaga      60
gcccaaacct ggagacctga ttgagatttt ccgccttggc tatgagcact gggccctgta     120
ataggagat ggctacgtga tccatctggc tcctccaagt gagtaccccg gggctggctc      180
ctccagtgtc ttctcagtcc tgagcaacag tgcagaggtg aaacgggagc gcctggaaga     240
tgtggtggga ggctgttgct atcgggtcaa caacagcttg gaccatgagt accaaccacg     300
gcccgtggag gtgatcacca gttctgcgaa ggagatggtt ggtcagaaga tgaagtacag     360
tattgtgagc aggaactgtg agcactttgt cacccagacc t                          401
```

<210> SEQ ID NO 197
<211> LENGTH: 471
<212> TYPE: DNA
<213> ORGANISM: Homo sapiens

<400> SEQUENCE: 197

```
ctgtaatgat gtgagcaggg agccttcctc cctgggccac ctgcagagag ctttcccacc      60
aactttgtac cttgattgcc ttacaaagtt atttgtttac aaacagcgac catataaaag     120
cctcctgccc caaagcttgt gggcacatgg gcacatacag actcacatac agacacacac     180
atatatgtac agacatgtac tctcacacac acaggcacca gcatacacac gttttctag      240
gtacagctcc caggaacagc taggtgggaa agtcccatca ctgagggagc ctaaccatgt     300
ccctgaacaa aaattgggca ctcatctatt ccttttctct tgtgtcccta ctcattgaaa     360
ccaaactctg gaaaggaccc aatgtaccag tatttatacc tctagtgaag cacagagaga     420
ggaagagagc tgcttaaact cacacaacaa tgaactgcag acacagacct g               471
```

<210> SEQ ID NO 198
<211> LENGTH: 201
<212> TYPE: DNA
<213> ORGANISM: Homo sapiens

<400> SEQUENCE: 198

```
ggtccattga ggctctgtcg gccatgccca cagttcgaag ctttgccaac gaggagggcg      60
aagcccagaa gtttagggaa aagctgcaag aaataaagac actcaaccag aaggaggctg     120
```

```
tggcctatgc agtcaactcc tggaccacta gtatttcagg tatgctgctg aaagtgggaa      180
tcctctacat tggtgggcag a                                               201

<210> SEQ ID NO 199
<211> LENGTH: 551
<212> TYPE: DNA
<213> ORGANISM: Homo sapiens

<400> SEQUENCE: 199
tctggcacag atcttcaccc acacggcggt ccacgtgctg atcatcttcc gggtctcacc      60
gggcctggaa cacaccatct tccccatgag cccggtgccc agtctggtga cttccatctt     120
ggcccctggc cttatgtccc agttatgacc cctgacttca actctggctc ttaccctgta     180
actccagtcc atctctgaca ttttaacac ccggccttgt gaccgtggac atagctcctg      240
acctcgattc ccatcttgag cccagtgtta gtccatgaga tcatgacctg actcctggtc     300
tccaaccttg tgatcctaat tctgggacct caatcctagc ctctgaactt gggaccctgg    360
agctcctgac cttagtcctg accgctaccc ttgattctga cctttgatcc tgtaacttag    420
gggtggcccc tgaccttatt actgtcattt agctccttga ccttgccact tcaatcctgg    480
ctttatgacc tcctactctc aattttaact ttaaccaaat gaccaaattt gtgacactaa    540
atgaccacaa t                                                          551

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200
cagctcancg ggcgacatgc ccctacaagt tggcanaagn ggctgccact gctgggtttg      60
tgtaagagag gctgctgnca ccattacctg cagaaacctt ctcataggg ctacgatcgg      120 tactgctagg gggcacatag cgcccatggg tgtggtaggt ggggnactcn ntnataggat     180
ggtaggtatc ccgggctgga aanatgnnca g                                    211

<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttct      60
taatttccac actatttctc ccatattcct taaacttctt ggcatccacc t              111

<210> SEQ ID NO 202
<211> LENGTH: 331
<212> TYPE: DNA
<213> ORGANISM: Homo sapiens

<400> SEQUENCE: 202
tgaaaataca gaataccagg tggtcccaaa tgtttgaagt tctttgaaca gaaagagaga      60
ggagagagag agagaggaaa attccctaac ccttggttta aagacaatat tcatttattg     120
ctcaaatgat gcttttaagg gaggacagtg gaataaaata aactttttt ttctccctac      180
```

| | |
|---|---|
| aatacataga agggttatca aaccactcaa gtttcaaaat ctttccaggg tccaatatca | 240 |
| cttttttct ttcggttcaa tgaaaagcta aatgtaataa tactaattat agataaaatt | 300 |
| ttattttact ttttaaaaat ttgtccagac c | 331 |

<210> SEQ ID NO 203
<211> LENGTH: 491
<212> TYPE: DNA
<213> ORGANISM: Homo sapiens

<400> SEQUENCE: 203

| | |
|---|---|
| agtcacccag tctacttagt acctggttgc tgcctctgac cttttcagct tgatacctg | 60 |
| ggctttagtg taaccaataa atctgtagtg accttacctg tattcctgt gctatcctgt | 120 |
| gggaaggtag gaatgggcta agtatgatga atgtataggt tagggatctt ttggttttaa | 180 |
| atcacagaaa acctaattca aactggctta aaataaaaag gatttattgg ttcatgtaac | 240 |
| tagaaagtcc ataggtagtg ctggctccag gtgaagactt gacccagtag ttcagtatgt | 300 |
| ctctaaatac cggactgact ttttctcac tgttgcatct tctgtaggac catttaagtc | 360 |
| tgggccactt aatggctgcc agcattccta agattacact ttttcccatt tatgtccaat | 420 |
| cagaaaaaga aggcatcttt gtaccagaaa tctcagcaaa agccctaata ttcacactga | 480 |
| ttaggacctg c | 491 |

<210> SEQ ID NO 204
<211> LENGTH: 361
<212> TYPE: DNA
<213> ORGANISM: Homo sapiens

<400> SEQUENCE: 204

| | |
|---|---|
| tcccttcctc ccccatgtga taaatgggtc cagggctgat caaagaactc tgactgcaga | 60 |
| actgccgctc tcagtggaca gggcatctgt tatcctgaga cctgtggcag acacgtcttg | 120 |
| ttttcatttg attttgtta agagtgcagt attgcagagt ctagaggaat ttttgtttcc | 180 |
| ttgattaaca tgattttcct ggttgttaca tccaggcat ggcagtggcc tcagccttaa | 240 |
| actttgttc ctactcccac cctcagcgaa ctgggcagca cggggagggt ttggctaccc | 300 |
| ctgcccatcc ctgagccagg taccaccatt gtaaggaaac actttcagaa attcagacct | 360 |
| c | 361 |

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<221> NAME/KEY: misc_feature
<222> LOCATION: (3)
<223> OTHER INFORMATION: n=A,T,C or G

<400> SEQUENCE: 205

| | |
|---|---|
| cnngtacagt tcttcctgga tggccgacac agatcctggg gaaaggcaat cctggcactg | 60 |
| ctctgaaacc agagctcctc ctccctcccc gggcagggtg gagctgagaa gggctgctct | 120 |
| agcgttggga ctccacctcc atacacctga tattttgata gggcaggtcc ctgctatggg | 180 |
| ccactgttct gggcagtata gtatgcttga cagcatcctt ggcatctatc caccagatcc | 240 |
| cagagcaccc gctactagct gtgacaacat cctccaaaca ttgcaaaatt tcccctggga | 300 |

| | | |
|---|---|---|
| ggcaagattg cctcagatgg gagaatcacg ctctagggaa atctgctggt atgagaaccc | 360 | |
| caactcccca ctccactgag cctccagatg gcgagcaggc tgcagctcca gcacagacac | 420 | |
| gaagctccct ccagccactg acggtccatg gctggggtta cccaggacct c | 471 | |

<210> SEQ ID NO 206
<211> LENGTH: 261
<212> TYPE: DNA
<213> ORGANISM: Homo sapiens

<400> SEQUENCE: 206

| | | |
|---|---|---|
| tagagtattt agagtcctga gataacaagg aatccaggca tcctttagac agtcttctgt | 60 | |
| tgtcctttct tcccaatcag agatttgtgg atgtgtggaa tgacaccacc accagcaatt | 120 | |
| gtagccttga tgagagaatc caattcttca tctccacgaa tagcaagttg caagtgacga | 180 | |
| ggggtaatac gctttacctt taagtctttt gatgcatttc ctgccagttc aagtacctct | 240 | |
| gcggtgaggt actccaggat g | 261 | |

<210> SEQ ID NO 207
<211> LENGTH: 361
<212> TYPE: DNA
<213> ORGANISM: Homo sapiens

<400> SEQUENCE: 207

| | | |
|---|---|---|
| gctctccggg agcttgaaga agaaactggc tacaaagggg acattgccga atgttctcca | 60 | |
| gcggtctgta tggacccagg cttgtcaaac tgtactatac acatcgtgac agtcaccatt | 120 | |
| aacggagatg atgccgaaaa cgcaaggccg aagccaaagc caggggatgg agagtttgtg | 180 | |
| gaagtcattt ctttacccaa gaatgacctg ctgcagagac ttgatgctct ggtagctgaa | 240 | |
| gaacatctca cagtggacgc cagggtctat tcctacgctc tagcactgaa acatgcaaat | 300 | |
| gcaaagccat tgaagtgcc cttcttgaaa ttttaagccc aaatatgaca ctggacctgc | 360 | |
| c | 361 | |

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208

| | | |
|---|---|---|
| agaggagatn tttgccatgc ctgaatnctt tcctatncca ccctancact taacatatta | 60 | |
| cttagtctgc tttgntaaaa gcaagtatta ccttnaactt gnctcttact ctttgccctt | 120 | |
| tagctaacta ataaagnttg atntaggcat tattatataa ttctgagtca ttcatggtat | 180 | |
| ctctcatgtt tgatgtattt tncaaactaa gatctatgat agttttttt ccanagttcc | 240 | |
| attaaatcat ttatttcctt tactttctca cctctgtnga aacatttaga aactggattt | 300 | |
| gggaacccan ttttggaaaa ccagattcat agtcatgaaa atggaaactt ncatattctg | 360 | |
| tttttgaaaa gatgtggacc t | 381 | |

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: (83)
<223> OTHER INFORMATION: n=A,T,C or G

<400> SEQUENCE: 209

```
gtggagagca agtgatttat taaagcaaga cgttgaaacc tttacattct gcagtgaaga      60
tcagggtgtc attgaaagac agnggaaacc aggatgaaag ttttacatg tcacacacta     120
catttcttca atattttcac caggacttcc gcaatgaggc ttcgtttctg aagggacatc    180
tgatccgtgc atctcttcac tcctaacttg gctgcaacag cttccacctg c             231
```

<210> SEQ ID NO 210
<211> LENGTH: 371
<212> TYPE: DNA
<213> ORGANISM: Homo sapiens

<400> SEQUENCE: 210

```
tccatcctgg ttttgcagag atcaggttgt tgacagttcc tggttgaccc acagctaccc     60
atgtcagtta tctccactaa catatccaag aatctttgta ggacaatttc tccacctgca    120
aggtttttta ggtagaactc ttcttttaag gcaattagcc cattgccaaa aggttttact    180
gtcttaaagc tgtctttctg agatctaatt ccaaggactt ctccacagct aagtgagatg    240
cctcacacca ttaggtgatg cttttggacag aacagagtat tttcatcttg tgtttaaagc   300
aattccttgg cttcggctcc tcaccacttt ctatgccagt ctcccattta tgtccctagt    360
aatgcctatg c                                                         371
```

<210> SEQ ID NO 211
<211> LENGTH: 471
<212> TYPE: DNA
<213> ORGANISM: Homo sapiens

<400> SEQUENCE: 211

```
tttatttaa aagaaaaaaa ttaaaataga gccaacaaat gcaattaaga aaaaaaagt       60
attgagacac aagggacct acatgttctg gtctaagaag catgcaagta ttacaaagca    120
ttccagatac agtatgacag aggaacagtg aacaagcatt ggaacgatgc tctttctttc   180
agaaacggga agtctaacag ttatgttttc acaatggtag tgattaaacc atcttttattt  240
ttaaggaatt ttataggaag aattttagca ccatcattaa aggaaaaata ataataccctt  300
tttagccctg cctatctcca gtcttggaat aataacagaa gcatagcacc tttcagtatc   360
taaaatataa acaagaatag taagtccatc ccagcttcta gagatgaggt agctcatgct   420
aagaaatgtt gggtcatttt tcctatgaaa gttcaaaggc caaatggtca c             471
```

<210> SEQ ID NO 212
<211> LENGTH: 401
<212> TYPE: DNA
<213> ORGANISM: Homo sapiens

<400> SEQUENCE: 212

```
tggcctgtct ccttcacata gtccatatca ccacaaatca cacaacaaaa gggagaggat     60
atattttggg ttcaaaaaaa gtaaaaagat aatgtagctg catttctttg gttattttgg   120
gccccaaata tttcctcatc ttttttgttgt tgtcatggat ggtggtgaca tggacttgtt  180
tatagaggac aggtcagctc tctggctcgg tgatctacat tctgaagttg tctgaaaatg   240
tcttcatgat taaattcagc ctaaacgttt tgccgggaac actgcagaga caatgctgtg   300
agtttccaac ctcagcccat ctgcgggcag agaaggtcta gtttgtccat caccattatg   360
```

```
atatcaggac tggttacttg gttaaggagg ggtctacctc g                          401
```

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G

<400> SEQUENCE: 213

```
tgtgaagcat acataaataa atgaagtaag ccatactgat ttaatttatt ggatgttatt       60
ttccctaaga cctgaaaatg aacatagtat gctagttatt tttcagtgtt agccttttac     120
tttcctcaca caatttggaa tcatataata taggtacttt gtccctgatt aaataatgtg     180
acggatagaa tgcatcaagt gtttattatg aaaagagtgg aaaagtatat agcttttanc     240
aaaaggtgtt tgcccattct aagaaatgag cgaatatata gaaatagtgn gggcatttct     300
tcctgttagg tggagtgtat gtgttgacat ttctccccat ctcttcccac tctgttttnnt   360
ccccattatt tgaataaagt gactgctgaa nangactttg aatccttatc cacttaattt     420
aatgtttaaa gaaaaaccta taatggaaag tgagactcct t                          461
```

<210> SEQ ID NO 214
<211> LENGTH: 181
<212> TYPE: DNA
<213> ORGANISM: Homo sapiens

<400> SEQUENCE: 214

```
cctgagcttc tactcctttc ccttaagatt cctccaaagc accagctcca taaaatcctt       60
cagctcccca gacccacacc aagaacccca catgttaatt ggatcagcca aatctacaag     120
cagataagtc ctaaggagaa tgccgaagcg ttttcttct tcctcaagcc tagcatgaga     180
c                                                                     181
```

<210> SEQ ID NO 215
<211> LENGTH: 581
<212> TYPE: DNA
<213> ORGANISM: Homo sapiens

<400> SEQUENCE: 215

```
ctgctttaag aatggttttc cacctttttcc ccctaatctc taccaatcag acacatttta      60
ttatttaaat ctgcacctct ctctatttta tttgccaggg gcacgatgtg acatatctgc     120
agtcccagca cagtgggaca aaaagaattt agaccccaaa agtgtcctcg gcatggatct     180
tgaacagaac cagtatctgt catggaactg aacattcatc gatggtctcc atgtattcat     240
ttattcactt gttcattcaa gtatttattg aatacctgcc tcaagctaga gagaaaagag     300
agtgcgcttt ggaaatttat tccagttttc agcctacagc agattatcag ctcggtgact     360
tttctttctg ccaccattta ggtgatggtg tttgattcag agatggctga atttctattc     420
ttagcttatt gtgactgttt cagatctagt ttgggaacag attagaggcc attgtcctct     480
gtcctgatca ggtggcctgg ctgtttcttt ggatccctct gtcccagagc cacccagaac     540
cctgactctt gagaatcaag aaaacaccca gaaaggacct c                         581
```

<210> SEQ ID NO 216
<211> LENGTH: 281
<212> TYPE: DNA
<213> ORGANISM: Homo sapiens

```
<220> FEATURE:
<221> NAME/KEY: misc_feature
<222> LOCATION: (1)...(281)
<223> OTHER INFORMATION: n=A,T,C or G

<400> SEQUENCE: 216
ccgatgtcct gcttctgtgg accagggct cctctgnngg tggcctcaac cacggctgag      60
atccctagaa gtccaggagc tgtggggaag agaagcactt agggccagcc agccgggcac    120
ccccacttgc gccccgaccc acgctcacgc accagacctg cccnggcggt cgctcnaaag    180
ggcgaattct gcagatatcc atcacactgg cggacgctcg agcatgcatc tagagggccc    240
aattcaccct atantgagtc gtattacaat tcactggccg t                        281

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: (1)...(356)
<223> OTHER INFORMATION: n=A,T,C or G

<400> SEQUENCE: 217
atagcaggtt tcaacaattg tcttgtagtt tgnagtaaaa agacataaga aagagaaggt     60
gtggtttgca gcaatccgta gttggtttct caccataccc tgcagttctg tgagccaaag   120
gtcttgcaga aagttaaaat aaatcacaaa gactgctgtc atatattaat tgcataaaca   180
cctcaacatt gctcagagtt tcatccgttt ggttaagaaa acattccttc aattcatcta   240
tggcatttgt agtggcattg tcgtctatga actcttgaag aagttctttg tattcagtct   300
tagacacttg tggattgatt gncttggaaa tcacattctc caataaggga cctcgg       356

<210> SEQ ID NO 218
<211> LENGTH: 321
<212> TYPE: DNA
<213> ORGANISM: Homo sapiens

<400> SEQUENCE: 218
ttgtccatcg ggagaaaggt gtttgtcagt tgtttcataa accagattga ggaggacaaa     60
ctgctctgcc aatttctgga tttctttatt ttcagcaaac actttcttta aagcttgact   120
gtgtgggcac tcatccaagt gatgaataat catcaagggt tgttgcttg tcttggattt     180 atatagagct tcttcatatg tctgagtcca gatgagttgc tcaccccaac ctctggagag   240
ggtctggggc agtttgggtc gagagtcctt tgtgtccttt ttggctccag gtttgactgt   300
ggtatctctg gacctgcctg g                                              321

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219
ccggttaggt ccacgcgggg gcagtggagg cacaggctca ngtggccgg gctacctggc      60 acccatggc ttacaaagta gagttggccc agtttccttc cacctgaggg gagcactctg    120
actcctaaca gtcttccttg ccctgccatc atctggggtg gctggctgtc aagaaaggcc   180
```

-continued

| gggcatgctt tctaaacaca gccacaggag gcttgtaggg catcttccag gtggggaaac | 240 |
| agtcttagat aagtaaggtg acttgtctaa g | 271 |

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n=A,T,C or G

<400> SEQUENCE: 220

| gtcctacgac gaggaccagc ttttcttctt cnactttttcc canaacactc gggtgcctcg | 60 |
| cctgcccgaa tttgctgact gggctcagga acagggagat gctcctgcca ttttatttga | 120 |
| caaagagttc tgcgagtgga tgatccagca ataggggcca aaacttgatg ggaaaatccc | 180 |
| ggtgtccaga gggtttccta tcgctgaagt gttcacgctg aagcccctgg agtttggcaa | 240 |
| gcccaacact ttggtctgtt ttgtcagtaa tctcttccca cccatgctga cagtgaactg | 300 |
| gtagcatcat tccgtccctg tggaaggatt tgggcctact tttgtctcag a | 351 |

<210> SEQ ID NO 221
<211> LENGTH: 371
<212> TYPE: DNA
<213> ORGANISM: Homo sapiens

<400> SEQUENCE: 221

| gtctgcagaa gcgtgtctga ggtgtccggt ggaggtggca gccgagctct gggactaatc | 60 |
| accgtgctgg ggacggcacc gcgtcaggat gcaggcagat ccctgcagaa gtgtctaaaa | 120 |
| ttcacactcc tcttctggag ggacgtcgat ggtattagga tagaagcacc aggggacccc | 180 |
| acgaacggtg tcgtcgaaac agcagccctt atttgcacac tggagggcg tgacaccagg | 240 |
| aaaaccacaa ttctgtcttt cacggggggc cactgtacac gtctctgtct gggcctcggc | 300 |
| cagggtgccg agggccagca tggacaccag gaccagggcg cagatcacct tgttctccat | 360 |
| ggtggacctc g | 371 |

<210> SEQ ID NO 222
<211> LENGTH: 471
<212> TYPE: DNA
<213> ORGANISM: Homo sapiens

<400> SEQUENCE: 222

| gtccatgttc catcattaat gttccaacat caccagggac acaaagctgc aaaaatgaga | 60 |
| agggaaataa ggttagagaa aggatccggg caatcttaag gactgaggaa gacatgttcc | 120 |
| ccaacccttg aactcacaaa ccctgaagct caaggattgc atccttcctc caaatctcac | 180 |
| tcaacataat aagtgcagaa caacatgcca aagcactgta tgaagcacta gggacaaaga | 240 |
| caaggtcaaa atccttgtaa ccaaatttaa tggtattgta atgcagtgtt aacacaggac | 300 |
| agtaacagaa cacccaagaa ccaaacagaa gagggtaggg ataagcataa atgaagtaac | 360 |
| atgaaataaa cttccaaatg gaaaacttgt ccatacccccc agggcaagtc aactacagtc | 420 |
| tcccaaagga cataaattcc acttagggca cactagacag aaaacaatat t | 471 |

<210> SEQ ID NO 223
<211> LENGTH: 411
<212> TYPE: DNA
<213> ORGANISM: Homo sapiens

<400> SEQUENCE: 223

```
agttgctcta caatgacaca caaatcccgt taaataaatt ataaacaagg gtcaattcaa        60
atttgaagta atgttttagt aaggagagat tagaagacaa caggcatagc aaatgacata       120
agctaccgat taactaatcg gaacatgtaa aacagttaca aaaataaacg aactctcctc       180
ttgtcctaca atgaaagccc tcatgtgcag tagagatgca gtttcatcaa agaacaaaca       240
tccttgcaaa tgggtgtgac gcggttccag atgtggattt ggcaaaacct catttaagta       300
aaaggttagc agagcaaagt gcggtgcttt agctgctgct tgtgccgctg tggcgtcggg       360
gaggctcctg cctgagcttc cttccccagc tttgctgcct gagaggaacc a                411
```

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: (31)
<223> OTHER INFORMATION: n=A,T,C or G

<400> SEQUENCE: 224

```
ggtctgaagt ttgataacaa agaaatatat ntaagacaaa aatagacaag agttaacaat        60
aaaaacacaa ctatctgttg acataacata tggaaacttt ttgtcagaaa gctacatctt       120
cttaatctga ttgtccaaat cattaaaata tggatgattc agtgccattt tgccagaaat       180
tcgtttggct ggatcataga ttaacatttt cgagagcaaa tccaagccat tttcatccaa       240
gttttttgaca tgggatgcta ggcttcctgg tttccatttg ggaaatgtat tcttatagtc       300
ctgtaaagat tccacttctg g                                                 321
```

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225

```
atgtctgggg aaagagttca ttggcaaaag tgtnctccca agaatggttt acaccaagca        60
gagaggacat gtcactgaat ggggaaaggg aaccccccgta tccacagtca ctgtaagcat       120
ccagtaggca ggaagatggc tttgggcagt ggctggatga aagcagattt gagatacccca      180
gctccggaac gaggtcatct tctacaggtt cttccttcac tgagacaatg aattcagggt       240
gatcattctc t                                                            251
```

<210> SEQ ID NO 226
<211> LENGTH: 331
<212> TYPE: DNA
<213> ORGANISM: Homo sapiens
<220> FEATURE:
<221> NAME/KEY: misc_feature
<222> LOCATION: (1)...(331)
<223> OTHER INFORMATION: n=A,T,C or G

<400> SEQUENCE: 226

```
gttaggtccc aggcccccccg ccaagnggtt accnnnntna ccactcctga cccaaaaatc        60
aggcatggca ttaaaacgtt gcaaattcct ttactgttat ccccccccacc accaggacca      120
```

```
tgtagggtgc agtctttact ccctaacccg tttcccgaaa aaggtgctac ctcctttcca    180
gacagatgag agagggcagg acttcaggct ggatccacca ctgggctctc cctcccccag    240
cctggagcac gggaggggag gtgacggctg gtgactgatg gatgggtagt gggctgagaa    300 gagggggacta ggaagggcta ttccaggctc a                                  331
```

<210> SEQ ID NO 227
<211> LENGTH: 391
<212> TYPE: DNA
<213> ORGANISM: Homo sapiens

<400> SEQUENCE: 227

```
aggtctgccc ttgaagtata ggaaggaatc atagttggag gacttctgca ttatttgttg    60
gctgaagcta gaagtgcaac cccctcctga tttctgcagc aagatgaact gccttatccc    120
cagcccgcag gaatgttcat atctgagcaa tcaatgggca ctgtgttcaa ccacgccatt    180
ttcaagattg gctccttaaa ccacccacaa ggcaccagct ctgggagaag ctgcagggag    240
aagagaacaa agccctcgct gtgatcagga tgggtgtctc atacctttc tctgggtca     300 ttccaggtat gagacagagt tgaacctgcg catgagcgtg gaggccgaca tcaacggcct    360
gcgcagggtg ctggatgagc tgaccctgga c                                   391
```

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228

```
gttgtccata gccacctcct gggatagaag ctttntagtt catagttcga ttagtgtgtc    60
cttaggacat aggtccagcc ctacagatta gctgggtgaa aaggcaagt gtctcgacag     120 ggcttagtct ccaccctcag gcatggaacc attcaggtg aagcctggga tgtgggcaca    180
ggagactcag gctgatataa aataacaaa atcagtaata aaaaaattat aaaacctgtt    240
gcttgtctga atagatttga gcaacagtct tgcttttgtt aaaatcctgg agccgttaag    300
tcctgaatat tcttctggac atcattgctg gctggagaaa ggagccccag gcccggctcg    360
gctgacatct gtcaggtttg gaagtctcat c                                   391
```

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229

```
gtccatggct tctcacccag acagtctttc tgggcaactt ggggaagccc ctgttctgct    60
caagtctcac cccatggaag aggtggggga aggggccctt ggttttcag gaagacgggt     120 tggagagcac gagtcactac aaagcagtaa aagtgaatgg tgtctccagg ggctgggtcc    180
agaacaccgc ggagagcccc anccataaag gtgtgttccg cctctggcct gcaggaatct    240 cttttgaatct ctttgattgg tggctccaag agcaatggga agtcaacagc caggaggctg    300
gactgggttc cctgggaccc cgaggtccca gaggctgctg g                       341
```

<210> SEQ ID NO 230
<211> LENGTH: 511
<212> TYPE: DNA
<213> ORGANISM: Homo sapiens

<400> SEQUENCE: 230

| | | |
|---|---|---|
| gtccaagcca aggaaaccat tcccttacag gagacctccc tgtacacaca ggaccgcctg | 60 |
| gggctaaagg aaatggacaa tgcaggacag ctagtgtttc tggctacaga aggggaccat | 120 |
| cttcagttgt ctgaagaatg gttttatgcc cacatcatac cattccttgg atgaaacccg | 180 |
| tatagttcac aatagagctc agggagcccc taactcttcc aaaccacatg ggagacagtt | 240 |
| tccttcatgc ccaagcctga gctcagatcc agcttgcaac taatccttct atcatctaac | 300 |
| atgccctact tggaaagatc taagatctga atcttatcct ttgccatctt ctgttaccat | 360 |
| atggtgttga atgcaagttt aattaccatg gagattgttt tacaaacttt tgatgtggtc | 420 |
| aagttcagtt ttagaaaagg gagtctgttc cagatcagtg ccagaactgt gcccaggccc | 480 |
| aaaggagaca actaactaaa gtagtgagat a | 511 |

<210> SEQ ID NO 231
<211> LENGTH: 311
<212> TYPE: DNA
<213> ORGANISM: Homo sapiens

<400> SEQUENCE: 231

| | | |
|---|---|---|
| ggtccaagta agctgtgggc aggcaagccc ttcggtcacc tgttggctac acagacccct | 60 |
| cccctcgtgt cagctcaggc agctcgaggc ccccgaccaa cacttgcagg ggtccctgct | 120 |
| agttagcgcc ccaccgccgt ggagttcgta ccgcttcctt agaacttcta cagaagccaa | 180 |
| gctccctgga gccctgttgg cagctctagc tttgcagtcg tgtaattggc ccaagtcatt | 240 |
| gttttttctcg cctcactttc caccaagtgt ctagagtcat gtgagcctcg tgtcatctcc | 300 |
| ggggtggacc t | 311 |

<210> SEQ ID NO 232
<211> LENGTH: 351
<212> TYPE: DNA
<213> ORGANISM: Homo sapiens

<400> SEQUENCE: 232

| | | |
|---|---|---|
| tcgtttagct aataatccct tccttgatga tacactccaa cttcttgttt ttctttattt | 60 |
| ctaaaaagcg gttctgtaac tctcaatcca gagatgttaa aaatgtttct aggcacggta | 120 |
| ttagtaaatc aagtaaattt catgtcctct taaaggacaa acttccagag atttgaatat | 180 |
| aaatttttat atgtgttatt gattgtcgtg taacaaatgg ccccacaaa ttagtagctt | 240 |
| aaaatagcat ttatgatgtc actgttttct ttgccttttc attaatgttc tgtacagacc | 300 |
| tatgtaaaca acttttgtat atgcatatag gatagctttt tgagggtat a | 351 |

<210> SEQ ID NO 233
<211> LENGTH: 511
<212> TYPE: DNA
<213> ORGANISM: Homo sapiens

<400> SEQUENCE: 233

| | | |
|---|---|---|
| aggtctggat gtaaggatgg atgctctcta tacatgctgg gttggggatg ctgggactgc | 60 |
| acagccaccc ccagtatgcc gctccaggac tctgggacta gggcgccaaa gtgtgcaaat | 120 |

-continued

| | |
|---|---|
| gaaaatacag gatacccagg gaactttgaa tttcagattg tgaaaagaaa acaaatcttg | 180 |
| agactccaca atcaccaagc taaaggaaaa agtcaagctg ggaactgctt agggcaaagc | 240 |
| tgcctcccat tctattcaca gtcatccccc tgaggctcac ctgcatagct gattgcttcc | 300 |
| tttcccctat cgcttctgta aaaatgcaga ctcactgagc cagactaaat tgtgtgttca | 360 |
| gtggaaggct gatcaagaac tcaaaagaat gcaaccttt gtctcttatc tactacaacc | 420 |
| aggaagcccc cacttaaggg ttgtcccacc ttactggact gaaccaaggt acatcttaca | 480 |
| cctactgatt gatgtctcat gtcccctaa g | 511 |

<210> SEQ ID NO 234
<211> LENGTH: 221
<212> TYPE: DNA
<213> ORGANISM: Homo sapiens

<400> SEQUENCE: 234

| | |
|---|---|
| caggtccagc gaagggctt cataggctac accaagcatg tccacataac cgaggaagct | 60 |
| ctctccatca gcatagcctc cgatgaccat ggtgttccac aaagggttca tcttcgagcg | 120 |
| ccggctgtac atggccctgg tcagccatga atgaatagct ctaggactat agctgtgtcc | 180 |
| atctcccaga agctcctcat caatcaccat ctggccgaga c | 221 |

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235

| | |
|---|---|
| ggtccaagaa agggacatct atgtgaaagt ganactgaga cagtgctggt cacaggtcat | 60 |
| gctgcagaat aatacattcc caggcactgt cacgtggggg acccaagagg ccccaggagt | 120 |
| gacctataac ctctccagaa agaccactct gtgtggcatc acagtccaca cagtttaagg | 180 |
| aaatatttag acttaacaat cagacaccag ctcttactca cacttacact cacagcccac | 240 |
| acacaagtgt gcaaacatac acacacatat atatttcctg atacattcat ggaatatcag | 300 |
| agccctgccc tgaagtcgtt agtgtctctg ctccccaaac cgctgctccc acattggcta | 360 |
| agctccctca agagacctca g | 381 |

<210> SEQ ID NO 236
<211> LENGTH: 441
<212> TYPE: DNA
<213> ORGANISM: Homo sapiens

<400> SEQUENCE: 236

| | |
|---|---|
| aggtcctgtt gcccctttct tttgcccaac ttcgccattt gggaattgga atatttaccc | 60 |
| aacacctgta ctgcattgaa tattggaagc aaataacttg gctttgatct tataggctca | 120 |
| cagatggagg aacgtaccttt gaagttcaga tgagatttcg acttttgag ttgatgctga | 180 |
| aacagcttga gattttggg gactactgag agatgataat tgtattgtgc aatatgagaa | 240 |
| ggacatgaga tttggtgggc ataggtgtga atgacattg tttggatgtg tttaccctcc | 300 |
| aaatctcttg ttgaatgtga tcttaaacgt tggtggtggg cctagtggaa ggtgttgaat | 360 |
| catgggggtg gactcttcat aatttgctta gctccatccc cttggtgatg agcaagtcct | 420 |
| tgctctgttg tgtcacatga g | 441 |

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237
tcctaaaaaa ttagctgacc ttgttaaaaa tgttggcgtg agcagtatat tattacctat        60 cttttttat tgtgtgtgtg ngtgtgtgtn ttaaactaat tggctgaaat atctgcctgt        120
ttccctcttt acattttct tgtttctttc cttatttatc tttgtccatc ttgagatcta        180
ctgtaaagtg aatnttttaa tgaaaacann nccaagttnt actctcactg ggnttgggac        240
atcagatgta attgagaggc aacaggtaa gtcttcatgt c                            281

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: (1)...(141)
<223> OTHER INFORMATION: n=A,T,C or G

<400> SEQUENCE: 238
gtctgcctcc tcctactgtt tccctctatn aaaagcctc cttggcgcag gttccctgag        60
ctgtgggatt ctgcactggt gcttnggatt ccctgatatg ttccttcaaa tccactgaga        120
attaaataaa catcgctaaa g                                                 141

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239
aacaatctaa acaaatccct cggttctann atacaatgga ttccccatat tggaaggact        60
ctgangcttt attccccac tatgcntatc ttatcatttt attattatac acacatccat        120
cctaaactat actaaagccc ttttcccatg catggatgga aatggaagat ttttttttaa        180
cttgttctag aagtcttaat atgggctgtt gccatgaagg cttgcagaat tgagtccatt        240
ttctagctgc ctttattcac atagtgatgg ggtactaaaa gtactgggtt gactcagaga        300
gtcgctgtca ttctgtcatt gctgctactc taacactgag caacactctc ccagtggcag        360
atcccctgta tcattccaag aggagcattc atcccttgc tctaatgatc aggaatgatg        420
cttattagaa aacaaactgc ttgacccagg aacaagtggc ttagcttaag naaacttggc        480
tttgctcana tccctgatcc t                                                 501

<210> SEQ ID NO 240
<211> LENGTH: 451
<212> TYPE: DNA
<213> ORGANISM: Homo sapiens

<400> SEQUENCE: 240

```
tgtcctgaaa ggccattact aatagaaaca cagcctttcc aatcctctgg aacatattct      60
gtctgggttt ttaatgtctg tggaaaaaaa ctaaacaagt ctctgtctca gttaagagaa     120
atctattggt ctgaaggttt ctgaacctct ttctggttct cagcagaagt aactgaagta     180
gatcaggaag gggctgcctc aggaaaattc ctagatccta ggaattcagt gagaccctgg     240
gaaggaccag catgctaatc agtgtcagtg aatccacagt cttacttcc tgcctcataa      300 agggccaggt ctccccagta ccaagtcctt tcctcatgaa gttgtgttgc ctcaggctgt     360
ttagggacca ttgcctgtct tggtcacatg agtctgtctc cttactttag tccctgggca     420
atccttgctt aatgcttttg ttgactcaac g                                    451
```

<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n=A,T,C or G

<400> SEQUENCE: 241

```
aatctccagt gtgatggtat cggggttaga gcttcaatct ccagtgtgat ggtactgcag      60
cnagagcttc aatctccagt gngatggtat tagggttaga tcttcaatct ccagtgtgat     120
ggtatcaggg ttagagcttc agcctccagt gtgatggtat cagggttaga gcttcagcct     180
ccagtgtgat ggtatcgggg ttagatcttc aatccccagt ggtggtggtt agagcttcaa     240
tctccagtgt gatggtattg gggttagagc ttcaatctcc agtctgatgg tgtttcggga     300
tggggctttt aagatgtaat tagggtttaa gatcataagg gacctggtct gatgggatt     360 agtncgcttn tatgaagaga cacangaggg cttgctctat ctctgactct c               411
```

<210> SEQ ID NO 242
<211> LENGTH: 351
<212> TYPE: DNA
<213> ORGANISM: Homo sapiens

<400> SEQUENCE: 242

```
ttccccttca caacagtaga gacctacaca gtgaactttg gggacttctg agatcagcgt      60
cctaccaaga ccccagccca actcaagcta cagcagcagc acttcccaag cctgctgacc     120
acagtcacat cacccatcag cacatggaag gcccctggta tggacactga aggaagggc      180 tggtcctgcc cctttgaggg ggtgcaaaca tgactgggac ctaagagcca gaggctgtgt     240
agaggctcct gctccacctg ccagtctcgt aagaaatggg gttgctgcag tgttggagta     300
ggggcagagg gagggagcca aggtcactcc aataaaacaa gctcatggca c               351
```

<210> SEQ ID NO 243
<211> LENGTH: 241
<212> TYPE: DNA
<213> ORGANISM: Homo sapiens

<400> SEQUENCE: 243

```
gtctgtgctt tatcaggaaa agcacaagaa tatgttttc tacctaaaac cctcttctac       60
tttaaaaatg gtttgctgaa ttttctatg ttttaaaat gtttttatgc tttttttaa        120 acacgtaaag gatggaacct aatcctctcc cgagacgcct cctttgtgtt aatgcctatt     180
cttacaacag agaaacaagt acattaatat aaaaacgagt tgattattgg ggtataaaat     240
a                                                                     241
```

<210> SEQ ID NO 244
<211> LENGTH: 301
<212> TYPE: DNA
<213> ORGANISM: Homo sapiens

<400> SEQUENCE: 244

```
ggtccagagc aatagcgtct gtggtgaagc gcctgcactc ctcgggagac atgcctggct      60
tatatgctgc atccacataa ccatagataa aggtgctgcc ggagccacca atggcaaaag     120
gctgtcgagt cagcattcct cccagggttc catatacctg acctccttca cgttggtccc     180
agccagctac catgagatgt gcagacaagt cctctcgata tttatagctg atatttctca     240
ccacatttgc agcagccaaa acaagtggag gttcctccag ttctatccca tggagctcca     300
g                                                                    301
```

<210> SEQ ID NO 245
<211> LENGTH: 391
<212> TYPE: DNA
<213> ORGANISM: Homo sapiens

<400> SEQUENCE: 245

```
ctgacactgc tgatgtgggc cggggggcgc cgaggcacaa ctggtggccg gaccattgag      60
gcacctggag ggtaggcagc ttgtggtgca gacaccacag agagagaaaa gttggatgga     120
gtggtgggaa taatcagggt ggcacactgt gcctagaagc ttccagggcc accaagagaa     180
tgggaaggga aactacaaca ttcacaacag aaataggagt caattcactt agacccagaa     240
ctccagaaag ggggagtgta ggaatctaca atttcaaagc cagctcgtgt ctacctagag     300
ccccaaactg cataagcacc aggattgtac accttagtcc ctcaagatag tttcaagtga     360
gcgtgcaatt cactcttaca gaggagggcc t                                    391
```

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246

```
tcctccacag gggaagcagg aagttngacc agcttcaggc tggaacgtgc ccagggcaca      60
gagctggcaa ggtgcaaagn cntctgcaga atattcacca ggttgacaca gacctccaca     120
ttcagacata ttccaagctt ctggggtctt cagggcccca gaatttcctg gtcttggca      180
tggtncacaa gtcatttgtc cttcctcatt ttggaaggtt ccatttggac ataaaatgca     240
agcgttctcg tgctncatna taataggtcc cagcctgcac tgacacattt g              291
```

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247

```
cactgagtga atgagtatat aatttatgaa aacagaaaag tgctttggaa aaaaaaaag       60
```

```
acaacaggag tacatacagn gaaccaaaaa gagtgtacca ggaggagcan accctgaaca      120
gttanaacta tggaaatcgc tatgctttgt gttgtcacag gagttaaaat aggaataccc      180
tgcatacaat aaatatttat tggataaata actaagcctg ataccctttt caatgcgtta      240
tacanactnt atcatcacac cactaatcta agttctcana agttaaacat tacaagactt      300
cagaacaaca taggcgtntt tggctccatt taacanaana aggaccatag tgatcattta      360
atctctatga gtctgtctta tcttctggaa aaggggccta acaccatttc cttttgcaaa      420
aaggtagctg ccttgcttcc agttctacca tcctntagca acccatcttt n               471

<210> SEQ ID NO 248
<211> LENGTH: 551
<212> TYPE: DNA
<213> ORGANISM: Homo sapiens

<400> SEQUENCE: 248
ccatgggatc aggaatgggg tcaggtcagt tgacctgagc atacccatta aacatgttca       60
aatgtcccca tcccacccac tcacatgaca tggctcccga gccctgagat ctgtatccca      120
agaacctcag ttgagaaata tttatggcag cttcactgtt gctcaagagc ctgggtattg      180
tagcagcctg ggggcaggtt gtccctaatg ttctccaagt tcttcacatc agccagaatc      240
ccatctatgc ttgtctccag caaatggagg tggcccctct gctgacgtgc cctctcttcc      300
agctctgaca tcatgggccg cagttggctg ttgatctggg tcttggctcg ggaaagcttc      360
tgctccagta agaccagccc ctcttcatct acactgagag gctggtccat cagatgcagg      420
aggccgtcta atgtgttgag tgtgtcttgg attgtaaccc cagcgttctt ggctctggta      480
tcaaccttct gggcttctgt aatcaccatc tgtactgcat ccatattcgt gtcgaactcc      540
agctccttcc t                                                            551

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249
atntccagag ggaccgtaag actggtacaa gtttacacca taagaggcga cgtggtcagc       60
cacaatgtct tcacctccac aggggctcat cacggnggtc agggcaaggg cccccagcat      120
cagagctttg tttaggatca tcctcttccc aaggcagcct tagcagttgc tgacctgccc      180
g                                                                       181

<210> SEQ ID NO 250
<211> LENGTH: 551
<212> TYPE: DNA
<213> ORGANISM: Homo sapiens

<400> SEQUENCE: 250
tctgtagcta ggatgagctg gctctcaagc aaaagtttgt cttcctgggt ccatttgtgg       60
ttatcacttg ttattgaatg tacatcacaa attaaagtct gcattgttgg acgtaagaga      120
atgtgccgac tttggtaacc aggagatttc atgttactgg actgcctgta gtcacgtatt      180
tctgctatga cacatccgca atgaaaaata ttaacctgag attttctag gagatcaacc      240 aaaataggag gtaattcttc tgcatccaaa tattcaagca actctccttc ttcatagggc      300
```

```
agtcgaatgg tctcggaatc tgatccgttt tttccctga gcatcagaga atatccctca      360
tttcctgggt atagattgac cactaaacat gacaaagtct cttgcataac aagcttctct      420
aacaagttca catttcttct taatttctta acttcaggtt ctttttcaca ttcttcaata      480
tacaagtcat aaagttttg aaatacagat tttcttccac ttgataggta tttccttta       540 ggaggtctct g                                                          551
```

<210> SEQ ID NO 251
<211> LENGTH: 441
<212> TYPE: DNA
<213> ORGANISM: Homo sapiens

<400> SEQUENCE: 251

```
tgtctgctct cccatcctgg ttactatgag tcgctcttgg cagaaaggac cacagatgga       60
gagcttggca ctcgctccaa ctttgccgaa agaggacaa ccaccaaagt agtaggtaaa      120
aacacaattt tagcagcagt gaaataaaaa gaggaagtga ggatgggcc aggccgcaac      180 tataattaaa ctgtctgttt aggagaagct gaatccagaa gaaacacaag ctgtaaagtg     240
agagaggaca gggagcaggg cctttggaga gcaggagagg acaggctgtc accaagcgct     300
gctcggactc tgccctgaaa gatttgaatt ggacactgtc cagtcacgtg tgtggcaaac     360
cgtactccaa gcacttttct cacggcagag gaaggagctg ccatggctgt accctgaac      420 gtttgtgggg ccagcgatgt g                                               441
```

<210> SEQ ID NO 252
<211> LENGTH: 406
<212> TYPE: DNA
<213> ORGANISM: Homo sapiens

<400> SEQUENCE: 252

```
ttttttttg aacaagtaaa aatttcttta tttgctgaca ataagataac ctacagggaa       60
aacctgatga aatctattaa aaagttacta aaactaataa aagaatttag gaaggttata    120
gaatgtaaga ccaagacaca aaaatcaatt acatttctat ataatagcaa tgaacagata   180
ctgaaatttt aaaaactaaa tcattttaca aagtatcac aatatgaaac actccgggat    240
aaattggata aaagatgtgc aagactgtac aaaagctaca aacatttat gaaggaaatt    300 ggaagataga aacaagatag aaaatgaaaa tattgtcaag agtttcagat agaaaatgaa    360
aaacaagcta agacaagtat tggagaagta tagaagatag aaaaat                   406
```

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253

```
gaaggagttc agtagcaaag tcacacctgt ccaattccct gagctttgct cactcagcta       60
atgggatggc aaaggtggtg gtgctttcat cttcaggcag aagcctctgc ccatccccct     120
caagggctgc aggcccagtt tcatgctgc ccttgggtgg gcatctgtta acagaggaga      180
acgtctgggg gcggcagca gctttgctct gagtgcctac aaanctaatg cttggtgcta      240
gaaacatcat cattattaaa cttcagaaaa gcagcagcca tgttcagtca ggctcatgct     300
```

```
gcctcactgc ttaagtgcct gcaggagccg cctgccaagc tcccttcct acacctggca      360 cactggggtc tgcacaaggc tttgtcaacc aaagacagct tcccccttt gattgcctgt      420 agactttgga gccaagaaac actctgtgtg actctacaca cacttcaggt ggtttgtgct     480
tcaaagtcat tgatgcaact tgaaaggaaa cagtttaatg gtggaaatga actaccattt     540
ataa                                                                  544
```

<210> SEQ ID NO 254
<211> LENGTH: 339
<212> TYPE: DNA
<213> ORGANISM: Homo sapiens

<400> SEQUENCE: 254

```
tggcattcag ggcagtgtct tctgcatctc ctaggaacct cgggagcggc agctccggcg      60
cctggtagcg agaggcgggt tccggagatc ccggcctcac ttcgtcccac tgtggttagg     120
ggtgagtcct gcaaatgtta agtgatttgc tcaaggtgcc catttcgcag gaattggagc     180
ccaggccagt tctctgagcc tatcattagg gctaaaggag tgcgtgatca gaatggtgtc     240
tggacggttc tacttgtcct gcctgctgct ggggtccctg ggctctatgt gcatcctctt     300
cactatctac tggatgcagt actggcgtgg tggctttgc                             339
```

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255

```
gaggttttt nttttttttt ttttttttt caattaaana tttgatttat tcaagtatgt        60
gaaaacattn tacaatggaa acttttntta aatgctgcat gtnctgtgct atggaccacn     120
cacatacagc catgctgttt caaaaaactt gaaatgccat tgatagttta aaaactntac     180
ncccgatgga aaatcgagga aaacaattta atgtttcatn tgaatccana ggngcatcaa     240
attaaatgac agctccactt ggcaaataat agctgttact tgatggtatc caaaaaaaaa     300
tggttgggga tggataaatt caaaaatgct tccccaaagg ngggnggttt ttaaaaagtt     360
tcaggncaca acccttgcan aaaacactga tgcccaacac antga                     405
```

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256

```
gggcangtct ggtcctctcc ccacatgtca cactctcctc agcctctccc caaccctgc       60 tctccctcct cccctgccct agcccaggga cagagtctag gaggagcctg ggcagagct      120 ggaggcagga agagagcact ggacagacag ctatggtttg gattggggaa gaggttagga     180
agtaggttct taaagaccct tttttagta                                        209
```

<210> SEQ ID NO 257
<211> LENGTH: 343

```
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257
tctggacacc ataatccctt ttaagtggct ggatggtcac acctctccca ttgacaagct      60
gggttaagtc aataggttga ctaggatcaa cacgacccaa atcaataaga tactgcagtc     120
tattgagact caaaggctta tactggcgtc tgaaactatg tccttcgtta aacccgtatt     180
ttgggattcg gatgtaaaat ggagtctggc ctccctcaaa gcccaagcgg ggccgggttc     240
ctctttgcct ttctccttta tggcctctgc cacattttct acctcttctc cgacctcttg     300
gtcttntctc nggtttcttg gagccgggat tcggctttaa gtn                      343

<210> SEQ ID NO 258
<211> LENGTH: 519
<212> TYPE: DNA
<213> ORGANISM: Homo sapiens

<400> SEQUENCE: 258
gcggcttctg acttctagaa gactaaggct ggtctgtgtt tgcttgtttg cccacctttg      60
gctgataccc agagaacctg ggcacttgct gcctgatgcc caccctgcc agtcattcct     120 ccattcaccc agcgggaggt gggatgtgag acagcccaca ttggaaaatc agaaaaccg     180 ggaacaggga tttgcccttc acaattctac tccccagatc ctctcccctg acacaggag     240 acccacaggg caggaccta agatctgggg aaaggaggtc ctgagaacct tgaggtaccc     300
ttagatcctt ttctacccac tttcctatgg aggattccaa gtcaccactt ctctcaccgg     360
cttctaccag ggtccaggac taaggcgttt tctccatagc ctcaacatttt tgggaatctt    420 cccttaatca cccttgctcc tcctgggtgc ctggaagatg gactggcaga gacctctttg     480
ttgcgttttg tgctttgatg ccaggaatgc cgcctagtt                            519

<210> SEQ ID NO 259
<211> LENGTH: 371
<212> TYPE: DNA
<213> ORGANISM: Homo sapiens

<400> SEQUENCE: 259
attgtcaact atatacacag tagtgaggaa taaaatgcac acaaacaat ggatagaata      60 tgaaaatgtc ttctaaatat gaccagtcta gcatagaacc ttcttctctt ccttctcagg    120
tcttccagct ccatgtcatc taacccactt aacaaacgtg gacgtatcgc ttccagaggc    180
cgtcttaaca actccatttc caaaagtcat ctccagaaga catgtatttt ctatgatttc    240
ttttaaacaa atgagaattt acaagatgtg taactttcta actctatttt atcatacgtc    300
ggcaacctct ttccatctag aagggctaga tgtgacaaat gttttctatt aaaaggttgg    360
ggtggagttg a                                                        371

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n=A,T,C or G
```

<400> SEQUENCE: 260

```
ttggattttt tgacttgcga tttcagtttt tttacttttt tttttttttt ttttganaaa      60
tactatattt attgtcaaag agtggtacat aggtgagtgt tcatcttccc tctcatgccg     120
gtatactctg cttcgctgtt tcagtaaaag ttttccgtag ttctgaacgt cccttgacca     180
caccataana caagcgcaag tcactcanaa ttgccactgg aaaactggct caactatcat     240
ttgaggaaag actganaaag cctatcccaa agtaatggac atgcaccaac atcgcggtac     300
ctacatgttc ccgtttttct gccaatctac ctgtgtttcc aagataaatt accacccagg     360
gagtcacttc ctgctatgtg aacaaaaacc cggtttcttt ctggaggtgc ttgactactc     420
tctcgngagc                                                            430
```

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: (178)
<223> OTHER INFORMATION: n=A,T,C or G

<400> SEQUENCE: 261

```
tcctgacgat agccatggct gtaccactta actatgattc tattccaact gttcagaatc      60
atatcacaaa atgacttgta cacagtagtt tacaacgact cccaagagag gaaaaaaaaa     120
aaaaaagacg cctcaaaatt cactcaactt ttgagacagc aatggcaata ggcagcanag     180
aagctatgct gcaactgagg gcacatatca ttgaagatgt cacaggagtt taagagacag     240
gctggaaaaa atctcatact aagcaaacag tagtatctca taccaagcaa aaccaagtag     300
tatctgctca gcctgccgct aacagatctc acaatcacca actgtgcttt aggactgtca     360
ccaaa                                                                 365
```

<210> SEQ ID NO 262
<211> LENGTH: 500
<212> TYPE: DNA
<213> ORGANISM: Homo sapiens

<400> SEQUENCE: 262

```
cctagatgtc atttgggacc cttcacaacc attttgaagc cctgtttgag tccctgggat      60
atgtgagctg tttctatgca taatggatat tcggggttaa caacagtccc ctgcttggct     120
tctattctga atccttttct ttcaccatgg ggtgcctgaa gggtggctga tgcatatggt     180
acaatggcac ccagtgtaaa gcagctacaa ttaggagtgg atgtgttctg tagcatccta     240
tttaaataag cctatttat cctttggccc gtcaactctg ttatctgctg cttgtactgg      300
tgcctgtact tttctgactc tcattgacca tattccacga ccatggttgt catccattac     360
ttgatcctac tttacatgtc tagtctgtgt ggttggtggt gaataggctt cttttttacat    420
ggtgctgcca gcccagctaa ttaatggtgc acgtggactt ttagcaagcg ggctcactgg     480
aagagactga acctggcatg                                                 500
```

<210> SEQ ID NO 263
<211> LENGTH: 413
<212> TYPE: DNA
<213> ORGANISM: Homo sapiens

<400> SEQUENCE: 263

```
ctcagagagg ttgaaagatt tgcctacgaa agggacagtg atgaagctaa gctctagatc      60
```

```
caggatgtct gacttcaaat tgaaactccc aaagtaatga gtttggaagg gtggggtgtg      120
gcctttccag gatggggtc ttttctgctc ccagcggata gtgaaacccc tgtctgcacc       180
tggttgggcg tgttgctttc ccaaaggttt ttttttttagg tccgtcgctg tcttgtggat    240
taggcattat tatctttact ttgtctccaa ataacctgga gaatggagag agtagtgacc     300
agctcagggc cacagtgcga tgaggaccat cttctcacct ctctaaatgc aggaagaaac    360
gcagagtaac gtggaagtgg tccacaccta ccgccagcac attgtgaatg aca           413
```

<210> SEQ ID NO 264
<211> LENGTH: 524
<212> TYPE: DNA
<213> ORGANISM: Homo sapiens

<400> SEQUENCE: 264

```
tccaatgggg ccctgagagc tgtgacagga actcacactc tggcactggc agcaaaacac     60
cattccaccc cactcatcgt ctgtgcacct atgttcaaac tttctccaca gttccccaat    120
gaagaagact catttcataa gtttgtggct cctgaagaag tcctgccatt cacagaaggg    180
gacattctgg agaaggtcag cgtgcattgc cctgtgtttg actacgttcc cccagagctc    240
attaccctct ttatctccaa cattggtggg aatgcaccatt cctacatcta ccgcctgatg   300
agtgaactct accatcctga tgatcatgtt ttatgaccga ccacacgtgt cctaagcaga   360
ttgcttaggc agatacagaa tgaagaggag acttgagtgt tgctgctgaa gcacatcctt    420
gcaatgtggg agtgcacagg agtccaccta aaaaaaaaaa tccttgatac tgttgcctgc    480 cttttttagtc accccgtaac aagggcacac atccaggact gtgt                     524
```

<210> SEQ ID NO 265
<211> LENGTH: 344
<212> TYPE: DNA
<213> ORGANISM: Homo sapiens

<400> SEQUENCE: 265

```
tcctttcttc tacttcagga gatgattcaa agttacttgt ggacatttct ttaagttctg     60
aagacaaatg agacaggatt tggcctgcgg gttcttcaga cttctctacc acctccatta   120
actcttcatc ttggcttgac gtaggcaatg cactattttg ctcttttgtt tctggagatg    180
acccagcacc acttctttct cttggcgggg ttctaagtgt gtctttgaat accagtgaag   240
actcaggcct atcctgtact ggaaagggac taaatttgtc tttctgtcta ggaggtgatg    300
cagtagcatc ctcctgaggg ggtaaggcca ttttctcttt ttga                    344
```

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

```
ccacaatgtc cataacttga gcaggctttg gcatcccacc acccccttca gaccaataca     60
cactatgttg gaggaacnac tttaaaatgt aaaatgagaa atgggcactg aacactccat   120
cctcactccc aacagcccac ccacacacct cttcaactgc tatccaaaca tggaggagct    180
cttgtggaag agaggctcaa caccaaataa                                      210
```

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n = A,T,C or G

<400> SEQUENCE: 267

```
tcggncctcc caccctctna ctgaaattct ntgaaattct cccctttggg atgaggatgg     60
caacccagg  catgtaccct cccaacctgg gacccgacct aataccctaa catcctgctg    120
acagtggctg ttctcgctgg gcaggcgtcc caaagcacat cgagccagat tcaggcagag    180
tggaactggc ccctcagcca tcagtggagg tggcctggga ggctctaccc tgaacggg     238
```

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: (459)
<223> OTHER INFORMATION: n=A,T,C or G

<400> SEQUENCE: 268

```
tcctcaagga catgcccctt gatagaaact cagttcctgt ctccagttcc ctcctggacc     60
tgatccccca aatgcaggge ctgggactat atccagttcc ttatttcag  aggcccatgc    120
acaagatgca cagcaaataa gtgctgaata agacccagc  tactgctagc ttaccctgct    180
ccaaacattc accaagtcct cagcaaagag ggccatccat tcacctcttc taaaaacaca    240
ctgagctccc cagtctatac cccaagatat gcttggctcc caactatccc tcctctctca    300
tctccaagcc agtttcccct ttctaagtat actgatatta ccaaagacac tgacaatctt    360
cttttcctac ctctccccag tgactaggtt tgcagcagga gctctataag tcctagtata    420
cagcagaagc tccataaatg tgtgctgacc taacattang c                       461
```

<210> SEQ ID NO 269
<211> LENGTH: 434
<212> TYPE: DNA
<213> ORGANISM: Homo sapiens

<400> SEQUENCE: 269

```
ctgtgttggt gagcaccgat tcccactcaa tatggcgtgg cttacagtct tcattaggtt     60
cccgctccca accagaatga ggaatgatca cttcatctgt caaggcatgc agtgcatggt    120
ccacaatctc cattttgatt gagtcatggg atgaaagatt ccacagggtt ccggtaataa    180
cttcagtaag gtccatatca cgagcctttc gaagcaatcg cacaagggca ggcacaccat    240
cacagttttt tatggcaatc ttgttatcct ggtcacgtcc aaaagagata ttcttgagag    300
ctccacaggc tccaaggtgc acttcctttt tgggatggtc taacaatccc accagtactg    360
ggatgcccctt gagcttccgc acgtcagtct tcaccttgtc attgcggtag cataagtgtt    420
gcaggtatgc aaga                                                     434
```

<210> SEQ ID NO 270
<211> LENGTH: 156
<212> TYPE: DNA
<213> ORGANISM: Homo sapiens

<400> SEQUENCE: 270

```
ctgcaccagc gattaccagt ggcattcaaa tactgtgtga ctaaggattt tgtatgctcc      60
ccagtagaac cagaatcaga caggtatgag ctagtcaaca gcaagtcttt gttggattcg     120
agtaggctca ggatctgctg aaggtcggag gagtta                               156

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271
ccactgtcac ggtctgtctg acacttactg ccaaacgcat ggcaaggaaa aactgcttag      60
tgaagaactt agaagctgtg gagaccttgg ggtccacgtn caccatctgc tctgataaaa     120
ctggaactct gactcanaac cggatgacag tgcccacat gtggtttgac aatcaaatcc      180
atgaagctga tacgacagag aatcagagtg gtgtctcttt tgacaagact tcagctacct     240
ggcttgctct gtccagaatt gcaggtcttt gtaacagggc agtgtttcag gctaaccagg     300
aaaacctacc tattcttaag cgggcagttg caggagatgc ctctgagtca gcactcttaa     360
agtgcataga gctgtgctgt ggntncgtga aggagatgag agaaagatac nccaaaatcg     420
tcgagatacc cttcaactcc accaacaagt accagttgtc tattcataag aaccccaaca     480
catcggagcc ccaacacctg ttggtgatga agggcgcccc agaaaggatc cta            533

<210> SEQ ID NO 272
<211> LENGTH: 630
<212> TYPE: DNA
<213> ORGANISM: Homo sapiens

<400> SEQUENCE: 272
tggtattttt ctttttcttt tggatgtttt atactttttt ttcttttttc ttctctattc      60
ttttcttcgc cttcccgtac ttctgtcttc cagttttcca cttcaaactt ctatcttctc     120
caaattgttt catcctacca ctcccaatta atctttccat tttcgtctgc gtttagtaaa     180
tgcgttaact aggcttttaaa tgacgcaatt ctccctgcgt catggatttc aaggtctttt   240
aatcaccttc ggtttaatct cttttttaaaa gatcgcccttc aaattatttt aatcacctac   300
aacttttaaa ctaaacttta agctgtttaa gtcaccttca ttttaatcta aaagcattgc    360
ccttctattg gtattaattc ggggctctgt agtcctttct ctcaatttc ttttaaatac     420 atttttact ccatgaagaa gcttcatctc aacctccgtc atgttttaga aacctttat     480 cttttccttc ctcatgctac tcttctaagt cttcatattt tctcttaaaa tcttaagcta    540
ttaaaattac gttaaaaact taacgctaag caatatctta gtaacctatt gactatattt    600
tttaagtagt tgtattaatc tctatctttc                                     630

<210> SEQ ID NO 273
<211> LENGTH: 400
<212> TYPE: DNA
<213> ORGANISM: Homo sapiens

<400> SEQUENCE: 273
tctggtttgc cctccagttc attctgaatc tagacttgct cagcctaatc aagttcctgt     60
acaaccagaa gcgacacagg ttcctttggt atcatccaca agtgagggt acacagcatc     120
```

| | |
|---|---|
| tcaaccettg taccagcctt ctcatgctac agagcaacga ccacagaagg aaccaattga | 180 |
| tcagattcag gcaacaatct ctttaaatac agaccagact acagcatcat catcccttcc | 240 |
| tgctgcgtct cagcctcaag tatttcaggc tgggacaagc aaacctttac atagcagtgg | 300 |
| aatcaatgta aatgcagctc cattccaatc catgcaaacg gtgttcaata tgaatgcccc | 360 |
| agttcctcct gttaatgaac cagaaacttt aaaacagcaa | 400 |

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

<400> SEQUENCE: 274

| | |
|---|---|
| tntgagtatg tcccagagaa ggtgaagaaa gcggaaaaga aattagaaga gaatccatat | 60 |
| gaccttgatg cttggagcat tctcattcga gaggcacaga atcaacctat agacaaagca | 120 |
| cggaagactt atgaacgcct tgttgcccag ttccccagtt ctggcagatt ctggaaactg | 180 |
| tacattgaag cagaggttac tatttttattt tatttttcct tatatcagta ttgcagcatt | 240 |
| cactgtagtg atagaaaaca agttaggaac atagccaatt aggacaagga ggatttaaat | 300 |
| gtgtcttacc tttatttgt aaaataggta taaggagta attaaaatga a | 351 |

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275

| | |
|---|---|
| gcgnggtcgc nnncgaggtc tgagaagccc ataccactat tgttgagaa atgtgtggaa | 60 |
| tttattgaag atacagggtt atgtaccgaa ggactctacc gtgtcagcgg gaataaaact | 120 |
| gaccaagaca atattcaaaa gcagtttgat caagatcata atatcaatct agtgtcaatg | 180 |
| gaagtaacag taaatgctgt agctggagcc cttaaagctt tctttgcaga tctgccagat | 240 |
| cctttaattc catattctct tcatccagaa ctattggaag cagcaaaaat cccggataaa | 300 |
| acagaacgtc ttcatgcctt gaaagaaatt gttaagaaat ttcatcctgt aaactatgat | 360 |
| gtattcagat acgtgataac a | 381 |

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276

| | |
|---|---|
| gctcngactc cggcgggacc tgctcggagg aatggcgccg ccgggttcaa gcactgtctt | 60 |
| cctgttggcc ctgacaatca tagccagcac ctgggctctg acgcccactc actacctcac | 120 |
| caagcatgac gtggagagac taaaagcctc gctggatcgc cctttcacaa atttggaatc | 180 |
| tgccttctac tccatcgtgg gactcagcag ccttggtgct caggtgccag atgcaaagaa | 240 |

```
agcatgtacc tacatcagat ctaaccttga tcccagcaat gtggattccc tcttctacgc      300
tgcccaggcc agccaggccc tctcaggatg tgagatctct atttcaaatg agaccaaaga      360
tctgcttctg gcagacctcg gccgcgacca                                       390

<210> SEQ ID NO 277
<211> LENGTH: 378
<212> TYPE: DNA
<213> ORGANISM: Homo sapiens

<400> SEQUENCE: 277
tgggaacttc tggggtagga cgttgtctgc tatctccagt tccacagacc caaccagtta       60
cgatggtttt ggaccattta tgccgggatt cgacatcatt ccctataatg atctgcccgc      120
actggagcgt gctcttcagg atccaaatgt ggctgcgttc atggtagaac caattcaggg      180
tgaagcaggc gttgttgttc cggatccagg ttacctaatg ggagtgcgag agctctgcac      240
caggcaccag gttctctttta ttgctgatga aatacagaca ggattggcca gaactggtag      300
atggctggct gttgattatg aaaatgtcag acctgatata gtcctccttg gaaaggccct      360 ttctggggc ttataccc                                                     378

<210> SEQ ID NO 278
<211> LENGTH: 366
<212> TYPE: DNA
<213> ORGANISM: Homo sapiens

<400> SEQUENCE: 278
ggagggcaca ttccttttca cctcagagtc ggtcggggaa ggccacccag ataagatttg       60
tgaccaaacc agtgatgctg tccttgatgc ccaccttcag caggatcctg atgccaaagt      120
agcttgtgaa actgttgcta aaactggaat gatccttctt gctggggaaa ttacatccag      180
agctgctgtt gactaccaga agtggttcg tgaagctgtt aaacacattg gatatgatga      240
ttcttccaaa ggttttgact acaagacttg taacgtgctg gtagccttgg agcaacagtc      300
accagatatt gctcaaggtg ttcatcttga cagaaatgaa gaagacattg gtgctggaga      360
ccaggg                                                                 366

<210> SEQ ID NO 279
<211> LENGTH: 435
<212> TYPE: DNA
<213> ORGANISM: Homo sapiens

<400> SEQUENCE: 279
cctaagaact gagacttgtg acacaaggcc aacgacctaa gattagccca gggttgtagc       60
tggaagacct acaacccaag gatggaaggc ccctgtcaca agcctacct agatggatag      120 aggacccaag cgaaaaagat atctcaagac taacggccgg aatctggagg cccatgaccc      180
agaacccagg aaggatagaa gcttgaagac ctggggaaat cccaagatga gaaccctaaa      240
ccctacctct tttctattgt ttacacttct tactcttaga tatttccagt tctcctgttt      300
atctttaagc ctgattcttt tgagatgtac ttttttgatgt tgccggttac ctttagattg      360
acaagtatta tgcctggcca gtcttgagcc agctttaaat cacagctttt acctatttgt      420
taggctatag tgttt                                                       435

<210> SEQ ID NO 280
<211> LENGTH: 435
<212> TYPE: DNA
```

<213> ORGANISM: Homo sapiens

<400> SEQUENCE: 280

```
tctggatgag ctgctaactg agcacaggat gacctgggac ccagcccagc caccccgaga      60
cctgactgag gccttcctgg caaagaagga gaaggccaag gggagccctg agagcagctt     120
caatgatgag aacctgcgca tagtggtggg taacctgttc cttgccggga tggtgaccac     180
ctcgaccacg ctggcctggg gcctcctgct catgatccta cacctggatg tgcagcgtga     240
gcccagacct gtccgggcgg ccgctcgaaa ttccagcaca ctggcggccg ttactagtgg     300
atccgagctc ggtaccaagc ttggcgtaat catggtcata gctgtttcct gtgtgaaatt     360
gttatccgct cacaattcca cacaacatac gagccggaag cataaagtgt aaagcctggg     420
gtgcctaatg agtga                                                     435
```

<210> SEQ ID NO 281
<211> LENGTH: 440
<212> TYPE: DNA
<213> ORGANISM: Homo sapiens

<400> SEQUENCE: 281

```
catctgatct ataaatgcgg tggcatcgac aaaagaacca ttgaaaaatt tgagaaggag      60
gctgctgaga tgggaaaggg ctccttcaag tatgcctggg tcttggataa actgaaagct     120
gagcgtgaac gtggtatcac cattgatatc tccttgtgga aatttgagac cagcaagtac     180
tatgtgacta tcattgatgc cccaggacac agagacttta tcaaaaacat gattacaggg     240
acatctcagg ctgactgtgc tgtcctgatt gttgctgctg gtgttggtga atttgaagct     300
ggtatctcca agaatgggca gacccgagag catgcccttc tggcttacac actgggtgtg     360
aaacaactaa ttgtcggtgt taacaaaatg gattccactg agcccctac agccagaaga     420
gatatgagga aattgttaag                                                440
```

<210> SEQ ID NO 282
<211> LENGTH: 502
<212> TYPE: DNA
<213> ORGANISM: Homo sapiens

<400> SEQUENCE: 282

```
tctgtggcgc aggagccccc tcccccggca gctctgacgt ctccaccgca gggactggtg      60
cttctcggag ctcccactcc tcagactccg gtggaagtga cgtggacctg atcccactg     120
atggcaagct cttccccagc gatggttttc gtgactgcaa gaaggggat cccaagcacg     180
ggaagcggaa acgaggccgg ccccgaaagc tgagcaaaga gtactgggac tgtctcgagg     240
gcaagaagag caagcacgcg cccagaggca cccacctgtg ggagttcatc cgggacatcc     300
tcatccaccc ggagctcaac gagggcctca tgaagtggga aatcggcat gaaggcgtct     360
tcaagttcct gcgctccgag gctgtggccc aactatgggg ccaaaagaaa agaacagca     420
acatgaccta cgagaagctg agccgggcca tgaggtacta ctacaaacgg gagatcctgg     480
aacgggtgga tggccggcga ct                                            502
```

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n=A,T,C or G

<400> SEQUENCE: 283

| ccatattaga | ttactggaac | atctaagcat | cagtgtgtga | ccatgcgaac | aaaagacttc | 60 |
| gggagtgtc | tattttaaa | aaggtttatg | tgtgtcgagg | cagttgtaaa | agatttactg | 120 |
| cagaatcaan | cccactttta | ggcttangac | caggttctaa | ctatctaaaa | atattgactg | 180 |
| ataacaaaaa | gtgttctaaa | tgtggctatt | ctgatccata | nttgntttt | aaagaaaaaa | 240 |
| antgtntata | cagaaagagt | ntaaaagttc | tgtgaattna | atgcaaatta | gncnccantc | 300 |
| ttgacttccc | aaanacttga | ttnatacctt | tnactcctnt | cnnttcctgn | ncttcnttaa | 360 |
| nntcaatnat | tnggnagtnn | anggccntcn | gnanaacacc | nttncncgnt | ccncgcaatc | 420 |
| canccgcctt | nan | | | | | 433 |

<210> SEQ ID NO 284
<211> LENGTH: 479
<212> TYPE: DNA
<213> ORGANISM: Homo sapiens

<400> SEQUENCE: 284

| tctggaagga | tcagggatct | gagcaaagcc | aagtttactt | aagctaagcc | acttgttcct | 60 |
| gggtcaagca | gtttgttttc | taataagcat | cattcctgat | cattagagca | aagggatgaa | 120 |
| tgctcctctt | ggaatgatac | agggatctg | ccactgggag | agtgttgctc | agtgttagag | 180 |
| tagcagcaat | gacagaatga | cagcgactct | ctgagtcaac | ccagtacttt | tagtaccccg | 240 |
| tcactatgtg | aataaaggca | gctagaaaat | ggactcaatt | ctgcaagcct | tcatggcaac | 300 |
| agcccatatt | aagacttcta | gaacaagtta | aaaaaaaatc | ttccatttcc | atccatgcat | 360 |
| gggaaaggg | ctttagtata | gtttaggatg | gatgtgtgta | taataataaa | atgataagat | 420 |
| atgcatagtg | ggggaataaa | gcctcagagt | ccttccagta | tggggaatcc | attgtatct | 479 |

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285

| tttttttt | tttttttt | tcaatanaaa | tgccataatt | tattccattg | tataaaaag | 60 |
| tcatccttat | gtaacaaaat | gtnttcttan | aanaanaaat | atattatttc | aggtcataaa | 120 |
| taatcagcaa | acatacaact | gttggcaact | aaaaaaaaac | ccaacactgg | tattttccat | 180 |
| cagngctgaa | acaaacctg | cttaaanata | tatttacagg | gatagtncag | tnctcaaaaa | 240 |
| caaaaattga | ggtattttgg | ttcttctagg | agtagacaat | gacatttgg | ganggcaga | 300 |
| ccctnnccc | aaaaaataaa | ataagggnat | nttcttcant | atngaananm | ggggcgccc | 360 |
| cgggaaaan | naaaccttgg | gnnggggggtt | tggcccaagc | ccttgaaaaa | aaantttntt | 420 |
| tcccaaaaaa | aacng | | | | | 435 |

<210> SEQ ID NO 286
<211> LENGTH: 301
<212> TYPE: DNA
<213> ORGANISM: Homo sapiens

<400> SEQUENCE: 286

```
cctggtttct ggtggcctct atgaatccca tgtagggtgc agaccgtact ccatccctcc      60
ctgtgagcac cacgtcaacg gctcccggcc cccatgcacg ggggagggag ataccccccaa    120 gtgtagcaag atctgtgagc ctggctacag cccgacctac aaacaggaca agcactacgg    180
atacaattcc tacagcgtct ccaatagcga gaaggacatc atggccgaga tctacaaaaa    240
cggccccgtg gagggagctt tctctgtgta ttcggacttc ctgctctaca agtcaggagt    300
g                                                                   301
```

<210> SEQ ID NO 287
<211> LENGTH: 432
<212> TYPE: DNA
<213> ORGANISM: Homo sapiens

<400> SEQUENCE: 287

```
tccagcttgt tgccagcatg agaaccgcca ttgatgacat tgaacgccgg gactggcagg     60
atgacttcag agttgccagc caagtcagcg atgtggcggt acaggggggac ccccttctca   120 acggcaccag ctttgcagac ggcaagggac accccccagaa tggcgttcgc accaaaactta  180 gatttatttt ctgttccatc catctcgatc atcagtttgt caatcttctc ttgttctgtg    240
acgttcagtt tcttgctaac cagggcaggc gcaatagttt tattgatgtg ctcaacagcc    300
tttgagacac ccttccccat atagcgagtc ttatcattgt cccggagctc tagggcctca    360
tagataccag ttgaagcacc actgggcaca gcagctctga agagaccttt tgaggtgaag    420
agatcaacct ca                                                       432
```

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288

```
tctggctcaa gtcaaagtcc tggtcctctt ctccgcctcc ttcttcatca tagtaataaa      60
cgttgtcccg ggtgtcatcc tctggggggca gtaaggggctc tttgaccacc gctctcctcc   120
gaagaaacag caagagcagc agaatcagaa ttagcaaagc aagaattcct ccaagaatcc    180
ccagaatggc aggaatttgc aatcctgctt cgacaggctg tgccttccta cagacgccgg    240
cggccccttc acantcacac acgctgacct ctaaggtggt cacttggtct ttattctggt    300
tatccatgag cttgagattg attttg                                        326
```

<210> SEQ ID NO 289
<211> LENGTH: 451
<212> TYPE: DNA
<213> ORGANISM: Homo sapiens

<400> SEQUENCE: 289

```
gtcccggtgt ggctgtgccg ttggtcctgt gcggtcactt agccaagatg cctgaggaaa     60
cccagaccca agaccaaccg atggaggagg aggaggttga gacgttcgcc tttcaggcag    120
aaattgccca gttgatgtca ttgatcatca atactttcta ctcgaacaaa gagatctttc    180
tgagagagct catttcaaat tcatcagatg cattggacaa aatccggtat gaaagcttga    240
cagatcccag taaattagac tctggaaaag agctgcatat taaccttata ccgaacaaac    300
aagatcgaac tctcactatt gtggatactg gaattggaat gaccaaggct gacttgatca    360
```

```
ataaccttgg tactatcgcc aagtctggga ccaaagcgtt catggaagct ttgcaggctg    420
gtgcagatat ctctatgatt ggacctcggc c                                  451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (421)
<223> OTHER INFORMATION: n=A,T,C or G

<400> SEQUENCE: 290

```
ttttttttt tcaaaacagt atattttatt ttacaatagc aaccaactcc ccagtttgtt      60
tcaattgtga catctagatg cttaagatt actttctggt ggtcacccat gctgaacaat     120 attttcaat cttccaaaca gcaaagactc aaaagagatt ctgcatttca catcagttca    180
caagttcaag agtcttccat ttatcttagc ttttggaata aattatcttt gaggtagaag   240
gacaatgacg aagccactta attccttgtg tctgcataaa agcagattta ttcatcacaa   300
cttcatttat gtgaataaag cagatgatga taaaatgttc tcttattctt gtttaatcag   360
tagtggtagt gatgccagaa acttgtaaat gcacttcaaa ccaattgtgg ctcaagtgta   420
ngtggttccc caaggctggt accaatgaga ctggggtttg ggaattagtt ggtcatcatc   480
cctcctgctg ccca                                                     494
```

<210> SEQ ID NO 291
<211> LENGTH: 535
<212> TYPE: DNA
<213> ORGANISM: Homo sapiens

<400> SEQUENCE: 291

```
tcgcgtgctt aacatgaaaa caaactttgt gctgtttggt tcattgtatg cattgatgga     60
gtcttgtctc tcatcatggg gtgtctgacc atccaacctg cagtactcat aatttctcca    120
catgcaataa tcttccaaaa tgtccaatac ccttgtcatt tgactgaaga ttagtactcg    180
tgaaccttgt tcttttaact tagggagcag cttgtctaaa accaccattt tgccactgtt    240
ggttactaga tgcatatctg ttgtataagg tggaccaggt tctgctccat caaagagata    300
tggatgatta caacattttc tcaactgcat taggatgttc aataacctca ttttgtccat    360
cttgcctgct gagttgagta tatctatatc cttcattaat atccgagtat accattccct    420
ttgcattttg ctgaggccca catagatttt tacttccttc tttggaggca aactcttttc    480
aacatcagcc ttaattcgac gaaggaggaa tggacgcaaa accatatgaa gcctc         535
```

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292

```
tacnagcccg tgctgatcga gatcctggtg gaggtgatgg atccttcctt cgtgtgcttg     60
aaaattggag cctgcccctc ggcccataag cccttgttgg gaactgagaa gtgtatatgg    120
ggcccaagct actggtgcca gaacacagag acagcagccc agtgcaatgc tgtcgagcat    180
```

```
tgcaaacgcc atgtgtggaa ctaggaggag gaatattcca tcttggcaga aaccacagca    240 ttggttttt tctacttgtg tgtctggggg aatgaacgca cagatctgtt tgactttgtt    300
ataaaaatag ggctccccca cctcccccat ttttgtgtcc tttattgnag cattgctgtc    360
tgcaagggag cccta                                                    376
```

<210> SEQ ID NO 293
<211> LENGTH: 320
<212> TYPE: DNA
<213> ORGANISM: Homo sapiens

<400> SEQUENCE: 293

```
tcggctgctt cctggtctgg cggggatggg tttgctttgg aaatcctcta ggaggctcct    60
cctcgcatgg cctgcagtct ggcagcagcc ccgagttgtt tcctcgctga tcgatttctt   120
tcctccaggt agagttttct ttgcttatgt tgaattccat tgcctctttt ctcatcacag   180
aagtgatgtt ggaatcgttt cttttgtttg tctgatttat ggttttttta agtataaaca   240 aaagttttt attagcattc tgaaagaagg aaagtaaaat gtacaagttt aataaaaagg   300
ggccttcccc tttagaatag                                               320
```

<210> SEQ ID NO 294
<211> LENGTH: 359
<212> TYPE: DNA
<213> ORGANISM: Homo sapiens

<400> SEQUENCE: 294

```
ctgtcataaa ctggtctgga gtttctgacg actccttgtt caccaaatgc accatttcct    60
gagacttgct ggcctctccg ttgagtccac ttggctttct gtcctccaca gctccattgc   120
cactgttgat cactagcttt ttcttctgcc cacaccttct tcgactgttg actgcaatgc   180
aaactgcaag aatcaaagcc aaggccaaga gggatgccaa gatgatcagc cattctggaa   240
tttggggtgt ccttatagga ccagaggttg tgtttgctcc accttcttga ctcccatgtg   300
agtgtccatc tgattcagat ccatgagtgg tatgggaccc cccactgggg tggaatgtg    359
```

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295

```
cctgagttgg gctgactgcc agagacagac ccctctgggt ctcggtgaac cagccaggca    60
tttacctcag tggttggcac ctggaacctg tccagggccc tcacctgact gaggagccgc   120
cgggcagtga agtaattgtc caggtctatg ctcttggggt ggataccata gccatccaag   180
gtattcctca ggttgtggaa ctgggtctga gtataggcag aactgggccc caggatgatc   240
tcccggagtg ggggaagctg tgaggtcagg taagtatcca cgtccacccg tacccccaatc   300 aaactcagca gaatggtgaa ctggagaagt ccttccgtta agtatttctt cagagaaagc   360
attgctgaag gaccagaatg tttatgcttt ttggttttta aaatcttcca aaagacaaat   420
caaggccact gctctgccgc tccagccagc aggttaccct cctcagtgtc aaacccgta    480 ccccacccctg gcagaacaca agggatgagc tccctgacgg ccccagagga agcacaccc   540 tgtggagcca aggccaanga cacactccag accacattca cttt                    584
```

<210> SEQ ID NO 296
<211> LENGTH: 287
<212> TYPE: DNA
<213> ORGANISM: Homo sapiens

<400> SEQUENCE: 296

```
ccttatcatt cattcttagc tcttaattgt tcattttgag ctgaaatgct gcattttaat      60
tttaaccaaa acatgtctcc tatcctggtt tttgtagcct tcctccacat cctttctaaa    120
caagatttta aagacatgta ggtgtttgtt catctgtaac tctaaaagat ccttttttaaa   180
ttcagtccta agaaagagga gtgcttgtcc cctaagagtg tttaatggca aggcagccct    240
gtctgaagga cacttcctgc ctaagggaga gtggtatttg cagacta                  287
```

<210> SEQ ID NO 297
<211> LENGTH: 457
<212> TYPE: DNA
<213> ORGANISM: Homo sapiens

<400> SEQUENCE: 297

```
ccaattgaaa caaacagttc tgagaccgtt cttccaccac tgattaagag tggggtggca     60
ggtattaggg ataatattca tttagccttc tgagctttct gggcagactt ggtgaccttg   120
ccagctccag cagccttctt gtccactgct ttgatgacac ccaccgcaac tgtctgtctc   180
atatcacgaa cagcaaagcg acccaaaggt ggatagtctg agaagctctc aacacacatg   240
ggcttgccag gaaccatatc aacaatggca gcatcaccag acttcaagaa tttagggcca   300
tcttccagct ttttaccaga acggcgatca atcttttcct tcagctcagc aaacttgcat   360
gcaatgtgag ccgtgtggca atccaataca ggggcatagc cggcgcttat ttggcctgga   420
tggttcagga taatcacctg agcagtgaag ccagacc                            457
```

<210> SEQ ID NO 298
<211> LENGTH: 469
<212> TYPE: DNA
<213> ORGANISM: Homo sapiens

<400> SEQUENCE: 298

```
tctttgactt tccttgtcta cctcctctgg agatctcaaa ttctccaggt tccatgctcc     60
cagagatctc aatgattcct gattctcctc ttccaggagt ctgaatgtct cttggttcac   120
ttccacagac tccagtggtt cttgaatttc cttttctaga ggattcattg cccctgatt    180
tatttcttct ggagtccaca gtggtgcttg agtttctgga gatttcagtg tttccaggtt   240
ctcttgtccc gcagacttca gtgattctag gatctctgtt tctaaagatt ttactgcctc   300
tatgctctct tctttgagtg actttaagaa ctcttgattc tcattttcaa gaggtctagc   360
tatctcctgg tcaagagact tcagtggttc tagatccact ttttctgggg gtcttaatgt   420
catctgatcc tgttcccta gagacctccg tcgctgttga gtctctttt                469
```

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G

<400> SEQUENCE: 299

-continued

| | |
|---|---|
| tctgtggaga ggatgaggtt gagggaggtg gggtatntcg ctgctctgac cttaggtaga | 60 |
| gtcctccaca gaagcatcaa antggactgg cacatatgga ctcccttcac aggccacaat | 120 |
| gatgtgtctc tccttcgggc tggnccggta tgcacagttg ggta | 165 |

<210> SEQ ID NO 300
<211> LENGTH: 506
<212> TYPE: DNA
<213> ORGANISM: Homo sapiens

<400> SEQUENCE: 300

| | |
|---|---|
| tctgaggaaa gtttgggctt attagtattt gctccagcga acctccaagt tttctccatt | 60 |
| gcggacaacg taactaccag ctccttggct cagtggttcg cctccactca gaagttccca | 120 |
| gtaggttctg tcattattgt tggcacatag gccctgaata caggtgatat agggccccca | 180 |
| tgagcgctcc tccattgtga aaccaaatat agtatcattc attttctggg ctttctccat | 240 |
| cacactgagg aagacagaac catttagcac agtgacattg gtgaaatatg ttcattgat | 300 |
| tctcacagag taattgacgg agatatatga ttgtgagtca ggaggtgtca cagttatagg | 360 |
| ctcatcagcg gagatgttga agttacctga agcagagacg caagaagagt ctttgttaat | 420 |
| atccaagaag gtctttccca tcagggcagg taagacctgg gctgcagcgt ttggattgct | 480 |
| gaatgctcct tgagaaattt ccgtga | 506 |

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301

| | |
|---|---|
| tcctaaggca gagcccccat cacctcaggc ttctcagttc ccttagccgt cttactcaac | 60 |
| tgccccttc ctctccctca gaatttgtgt ttgctgcctc tatcttgttt tttgtttttt | 120 |
| cttctggggg gggtctagaa cagtgcctgg cacatagtag gcgctcaata aatacttgtt | 180 |
| tgttgaatgt ctcctctctc tttccactct gggaaaccta ngnttctgcc attctgggtg | 240 |
| accctgtatt tntttctggt gcccattcca tttgnccagn taatacttcc tcttaaaaat | 300 |
| ctcc | 304 |

<210> SEQ ID NO 302
<211> LENGTH: 492
<212> TYPE: DNA
<213> ORGANISM: Homo sapiens

<400> SEQUENCE: 302

| | |
|---|---|
| ttttcagtaa gcaacttttc catgctctta atgtattcct ttttagtagg aatccggaag | 60 |
| tattagattg aatggaaaag cacttgccat ctctgtctag gggtcacaaa ttgaaatggc | 120 |
| tcctgtatca catacggagg tcttgtgtat ctgtggcaac agggagtttc cttattcact | 180 |
| ctttatttgc tgctgtttaa gttgccaacc tcccctccca ataaaaattc acttacacct | 240 |
| cctgcctttg tagttctggt attcacttta ctatgtgata gaagtagcat gttgctgcca | 300 |
| gaatacaagc attgcttttg gcaaattaaa gtgcatgtca tttcttaata cactagaaag | 360 |
| gggaaataaa ttaaagtaca caagtccaag tctaaaactt tagtactttt ccatgcagat | 420 |
| ttgtgcacat gtgagagggt gtccagtttg tctagtgatt gttatttaga gagttggacc | 480 |

```
actattgtgt gt                                                      492

<210> SEQ ID NO 303
<211> LENGTH: 470
<212> TYPE: DNA
<213> ORGANISM: Homo sapiens

<400> SEQUENCE: 303
tctggggcag caggtactcc ctacggcact agtctacagg gggaaggacg ctctgtgctg     60
gcagcggtgg ctcacatggc ctgtctgcac tgtaaccaca ggctgggatg tagccaggac   120
ttggtctcct tggaagacag gtctgatgtt tggccaatcc agtccttcag accctgcctg   180
aaacttgtat cttacgtgaa cttaaagaat aaaatgcatt tctacccgga tctcgccccc   240
aggactggca cgacaggccc acggcagatt agatcttttc ccagtactga tcggtgcgtg   300
gaattccagc caccacttct gattcgattc cacagtgatc ctgtcctctg agtattttaa   360
agaagccatt gtcaccccag tcagtgttcc aggagttggc aaccagccag tagggtgtgc   420
cattctccac tccccagccc aggatgcgga tggcatggac ctcggccgcg              470

<210> SEQ ID NO 304
<211> LENGTH: 79
<212> TYPE: DNA
<213> ORGANISM: Homo sapiens

<400> SEQUENCE: 304
tgtcccattg ttaactcagc ctcaaatctc aactgtcagg ccctacaaag aaaatggaga    60
gcctcttctg gtggatgcg                                                 79

<210> SEQ ID NO 305
<211> LENGTH: 476
<212> TYPE: DNA
<213> ORGANISM: Homo sapiens

<400> SEQUENCE: 305
tcactgagcc accctacagc cagaagagat atgaggaaat tgttaaggaa gtcagcactt    60
acattaagaa aattggctac aaccccgaca cagtagcatt tgtgccaatt tctggttgga   120
atggtgacaa catgctggag ccaagtgcta acgtaagtgg ctttcaagac cattgttaaa   180
aagctctggg aatggcgatt tcatgcttac acaaattggc atgcttgtgt ttcagatgcc   240
ttggttcaag ggatggaaag tcacccgtaa ggatggcaat gccagtggaa ccacgctgct   300
tgaggctctg gactgcatcc taccaccaac tcgtccaact gacaagccct gcgcctgcc    360 tctccaggat gtctacaaaa ttggtggtaa gttggctgta aacaaagttg aatttgagtt   420
gatagagtac tgtctgcctt cataggtatt tagtatgctg taaatatttt taggta       476

<210> SEQ ID NO 306
<211> LENGTH: 404
<212> TYPE: DNA
<213> ORGANISM: Homo sapiens

<400> SEQUENCE: 306
tctgtctcgg agctcagggc gcagccagca cacacaggag cccacaggac agccacgtct    60
tcacagaaac tacagaagtc aggacccagg cgaggacctc aggaacaagt gccccctgca   120
gacagagaga cgcagtagca acagcttctg aacaactaca taataatgcg gggagaatcc   180
tgaagaccac tgcatcccac aagcactgac aaccacttca ggatttttatt tcctccactc   240
```

```
taacccccag atccatttat gagaagtgag tgaggatggc aggggcatgg agggtgaagg        300
gacagcaagg atggtctgag ggcctggaaa caatagaaaa tcttcgtcct ttagcatatc        360
ctggactaga aaacaagagt tggagaagag gggggttgat acta                         404
```

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n=A,T,C or G

<400> SEQUENCE: 307

```
tcctgcctan acatctgtga gggcctcaag ggctgctgcc tcgactttct ccctagctaa         60
gtccacccgt ccagggacac agccagggca ctgctctgtg ctgacttcca ctgcagccaa        120
gggtcaaaat gaagcatctg cggaggccag gactccttgg catcggacac agtcagggga        180
aaagccaccc tgactctgca ggacagaggg tctagggtca tttggcagga gaacactggt        240
gtgccaaggg aagcnancat                                                    260
```

<210> SEQ ID NO 308
<211> LENGTH: 449
<212> TYPE: DNA
<213> ORGANISM: Homo sapiens

<400> SEQUENCE: 308

```
tctgtgctcc cgactcctcc atctcaggta ccaccgactg cactgggcgg ggccctctgg         60
ggggaaaggc tccacggggc aggatacat ctcgaggcca gtcatcctct ggaggcagcc        120
caatcaggtc aaagattttg cccaactggt cggcttcaga gtttccacag aagagaggct       180
ttcgacgaaa catctctgca aagatacagc caacactcca catgtccaca ggtgttgcat       240
atgtggactg cagaagaact tcgggagctc ggtaccagag tgtaacaacc ttgatcgttt       300
cggctggcaa gcctggtggg ggtgccttgt ccagatatgt ccttaggtcc tggtctacat       360
gctcaaacac cagggttacc ttgatctccc ggtcagttcg ggatgtggca cagacgtcca       420
tcagccggac aacattggga tgctcaaaa                                         449
```

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309

```
ctgtggaaac ctggggtgcc gggtaaatgg agaactccag cttggatttc ttgccataat         60
caactgagag acgttccatg agcagggagg tgaacccaga accagttccc ccaccaaagc       120
tgtggaaaac caagaagccc tgaagaccgg tgcactggtc agccagcttg cgaattcggt       180
ccaacacaag gtcaatgatc tccttgccaa tggtgtagtg ccctcgggca tagttattgg       240
cagcatcttc cttgcctgtg atgagctgct cagggtggaa gagctggcgg taggtgccag       300
tgcgaacttc atcaatgact gtgggttcca agtctacaaa cacagcccgg ggcacgtgct       360
tgccagcgcc cgtctcactt gaanaagggt gtttgaagga agtcatctcc t                411
```

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310

| | | | | | |
|---|---|---|---|---|---|
| tcctcgtcca | gcttgactcg | attagtcctc | ataaggtaag | caaggcagat | ggtggctgac | 60 |
| cgggaaatgc | ctgcctggca | gtggacaaac | accttcctc  | cagcattctt | gatggagtct | 120 |
| atgaagtcaa | tggcctcgtt | gaaccaggag | ctgatgtctg | ccttgtggtt | gtcctccaca | 180 |
| gggatgctct | tgtactggta | gtgaccctca | aaatggttgg | acaattggc  | tgagacgttg | 240 |
| atcaaggcan | ttatgcccaa | ggcatccagc | atgtccttgc | gggaagcgtg | atacgcactg | 300 |
| cccaggtaca | gaaagggcag | | | | | 320 |

<210> SEQ ID NO 311
<211> LENGTH: 539
<212> TYPE: DNA
<213> ORGANISM: Homo sapiens

<400> SEQUENCE: 311

| | | | | | |
|---|---|---|---|---|---|
| tctggcccat | gaagctgaag | ttgggagaga | tgatgcttcg | cctctgcttc | acaaactcaa | 60 |
| aggcctcgtc | cagcttgact | cgattagtcc | tcataaggta | agcaaggcag | atggtggctg | 120 |
| accgggaaat | gcctgcctgg | cagtggacaa | acaccttcc  | tccagcattc | ttgatggagt | 180 |
| ctatgaagtc | aatggcctcg | ttgaaccagg | agctgatgtc | tgccttgtgg | ttgtcctcca | 240 |
| cagggatgct | cttgtactgg | tagtgaccct | caaaatggtt | gggacaattg | gctgagacgt | 300 |
| tgatcaaggc | agttatgccc | aaggcatcca | gcatgtcctt | gcgggaagcg | tgatacgcac | 360 |
| tgcccaggta | cagaaagggc | aggatttcca | ccgggccacc | ctgaaatcca | gaaatatcca | 420 |
| acattcatca | agcttgctca | aagccaaggc | cagtgcccat | acccacaaaa | actttctgct | 480 |
| ggaaaagtca | atttcagata | ccgagtgaac | tcagttctgt | tgctggagga | taaataaat  | 539 |

<210> SEQ ID NO 312
<211> LENGTH: 475
<212> TYPE: DNA
<213> ORGANISM: Homo sapiens

<400> SEQUENCE: 312

| | | | | | |
|---|---|---|---|---|---|
| tcaaggatct | tcctaaagcc | accatgtgag | aggattcgga | cgagagtctg | agctgtatgg | 60 |
| cagaccatgt | cctgctgttc | tagggtcatg | actgtgtgta | ctctaaagtt | gccactctca | 120 |
| cagggtcag  | tgatacccac | tgaacctggc | aggaacagtc | ctgcagccag | aatctgcaag | 180 |
| cagcgcctgt | atgcaacgtt | tagggccaaa | ggctgtctgg | tggggttgtt | catcacagca | 240 |
| taatggccta | gtaggtcaag | gatccagggt | gtgagggct  | caaagccagg | aaaacgaatc | 300 |
| ctcaagtcct | tcagtagtct | gatgagaact | ttaactgtgg | actgagaagc | attttcctcg | 360 |
| aaccagcggg | catgtcggat | ggctgctaag | gcactctgca | atactttgat | atccaaatgg | 420 |
| agttctggat | ccagttttcg | aagattgggt | ggcactgttg | taatgagaat | cttca      | 475 |

<210> SEQ ID NO 313
<211> LENGTH: 456
<212> TYPE: DNA
<213> ORGANISM: Homo sapiens

```
<400> SEQUENCE: 313
tccacttaaa gggtgcctct gccaactggt ggaatcatcg ccacttccag caccacgcca    60
agcctaacat cttccacaag gatcccgatg tgaacatgct gcacgtgttt gttctgggcg   120
aatggcagcc catcgagtac ggcaagaaga agctgaaata cctgccctac aatcaccagc   180
acgaatactt cttcctgatt gggccgccgc tgctcatccc catgtatttc cagtaccaga   240
tcatcatgac catgatcgtc cataagaact gggtggacct ggcctgggcc gtcagctact   300
acatccggtt cttcatcacc tacatccctt tctacggcat cctgggagcc ctccttttcc   360
tcaacttcat caggttcctg gagagccact ggtttgtgtg ggtcacacag atgaatcaca   420
tcgtcatgga gattgaccag gaggacctcg gcccgc                             456

<210> SEQ ID NO 314
<211> LENGTH: 477
<212> TYPE: DNA
<213> ORGANISM: Homo sapiens

<400> SEQUENCE: 314
tgcgtgggct tctggaagcc tggatctgga atcattcacc agattattct ggaaaactat    60
gcgtaccctg gtgttcttct gattggcact gactcccaca cccccaatgg tggcggcctt   120
gggggcatct gcattggagt tggggtgcc gatgctgtgg atgtcatggc tgggatcccc    180
tgggagctga gtgccccaa ggtgattggc gtgaagctga cgggctctct ctccggttgg    240
tcctcaccca aagatgtgat cctgaaggtg gcaggcatcc tcacggtgaa aggtggcaca   300
ggtgcaatcg tggaatacca cgggcctggt gtagactcca tctcctgcac tggcatggcg   360
acaatctgca acatgggtgc agaaattggg gccaccactt ccgtgttccc ttacaaccac   420
aggatgaaga gtatctgag caagaccggc cgggaagaca ttgccaatct agctgat      477

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 315
caggtactgg atgtcaggtc tgcgaaactt cttanatttt gacctcagtc cataaaccac    60
actatcacct cggccatcat atgtgtctac tgtggggaca actggagtga aaacttcggt   120
tgctgcaggt ccgtgggaaa atcagtgacc agttcatcag attcatcaga atggtgagac   180
tcatcagact ggtgagaatc atcagtgtca tctacatcat cagagtcgtt cgagtcaatg   240
g                                                                   241

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 316
nttntgtgat agtgtggttt atggactgag gncaaaatnt aagaagtttc gcagacctga    60
catccaancc tgcccgngcg gncgctcgaa aggncgaatt ctgcagatat ccatcacact   120
```

```
ggcggccgct cgagcatgca tctagagggc ccaattcgcc ctatantgag tnatattaca      180
attcactggc cgtcnnttta caacgtcgtg actgggaaaa ccctggcgtt acccaactta      240
a                                                                      241
```

<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 317

```
aggtaccctg ctcancagcc tgggngcctg ggttgtctcc ttgtccatcc actggtccat       60
tctgctctgc attttttgt tcctcttttg gaggttccac tttgggtttg ggcttttgaaa     120 ttatagggct acaantacct cggccgaaac cacnctaagg gcgaattctg cagatatcca     180
tcacactggc ggncgctcga gcatgcatct agagggccca attcgcccta tagtgagtcg     240
t                                                                      241
```

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 318

```
cgngnacaan ntacattgat ggannggtntg nggntctgan tntttantta cantggagca      60
ttaatatttt cttnaacgtn cctcaccttc ctgaantaaa nactctgggt tgtagcgctc     120
tgtgctnana accacntnaa ctttacatcc ctcttttgga ttaatccact gcgcggccac     180
ctctgccgcg accacgctaa gggcnaattc tgcagatatc catcacactg gcggccgctc     240 n                                                                      241
```

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 319

```
caggtactga tcggtgcgtg gaantccagc caccanttnt gattcgattc cacagtgatc      60
ctgtcctctg agtattttaa agaagccatt gtcaccccag tcagtgttcc aggagttggc     120
aaccagccag tagggtgtgc cattctccac tccccagccc aggatgcgga tggcatggcc     180
acccatcatc tctccggtga cgtgttggta cctcggccgc gaccacgcta agggcgaatt     240
c                                                                      241
```

<210> SEQ ID NO 320
<211> LENGTH: 241
<212> TYPE: DNA
<213> ORGANISM: Homo sapiens
<220> FEATURE:

```
<221> NAME/KEY: misc_feature
<222> LOCATION: (1)...(241)
<223> OTHER INFORMATION: n = A,T,C or G

<400> SEQUENCE: 320
ggcaggtacc aacagagctt agtaatntct aaaaagaaaa aatgatcttt ttccgacttc      60
taaacaagtg actatactag cataaatcat tctagtaaaa cagctaaggt atagacattc     120
taataatttg ggaaaaccta tgattacaag tgaaaactca gaaatgcaaa gatgttggtt    180
ttttgtttct cagtctgctt tagcttttaa ctctnnnaan cncatgcaca cttgnaactc    240
t                                                                    241

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 321
angtaccaac agagcttagt aattnntaaa aagaaaaaat gatcttttc cgacttctaa      60 acaagtgact atactagcat aaatcattct agtaaaacag ctaaggtata gacattctaa    120
taatttggga aacctatga ttacaagtga aaactcagaa atgcaaagat gttggttttt    180
tgtttctcag tctgctttag cttttaactc tggaagcgca tgcacacntg aactctgctc    240
a                                                                    241

<210> SEQ ID NO 322
<211> LENGTH: 241
<212> TYPE: DNA
<213> ORGANISM: Homo sapiens

<400> SEQUENCE: 322
ggtaccaaca gagcttagta atttctaaaa agaaaaaatg atcttttcc gacttctaaa     60 caagtgacta tactagcata aatcattctt ctagtaaaac agctaaggta tagacattct    120
aataatttgg gaaacctat gattacaagt aaaaactcag aaatgcaaag atgttggttt    180
tttgtttctc agtctgcttt agcttttaac tctggaagcg catgcacact gaactctgct    240
c                                                                    241

<210> SEQ ID NO 323
<211> LENGTH: 241
<212> TYPE: DNA
<213> ORGANISM: Homo sapiens

<400> SEQUENCE: 323
cgaggtactg tcgtatcctc agccttgttc tatttcttta ttttagcttt acagagatta     60
ggtctcaagt tatgagaatc tccatggctt cagggctta acttttctg ccattctttt    120 gctcttaccg ggctcagaag gacatgtcag gtgggatacg tgtttctctt tcagagctga    180
agaaagggtc tgagctgcgg aatcagtaga gaaagccttg gtctcagtga ctccttggct    240
t                                                                    241

<210> SEQ ID NO 324
<211> LENGTH: 241
<212> TYPE: DNA
<213> ORGANISM: Homo sapiens
```

<400> SEQUENCE: 324
aggtactgtc gtatcctcag ccttgttcta tttctttatt ttagctttac agagattagg      60
tctcaagtta tgagaatctc catggctttc aggggctaaa cttttctgcc attcttttgc     120
tcttaccggg ctcagaagga catgtcaggt gggatacgtg tttctctttc agagctgaag     180
aaagggtctg agctgcggaa tcagtagaga aagccttggt ctcagtgact ccttggcttt     240
c                                                                    241

<210> SEQ ID NO 325
<211> LENGTH: 241
<212> TYPE: DNA
<213> ORGANISM: Homo sapiens

<400> SEQUENCE: 325
ggcaggtaca tttgttttgc ccagccatca ctctttttgt gaggagcct aaatacattc       60 ttcctggggt ccagagtccc cattcaaggc agtcaagtta agacactaac ttggcccttt    120
cctgatggaa atatttcctc catagcagaa gttgtgttct acaagactg agagagttac     180 atgttgggaa aaaaaagaa gcattaactt agtagaactg aaccaggagc attaagttct    240
g                                                                    241

<210> SEQ ID NO 326
<211> LENGTH: 241
<212> TYPE: DNA
<213> ORGANISM: Homo sapiens

<400> SEQUENCE: 326
gcaggtacat ttgttttgcc cagccatcac tctttttgt gaggagccta aatacattct       60
tcctggggtc cagagtcccc attcaaggca gtcaagttaa gacactaact tggcccttc     120 ctgatggaaa tatttcctcc atagcagaag ttgtgttctg acaagactga gagagttaca    180
tgttgggaaa aaaagaagc attaacttag tagaactgat ccaggagcat taagttctga    240
a                                                                    241

<210> SEQ ID NO 327
<211> LENGTH: 241
<212> TYPE: DNA
<213> ORGANISM: Homo sapiens

<400> SEQUENCE: 327
ggtaccagac caagtgaatg cgacagggaa ttatttcctg tgttgataat tcatgaagta     60
gaacagtata atcaaaatca attgtatcat cattagtttt ccactgcctc acactagtga    120
gctgtgccaa gtagtagtgt gacacctgtg ttgtcatttc ccacatcacg taagagcttc    180
caaggaaagc caaatcccag atgagtctca gagagggatc aatatgtcca tgattatcag    240
g                                                                    241

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 328

-continued

```
ggtacnagac caaatgaang ccacagggaa ttatttcctg tgttgataat tcatgaagta      60
gaacantata atcaaaatca attgtatcat cattagtttt ccactgcctc acactagtga     120
gctgtgccaa gtagtagtgt gacacctgtg ttgtcatttc ccacatcacg taagagcttc     180
caaggaaagc caaatcccag atgagtctca gagagggatc aatatgtcca tnatcatcan    240
g                                                                     241
```

<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 329

```
ttcaggtcga gttggctgca gatttgtggt gcnttctgag ccgtctgtcc tgcgccaaaa      60
ngcttcaaag tattattaaa aacatatgga tccccatgaa gccctactac accaaagttt    120
accaggagat ttggatagga atggggctga tgggcttcat cgtttataaa atccgggctg    180
ctgataagaa gtaaggcttt gaaagcttca gcgcctgctn ctggtcanna ctaaccatan    240 n                                                                     241
```

<210> SEQ ID NO 330
<211> LENGTH: 241
<212> TYPE: DNA
<213> ORGANISM: Homo sapiens

<400> SEQUENCE: 330

```
ttttgtgcag atttgtggtg cgttctgagc cgtctgtcct gcgccaagat gcttcaaagt     60
attattaaaa acatatggat ccccatgaag ccctactaca ccaaagttta ccaggagatt    120
tggataggaa tggggctgat gggcttcatc gtttataaaa tccgggctgc tgataaagaa    180
agtaaggctt tgaaagcttc agcgcctgct cctggtcatc actaaccaga tttacttgga    240
g                                                                     241
```

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 331

```
nttttaggna ctttgggctc cagacttcac tggtcttagg nattgaaacc atcacctggn     60
ntgcattcct catgactgag gttaacttaa aacaaaatg gtaggaaagc tttcctatnc    120
ttcnggtaag anacaaatnt nctttaaaaa aangtggaag gcatgacnta cgtgagaact    180
gcacaaactg gccactgaca aaaatgaccc ccatttgtgt gacttcattg agacacatta    240
c                                                                     241
```

<210> SEQ ID NO 332
<211> LENGTH: 241
<212> TYPE: DNA
<213> ORGANISM: Homo sapiens

<400> SEQUENCE: 332
tgtgaggaga gggaacatgc tgagaaactg atgaagctgc agaaccaacg aggtggccga    60
atcttccttc aggatatcaa gaaaccagac tgtgatgact gggagagcgg gctgaatgca   120
atggagtgtg cattacattt ggaaaaaaat gtgaatcagt cactactgga actgcacaaa   180
ctggccactg acaaaaatga cccccatttg tgtgacttca ttgagacaca ttacctgaat   240
g                                                                  241

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 333
caggtacaag cttttttttt tttttttttt tttttttttt ttgnaaatac tntttattgn    60
aaatattcta tcctaaattc catatagcca attaattntt acanaatntt ttgttaattt   120
ttgngngtat aaattttaca aaaataaagg gtatgtttgt tgcacacaac ttacaaataa   180
taataaactn tttattgnaa atattnttta ttgnaaatat tctttatcct aaattccata   240
t                                                                  241

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 334
tacctgctgn agggntgaa gncntctctg ctgccccagg catctgcanc ccctgctgct    60
ggttctgccc ctgctgcagc agaggagaag aaagatgaga agaaggagga gtctgaagag   120
tcagatgatg acatgggatt tggcctttttt gattaaannc ctgctcccct gcaaataaag   180
cctttttaca caaaaaaaaa aaaaaaaaaa aaaaaaaaaa aagcttgtac ctgcccnggc   240
g                                                                  241

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 335
ctatgtgctg ggatgactat ggagacccaa atgtctcana atgtatgtcc cagaaacctg    60
tggctgcttc aaccattgac agttttgctg ctgctggctt ctgcagacag tcaagctgca   120
gctcccccaa aggctgtgct gaaacttgag ccccgtggaa tcaacgtgct ccaggaggac   180
tctgtgactc tgacatgcca gggggctcgc agccctgaga gcgactccat tcagtggttc   240
c                                                                  241

<210> SEQ ID NO 336

<211> LENGTH: 241
<212> TYPE: DNA
<213> ORGANISM: Homo sapiens

<400> SEQUENCE: 336

```
taccaaccta tgcagccaag caacctcagc agttcccatc aaggccacct ccaccacaac      60
cgaaagtatc atctcaggga aacttaattc ctgcccgtcc tgctcctgca cctcctttat     120
atagttccct cacttgattt ttttaacctt cttttttgcaa atgtcttcag ggaactgagc    180
taatactttt ttttttcttg atgttttctt gaaaagcctt tctgttgcaa ctatgaatga    240
a                                                                    241
```

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 337

```
ggtactgtat gtagctgcac tacaacagat tcttaccgtc tccacanagg tcatanattg      60
taaatggtna atactgactt ttttttttatt cccttgactc aagacagcta acttcatttt    120
cagaactgtt ttaaaccttt gtgtgctggt ttataaaata atgtgtgtaa tccttgttgc    180
tttcctgata ccagactgtt tcccgtggtt ggttagaata tattttgntt tgatgcttat    240
a                                                                    241
```

<210> SEQ ID NO 338
<211> LENGTH: 241
<212> TYPE: DNA
<213> ORGANISM: Homo sapiens

<400> SEQUENCE: 338

```
aggtacaggt gtgcgctgag ccgagtttac acggaaagga taaagcccat ttagtttctt      60
ctcaaatgga gttttccact ttcctttgaa gtagacagca ttcaccagga tcatcctggt    120
atccccatct acagaacctt caggtaacaa gtttgggatt ttgcctttgg tttgagtctt    180
gacccaggaa ttaatctttt ttctagcttc ttctgcacat tctaggaagt ctactgcctg    240
g                                                                    241
```

<210> SEQ ID NO 339
<211> LENGTH: 241
<212> TYPE: DNA
<213> ORGANISM: Homo sapiens

<400> SEQUENCE: 339

```
taccgacggc tcctggaggg agagagtgaa gggacacggg aagaatcaaa gtcgagcatg      60
aaagtgtctg caactccaaa gatcaaggcc ataacccagg agaccatcaa cggaagatta    120
gttctttgtc aagtgaatga aatccaaaag cacgcatgag accaatgaaa gtttccgcct    180
gttgtaaaat ctattttccc ccaaggaaag tccttgcaca gacaccagtg agtgagttct    240
a                                                                    241
```

<210> SEQ ID NO 340
<211> LENGTH: 241
<212> TYPE: DNA
<213> ORGANISM: Homo sapiens

<400> SEQUENCE: 340

```
gtagccctca cacacacatg cccgtaacag gatttatcac aagacacgcc tgcatgtaga      60
ccagacacag ggcgtatgga aagcacgtcc tcaagactgt agtattccag atgagctgca     120
gatgcttacc taccacggcc gtctccacca gaaaaccatc gccaactcct gcgatcagct     180
tgtgacttac aaaccttgtt taaaagctgc ttacatggac ttctgtcctt aaaagcttc     240
c                                                                    241
```

<210> SEQ ID NO 341
<211> LENGTH: 241
<212> TYPE: DNA
<213> ORGANISM: Homo sapiens

<400> SEQUENCE: 341

```
gtaccgccta ctttcgtctc atgtctccga acttcttgct gatggccgtt ccaacgttgc      60
tgaaagctgc agttgccttt tgccctgcgt gactcagggt ttcatgtgtt ttcttgtagg     120
cagtggtagt ctgcatgtca tgccagcttt tgctgaagtt ctgttttaat tcattcatca     180
ggttcatgcc gagttttgtt ttatctcaac tagatgcctt tctttcgctg acaaaacttg     240
t                                                                    241
```

<210> SEQ ID NO 342
<211> LENGTH: 241
<212> TYPE: DNA
<213> ORGANISM: Homo sapiens

<400> SEQUENCE: 342

```
gtacattggt gctataaata taaatgctac ttatgaagca tgaaattaag cttcttttt      60
cttcaagttt tttctcttgt ctagcaatct gttaggcttc tgaaccaaga ccaaatgttt    120
acgttcctct gctgcatacc aacgttactc caaacaataa aaatctatca tttctgctct    180
gtgctgagga atggaaaatg aaacccccac cccctgaccc ctaggactat acagtggaaa    240
c                                                                    241
```

<210> SEQ ID NO 343
<211> LENGTH: 241
<212> TYPE: DNA
<213> ORGANISM: Homo sapiens

<400> SEQUENCE: 343

```
gtacatgtgg tagcagtaat tttttttgaag caactgcact gacattcatt tgagttttct      60
ctcattatca gattctgttc caaacaagta ttctgtagat ccaaatggat taccagtgtg    120
ctacagactt cttattatag aacagcattc tattctacat caaaaatagt ttgtgtaagt    180
tagttttggt taccatctaa aatatttta atgttctttt acataaaaat ttatgttgtg    240
t                                                                    241
```

<210> SEQ ID NO 344
<211> LENGTH: 241
<212> TYPE: DNA
<213> ORGANISM: Homo sapiens

<400> SEQUENCE: 344

```
ggtacaaaat tgttggaatt tagctaatag aaaaacatag taaatattta caaaaacgtt      60
gataacatta ctcaagtcac acacatataa caatgtagac aggtcttaac aaagtttaca    120
```

```
aattgaaatt atgagatttt cccaaaatga atctaatagc tcattgctga gcatggttat    180
caatataaca tttaagatct tggatcaaat gttgtccccg agtcttctgc aatccagtcc    240
t                                                                    241

<210> SEQ ID NO 345
<211> LENGTH: 241
<212> TYPE: DNA
<213> ORGANISM: Homo sapiens

<400> SEQUENCE: 345
ggtacgaagc tgagcgcacg ggggttgccc cagcgtggag cctggacctc aaacttcacg    60
gaaaatgctc tctctctttg acaggcttcc agctgtctcc taatttcctg gatgaactct   120
ccccggcgat ttaactgatc ctgaaaagtg gtgagaggac tgaggaagac aaccaggtca   180
gcgttagatc ggcctctgag ggtggtgccc ttgcctgagg agccacccct taccaccttg   240
g                                                                    241

<210> SEQ ID NO 346
<211> LENGTH: 241
<212> TYPE: DNA
<213> ORGANISM: Homo sapiens

<400> SEQUENCE: 346
caggtaccac tgagcctgag atggggatga gggcagagag aggggagccc cctcttccac    60
tcagttgttc ctactcagac tgttgcactc taaacctagg gaggttgaag aatgagaccc   120
ttaggtttta acacgaatcc tgacaccacc atctataggg tcccaacttg gttattgtag   180
gcaaccttcc ctctctcctt ggtgaagaac atcccaagcc agaaagaagt taactacagt   240
g                                                                    241

<210> SEQ ID NO 347
<211> LENGTH: 241
<212> TYPE: DNA
<213> ORGANISM: Homo sapiens

<400> SEQUENCE: 347
aggtacatct aaaggcatga agcactcaat tgggcaatta acattagtgt ttgttctctg    60
atggtatctc tgagaatact ggttgtagga ctggccagta gtgccttcgg gactgggttc   120 accccaggt ctgcggcagt tgtcacagcg ccagccccgc tggcctccaa agcatgtgca    180
ggagcaaatg gcaccgagat attccttctg ccactgttct cctacgtggt atgtcttccc   240
a                                                                    241

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 348
angtacttgg caagattnga tgctcttgng ctcantgaca tcattcataa cttgtnngtg    60
tgancagagg aggagnncat catcntgtcc tcattcgtca gnnncctctc ctctctgaat   120
ctcaaacaag ttgataatgg agaaaaattt gaattctcag gattgaggct ggactggttc   180
cgcctacang catacactag cgtggctaag gcccctctgc accctgcatg anaaccctga   240
``` c                                                                           241

<210> SEQ ID NO 349
<211> LENGTH: 241
<212> TYPE: DNA
<213> ORGANISM: Homo sapiens

<400> SEQUENCE: 349
gcaggtacca tttgtctgac ctctgtaaaa aatgtgatcc tacagaagtg gagctggata      60
atcagatagt tactgctacc cagagcaata tctgtgatga agacagtgct acagagacct    120
gctacactta tgacagaaac aagtgctaca cagctgtggt cccactcgta tatggtggtg    180
agaccaaaat ggtggaaaca gccttaaccc cagatgcctg ctatcctgac taatttaagt    240
c                                                                           241

<210> SEQ ID NO 350
<211> LENGTH: 241
<212> TYPE: DNA
<213> ORGANISM: Homo sapiens

<400> SEQUENCE: 350
aggtactgtg gatatttaaa atatcacagt aacaagatca tgcttgttcc tacagtattg     60
cgggccagac acttaagtga agcagaagt gtttgggtga cttttcctact taaaattttg    120 gtcatatcat ttcaaaacat ttgcatcttg gttggctgca tatgctttcc tattgatccc    180
aaaccaaatc ttagaatcac ttcatttaaa atactgagcg gtattgaata cttcgaagca    240
g                                                                           241

<210> SEQ ID NO 351
<211> LENGTH: 241
<212> TYPE: DNA
<213> ORGANISM: Homo sapiens

<400> SEQUENCE: 351
tacagaaatc atttggagcc gttttgagac agaagtagag gctctgtcaa gtcaatactg     60
cattgcagct tggtccactg aagaagccac gcctgagata caaaagatgc actcacttg    120 acccgcttta tgttcgcttc ctctcccctt ctctctcatc aactttatta ggttaaaaca    180
ccacatacag gctttctcca aatgactccc tatgtctggg gtttggttag aattttatgc    240
c                                                                           241

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 352
gtaccctgtn gagctgcacc aagattannt ggggccatca tgactgcanc cacnacgang     60
acgcaggcgt gnagtgcatc gtctgacccg gaaacccttt cacttctctg ctcccgaggt    120
gtcctcnggc tcatatgtgg gaaggcanan gatctctgan gagttncctg gggacaactg    180
ancagcctct ggagaggggc cattaataaa gctcaacatc attggcaaaa aaaaaaaaa    240 a                                                                           241

```
<210> SEQ ID NO 353
<211> LENGTH: 241
<212> TYPE: DNA
<213> ORGANISM: Homo sapiens

<400> SEQUENCE: 353
aggtaccagt gcattaattt gggcaaggaa agtgtcataa tttgatactg tatctgtttt      60
ccttcaaagt atagagcttt tggggaagga agtattgaa ctgggggttg gtctggccta     120
ctgggctgac attaactaca attatgggaa atgcaaaagt tgtttggata tggtagtgtg    180
tggttctctt ttggaatttt tttcaggtga tttaataata atttaaaact actataaaaa    240
c                                                                    241

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 354
ngcaggtccg ggcaggtacc aagattcatt ctcatcaaaa actagaaaca gaagggcaaa      60
ttccagtttc cttctgggat tgaatacttt caagtaaggt cttcgacaaa caatcagggg    120
gccaattaat ccactgtaga ggtccttaac ttgatccaca gttgaataat aagcccatgg    180
aatacaagca gaatcctctg ttccagctcc agatctttct gggattttcc atacgtaagt    240
g                                                                    241

<210> SEQ ID NO 355
<211> LENGTH: 241
<212> TYPE: DNA
<213> ORGANISM: Homo sapiens

<400> SEQUENCE: 355
ggtacccacc ctaaatttga actcttatca agaggctgat gaatctgacc atcaaatagg      60
ataggatgga cctttttttg agttcattgt ataaacaaat tttctgattt ggacttaatt    120
cccaaaggat taggtctact cctgctcatt cactctttca aagctctgtc cactctaact    180
tttctccagt gtcatagata gggaattgct cactgcgtgc ctagtctttc ttcacttacc    240
t                                                                    241

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 356
aggtactgta attgagcatc cggaatntgg agaagtaatt tagctacagg gtgaccaacg      60
caagaacata tgccagttcc tcgtagagat tggactggct aaggacgatc agctgaaggt    120
tcatgggttt taagtgcttg tggctcactg aagcttaagt gaggatttcc ttgcaatgag    180
tagaatttcc cttctctccc ttgtcacagg tttaaaaacc tcacagcttg tataatgtaa    240
c                                                                    241
```

<210> SEQ ID NO 357
<211> LENGTH: 241
<212> TYPE: DNA
<213> ORGANISM: Homo sapiens

<400> SEQUENCE: 357

| ttttgtacca | ccgatatgat | caaggaaaat | tctgcccatt | tttatggctg | aagttctaaa | 60 |
| aacctaattc | aaagttcttc | catgatccta | cactgcctcc | aagatggtcc | aggctggcat | 120 |
| aaggcctgag | cggcggtgag | atccgcggct | gccagcagct | tgtcgctctt | cagctggtat | 180 |
| gaagcccctc | ggccacccga | gtctccagga | cctgcccggg | cgccgctcga | agggcgaat | 240 |
| t | | | | | | 241 |

<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 358

| aggtacgggg | agtgggggtg | aagcntgttc | tctacatagg | caacacagcc | gcctaantca | 60 |
| caaagtcagt | ggtcggccgc | ttcgaccaac | atgtggtgag | cattccacgg | gcgcatgaag | 120 |
| tctgggtgct | gtgctcgagt | ctctgaatat | tttgatagga | agcgacaaga | aaattcaaac | 180 |
| tgctctttgc | tgactactgg | aaagtgaaaa | gatgctcaag | tttaccattc | aaagaaacca | 240 |
| t | | | | | | 241 |

<210> SEQ ID NO 359
<211> LENGTH: 241
<212> TYPE: DNA
<213> ORGANISM: Homo sapiens

<400> SEQUENCE: 359

| gaggtacaca | aaaggaatac | cttctgagag | ccagggagtg | aggaaagggg | aaggagactt | 60 |
| gacgtcaagg | gtgcttttga | ggaacatgac | gggccagcca | gcctgcccca | actttgaggc | 120 |
| cctgctgggc | tcttgtgact | ataaatatac | tgtctatttc | taatgcaatc | cgtctttcct | 180 |
| gaaagatctt | gttatctttt | actattgaga | catgctttca | tttttgtggt | cctgtttcca | 240 |
| a | | | | | | 241 |

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 360

| ngtactctat | actaattctg | ccttttata | cttaattcta | aatttctccc | ctctaattta | 60 |
| caacaaattt | tgtgatttt | ataagaatct | atgcctcccc | aattctcaga | ttcttctctt | 120 |
| ttctccttta | tttctttgct | taaattcagt | ataagctttc | ttggtatttt | aggcttcatg | 180 |
| cacattctta | ttcctaaaca | ccagcagttc | ttcagagacc | taaaatccag | tataggaata | 240 |

-continued a 241

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc 60
ccactttgta cttttcttac tatcctgtct agaatcatgt cttatgattt aacagatat 120 agaaccactc ctagaaaatg ttctttcact ttctcgtttc cttttttaatc tatcatcctg 180 actactgaac ttaaaatctt tttcttccct tttttgtttc tcttttcttt tatcctgttc 240
a 241

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 362
aggtactttt atacctngct tangtcagtg acagatttac caatgacaac acaattttaa 60
aattccaaca catatattac tttgtcctat gaagggcaaa aagtcaatat attttaaatt 120
ttaaaaacag aatggatata atgacctttt tacacatcag tgatatttaa aagacttaaa 180
gagacaatac tatggttgag acactggctt cctattccag ccctaattaa agaaaaaata 240
g 241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 363
ttangtacta aaaacaaaat cctaattctg ttttaaagag ctgggagatg ttaatcatat 60
gctcagtttt tccacgttat aatttcctaa atgcaaactt ttcaatcagg gcagttcaaa 120
ttcattacat cacagtaaat aacagtagcc aactttgatt ttatgcttat aggaaaaaaa 180
atcctgtaga tataaaaaca gcaaattttg acaaataaaa ctcaaaccat tcatccctaa 240
a 241

<210> SEQ ID NO 364
<211> LENGTH: 241
<212> TYPE: DNA
<213> ORGANISM: Homo sapiens

<400> SEQUENCE: 364
ggtacaagca gttagtcctg aaggcccctg ataagaatgt catcttctcc ccactgagca 60
tctccaccgc cttggccttc ctgtctctgg gggcccataa taccaccctg acagagattc 120
tcaaaggcct caagttcaac ctcacggaga cttctgaggc agaaattcac cagagcttcc 180
agcacctcct gcgcaccctc aatcagtcca gcgatgagct gcagctgagt atgggaaatg 240

|  |  |
|---|---|
| c | 241 |

<210> SEQ ID NO 365
<211> LENGTH: 241
<212> TYPE: DNA
<213> ORGANISM: Homo sapiens

<400> SEQUENCE: 365

| | | |
|---|---|---|
| cgaggtactg agattacagg catgagccac cacgcccggc caaaaacatt taaaaaatga | 60 |
| ctgtccctgc tcaaatactg cagtaggaaa tgtaatttga catatatcac ttccagaaaa | 120 |
| aaactttaaa tctttctata aaatgaattt gatacatcat cagcatgaag tgaagttaaa | 180 |
| atctcttaca aagtaaattc aggtatatca acaatgagat ccaaaagtat cggttcaaga | 240 |
| t | 241 |

<210> SEQ ID NO 366
<211> LENGTH: 241
<212> TYPE: DNA
<213> ORGANISM: Homo sapiens

<400> SEQUENCE: 366

| | |
|---|---|
| ggcaggtaca catcaaacac ttcattgcct aaatgcaggg acatgcttcc atctgaccac | 60 |
| ttgactatcc gagcattgct ttctttaatt tcatttcctt cttcatctcg gcgtatcctc | 120 |
| catcttatag tattttctac ctttaatttt aacctggttc taccttcttc atccagcatt | 180 |
| tcttcatctt caaattcatc ttcataatac tgggctctac acttgagaaa gttgggcagt | 240 |
| t | 241 |

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 367

| | |
|---|---|
| gcaggtacaa ataattcctg ttgtnacatt tagtggacgc gattatctgt atacctcaaa | 60 |
| ttttaattta agaaagtatc acttaaagag catctcattt tctatagatt gaggcttaat | 120 |
| tactgaaaag tgactcaacc aaaaagcaca taacctttta aaggagctac acctaccgca | 180 |
| gaaagtcaga tgccctgtaa ataactttgg tctttcaaaa tagtggcaat gcttaagata | 240 |
| c | 241 |

<210> SEQ ID NO 368
<211> LENGTH: 241
<212> TYPE: DNA
<213> ORGANISM: Homo sapiens

<400> SEQUENCE: 368

| | |
|---|---|
| tttgtacatt gttaatagtg accctcggag gaaatggatt tctcttctat taaaaactct | 60 |
| atggtatata agcattacat aataatgcta cttaaccacc ttttgtctca agaattatca | 120 |
| ccaaagtttt ctggaaataa gtccacataa gaattaaata tttaaaaggt gaaatgttcc | 180 |
| ttattttaac tttagcaaga tcttttcttt ttcattaaga aacactttaa taattttaaa | 240 |
| g | 241 |

<210> SEQ ID NO 369
<211> LENGTH: 241
<212> TYPE: DNA
<213> ORGANISM: Homo sapiens

<400> SEQUENCE: 369

| gcaggtactt tattcttatt tcttatccta tattctgtgt tacagaaaaa ctactaccat | 60 |
| aaacaaaaca ccaaccagcc acagcagttg tgtcaagcat gacaattggt ctagtcttca | 120 |
| cattttatta gtaagtctat caagtaagag atgaagggtc tagaaaacta gacacaaagc | 180 |
| aaccagggtc caaatcacca aggtagatct gtgcttagct aaagggaaac acccgaagat | 240 |
| t | 241 |

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 370

| ngttcacagt gcccctccgg cctcgccatg aggctcttcc tgtcgctccc ggtcctggtg | 60 |
| gtggttctgt cgatcgtctt ggaaggccca gccccagccc aggggacccc agacgtctcc | 120 |
| agtgccttgg ataagctgaa ggagtttgga acacactgg aggacaaggc tcgggaactc | 180 |
| atcagccgca tcaaacagag tgaactttct gccaagatgc gggagtggtt ttcagaagac | 240 |
| a | 241 |

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 371

| ggcaggtcat cttgagcctt gcacatgata ctcagattcc tcacccttgc ttaggagtaa | 60 |
| aacaatatac tttacagggt gataataatc tccatagtta tttgaagtgg cttgaaaaag | 120 |
| gcaagattga cttttatgac attggataaa atctacaaat cagccctcga gttattcaat | 180 |
| gataactgac aaactaaatt atttccctag aaaggaagat gaaaggnagt ggagtgtggt | 240 |
| t | 241 |

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 372

| aggtacagca aagcgaccct tggtgnnata gatcagacgg aaattctctc ccgtcttgnc | 60 |
| aatgctgatg acatccatga atccagcagg gtaggttata tcagttcgga ccttgccatc | 120 |
| gattttaatg aaccgctgca tgcaaatctt ctttacttca tctcctgtca gggcatactt | 180 | aagtctgttc ctcaggaaaa tgatgagggg gagacactct ctcaacttgt ggggaccggt      240 g                                                                       241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca       60
gaagcagtag aaaatcttag cattccaatg gaaggcatgt atttgtaaaa tattctaaaa      120
tcagctctat agtttccttg tcctctttga taagggatca gacagagggt gtgtcccect      180 tcagcagcta cccttcttga caaactggtc tccaataata cctttcagaa acttacaaga     240
c                                                                       241

<210> SEQ ID NO 374
<211> LENGTH: 241
<212> TYPE: DNA
<213> ORGANISM: Homo sapiens

<400> SEQUENCE: 374
caggtactaa aacttacaat aaatatcaga gaagccgtta gttttacag catcgtctgc       60 ttaaaagcta agttgaccag gtgcataatt tcccatcagt ctgtccttgt agtaggcagg     120
gcaatttctg ttttcatgat cggaatactc aaatatatcc aaacatcttt ttaaaacttt     180
gatttatagc tcctagaaag ttatgttttt taatagtcac tctactctaa tcaggcctag     240
c                                                                       241

<210> SEQ ID NO 375
<211> LENGTH: 241
<212> TYPE: DNA
<213> ORGANISM: Homo sapiens

<400> SEQUENCE: 375
aggtacaaag gaccagtatc cctacctgaa gtctgtgtgt gagatggcag agaacggtgt      60
gaagaccatc acctccgtgg ccatgaccag tgctctgccc atcatccaga agctagagcc     120
gcaaattgca gttgccaata cctatgcctg taagggcta gacaggattg aggagagact      180
gcctattctg aatcagccat caactcagat tgttgccaat gccaaaggcg ctgtgactgg     240
g                                                                       241

<210> SEQ ID NO 376
<211> LENGTH: 241
<212> TYPE: DNA
<213> ORGANISM: Homo sapiens

<400> SEQUENCE: 376
ggtacatttt actttccttc tttcagaatg ctaataaaaa acttttgttt atacttaaaa      60
aaaccataaa tcagacaaac aaaagaaacg attccaacat cacttctgtg atgagaaaag    120
aggcaatgga attcaacata agcaaagaaa actctacctg gaggaaagaa atcgatcagc    180
gaagaaacaa ctcggggctg ctgccagact gcaggccatg cgaggaggag cctcctagag    240
g                                                                       241

<210> SEQ ID NO 377

```
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 377
tcctttctgt ccaggtgatt cacagactag acctttctta tcctcctcct agagttttga      60
cttgggactc tagtgttaag atgatgagcc cgtgcatcag gtccttctgc actttggtgg     120
aagtctccca gggtaggttt cctatttgaa acagtggaat catgtttcca gtgataaagt     180
ttaatgacct catccttttt ttttttttttc tcatctgcca tttgtgtgtc ttanatgggt     240
t                                                                    241

<210> SEQ ID NO 378
<211> LENGTH: 241
<212> TYPE: DNA
<213> ORGANISM: Homo sapiens

<400> SEQUENCE: 378
aggtcagcga tcaggtcctt tatgggcagc tgctgggcag ccccacaagc ccagggccag      60
ggcactatct ccgctgcgac tccactcagc ccctcttggc gggcctcacc cccagcccca     120
agtcctatga gaacctctgg ttccaggcca gcccctttggg gaccctggta accccagccc    180
caagccagga ggacgactgt gtctttgggc cactgctcaa cttcccccctc ctgcagggga    240 t                                                                    241

<210> SEQ ID NO 379
<211> LENGTH: 241
<212> TYPE: DNA
<213> ORGANISM: Homo sapiens

<400> SEQUENCE: 379
tacggagcaa tcgaagaggc atatccacac ttggggtggc tatagggctg gaaaatgctg      60
aagatgactg ctttcactga ggtcaaggat tgtaatattg ccagctttgt aaagccatta     120
aagcagaagt tcttcagtg atcttctctc taagaaacac catcacctcc atgtgccttta    180 cagaggcccc ctgcgttctg ctgcattgct tttgcgcaat cccttgatga tgaagatggt    240
c                                                                    241

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 380
acgtacacgc agaccgacat gggnnnttca ggcntnagat caaactcaaa acctgnaatg      60
atatccactc tcttttttctt aagctcaggg aaatattcca agtagaagtc canaaagtca   120
tcggctaana tgcttcngaa tttgaattca tgcacatagg ccttgaaaaa actgtcaaac    180
tgannctgat caccccaccaa gtgggccntn tatgacacaa agcagaaacc tttctcntan   240
g                                                                    241
```

<210> SEQ ID NO 381
<211> LENGTH: 241
<212> TYPE: DNA
<213> ORGANISM: Homo sapiens

<400> SEQUENCE: 381

```
aggtacaact taatggatta gcttttgggt ttaactgaat atatgaagaa attgggtctg    60
tctaaagaga gggtatttca tatggctttt agttcacttg tttgtatttc atcttgattt   120
ttttctttgg aaaataaagc attctatttg gttcagattt ctcagatttg aaaaaggctc   180
tatctcagat gtagtaaatt atttcctttc agtttgtgaa agcaggattt gactctgaaa   240
g                                                                  241
```

<210> SEQ ID NO 382
<211> LENGTH: 241
<212> TYPE: DNA
<213> ORGANISM: Homo sapiens

<400> SEQUENCE: 382

```
gtactgctat aatcaatacg tctgatagac aggtttatcc actatattga ccctacctct    60
aaaaggattg tcataattta tatgctttat gtttacacct atgatacagt tgccttggaa   120
cacaaaattt ttcattgtaa ttaaaaaaag aagagttgtg cagacagaag aaatcaaatc   180
taagaaaatc acaggagtag ataaatactc tagaattcat ataccttggg aagatgggtt   240
t                                                                  241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact    60
gtatttaagt ctgtgcaaat aatccttcag aagaaatatc caagattctg tttgcagagg   120
tcattttgtc tctcaaagat gattaaatga gtttgtcttc agataaagtg ctcctgtcca   180
gcagaactca aaaggccttc aagctgttca gtaagtgtag ttcagataag actccgtcat   240
a                                                                  241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag    60
attctataaa atcagttata tcaacatata aaggagtgtg attttcagtt tgttttttta   120
agtaaatatg accaaactga ctaaataaga aggcaaaaca aaaattatg cttccttgac    180
aaggcctttg gagtaaacaa aatgctttaa ggctcctggt gaatgggtt gcaaggatga    240
a                                                                  241
```

<210> SEQ ID NO 385
<211> LENGTH: 241
<212> TYPE: DNA
<213> ORGANISM: Homo sapiens

<400> SEQUENCE: 385

-continued

```
ggcaggtcta caatggctct gtccttctg tggaatcgtt acaccaagag gtctcagtcc      60
tggtccctga ccccacagtg agctgtttag atgatccttc acatcttcct gatcaactgg     120
aagacactcc aatcctcagt gaagactctc tggagccctt caactctctg caccaggta     180 ggtttggagg ctatgtccct ttaacttatc catgcagagt agccaaactt tacctgaaag     240
a                                                                     241

<210> SEQ ID NO 386
<211> LENGTH: 241
<212> TYPE: DNA
<213> ORGANISM: Homo sapiens

<400> SEQUENCE: 386
aggtaccttt ttcctctcca aggaacagt ttctaaagtt ttctgggggg aaaaaaaact      60
tacatcaaat ttaaaccata tgttaaactg catattagtt gtgttacacc aaaaaattgc     120
ctcagctgat ctacacaagt ttcaaagtca ttaatgcttg atataaattt actcaacatt     180
aaattatctt aaattattaa ttaaaaaaaa aactttctaa gggaaaaata aacaaatgta     240
g                                                                     241

<210> SEQ ID NO 387
<211> LENGTH: 241
<212> TYPE: DNA
<213> ORGANISM: Homo sapiens

<400> SEQUENCE: 387
accccactgg ccgctgtgga gtatctccac tctcccctcg tgagggccgc tcccaccgac     60
cagtcgaact ttcgtaaatg gagttaatgt gtttccactc ccctttcccc ctttctggcc     120
ttttggtcca gaatttcctg gccttccggc atatcctggg agtcctcgac ttccaggaaa     180
gccaattgct ccccgatcac ctttaagacc cggaggacct attggacctg gaaatcctcg     240
t                                                                     241

<210> SEQ ID NO 388
<211> LENGTH: 241
<212> TYPE: DNA
<213> ORGANISM: Homo sapiens

<400> SEQUENCE: 388
tttgtactct tgtccacagc agagacattg agtataccat tggcatcaat gtcaaaagtg     60
acttcaatct gaggaacacc tcggggtgca ggaggtatgc ctgtgagttc aaacttgcca     120
agcaggttgt tatcctttgt catggcacgc tcgccttcat aaacctgaat aagtacacca     180
ggctggttgt cagaataggt agtgaaggtc tgtgtctgct tggtaggaat ggtggtatta     240
c                                                                     241

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 389
tacctntgtt agtgagcacc ttgtcttntg tgcttatntc ttnaagataa atacatggaa     60
ggatgtgaaa atcggaacac caactatgtg tctcactgca tctaagtgaa gcagccacag    120
```

```
ctgtgagagt tttcaaagca gaaagatgct gatgtgacct ctggaattca gacatactga      180
gctatgggtc agaagtgttt tacttaaaaa gcaaacaatc cccaggaaat actgaatagg      240
a                                                                     241

<210> SEQ ID NO 390
<211> LENGTH: 241
<212> TYPE: DNA
<213> ORGANISM: Homo sapiens

<400> SEQUENCE: 390
gcaggtacat ccacatgttc ctccaaatga cgtttggggt cctgcttgcc aacattcttt       60
attgccagct gttcaggtgt catcttatct tcttcttcta cagccttatt gtaattcttg      120
gctaattcca acatctcttt taccactgat tcattgcgtt tacaatgttc actgtagtcc      180
tgaagtgtca aaccttccat ccaactcttc ttatgcaaat ttagcaacat cttctgttcc      240
a                                                                     241

<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 391
cnggcacaan cttntgtttt tnntnttttt tttttttttn tctttatttn tttttantnt       60
taaanaaaaa nnntannnaa annngggttt aaatnctntn nncagancat taaaactgaa      120
ggggaaaaaa aaaccaaaaa cgagcttntt anttnacntg ggnttgggnn gntgctgatn      180
tnaagaagca anntttanan cnngcnnnat ganngagngn tcannttgaa atttnnaccc      240
t                                                                     241

<210> SEQ ID NO 392
<211> LENGTH: 241
<212> TYPE: DNA
<213> ORGANISM: Homo sapiens

<400> SEQUENCE: 392
gaggtactaa atggtatcct tagattaaaa ttttgtgctt gataacagct gttttttcta       60
cattagaaat aagatgccac acaaggaact acattccaga tttaaagaaa tgaaaggata      120
ccattagtgt gtataacaga ttattgttca tacttgtaaa gcatcttatg tcattgagaa      180
tataaagaac agtgccttag aagacagtga aaggtaagct ctagcttaat gtctatgatt      240
t                                                                     241

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 393
ggcaggtaca taagcataat cagttatgga cagcttcttg tataaattgc tattcancaa       60
```

| tacataaact gcctnaaaga tttatgctta caggtagaca ttcaatttac caataaaaca | 120 |
| gcatgttctg aaaatatggg cacattttaa aacatattaa gacagttctg ttaaccataa | 180 |
| tagtcccaca gtatgactga gtaataagaa tctacttcaa aagnaaaaaa aaaattaatc | 240 |
| a | 241 |

<210> SEQ ID NO 394
<211> LENGTH: 241
<212> TYPE: DNA
<213> ORGANISM: Homo sapiens

<400> SEQUENCE: 394

| aggtacagca gcagtagatg gctgcaacaa ccttcctcct accccagccc agaaaatatt | 60 |
| tctgccccac cccaggatcc gggaccaaaa taaagagcaa gcaggccccc ttcactgagg | 120 |
| tgctgggtag ggctcagtgc cacattactg tgctttgaga aagaggaagg ggatttgttt | 180 |
| ggcactttaa aaatagagga gtaagcagga ctggagaggc cagagaagat accaaaattg | 240 |
| g | 241 |

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 395

| nggcnggnnc caanatatga aatntnanta tnatacatga tnaaaagctt tatntatttt | 60 |
| agtgagtaat taagtttaca ctgtgaataa ggattaattc ccagatgacc atctacagtt | 120 |
| actaccacat agagggtata cacggatgga tcgattacaa gaatataaaa cttatttttcc | 180 |
| ttcctgtatc cacatttctt tgcaatgtga atttgcaggc cctctcaaga agtggagtct | 240 |
| a | 241 |

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 396

| gaggtacacc ttgaatgaca atgctngag cccccctgtg gtcatcgacg cctccactgc | 60 |
| cattgatgca ccatccaacc tgcgtttcct ggccaccaca cccaattcct tgctggtatc | 120 |
| atggcagccg ccacgtgcca ggattaccgg ctacatcatc aagtatgaga agcctgggtc | 180 |
| tcctcccaga gaagtggtcc ctcggccccg ccctggtgtc acagaggcta ctattactgg | 240 |
| c | 241 |

<210> SEQ ID NO 397
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 397

```
ggcaggtacc agcagggga tgtgtttctg gggaattgtg gctctggaag cttcacggtt      60
tcccagaatg tggaaaatat atctgtgcan gatagaaatc ctgcccagag gctgtttctg    120
tctcatttga gctctccttc atgtggcaga gctgactgtg gcggtttagg agcctacatt    180
ttagaaaagc ttacctcaaa gttctgcatt gagcctgagc actggaaagg agataaaata    240
a                                                                    241
```

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 398

```
gangtgacca ngacatcacc tnacacntgg aaagcganga nttgaatggt gcntacaang     60
ccntacccnt tgcccannac ctgaacgcgc cttntgattg ggacagccgt gggaaggaca    120
gttatgaaac nantcanctg gatgaccana gtgntgaaac cnacanncac angcnntcna    180
cattatataa ncggaaagct aatgatgaga gcaatgatca ttccgatgtn attgatagtc    240
a                                                                    241
```

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 399

```
cagagtgaga tgggagtggg agggccaatc tgatacagaa gggggtgaag ggtagggccc     60
ctgagcagcc cacccttac cctgacgaag gcaatcctcc tctggaatgt ctcttccctc    120
ttcagtctgg gttctgcctc agccacgaac tgggaaggag tgaggaacat cccaacggca    180
atgagagtat cccagtgact ccaaacagga angaatcagt gttcanaaag tcagggccct    240
t                                                                    241
```

<210> SEQ ID NO 400
<211> LENGTH: 241
<212> TYPE: DNA
<213> ORGANISM: Homo sapiens

<400> SEQUENCE: 400

```
ggtactcttg ctcttttagc tagagtgtat gtgaaaataa agaaatacat cattgtattc     60
acaaccatgt gtcttcattt ataactttt gtttaaaaaa tttttagttc aagtttagtt    120
cattgatatt atcctctgaa tgcagttaag gctgggcaga aattctactc atgtgacatc    180
tgccacaggt ctattttgaa gcttttcttc taatgggcaa tgtttgtcct taccaggatt    240
t                                                                    241
```

<210> SEQ ID NO 401
<211> LENGTH: 241
<212> TYPE: DNA

<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 401
nncaggtact tgtagagca gagagaggct ttggttcctc ctttcttcaa tcacgtggag    60
atgtgtcatc acctgggatt tcatctgggc cgccttttct gggtcaacag ccaacacatg   120
ctggtaatga cggatggtat gtaagcgatc tttgttctca gcacggacat aacgccgtaa   180
ggcctggaga atgcgatgag gccgtggcgg gtcagactgc aaggcagcca ggtagttctc   240
c                                                                  241

<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 402
ggcaggtcca aaaaaaacct aaaaanngtt tcaggaatgt agagaaatat ccaacttaaa    60
tagcgaaaaa gtgcaccata attactgctg cactgcagtc atttctgcaa ttcccatgtt   120
tcttaaataa ctatcttgtc agataacaca caatataaag agcaattatg aaaaacagac   180
atttacatat acttctaaag tcttattggg aatatcctgt ttggccattg ggataaccaa   240
t                                                                  241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 403
aggtgttaac tacccgctcc gagacgggat tgatgacgag tcctatgang ccattttcaa    60
gccggtcatg tccaaagtaa tggagatgtt ccagcctagt gcggtggtct tacagtgtgg   120
ctcagactcc ctatctgggg atcggttagg ttgcttcaat ctaactatca aggacacgc   180
caagtgtgtg gaatttgtca agagctttaa cctgcctatg ctgatgctgg gaggcggtgg   240
t                                                                  241

<210> SEQ ID NO 404
<211> LENGTH: 241
<212> TYPE: DNA
<213> ORGANISM: Homo sapiens

<400> SEQUENCE: 404
caggtactgc aacccataaa atactgtttc ctcatatttc accttcctta atttggagtt    60
ttctgtcttc ttttcacggc attcaaagta ggaataaact ttgcttgtgt tgggtggata   120
ttgtttatag tgagtaacct tgtaggagtc ggtggccagg aggatgttga actcggcttc   180
tgccgcagga ttcatctcgg gccggaggac aaggggcccg cgcgccgcga gctccctgac   240
c                                                                  241

<210> SEQ ID NO 405
<211> LENGTH: 266
<212> TYPE: DNA
<213> ORGANISM: Homo sapiens

<400> SEQUENCE: 405

| ttctgggctg | gggagtggag | agaaagaagt | tgcagggctt | acaggaaatc | ccagagcctg | 60 |
| aggttttctc | ccagatttga | gaactctaga | ttctgcatca | ttatctttga | gtctatattc | 120 |
| tcttgggctg | taagaagatg | aggaatgtaa | taggtctgcc | ccaagccttt | catgccttct | 180 |
| gtaccaagct | tgtttccttg | tgcatccttc | ccaggctctg | gctgcccctt | attggagaat | 240 |
| gtgatttcca | agacaatcaa | tccaca | | | | 266 |

<210> SEQ ID NO 406
<211> LENGTH: 231
<212> TYPE: DNA
<213> ORGANISM: Homo sapiens

<400> SEQUENCE: 406

| ttggtgaaga | accattcctc | ggcatccttg | cggttcttct | ctgccatctt | ctcatactgg | 60 |
| tcacgcatct | cgttcagaat | gcggctcagg | tccacgccag | gtgcagcgtc | catctccaca | 120 |
| ttgacatctc | cacccacctg | gcctctcagg | gcattcatct | cctcctcgtg | gttcttcttc | 180 |
| aggtaggcca | gctcctcctt | caggctctca | atctgcatct | ccaggtcagc | t | 231 |

<210> SEQ ID NO 407
<211> LENGTH: 266
<212> TYPE: DNA
<213> ORGANISM: Homo sapiens

<400> SEQUENCE: 407

| cagcatcatt | gtttataatc | agaaactctg | gtccttctgt | ctggtggcac | ttagagtctt | 60 |
| ttgtgccata | atgcagcagt | atggagggag | gattttatgg | agaaatgggg | atagtcttca | 120 |
| tgaccacaaa | taaataaagg | aaaactaagc | tgcattgtgg | gttttgaaaa | ggttattata | 180 |
| cttcttaaca | attcttttt | tcagggactt | ttctagctgt | atgactgtta | cttgaccttc | 240 |
| tttgaaaagc | attcccaaaa | tgctct | | | | 266 |

<210> SEQ ID NO 408
<211> LENGTH: 261
<212> TYPE: DNA
<213> ORGANISM: Homo sapiens

<400> SEQUENCE: 408

| ctgtgtcagc | gagcctcggt | acactgattt | ccgatcaaaa | gaatcatcat | ctttaccttg | 60 |
| acttttcagg | gaattactga | actttcttct | cagaagatag | ggcacagcca | ttgccttggc | 120 |
| ctcacttgaa | gggtctgcat | ttgggtcctc | tggtctcttg | ccaagtttcc | cagccactcg | 180 |
| agggagtaat | atctggaggg | caaagaagag | acttatgtta | ttgttgaacc | tccagccaca | 240 |
| gggaggagca | tgggcatggg | t | | | | 261 |

<210> SEQ ID NO 409
<211> LENGTH: 266
<212> TYPE: DNA
<213> ORGANISM: Homo sapiens

<400> SEQUENCE: 409

```
gctgacagta atacactgcc acatcttcag cctgcaggct gctgatggtg agagtgaaat    60
ctgtcccaga cccgctgcca ctgaatcggt cagggatccc ggattccgg gtagatgccc    120 agtaaatgag cagtttagga ggctgtcctg gtttctgctg gtaccaagct aagtagttct    180
tattgttgga gctgtctaaa acactctggc tggtcttgca gttgatggtg ccctctcgc    240 ccagagacac agccagggag tgtgga                                        266
```

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 410

```
caaaaggtnc tttttgntca aaancnattt ttattccttg atattttct tttttttttt     60 tttgnggatg gggacttgtg aattttttcta aagggnnnn ttnannnngg aagaaaaccn   120
ngntccggtt ccagccaaac cngtngctna ctttccacct tntttccacc tccctcnggt   180
t                                                                    181
```

<210> SEQ ID NO 411
<211> LENGTH: 261
<212> TYPE: DNA
<213> ORGANISM: Homo sapiens

<400> SEQUENCE: 411

```
gccctgcag tacttggccg atgtggacac ctctgatgag gaaagcatcc gggctcacgt     60
gatggcctcc caccattcca gcggagagg ccgggcgtct tctgagagtc agggtctagg   120
tgctggagtg cgcacggagg ccgatgtaga ggaggaggcc ctgaggagga agctggagga   180
gctggccagc aacgtcagtg accaggagac ctcgtccgag gaggaggaag ccaaggacga   240
aaaggcagag cccaacaggg a                                              261
```

<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412

```
nttttntctt tacaattcag tcttcaacaa cttgagagct ttcttcatgt tgncaagcaa    60
cagagctgta tctgcaggnt cgtaagcata nagacngttt gaatatcttc cagngatatc   120
ggctctaact gncagagatg ggtcaacaaa cataatcctg gggacatact g             171
```

<210> SEQ ID NO 413
<211> LENGTH: 266
<212> TYPE: DNA
<213> ORGANISM: Homo sapiens

<400> SEQUENCE: 413

```
ttaggaccaa agatagcatc aactgtattt gaaggaactg tagtttgcgc attttatgac    60 attttttataa agtactgtaa ttctttcatt gagggctat gtgatggaga cagactaact   120
cattttgtta tttgcattaa aattattttg ggtctctgtt caaatgagtt tggagaatgc   180
```

```
ttgacttgtt ggtctgtgta aatgtgtata tatatatacc tgaatacagg aacatcggag        240
acctattcac tcccacacac tctgct                                              266
```

<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 414

```
tttgccataa ttgagtgaaa agtggcagat ggcattaact ctgctccgct tcaagctggc         60
tccatgacca ctcaaggcct ccccancctg ttcgtcaagt tgtcctcaag tccaagcaat        120
ggaatccatg tgtttgcaaa aaaagtgtgc tanttttaag gnctttcgta taagaatnaa        180
tganacaatt ttcctaccaa aggangaaca aaaggataaa tataatacaa aatatatgta        240
tatggttgtt tgacaaatta tataac                                              266
```

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 415

```
cctccatcca gtctattaat tgttgccggg aagctanagt aagtagttcg ccagttaata         60
gtttgcgcaa cgttgttgcc attgctacag gcatcgtggt gtnacgctcg tcgattggta        120
tggcttcatt cagctccggt tcccaacgat caaggcgagt tacatgatcc cccatgttgt        180
gcaaaaaagc ggttagctcc ttcggtcctc cgatcgttgt canaagtaag ttggccgcag        240
tgttatcact catggttatg gcagca                                              266
```

<210> SEQ ID NO 416
<211> LENGTH: 878
<212> TYPE: DNA
<213> ORGANISM: Homo sapiens

<400> SEQUENCE: 416

```
cctgacgata gccatggctg taccacttaa ctatgattct attccaactg ttcagaatca         60
tatcacaaaa tgacttgtac acagtagttt acaacgactc ccaagagagg aaaaaaaaaa        120
aaaaagacgc ctcaaaattc actcaacttt tgagacagca atggcaatag gcagcagaga        180
agctatgctg caactgaggg cacatatcat tgaagatgtc acaggagttt aagagacagg        240
ctggaaaaaa tctcatacta agcaaacagt agtatctcat accaagcaaa accaagtagt        300
atctgctcag cctgccgcta acagatctca caatcaccaa ctgtgcttta ggactgtcac        360
caaagtcaga ttcggtgcta accaggtggc atctatgatc aacgtcgccc ctcttattta        420
acaaagggct ctgaaggagg tgttctccaa gcaacaagga gactgcttca gtacaagact        480
ttgcaccttg aattcaattg catcaagtgt ggatagcaaa ataagtatct taccattgaa        540
atatgtgttc agcctaagat tttacccacc agcagaacaa aagtgagggt gagagggatg        600
ggccagtgag gggatggggg agaaaaaaaa atcacaggat taccaccaaa gccttgtttt        660
```

| | |
|---|---|
| aaaagggctc ccttcactat tcaggaaggg aagtggaagg agaaattaac caattcctgc | 720 |
| cacagcagcc cttttggct gcttccacaa tagatacttt atggagtggc acagccaacc | 780 |
| ctatctgtga cctgccctgc ggataaacac agccaagcag gtttaattag atcaaagaca | 840 |
| caaagggcta ttccctcctt tcataacaac gcagacct | 878 |

<210> SEQ ID NO 417
<211> LENGTH: 514
<212> TYPE: DNA
<213> ORGANISM: Homo sapiens

<400> SEQUENCE: 417

| | |
|---|---|
| ttctgacttc tagaagacta aggctggtct gtgtttgctt gtttgcccac ctttggctga | 60 |
| tacccagaga acctgggcac ttgctgcctg atgcccaccc ctgccagtca ttcctccatt | 120 |
| cacccagcgg gaggtgggat gtgagacagc ccacattgga aaatccagaa accgggaac | 180 |
| agggatttgc ccttcacaat tctactcccc agatcctctc ccctggacac aggagaccca | 240 |
| cagggcagga ccctaagatc tggggaaagg aggtcctgag aaccttgagg tacccttaga | 300 |
| tcctttcta cccactttcc tatggaggat tccaagtcac cacttctctc accggcttct | 360 |
| accagggtcc aggactaagg cgttttctcc atagcctcaa cattttggga atcttccctt | 420 |
| aatcacccctt gctcctcctg ggtgcctgga agatggactg gcagagacct ctttgttgcg | 480 |
| ttttgtgctt tgatgccagg aatgccgcct agtt | 514 |

<210> SEQ ID NO 418
<211> LENGTH: 352
<212> TYPE: DNA
<213> ORGANISM: Homo sapiens

<400> SEQUENCE: 418

| | |
|---|---|
| ctgcaccagc gattaccagt ggcattcaaa tactgtgtga ctaaggattt tgtatgctcc | 60 |
| ccagtagaac cagaatcaga caggtatgag ctagtcaaca gcaagtcttt gttggattcg | 120 |
| agtaggctca ggatctgctg aaggtcggag gagttagtcc ccgcaatcaa gagcctgtct | 180 |
| tcctgaagcc cttggtgata ttttgccact cagccaagaa tgaggatgca tccttcagat | 240 |
| tctctatgtc ccgaacctgg aacccatcca cgccagcttg cagccaaaac tccagagcat | 300 |
| ccttcacctt ggtggaaaaa aaaaaaaaaa aaaaaaaaa aaaaaaaaa aa | 352 |

<210> SEQ ID NO 419
<211> LENGTH: 344
<212> TYPE: DNA
<213> ORGANISM: Homo sapiens

<400> SEQUENCE: 419

| | |
|---|---|
| ctggacacca taatcccttt taagtggctg gatggtcaca cctctcccat tgacaagctg | 60 |
| ggttaagtca ataggttgac taggatcaac acgacccaaa tcaataagat actgcagtct | 120 |
| attgagactc aaaggcttat actggcgtct gaaactatgt ccttcgttaa acccgtattt | 180 |
| tgggattcgg atgtaaaatg gagtctggcc tccctcaaag cccaagcggg gccgggttcc | 240 |
| tctttgcctt tctcctttat ggcctctgcc acattttcta cctcttctcc gacctcttgg | 300 |
| tcttctctcc ggtttcttgg agccgggatt cggctttaag ttgg | 344 |

<210> SEQ ID NO 420
<211> LENGTH: 935
<212> TYPE: DNA
<213> ORGANISM: Homo sapiens

<400> SEQUENCE: 420

```
cgaaagtcaa cgttaagggg ctcaggtgaa ccatgatgat gaccttctgt tgactttgaa      60
atattggctc ttgtgggtga caaaagccag acaagctgtg gctgtggtcc gattttaaga     120
cgaggttctc aaagatccaa aggagggaaa gggtattgga aacactgtgt atcatctgag     180
acacacgtgt cctcatgatc ttaaatgcct actttaaagc cacctaatac tgcccttcat     240
tgtggtcaga agagatttct acaaaagcac tcagaattct ggaggcagtt gtgattttgc     300
catgtggcag ttggtttgtg gagttgggca ggtgtgaaag ggtaaaactc cacttctgaa     360
tgctgcttct gcccctggg acccagcaca ttgttagacc atcttcttga ctgaaaattc     420
tctcctgatg ctgagccctg caccaccacc ttccttttcc taactatgaa ttgatggcaa     480
agtccactca aaacaaccag ttaagtgctc acgagagagt agtcaagcac ctccagaaag     540
aaacggggtt tttgttcaca tagcaggaag tgactccctg ggtggtaatt tatcttggaa     600
acacaggtag attggcagaa aacgggaac atgtaggtac cgcgatgttg gtgcatgtcc     660
attactttgg gataggcttt ctcagtcttt cctcaaatga tagttgagcc agttttccag     720
tggcaattct gagtgacttg cgcttgtctt atggtgtggt caagggacgt tcagaactac     780
ggaaaacttt tactgaaaca gcgaagcaga gtataccggc atgagaggga agatgaacac     840
tcacctatgt accactcttt gacaataaat atagtatttc tcaaaaaaaa aaaaaaaaaa     900
agtaaaaaaa ctgaaatcgc aagtcaaaaa atcca                                935
```

<210> SEQ ID NO 421
<211> LENGTH: 745
<212> TYPE: DNA
<213> ORGANISM: Homo sapiens

<400> SEQUENCE: 421

```
ggcttcgagc ggccgcccgg gcaggtccta gatgtcattt gggacccttc acaaccattt      60
tgaagccctg tttgagtccc tgggatatgt gagctgtttc tatgcataat ggatattcgg     120
ggttaacaac agtcccctgc ttggcttcta ttctgaatcc ttttctttca ccatggggtg     180
cctgaagggt ggctgatgca tatggtacaa tggcacccag tgtaaagcag ctacaattag     240
gagtggatgt gttctgtagc atcctattta aataagccta ttttatcctt tggcccgtca     300
actctgttat ctgctgcttg tactggtgcc tgtacttttc tgactctcat tgaccatatt     360
ccacgaccat ggttgtcatc cattacttga tcctacttta catgtctagt ctgtgtggtt     420
ggtggtgaat aggcttcttt ttacatggtg ctgccagccc agctaattaa tggtgcacgt     480
ggacttttag caagcgggct cactggaaga gactgaacct ggcatggaat tcctgaagat     540
gtttggggtt tttttctttc ttaatcgaaa gttaacattg tctgaaagt tttgttagaa     600
ctactgcgga acctcaaaat cagtagattt ggaagtgatt caaagctaaa cttttccctt     660
ggccctcctt gtgttctaat tgcttgcaag tgtaatacta ggatgtccaa gatgccagtt     720
tttgcttctt tgttagttgt cagac                                           745
```

<210> SEQ ID NO 422
<211> LENGTH: 764
<212> TYPE: DNA
<213> ORGANISM: Homo sapiens

<400> SEQUENCE: 422

```
gagttcagta gcaaagtcac acctgtccaa ttccctgagc tttgctcact cagctaatgg      60
```

```
gatggcaaag gtggtggtgc tttcatcttc aggcagaagc ctctgcccat ccccctcaag      120
ggctgcaggc ccagttctca tgctgccctt gggtgggcat ctgttaacag aggagaacgt      180
ctgggtggcg gcagcagctt tgctctgagt gcctacaaag ctaatgcttg gtgctagaaa      240
catcatcatt attaaacttc agaaaagcag cagccatgtt cagtcaggct catgctgcct      300
cactgcttaa gtcctgcag gagccgcctg ccaagctccc cttcctacac ctggcacact      360
ggggtctgca caaggctttg tcaaccaaag acagcttccc ccttttgatt gcctgtagac      420
tttggagcca agaaacactc tgtgtgactc tacacacact tcaggtggtt tgtgcttcaa      480
agtcattgat gcaacttgaa aggaaacagt ttaatggtgg aaatgaacta ccattataa       540 cttctgtttt tttattgaga aaatgattca cgaattccaa atcagattgc caggaagaaa      600
taggacgtga cggtactggg ccctgtgatt ctcccagccc ttgcagtccg ctaggtgaga      660
ggaaaagctc tttacttccg cccctggcag ggacttctgg gttatgggag aaaccagaga      720
tgggaatgag gaaaatatga actacagcag aagcccctgg gcag                      764
```

<210> SEQ ID NO 423
<211> LENGTH: 1041
<212> TYPE: DNA
<213> ORGANISM: Homo sapiens

<400> SEQUENCE: 423

```
ctcagagagg ttgaaagatt tgcctacgaa agggacagtg atgaagctaa gctctagatc      60
caggatgtct gacttcaaat tgaaactccc aaagtaatga gtttggaagg gtgggtgtg      120 gcctttccag gatggggtc ttttctgctc ccagcggata gtgaaacccc tgtctgcacc      180
tggttgggcg tgttgctttc ccaaaggttt ttttttttagg tccgtcgctg tcttgtggat      240
taggcattat tatctttact ttgtctccaa ataacctgga gaatggagag agtagtgacc      300
agctcagggc cacagtgcga tgaggaccat cttctcacct ctctaaatgc aggaagaaac      360
gcagagtaac gtggaagtgg tccacaccta ccgccagcac attgtgaatg acatgaaccc      420
cggcaacctg cacctgttca tcaatgccta caacaggtat tgggatgtag ttcagccaca      480
tcattgctat ttatgaggtg tcttctgtag atccgaaatg tgggacagat gagagggaga      540
gtataaaatg agcggaagag gcaggctctg agtttgagca aatagattaa taggacaggt      600
gtccccagga aggacacctg gcctgtaagc tggttcctgg cattcagctc gccttgcagg      660
gatctgaaca aacactccag accactgggg gtgcagacgt gagagggacg cagtcgcaca      720
ctcagagggt tgagagtaaa tatgtgtgcc cgctgctgac cttcacgaaa ggccaaatgt      780
aagaagagct aagtgagaga gcagcaaagc actcctggag gccggggata atccaggcag      840
gcttctggga gtttgtcatt ccaaggataa ggaggacctg aacatggcct ttgcctaagg      900
cgtggccctc tcaaccagca ctaggtgctt atctggagct cagctagggg aggagacagc      960
tcagggccat tggtgtcagc cagagactct gtaatcttcc agggagctcg ctcaacctgc     1020
tgagctcgct ctgccacgca c                                              1041
```

<210> SEQ ID NO 424
<211> LENGTH: 1288
<212> TYPE: DNA
<213> ORGANISM: Homo sapiens

<400> SEQUENCE: 424

```
ctaagaactg agacttgtga cacaaggcca acgacctaag attagcccag ggttgtagct       60
ggaagaccta caacccaagg atggaaggcc cctgtcacaa agcctaccta gatggataga      120
```

```
ggacccaagc gaaaaaggta tctcaagact aacggccgga atctggaggc ccatgaccca    180
gaacccagga aggatagaag cttgaagacc tggggaaatc ccaagatgag aaccctaaac    240
cctacctctt ttctattgtt tacacttctt actcttagat atttccagtt ctcctgttta    300
tctttaagcc tgattctttt gagatgtact ttttgatgtt gccggttacc tttagattga    360
cagtattatg cctgggccag tcttgagcca gcttaaatc acagctttta cctatttgtt     420
aggctatagt gttttgtaaa cttctgtttc tattcacatc ttctccactt gagagagaca    480
ccaaaatcca gtcagtatct aatctggctt ttgttaactt ccctcaggag cagacattca    540
tataggtgat actgtatttc agtcctttct tttgacccca gaagccctag actgagaaga    600 taaatggtc aggttgttgg ggaaaaaaa gtgccaggct ctctagagaa aaatgtgaag       660
agatgctcca ggccaatgag aagaattaga caagaaatac acagatgtgc cagacttctg    720
agaagcacct gccagcaaca gcttccttct ttgagcttag tccatccctc atgaaaaatg    780
actgaccact gctgggcagc aggagggatg atgaccaact aattcccaaa ccccagtctc    840
attggtacca gccttgggga accacctaca cttgagccac aattggtttt gaagtgcatt    900
tacaagtttc tggcatcact accactactg attaaacaag aataagagaa cattttatca    960
tcatctgctt tattcacata aatgaagttg tgatgaataa atctgctttt atgcagacac   1020
aaggaattaa gtggcttcgt cattgtcctt ctacctcaaa gataatttat tccaaaagct   1080
aagataaatg gaagactctt gaacttgtga actgatgtga aatgcagaat ctcttttgag   1140
tctttgctgt ttggaagatt gaaaaatatt gttcagcatg ggtgaccacc agaaagtaat   1200
cttaagccat ctagatgtca caattgaaac aaactgggga gttggttgct attgtaaaat   1260
aaaatatact gttttgaaaa aaaaaaac                                      1288

<210> SEQ ID NO 425
<211> LENGTH: 446
<212> TYPE: DNA
<213> ORGANISM: Homo sapiens

<400> SEQUENCE: 425
ccacttaaag ggtgcctctg ccaactggtg gaatcatcgc cacttccagc accacgccaa      60
gcctaacatc ttccacaagg atcccgatgt gaacatgctg cacgtgtttg ttctgggcga    120
atggcagccc atcgagtacg gcaagaagaa gctgaaatac ctgccctaca atcaccagca    180
cgaatacttc ttcctgattg ggccgccgct gctcatcccc atgtatttcc agtaccagat    240
catcatgacc atgatcgtcc ataagaactg ggtggacctg gcctgggccg tcagctacta    300
catccggttc ttcatcacct acatcccttt ctacggcatc ctgggagccc tcctttcct    360 caacttcatc aggttcctgg agagccactg gtttgtgtgg gtcacacaga tgaatcacat    420
cgtcatggag attgaccagg aggacc                                        446

<210> SEQ ID NO 426
<211> LENGTH: 874
<212> TYPE: DNA
<213> ORGANISM: Homo sapiens

<400> SEQUENCE: 426
tttttttttt tttttttttt tttttcaat taaagatttg atttattcaa gtatgtgaaa      60
acattctaca atgaaaactt ttattaaatg ctgcatgtac tgtgctatgg accacgcaca    120
tacagccatg ctgtttcaga agacttgaaa tgccattgat agtttaaaaa ctctacaccc    180
```

-continued

```
gatggagaat cgaggaagac aatttaatgt ttcatctgaa tccagaggtg catcaaatta    240
aatgacagct ccacttggca ataatagct gttacttgat ggtatccaag aagaaatggt    300
tggtgatgga taaattcaga aatgcttccc caaaggtggg tggttttttaa aaagttttca   360 ggtcacaacc cttgcagaaa acactgatgc ccaacacact gattcgcggt ccaggaaaca   420
cgggtcttcc aagttccaag gggctggggt tccccaacga tcaagttcct gtgctgtaat   480
caagagggtc ctttggactg gatagggagc acttgggagc tgtacaccat cagtcataat   540
ggatggcagt gtaaaagatg atccaaatga cctgagatgc tcctgaggag tggtgcacca   600
gacccaggag tgccactgta gggctgcttc tttgctttag tcatcacaca cacacacagc   660
tccagagcag caatggcctt tcctgtaaca ggaaaaaagc ctcctgctat tcccaagaac   720
cctcgtaatg gcaaaactcc ccaaatgaca cccaggacca cagcaatgat ctgtcggaac   780
cagtagatca catctaaaaa ttcatcctta tcctcccagg ccgcgtcgct ccgcagcacc   840
ttactccaga cggagacttt gagggccccg ttgg    874
```

<210> SEQ ID NO 427
<211> LENGTH: 638
<212> TYPE: DNA
<213> ORGANISM: Homo sapiens

<400> SEQUENCE: 427

```
acttgtaatt agcacttggt gaaagctgga aggaagataa ataacactaa actatgctat    60
ttgatttttc ttcttgaaag agtaaggttt acctgttaca ttttcaagtt aattcatgta   120
aaaaatgata gtgatttga tgtaatttat ctcttgtttg aatctgtcat tcaaaggcca   180
ataatttaag ttgctatcag ctgatattag tagctttgca accctgatag agtaaataaa   240
ttttatgggc gggtgccaaa tactgctgtg aatctatttg tatagtatcc atgaatgaat   300
ttatggaaat agatatttgt gcagctcaat ttatgcagag attaaatgac atcataatac   360
tggatgaaaa cttgcataga attctgatta aatagtgggt ctgtttcaca tgtgcagttt   420
gaagtattta ataaccact cctttcacag tttattttct tctcaagcgt tttcaagatc    480
tagcatgtgg attttaaaag atttgccctc attaacaaga ataacattta aaggagattg   540
tttcaaaata ttttttgcaaa ttgagataag gacagaaaga ttgagaaaca ttgtatattt   600
tgcaaaaaca agatgtttgt agctgtttca gagagagt    638
```

<210> SEQ ID NO 428
<211> LENGTH: 535
<212> TYPE: DNA
<213> ORGANISM: Homo sapiens

<400> SEQUENCE: 428

```
acaagatgat tcttcctcct caatttgaca gatcaaagaa gtatcccttg ctaattcaag    60
tgtatggtgg tccctgcagt cagagtgtaa ggtctgtatt tgctgttaat tggatatctt   120
atcttgcaag taaggaaggg atggtcattg ccttggtgga tggtcgagga acagcttttcc   180 aaggtgacaa actcctctat gcagtgtatc gaaagctggg tgtttatgaa gttgaagacc   240
agattacagc tgtcagaaaa ttcatagaaa tgggtttcat tgatgaaaaa agaatagcca   300 tatgggctg gtcctatgga ggatacgttt catcactggc ccttgcatct ggaactggtc   360
ttttcaaatg tggtatagca gtggctccag tctccagctg gaatattac gcgtctgtct   420 acacagagag attcatgggt ctcccaacaa aggatgataa tcttgagcac tataagaatt   480
caactgtgat ggcaagagca gaatatttca gaaatgtaga ctatcttctc atcca         535
```

<210> SEQ ID NO 429
<211> LENGTH: 675
<212> TYPE: DNA
<213> ORGANISM: Homo sapiens

<400> SEQUENCE: 429

```
actatttca ccctgagca ttaacactgc ataccaaggg ggggtgggtc aagaagctgg      60
ttagatcgaa gcacaagcac aagccactga tattctctat gtgatcaggt ttttacaaaa     120
aaatacatag ttttcaataa ataatgctta attttacaac tttgatacag caatgtcata    180
caccgtttca acacactaca ctctgcatgc tagatagtct acgagaagac gaaactttgc    240
catgcatttt ctttcccccc tagtgctatc aaacacttca tcctccagcg cactgcctca    300
ggtagctta ccttctctct gtttcacagc aataggccgt gcgctggcat gcaaactcta    360
aaaaggtcc cccccacaaa ccactcagac ttctacacaa aagggtttt cagcttttct     420
gctcccaaac ctggagtggc taagaaagta agtttcatgt ggccttggaa aatacacact    480
tgttaacagt gtcatgctga aaactgctct aaaacatcag gtggttctgt cctggtggcc    540
gtcacgaagc attatgggat gccataacca ctaggagtcc caaaccggaa aaaataggcc    600
tccgttttaa aacagtcaat tcaaaaaagg tgtcacagaa caaatgcaaa agactcttaa   660
acccacaaca tatgt                                                     675
```

<210> SEQ ID NO 430
<211> LENGTH: 434
<212> TYPE: DNA
<213> ORGANISM: Homo sapiens

<400> SEQUENCE: 430

```
acctctgcca gaagtccagc gagaggacct cacagtagag cacaggccac tccgggagtg     60
catcagaaga ttcatcctca tggaggaaga aggcttcaaa cgtgaatggg taggagaagt    120
gagccacctt gtccattgcc agggacttgg tggtgcaggt ctgtgttact cctgagagct    180
gctggaatgc tgggcttgac cagtgagcag ttggcaattc tacaaagaag tggacgtaga    240
gattgtcata ctcatagcct tgggctgaaa cgacctctcc atttacaaag agccggaggg    300
cacctgggac agtcatctca agtcggtgc ctacgaggct gctgagatac tccttgtgcc    360
ggccataaag atccttgaac actcgccgtt cccgctcctc ctcctccggc tgtgcgtggg    420
gggaaacatt gtcg                                                      434
```

<210> SEQ ID NO 431
<211> LENGTH: 581
<212> TYPE: DNA
<213> ORGANISM: Homo sapiens

<400> SEQUENCE: 431

```
acacaagcct ccagcccgac ccagcggcct aatgaaactc tggcaaccta tcctgggcgt     60
ggccacgagt atccagctcc aagcccaagt gaggcgggga gtcaacttcc ccatgattgc    120
caagtgacca agaccagaag cagggacgat taggctagtt ctgcggcaag gtgaactgga    180
gaccctgtct ctgccctcct tccctggcct gtcccacaga catcccgttg tttaacccac    240
tgcctttgca aggacctgct ctgtccactc caaatcaaag gatacttgca tccttcttac    300
acagactccc atctctctgc tcatagtggt cccaggctgc ccgagaaaaa gaaacttggg    360
tcagtagaag gctcattagt gtgaaggagt gagaggccag gccttcctgt gacataatgc    420
```

| | |
|---|---|
| ttctatgctt gtttcctaaa cacttggtcc acacacaata cctgggcagg aagagagaac | 480 |
| caagcaccac tggatggctc tggagccagg ggacttctat gcacatacaa ccaacatcac | 540 |
| cccactctgc tcatctgtgc ctccaccctg aacagcagag t | 581 |

<210> SEQ ID NO 432
<211> LENGTH: 532
<212> TYPE: DNA
<213> ORGANISM: Homo sapiens

<400> SEQUENCE: 432

| | |
|---|---|
| actccaactc aagtttacaa gttacacctt tgccacagcc ttggctaaat cttgaactag | 60 |
| tgcagaattc agctgtggta gagtgctgat cttagcatgc ttcgatgtgg catacttgtt | 120 |
| cttgacagtc atgtgctttg taagtccttg atttaccatg actacattct tagccaggtg | 180 |
| ctgcataact ggaagaagag attcttcagt atatgacagg taatgttgta gagttggtgt | 240 |
| ccattcacca ttatccagaa ttttcagtgc taagcaaaaa gctcctgctg caatttgaga | 300 |
| aggaggaaag tgcaccatgt catagtccaa catagttagt tccatcaggt atttggccaa | 360 |
| agtatgttgc tcgacatcaa cctctccaat cttagatgct ctccgaagga agtgcaaagg | 420 |
| tagaggccga cccagaccaa agtttaaagc tcttagaatc ttcatttcca tctgtctgat | 480 |
| ttggtgctta gtataagtgt tgtcagtcac aaaagcaaag tcaccaattt ct | 532 |

<210> SEQ ID NO 433
<211> LENGTH: 531
<212> TYPE: DNA
<213> ORGANISM: Homo sapiens

<400> SEQUENCE: 433

| | |
|---|---|
| acttggtttt acagctcctt tgaaaactct gtgtttggaa tatctctaaa aacatagaaa | 60 |
| acactacagt ggtttagaaa ttactaattt tacttctaag tcattcataa accttgtcta | 120 |
| tgaaatgact tcttaaatat ttagttgata gactgctaca ggtaataggg acttagcaag | 180 |
| ctcttttata tgctaaagga gcatctatca gattaagtta gaacatttgc tgtcagccac | 240 |
| atattgagat gacactaggt gcaatagcag ggatagattt tgttggtgag tagtctcatg | 300 |
| ccttgagatc tgtggtggtc ttcaaaatgg tggccagcca gatcaaggat gtagtatctc | 360 |
| atagttccca ggtgatattt ttcttattag aaaaatatta taactcattt gttgtttgac | 420 |
| acttatagat tgaaatttcc taatttattc taaattttaa gtggttcttt ggttccagtg | 480 |
| ctttatgttg ttgttgtttt tggatggtgt tacatattat atgttctaga a | 531 |

<210> SEQ ID NO 434
<211> LENGTH: 530
<212> TYPE: DNA
<213> ORGANISM: Homo sapiens

<400> SEQUENCE: 434

| | |
|---|---|
| acaagagaaa acccctaaaa aaaggatggc tttagatgac aagctctacc agagagactt | 60 |
| agaagttgca ctagctttat cagtgaagga acttccaaca gtcaccacta atgtgcagaa | 120 |
| ctctcaagat aaaagcattg aaaaacatgg cagtagtaaa atagaaacaa tgaataagtc | 180 |
| tcctcatatc tctaattgca gtgtagccag tgattattta gatttggata agattactgt | 240 |
| ggaagatgat gttggtggtg ttcaagggaa aagaaaagca gcatctaaag ctgcagcaca | 300 |
| gcagaggaag attcttctgg aaggcagtga tggtgatagt gctaatgaca ctgaaccaga | 360 |
| cttttgcacct ggtgaagatt ctgaggatga ttctgatttt tgtgagagtg aggataatga | 420 |

```
cgaagacttc tctatgagaa aaagtaaagt taaagaaatt aaaaagaaag aagtgaaggt        480
aaaatcccca gtagaaaaga aagagaagaa atctaaatcc aaatgtaatg                   530
```

<210> SEQ ID NO 435
<211> LENGTH: 677
<212> TYPE: DNA
<213> ORGANISM: Homo sapiens

<400> SEQUENCE: 435

```
accttatgat ctaattaata gatattagaa acagtagaaa gacaagttac acgtcaatgc         60
ccaatgacta gagtcaacat taaagagttg taatttaagt aatccaaact gacatctaat        120
tccaaaatca tttataaaat gtatttggct ttggaatcca caggacttca aacaagcaaa        180
gtttcactgc agatagtcac aaagatgcag atacactgaa atacttaaga gccttattaa        240 tgattttgt tattttggat cttctgtttt tttcttatta tggtccgaag cctccttaat         300
accaatttat cagacagaag catgtcatct tgttgttcaa gataatccag taaattttca       360
gtccattcaa gtgccgcttt atggctaata cgcttctctg gattcagttc tgttttcta        420 ctcttactgg aaggcttttg ctcagcagcc ttggtctggt cctcagcact ttcactgtca      480
gtcagcacct gacagcttga gtcactgctc cgagagtcga accactgatc aatattctca      540
atgtcaacat gttcacattc ttctgtgttc tgtaaaactg ttgctaaatt agctgctaaa      600
atggctcctt catcaatgtt catacctgaa ttctcttcat tgccagggaa aagttttttc      660
catgctttgg ttatggt                                                      677
```

<210> SEQ ID NO 436
<211> LENGTH: 573
<212> TYPE: DNA
<213> ORGANISM: Homo sapiens

<400> SEQUENCE: 436

```
acctcttagg gtgggagaaa tggtgaagag ttgttcctac aacttgctaa cctagtggac         60
agggtagtag attagcatca tccggataga tgtgaagagg acggctgttt ggataataat      120
taaggataaa atttggccag ttgacagatt ctgtttccag cagttttttac agcaacagtg     180 gagtgcttca gtattgtgtt cctgtaaatt taattttgat ccgcaatcat ttggtataca     240
atgctgtttg aagttttgtc ctattggaaa agtcttgtgt tgcagggggtg cagttaagat    300 cttttgtgatg aggaatggga tgggctaatt ttttgccgtt ttcttggaat tggggggcatg    360 gcaaatacag tagggtagtt tagttctta cacagaacat gataaactac acctgttgat     420
gtcaccgtct gtcaatgaat attatagaag gtatgaaggt gtaattacca taataacaaa      480
acaccctgtc tttagggctg acctttcgtc ctttgacctc ctcagcctcc attcccatct      540
tcgctcagac tgcaagtatg tttgtattaa tgt                                   573
```

<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 437

```
acaattggta tccatatctt gttgaaattg taatgggaaa acaatatatt tcaatctcta         60
```

```
tgtagatagt gggttttttgt tttcataata tattctttta gtttactgta tgagttttgc      120
aggactgcat aatagatcac cacaatcata acatcttagg accacagaca tttatgagat      180
catggcttct gtgggttaga agtatgctca tgtcttaact gggtcctctg ctcagtctta      240
tctggctgca atcaaggtgt cagctgggct gaattttcat ttggaatctt gactgggaaa      300
gagtctgctt ccaaggtcat gaagtttgct ggcaaaatgt atgtttttat gacagtatga      360
ctgaaatccc aagctatctc ctgacttttta gctgggtaat ctcaggccct aaatgttgcc      420
tacagttcct agaggctggt cacagttctt agccatgtgg atttcctcaa catggctgct      480
tgcttcatca agtcagcaag aatagcctgt catatcagtg tatatcaggc tcactcagga      540
taatttccct actgatgagc caaacactaa ctgattttag agcttaacta catctgcaaa      600
attcngttca ccagaggcaa gtcatattca gggaaggaga agtgt                      645

<210> SEQ ID NO 438
<211> LENGTH: 485
<212> TYPE: DNA
<213> ORGANISM: Homo sapiens

<400> SEQUENCE: 438
acagaattga gagacaagat tgcttgtaat ggagatgctt ctagctctca gataatacat       60
atttctgatg aaaatgaagg aaaagaaatg tgtgttctgc gaatgactcg agctagacgt      120
tcccaggtag aacagcagca gctcatcact gttgaaaagg ctttggcaat tctttctcag      180
cctacaccct cacttgttgt ggatcatgag cgattaaaaa atcttttgaa gactgttgtt      240
aaaaaaagtc aaaactacaa catatttcag ttggaaaatt tgtatgcagt aatcagccaa      300
tgtatttatc ggcatcgcaa ggaccatgat aaaacatcac ttattcagaa aatggagcaa      360
gaggtagaaa acttcagttg ttccagatga tgatgtcatg gtatcgagta ttctttatat      420
tcagttccta tttaagtcat ttttgtcatg tccgcctaat tgatgtagta tgaaaccctg      480
catct                                                                 485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc       60
aggttcaaca gtatggctcc aaatgatgaa atttcattct gattttctgg ctgaagacta      120
ttctgtttgt gtatgtccac cacagttact ttatcccttc atctgtggat gggcagaatg      180
aaacatatat ggaaatgttc tgtgcaataa aaacagcagt ggtaacacag atgtaggctc      240
tgagtgtctc actggagact gaagtccaca gatatgcaac aaagcctttg tctccctgat      300
gtttttgcct cctgctggtc atgtgctttc acacatcaag agaggacatt taacatttga      360
gccacagtgt catttgctgt tgtctgatgg ttggttggca gagaatttga actggagatg      420
aactttatta tccaggacgc tgagagtata acatgcatga cagagctttt agagcactgt      480
gatgtaacat gtcaagcaga aatagggagc atgtttacag ccattctatg aaa            533

<210> SEQ ID NO 440
<211> LENGTH: 341
<212> TYPE: DNA
<213> ORGANISM: Homo sapiens

<400> SEQUENCE: 440
```

```
catggggtag gggggtcggg gattcattga attgtggttg gcaggagcaa gccctgctca    60
cactctcaca ctcgcaccca gaattgtcaa agatacagat tgtaaaaatc tacgatccct   120
cagtctcact cacaaaaaat aaaatctcat gtccccaacg aacccagagt cagacgacag   180
ctggagcatt ggcagggaca gtcagaaagg agacaagtga aaacggtcag atggacacag   240
gcggaggaga aaagacagag ggagagagac catcgggaac aatcagaggg gccgagacga   300
tcagaaaagg gtcagcccga gacaggctga gccagagttt c                      341
```

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 441

```
aagtttgggg ataatttatt atgcagcaag agataataca caggacttct canagcactt    60
aatatgttaa tataaatctc caanaaaaaa gatatacaat gaaacattcc tcttagttat   120
ctggccaagg anactttntt tttttganaa tattcttcaa aaagctgatc taatgatatg   180
gctctggtcc tacaattcca tgtaacttct aaccttgatt ttatctcatg agcaaatcat   240
ttatccttcc agaacctcaa cttttccctt ttacaaagta gaaataaacc atctgccttt   300
acataaatca ttaatacagc cctggatggg cagattctga gctattttg gctgggggt    360 gggaaatagc ctgtggaggt cctaaaaaga tctacgggc tcgagatggt tctctgcaag   420
gtagcaggtg ggctcagggc ccatttcagt ctttgttccc caggccattt ccacaaaatg   480
gtgagaaata gtgtcttctt ttagcttgct cataactcaa agatgggggg catggacctg   540 ggccttttcta ggctagggca tgaacctcct cc                                572
```

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: (1)...(379)
<223> OTHER INFORMATION: n = A,T,C or G

<400> SEQUENCE: 442

```
tcccagctgc actgcttaca cgtcttcctt cgtnttcacc taccccgagg ctgactcctt    60
ccccagntgt gcagctgccc accgcaaggg cagcagcagc aatgagcctt cctctgactc   120
gctcagctca cccacgctgc tggccctgtg aggggcagg gaaggggagg cagccggcac    180
ccacaagtgc cactgcccga gctggtgcat tacagagagg agaaacacat cttccctaga   240
gggttcctgt agacctaggg aggaccttat ctgtgcgtga acacaccag gctgtgggcc    300 tcaaggactt gaaagcatcc atgtgtggac tcaagtcctt acctcttccg gagatgtagc   360
aaaacgcatg gagtgtgta                                                379
```

<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: (1)...(511)

<223> OTHER INFORMATION: n = A,T,C or G

<400> SEQUENCE: 443

```
acatgccccc aaaggctcgc ttcattgcta cgattctcta cttaaatcca cattcacagc      60
tattgcctca gaccctctgg aggaggggcc aggggttagc tggctttgaa tagcatgtag     120
agcacaggca gtgtggccac aaatgtcaca caggtgacca gggtgctata gatggtgttc    180
ctgttgactt gggcttctag tctctgctcc gtgtctgaca gtgccaagat catgctcccc    240
tgctccagca agaagctggg catagccccg tctgctggtt ccaccaggcc tgggtgtgct    300
gcagacttta caagctgaac cacccccagcc atttggctac aagtcttttc taggccatca    360
agctgctctc gtaagccttc tagacatgaa tggacttgcc tggaatgact aagctgctct    420
ttcaaggcag ctgaaaggac atcnacatct ctgtctctgg tcgggggact acctgcctgt    480
gacccagagt cctgccctgg cccagcagca t                                   511
```

<210> SEQ ID NO 444
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 444

```
acaggaagaa ttctacagtt aatctatcac agtgttccag caaagcatat gttgaaaact     60
acagttttca atctaacatc taaattttaa aaagtagcat ttcagcaaca aacaagctca    120
gagaggctca tggcaaaagt gaaataacag aactattgct cagatgtctg caaagtcaag    180
ctgctgccct cagctccgcc cacttgaagg cttaggcaga cacgtaaggt ggcggtggct    240
ccttggcagc accattcaca gtggcatcat catacgagg tagcagcacc gtagtgtcat    300
tgctggtaac ataaaccagg acatcagagg agttcctacc attgatgtat cggtagcagt    360
tccaaacaca gctaatcaag taaccettaa agtcaagat aatgctaata acagaagaa    420
taataaggac caaacaggta ggattcactg acatgacatc atctctgtag ggaaaattag    480
gaggcagttg ccgtatgtat tcctgaatgg agtttggata aataagcaca gtgattgcaa    540
ccaacancttt caggggcaaag tcaaagatct ggtaacagaa gaatgggatg atccaggctg    600
cgcgttgctt gt                                                        612
```

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 445

```
accatcctgt tccaacagag ccattgccta ttcctaaatt gaatctgact gggtgtgccc     60
ctcctcggaa cacaacagta gaccttaata gtggaaacat cgatgtgcct cccaacatga    120
caagctgggc cagctttcat aatggtgtgg ctgctggcct gaagatagct cctgcctccc    180
agatcgactc agcttggatt gtttacaata agcccaagca tgctgagttg gccaatgagt    240
atgctggctt tctcatggct ctgggtttga atgggcacct taccagctg gcgactctca    300
atatccatga ctacttgacc aagggccatg aaatgacaag cattggactg ctacttggtg    360
```

```
tttctgctgc aaaactaggc accatggata tgtctattac tcggcttgtt agcattcgca      420
ttcctgctct cttaccccca acgtccacag agttggatgt tcctcacaat gtccaagtgg      480
ctgcagtggt tggcattggc cttgtatatc aagggacagc tcacagacat actgcagaag      540
tcctgttggc tgagatagga cggcctcctg gtcctgaaat ggaatactgc actgacagag      600
agtcatactc cttagctgct ggcttggccc tgggcatggt ctncttgggg catggcagca      660
atttgatagg tatgtntgat ctcaatgtgc ctgagcagct ctatcagt                   708
```

<210> SEQ ID NO 446
<211> LENGTH: 612
<212> TYPE: DNA
<213> ORGANISM: Homo sapiens

<400> SEQUENCE: 446

```
acaagcaacg cgcagcctgg atcatcccat tcttctgtta ccagatcttt gactttgccc      60
tgaacatgtt ggttgcaatc actgtgctta tttatccaaa ctccattcag gaatacatac     120
ggcaactgcc tcctaatttt ccctacagag atgatgtcat gtcagtgaat cctacctgtt     180
tggtccttat tattcttctg tttattagca ttatcttgac ttttaagggt tacttgatta     240
gctgtgtttg gaactgctac cgatacatca atggtaggaa ctcctctgat gtcctggttt     300
atgttaccag caatgacact acggtgctgc tacccccgta tgatgatgcc actgtgaatg     360
gtgctgccaa ggagccaccg ccaccttacg tgtctgccta agccttcaag tgggcggagc     420
tgagggcagc agcttgactt tgcagacatc tgagcaatag ttctgttatt tcacttttgc     480
catgagcctc tctgagcttg tttgttgctg aaatgctact ttttaaaatt tagatgttag     540
attgaaaact gtagttttca acatatgctt tgctggaaca ctgtgataga ttaactgtag     600
aattcttcct gt                                                         612
```

<210> SEQ ID NO 447
<211> LENGTH: 642
<212> TYPE: DNA
<213> ORGANISM: Homo sapiens

<400> SEQUENCE: 447

```
actgaaagaa ttaaagtcag aagtcttccc aaaacaaaaa gaactgccca cagagaaaat      60
cctttctgat acttttcatt gctaaaataa acaggcgggg aaatgtggaa aagaaattca     120
acaaaataat gtagcaccag aagaacaagt cctagatgat tcaagttcaa aaggtaagct     180
ccagcaatgt ggaagaggta aagaccaatg tagacaagct gacgaggaat atcttctttt     240
ttggttttct ggaagtagag ttcaggaaaa gcatgaagcc agtaagccag ctgtgatatg     300
tagaaaaact tcatttgaaa tgtcatcagg ttatggggat aagccctcca taagatagtt     360
gggtctgaga tgtagttttc agagatgaga atgaatgtgc cccaaacaca ggcaaaaagg     420
tagaacgcac taagctgacc agattcatta aacttgctgt gttttgtttt ggagaagtgc     480
attcgcctgt taattttatc caacatatac tcttgaatta cggcatgaat aattatcgcc     540
actagcatgt agaagaaaac agtagccaaa tctttgatgc catagtaata aagggacact     600
gattcagtag cttgttcttc tgttgctggg agggtgacat tg                        642
```

<210> SEQ ID NO 448
<211> LENGTH: 394
<212> TYPE: DNA
<213> ORGANISM: Homo sapiens
<220> FEATURE:

```
<221> NAME/KEY: misc_feature
<222> LOCATION: (1)...(394)
<223> OTHER INFORMATION: n = A,T,C or G

<400> SEQUENCE: 448
accagaagac cttagaaaaa ggaggaaagg aggagaggca gataatttgg atgaattcct      60
caaagngttt gaaaatccag aggttcctag agaggaccag caacagcagc atcagcagcg    120
tgatgttatc gatgagccca ttattgaaga gccaagccgc ctccaggagt cagtgatgga    180
ggccagcaga acaaacatag atgagtcagc tatgcctcca ccaccacctc agggagttaa    240
gcgaaaagct ggacaaattg acccagagcc tgtgatgcct cctcagcagg tagagcagat    300
ggaaatacca cctgtagagc ttcccccaga agaacctcca aatatctgtc agctaatacc    360
agagttagaa cttctgccag aaaaagagaa ggag                                394

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: (1)...(494)
<223> OTHER INFORMATION: n = A,T,C or G

<400> SEQUENCE: 449
acaaaaaaca caaggaatac aacccaatag aaaatagtcc tgggaatgtg gtcagaagca     60
aaggcntgag tgtctttctc aaccgtgcaa agccgtgtt cttcccggga aaccaggaaa    120
aggatccgct actcaaaaac caagaattta aaggagtttc ttaaatttcg accttgtttc    180
tgaagctcac ttttcagtgc cattgatgtg agatgtgctg gagtggctat taacctttt     240
ttcctaaaga ttattgttaa atagatattg tggtttgggg aagttgaatt ttttataggt    300
taaatgtcat tttagagatg gggagaggga ttatactgca ggcagcttca gccatgttgt    360
gaaactgata aaagcaactt agcaaggctt cttttcatta tttttatgt ttcacttata     420
aagtcttagg taactagtag gatagaaaca ctgtgtcccg agagtaagga gagaagctac    480
tattgattag agcc                                                       494

<210> SEQ ID NO 450
<211> LENGTH: 547
<212> TYPE: DNA
<213> ORGANISM: Homo sapiens

<400> SEQUENCE: 450
actttgggct ccagacttca ctgtccttag gcattgaaac catcacctgg tttgcattct     60
tcatgactga ggttaactta aaacaaaaat ggtaggaaag cttttcctatg cttcgggtaa   120
gagacaaatt tgcttttgta gaattggtgg ctgagaaagg cagacagggc ctgattaaag    180
aagacatttg tcaccactag ccaccaagtt aagttgtgga acccaaaggt gacggccatg    240
gaaacgtaga tcatcagctc tgctaagtag ttaggggaag aaacatattc aaaccagtct    300
ccaaatggga tcctgtggtt acagtgaatg gccactcctg ctttatttt cctgagattg     360
ccgagaataa catggcactt atactgatgg gcagatgacc agatgaacat catcatccca    420
agaatatgga accaccgtgc ttgcatcaat agattttcc ctgttatgta ggcattcctg     480
ccatccattg gcacttggct cagcacagtt aggccaacaa ggacataata gacaagtcca    540
aaacagt                                                               547
```

```
<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 451
actacttnnt ggttaaaang ccactggtag agtcatctga ntgtaaacaa tgtccctgca      60
ctgctggaaa aatccactgg ctcccaagaa aagaaaatgg tctgaagcct ctgttgtggc     120
tctcacaact catctttccc taagtcatca agctccacat cactgaggtc aatgtcatcc     180
tccacgggaa gctcgccatc cctgccgtcc caaggctctc tctcaacgat ggtagggaaa     240
gccccgcctc ctacaggtgc cgtggagcca cgcccaaaag agagctccct gagaaactcg     300
ttgatgcctt gctcactgaa ggagcctttt agcagagcaa atttcatctt gcgtgcattg     360
atggcggcca tggcggggta ccca                                            384

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n = A,T,C or G

<400> SEQUENCE: 452
actctaaagt tgccactctc acaggggtca gtgataccca ctgaacctgg caggaacagt      60
cctgcagcca gaatctgcaa gcagcgcctg tatgcaacgt ttagggccaa aggctgtctg     120
gtggggttgt tcatcacagc ataatggcct agtaggtcaa ggatccaggg tgtgagggc      180
tcaaagccag gaaaacgaat cctcaagtcc ttcagtagtc tgatgagaac tttaactgtg     240
gactgagaag cattttcctc gaaccagcgg gcatgtcgga tggctgctaa ngcactctgc     300
aatactttga tatccaaatg gagttctgga tccagttttc naagattggg tggcactgtt     360
gtaatganaa tcttcactgt a                                               381

<210> SEQ ID NO 453
<211> LENGTH: 455
<212> TYPE: DNA
<213> ORGANISM: Homo sapiens

<400> SEQUENCE: 453
actgtgctaa acagcctata gccaagtttt aaagagttac aggaacaact gctacacatt      60
caaagaacag gcattcactg cagcctcctg atttgacctg atgggaggga caggagaatg     120
agtcactctg ccaccacttt tcctgccttg gatttgtaga ggatttgttt tgctctaatt     180
tgttttttcct atatctgccc tactaaggta cacagtctgg gcactttgaa aatgttaaag     240
ttttttaacgt ttgactgaca gaagcagcac ttaaaggctt catgaatcta ttttccaaaa     300
aaagtatgct ttcagtaaaa catttttacca ttttatctaa ctatgcactg acattttttgt   360
tcttcctgaa aagggggattt atgctaacac tgtattttta atgtaaaaat atacgtgtag    420
agatatttta acttcctgag tgacttatac ctcaa                                455

<210> SEQ ID NO 454
<211> LENGTH: 383
<212> TYPE: DNA
```

<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 454

```
acagagcanc tttacaagtt gtcacatttc tttataaatt ttttaaagc tacagtttaa      60
tacaaaatga attgcggttt tattacatta ataacctttc acctcagggt tttatgaaga    120
ggaaagggtt ttatgcaaaa gaaagtgcta caattcctaa tcattttaga cactttagga    180
gggggtgaag ttgtatgata aagcagatat tttaattatt tgttatcttt ttgtattgca    240
agaaatttct tgctagtgaa tcaagaaaac atccagattg acagtctaaa atggctactg    300
gtattttagt taattcaaaa atgaaacttt tcagtgattc actttactaa cattctattt    360
gagaaggctt attggtaaag ttt                                            383
```

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 455

```
actcctttan gacaaggaaa caggtatcag catgatggta gcagaaacct tatcaccaag     60
gtgcaggagc tgacttcttc caaagagttg tggttccggg cagcggtcat tgccgtgccc   120
attgctggag ggctgatttt agtgttgctt attatgttgg ccctgaggat gcttcgaagt   180
gaaaataaga ggctgcagga tcagcggcaa cagatgctct cccgtttgca ctacagcttt   240
cacggacacc attccaaaaa ggggcaggtt gcaaagttag acttggaatg catggtgccg   300
gtcagtgggc acgagaactg ctgtctgacc tgtgataaaa tgagacaagc agacctcagc   360
aacgataaga tcctctcgct tgt                                            383
```

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 456

```
acaaacattt tacaaaaaag aacattacca atatcagtgg cagtaagggc aagctgaaga     60
atangtagac tgagtttccg ggcaatgtct gtcctcaaag acatccaaac tgcgttcagg   120
cagctgaaac aggcttcttt cccagtgaca agcatatgtg gtcagtaata caaacgatgg   180
taaatgaggc tactacatag gcccagttaa caaactcctc ttctcctcgg gtaggccatg   240
atacaagtgg aactcatcaa ataatttaaa cccaaggcga taacaacact atttcccatc   300
taaactcatt taagccttca caatgtcgca atggattcag ttacttgcaa acgatcccgg   360
gttgtcatac agatacttgt tttttacaca taacgctgtg ccatcccttc cttcactgcc   420
ccagtcaggt ttcctgttgt tggaccgaaa ggggatacat tttagaaatg cttccctcaa   480
gacagaagtg agaagaaag gagaccctga ggccaggatc tattaaacct ggtgtgtgcg   540
caa                                                                  543
```

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 457

| | | | | | |
|---|---|---|---|---|---|
| actggtgcca | atattgncat | ggtgagctcc | tctctaatgt | cttccagggc | accaatatct | 60
| gcccatgtca | cattagggac | agtgacaaag | ccttcccttt | tggcagaggg | ttggactgag | 120
| gatagagcaa | caatgaaatc | attcagttca | atgcacagtc | cttgcatctg | ctcctctgag | 180
| agggatctt | ggtctcttag | caaccccagc | agcctttgta | attcatcctg | tgtttcagaa | 240
| gtgggctcag | ttcccagcct | ttcctcctgg | actcctttag | atggcaaatc | ttccatttca | 300
| ggatttttct | tctgctgttc | ctgtagcttc | attaagactc | tattgactgc | acacattgct | 360
| gcctctcggc | acagtgccat | gagatcagca | ccaacaaagc | ctggagttag | gtgtgctaag | 420
| tgacagaaat | caaaagcttg | aggaagcctc | agttttctgc | acaatgtttg | aagtattctt | 480
| tccctggatg | cttcatctgg | gatacctagg | catatttctc | ggtcgaacct | tcccgcacgt | 540
| ctca | | | | | 544

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458

| | | | | | |
|---|---|---|---|---|---|
| acctntaggc | tcaacggcag | aancttcacc | acaaaagcga | aatgggcaca | ccacagggag | 60
| aaaactggtt | gtcctggatg | tttgaaaagt | tggtcgttgt | catggtgtgt | tacttcatcc | 120
| tatctatcat | taactccatg | gcacaaagtt | atgccaaacg | aatccagcag | cggttgaact | 180
| cagaggagaa | aactaaataa | gtagagaaag | ttttaaactg | cagaaattgg | agtggatggg | 240
| ttctgcctta | aattgggagg | actccaagcc | gggaaggaaa | attccctttt | ccaacctgta | 300
| tcaattttta | caacttttttt | cctgaaagca | gtttagtcca | tactttgcac | tgacatactt | 360
| tttccttctg | tgctaaggta | ag | | | 382

<210> SEQ ID NO 459
<211> LENGTH: 168
<212> TYPE: DNA
<213> ORGANISM: Homo sapiens

<400> SEQUENCE: 459

| | | | | | |
|---|---|---|---|---|---|
| ctcgtactct | agccaggcac | gaaaccatga | agtagcctga | tccttcttag | ccatcctggc | 60
| cgccttagcg | gtagtaactt | tgtgttatga | atcacatgaa | agcatggaat | cttatgaact | 120
| taatcccttc | attaacagga | gaaatgcaaa | taccttcata | tcccctca | | 168

<210> SEQ ID NO 460
<211> LENGTH: 190
<212> TYPE: DNA
<213> ORGANISM: Homo sapiens
<220> FEATURE:

<221> NAME/KEY: misc_feature
<222> LOCATION: (1)...(190)
<223> OTHER INFORMATION: n = A,T,C or G

<400> SEQUENCE: 460

```
acanctgcta ccagggagcc gagagctgac tatcccagcc tcggctaatg tattctacgc     60
catggatgga gcttcacacg atttcctcct gcggcagcgg cgaaggtcct ctactgctac    120
acctggcgtc accagtggcc cgtctgcctc aggaactcct ccgagtgagg gaggaggggg    180
ctcctttccc                                                            190
```

<210> SEQ ID NO 461
<211> LENGTH: 495
<212> TYPE: DNA
<213> ORGANISM: Homo sapiens

<400> SEQUENCE: 461

```
acagacaggc ttctctgcta tcctccaggc agtgtaatag tcaaggaaaa gggcaacagt     60
attggatcat tccttagaca ctaatcagct ggggaaagag ttcattggca aaagtgtcct    120
cccaagaatg gtttacacca agcagagagg acatgtcact gaatgggaa agggaacccc    180
cgtatccaca gtcactgtaa gcatccagta ggcaggaaga tggctttggg cagtggctgg    240
atgaaagcag atttgagata cccagctccg gaacgaggtc atcttctaca ggttcttcct    300
tcactgagac aatgaattca gggtgatcat tctctgaggg gctgagaggt gcttcctcga    360
ttttcactac cacattagct tggctctctg tctcagaggg tatctctaag actagggct    420
tggtatatat gtggtcaaaa cgaattagtt cattaatggc ttccagcttg gctgatgacg    480
tccccactga cagag                                                      495
```

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: n = A,T,C or G

<400> SEQUENCE: 462

```
acactgaaac ataaatccgc aagtcaccac acatacaaca cccggcagga aaaaacaaa     60
aacagggngt ttacatgatc cctgtaacag ccatggtctc aaactcagat gcttcctcca    120
tctgccaagt gtgttttgga tacagagcac atcgtggctt ctggggtcac actcagctta    180
ggctgtgggt ccacagagca ctcatctggc tgggctatgg tggtggtggc tctactcaag    240
aagcaaagca gttaccagca cattcaaaca gtgtattgaa catcttttaa atatcaaagt    300
gagaaacaag aaggcaacat aataatgtta tcagaaagat gttaggaagt aaggacagct    360
gtgtaaagct tgaggctgaa aagtagcttg ccagcttcat ttctttggtt tcttgggtag    420
tgggcgccgg aacagcaaga tgtgaggttc tggttcatgg atcatataat ggacccatcc    480
ctgactctgc tga                                                        493
```

<210> SEQ ID NO 463
<211> LENGTH: 3681
<212> TYPE: DNA
<213> ORGANISM: Homo sapiens

<400> SEQUENCE: 463

```
tccgagctga ttacagacac caaggaagat gctgtaaaga gtcagcagcc acagccctgg     60
```

-continued

```
ctagctggcc ctgtgggcat ttattagtaa agttttaatg acaaaagctt tgagtcaaca      120
cacccgtggg taattaacct ggtcatcccc accctggaga gccatcctgc ccatgggtga      180
tcaaagaagg aacatctgca ggaacacctg atgaggctgc accttggcg aaagaacac       240
ctgacacagc tgaaagcttg gtggaaaaaa cacctgatga ggctgcaccc ttggtggaaa      300
gaacacctga cacggctgaa agcttggtgg aaaaaacacc tgatgaggct gcatccttgg      360
tggagggaac atctgacaaa attcaatgtt tggagaaagc gacatctgga aagttcgaac      420
agtcagcaga agaaacacct agggaaatta cgagtcctgc aaaagaaaca tctgagaaat      480
ttacgtggcc agcaaaagga agacctagga agatcgcatg ggagaaaaaa gaagacacac      540
ctagggaaat tatgagtccc gcaaaagaaa catctgagaa atttacgtgg gcagcaaaag      600
gaagacctag gaagatcgca tgggagaaaa agaaacacc tgtaaagact ggatgcgtgg       660
caagagtaac atcaataaa actaaagttt tggaaaaagg aagatctaag atgattgcat       720
gtcctacaaa agaatcatct acaaaagcaa gtgccaatga tcagaggttc ccatcagaat      780
ccaaacaaga ggaagatgaa gaatattctt gtgattctcg gagtctcttt gagagttctg      840
caaagattca agtgtgtata cctgagtcta tatcaaaa agtaatggag ataaatagag         900
aagtagaaga gcctcctaag aagccatctg ccttcaagcc tgccattgaa atgcaaaact      960
ctgttccaaa taaagccttt gaattgaaga tgaacaaac attgagagca gatccgatgt      1020
tcccaccaga atccaaacaa aaggactatg aagaaaattc ttgggattct gagagtctct      1080
gtgagactgt ttcacagaag gatgtgtgtt tacccaaggc tacacatcaa aaagaaatag     1140
ataaaataaa tggaaaatta gaagagtctc taataaaga tggtcttctg aaggctacct      1200
gcggaatgaa agtttctatt ccaactaaag ccttagaatt gaaggacatg caaactttca      1260
aagcagagcc tccggggaag ccatctgcct tcgagcctgc cactgaaatg caaaagtctg      1320
tcccaaataa agccttggaa ttgaaaaatg aacaaacatt gagagcagat gagatactcc      1380
catcagaatc caaacaaaag gactatgaag aaagttcttg ggattctgag agtctctgtg      1440
agactgtttc acagaaggat gtgtgtttac ccaaggctrc rcatcaaaaa gaaatagata      1500
aaataaatgg aaaattagaa gggtctcctg ttaaagatgg tcttctgaag gctaactgcg      1560
gaatgaaagt ttctattcca actaaagcct tagaattgat ggacatgcaa actttcaaag      1620
cagagcctcc cgagaagcca tctgccttcg agcctgccat tgaaatgcaa aagtctgttc      1680
caaataaagc cttggaattg aagaatgaac aaacattgag agcagatgag atactcccat      1740
cagaatccaa acaaaaggac tatgaagaaa gttcttggga ttctgagagt ctctgtgaga      1800
ctgtttcaca gaaggatgtg tgtttaccca aggctrcrca tcaaaaagaa atagataaaa      1860
taaatggaaa attagaagag tctcctgata atgatggttt tctgaaggct ccctgcagaa      1920
tgaaagtttc tattccaact aaagccttag aattgatgga catgcaaact ttcaaagcag      1980
agcctcccga agccatctg ccttcgagc ctgccattga atgcaaaag tctgttccaa         2040
ataaagcctt ggaattgaag aatgaacaaa cattgagagc agatcagatg ttcccttcag      2100
aatcaaaaca aaagaasgtt gaagaaaatt cttgggattc tgagagtctc cgtgagactg      2160
tttcacagaa ggatgtgtgt gtacccaagg ctacacatca aaaagaaatg gataaaataa      2220
gtggaaaatt agaagattca actagcctat caaaaatctt ggatacagtt cattcttgtg      2280
aaagagcaag ggaacttcaa aaagatcact gtgacaacg tacaggaaaa atggaacaaa       2340
tgaaaaagaa gttttgtgta ctgaaaaaga aactgtcaga agcaaaagaa ataaaatcac      2400
```

```
agttagagaa ccaaaaagtt aaatgggaac aagagctctg cagtgtgagg tttctcacac    2460
tcatgaaaat gaaaattatc tcttacatga aaattgcatg ttgaaaaagg aaattgccat    2520
gctaaaactg gaaatagcca cactgaaaca ccaataccag gaaaaggaaa ataaatactt    2580
tgaggacatt aagattttaa agaaaagaa tgctgaactt cagatgaccc taaaactgaa    2640
agaggaatca ttaactaaaa gggcatctca atatagtggg cagcttaaag ttctgatagc    2700
tgagaacaca atgctcactt ctaaattgaa ggaaaaacaa gacaaagaaa tactagaggc    2760
agaaattgaa tcacaccatc ctagactggc ttctgctgta caagaccatg atcaaattgt    2820
gacatcaaga aaaagtcaag aacctgcttt ccacattgca ggagatgctt gtttgcaaag    2880
aaaaatgaat gttgatgtga gtagtacgat atataacaat gaggtgctcc atcaaccact    2940
ttctgaagct caaggaaat ccaaaagcct aaaaattaat ctcaattatg cmggagatgc    3000
tctaagagaa aatacattgg tttcagaaca tgcacaaaga gaccaacgtg aaacacagtg    3060
tcaaatgaag gaagctgaac acatgtatca aaacgaacaa gataatgtga acaaacacac    3120
tgaacagcag gagtctctag atcagaaatt atttcaacta caaagcaaaa atatgtggct    3180
tcaacagcaa ttagttcatg cacataagaa agctgacaac aaaagcaaga taacaattga    3240 tattcattt cttgagagga aaatgcaaca tcatctccta aaagagaaaa atgaggagat    3300
atttaattac aataaccatt taaaaaaccg tatatatcaa tatgaaaaag agaaagcaga    3360
aacagaaaac tcatgagaga caagcagtaa gaaacttctt ttggagaaac aacagaccag    3420
atctttactc acaactcatg ctaggaggcc agtcctagca tcaccttatg ttgaaaatct    3480
taccaatagt ctgtgtcaac agaatactta ttttagaaga aaattcatg atttcttcct    3540 gaagcctaca gacataaaat aacagtgtga agaattactt gttcacgaat tgcataaagc    3600
tgcacaggat tcccatctac cctgatgatg cagcagacat cattcaatcc aaccagaatc    3660
tcgctctgtc actcaggctg g                                              3681
```

<210> SEQ ID NO 464
<211> LENGTH: 1424
<212> TYPE: DNA
<213> ORGANISM: Homo sapiens

<400> SEQUENCE: 464

```
tccgagctga ttacagacac caaggaagat gctgtaaaga gtcagcagcc acagccctgg      60
ctagctggcc ctgtgggcat ttattagtaa agttttaatg acaaaagctt tgagtcaaca     120
cacccgtggg taattaacct ggtcatcccc accctggaga gccatcctgc ccatgggtga     180
tcaaagaagg aacatctgca ggaacacctg atgaggctgc acccttggcg aaagaacac     240 ctgacacagc tgaaagcttg gtggaaaaaa cacctgatga ggctgcaccc ttggtggaaa     300
gaacacctga cacggctgaa agcttggtgg aaaaaacacc tgatgaggct gcatccttgg     360
tggagggaac atctgacaaa attcaatgtt tggagaaagc gacatctgga aagttcgaac     420
agtcagcaga agaaacacct agggaaatta cgagtcctgc aaaagaaaca tctgagaaat     480
ttacgtggcc agcaaaagga agacctagga agatcgcatg ggagaaaaaa gaagacacac     540
ctagggaaat tatgagtccc gcaaagaaaa catctgagaa atttacgtgg gcagcaaaag     600
gaagacctag gaagatcgca tgggagaaaa aagaaacacc tgtaaagact ggatgcgtgg     660
caagagtaac atctaataaa actaaagttt tggaaaaagg aagatctaag atgattgcat     720
gtcctacaaa agaatcatct acaaaagcaa gtgccaatga tcagaggttc ccatcagaat     780
ccaaacaaga ggaagatgaa gaatattctt gtgattctcg gagtctcttt gagagttctg     840
```

-continued

| | |
|---|---|
| caaagattca agtgtgtata cctgagtcta tatatcaaaa agtaatggag ataaatagag | 900 |
| aagtagaaga gcctcctaag aagccatctg ccttcaagcc tgccattgaa atgcaaaact | 960 |
| ctgttccaaa taaagccttt gaattgaaga atgaacaaac attgagagca gatccgatgt | 1020 |
| tcccaccaga atccaaacaa aaggactatg aagaaaattc ttgggattct gagagtctct | 1080 |
| gtgagactgt ttcacagaag gatgtgtgtt tacccaaggc tacacatcaa aaagaaatag | 1140 |
| ataaaataaa tggaaaatta gaaggtaaga accgtttttt atttaaaaat cagttgaccg | 1200 |
| aatatttctc taaactgatg aggagggata tcctctagta gctgaagaaa attacctcct | 1260 |
| aaatgcaaac catggaaaaa aagagaagtg caatggtcgt aagttgtatg tctcatcagg | 1320 |
| tgttggcaac agactatatt gagagtgctg aaaaggagct gaattattag tttgaattca | 1380 |
| agatattgca agacctgaga gaaaaaaaaa aaaaaaaaaa aaaa | 1424 |

<210> SEQ ID NO 465
<211> LENGTH: 674
<212> TYPE: DNA
<213> ORGANISM: Homo sapiens

<400> SEQUENCE: 465

| | |
|---|---|
| attccgagct gattacagac accaaggaag atgctgtaaa gagtcagcag ccacagccct | 60 |
| ggctagctgg ccctgtgggc atttattagt aaagttttaa tgacaaaagc tttgagtcaa | 120 |
| cacacccgtg ggtaattaac ctggtcatcc ccaccctgga gagccatcct gcccatgggt | 180 |
| gatcaaagaa ggaacatctg caggaacacc tgatgaggct gcacccttgg cggaaagaac | 240 |
| acctgacaca gctgaaagct tggtggaaaa aacacctgat gaggctgcac ccttggtgga | 300 |
| aagaacacct gacacggctg aaagcttggt ggaaaaaaca cctgatgagg ctgcatcctt | 360 |
| ggtggaggga acatctgaca aaattcaatg ttttggagaaa gcgacatctg gaaagttcga | 420 |
| acagtcagca gaagaaacac ctagggaaat tacgagtcct gcaaaagaaa catctgagaa | 480 |
| atttacgtgg ccagcaaaag gaagacctag gaagatcgca tgggagaaaa aagatgactc | 540 |
| agttaaggca aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaaaa aaaa | 674 |

<210> SEQ ID NO 466
<211> LENGTH: 1729
<212> TYPE: DNA
<213> ORGANISM: Homo sapiens
<220> FEATURE:
<221> NAME/KEY: misc_feature
<222> LOCATION: (1)...(1729)
<223> OTHER INFORMATION: n=A,T,C or G

<400> SEQUENCE: 466

| | |
|---|---|
| gaaagttcga ncagtcagca gaagaaacac ctagggaaat tacgagtcct gcaaaagaaa | 60 |
| catctgagaa atttacgtgg ccagcaaaag gaagacctag gaagatcgca tgggagaaaa | 120 |
| aagaagacac acctagggaa attatgagtc ccgcaaaaga aacatctgag aaatttacgt | 180 |
| gggcagcaaa aggaagacct aggaagatcg catgggagaa aaagaaaaca cctgtaaaga | 240 |
| ctggatgcgt ggcaagagta acatctaata aaactaaagt ttttggaaaaa ggaagatcta | 300 |
| agatgattgc atgtcctaca aaagaatcat ctacaaaagc aagtgccaat gatcagaggt | 360 |
| tcccatcaga atccaaacaa gaggaagatg aagaatattc ttgtgattct cggagtctct | 420 |

-continued

```
ttgagagttc tgcaaagatt caagtgtgta tacctgagtc tatatatcaa aaagtaatgg      480
agataaatag agaagtagaa gagcctccta agaagccatc tgccttcaag cctgccattg      540
aaatgcaaaa ctctgttcca aataaagcct tgaattgaa gaatgaacaa acattgagag       600
cagatccgat gttcccacca gaatccaaac aaaaggacta tgaagaaaat tcttgggatt     660
ctgagagtct ctgtgagact gtttcacaga aggatgtgtg tttacccaag gctacacatc    720 aaaagaaat agataaaata aatggaaat tagaagagtc tcctaataaa gatggtcttc       780
tgaaggctac ctgcggaatg aaagtttcta ttccaactaa agccttagaa ttgaaggaca    840
tgcaaacttt caaagcagag cctccgggga agccatctgc cttcgagcct gccactgaaa   900
tgcaaaagtc tgtcccaaat aaagccttgg aattgaaaaa tgaacaaaca ttgagagcag    960
atgagatact cccatcagaa tccaaacaaa aggactatga agaaaattct tgggatactg   1020
agagtctctg tgagactgtt tcacagaagg atgtgtgttt acccaaggct gcgcatcaaa   1080
aagaaataga taaataaat ggaaaattag aagggtctcc tggtaaanat ggtcttctga     1140
aggctaactg cggaatgaaa gtttctattc caactaaagc cttagaattg atggacatgc    1200
aaactttcaa agcagagcct cccgagaagc catctgcctt cgagcctgcc attgaaatgc   1260
aaaagtctgt tccaaataaa gccttggaat tgaagaatga acaaacattg agagcagatg    1320
agatactccc atcagaatcc aaacaaaagg actatgaaga aagttcttgg gattctgaga    1380
gtctctgtga actgtttca cagaaggatg tgtgtttacc caaggctgcg catcaaaaag     1440
aaatagataa aataaatgga aaattagaag gtaagaaccg tttttatt aaaaatcatt      1500 tgaccaaata tttctctaaa ttgatgagga aggatatcct ctagtagctg aagaaaatta    1560
cctcctaaat gcaaaccatg gaaaaaaaga gaagtgcaat ggtcataagc tatgtgtctc    1620
atcaggcatt ggcaacagac tatattgtga gtgctgaaga ggagctgaat tactagttta   1680
aattcaagat attccaagac gtgaggaaaa tgagaaaaa aaaaaaaaa                 1729
```

<210> SEQ ID NO 467
<211> LENGTH: 1337
<212> TYPE: DNA
<213> ORGANISM: Homo sapiens

<400> SEQUENCE: 467

```
aaaaagaaat agataaaata aatggaaat tagaagggtc tcctgttaaa gatggtcttc      60
tgaaggctaa ctgcggaatg aaagtttcta ttccaactaa agccttagaa ttgatggaca   120
tgcaaacttt caaagcagag cctcccgaga agccatctgc cttcgagcct gccattgaaa   180
tgcaaaagtc tgttccaaat aaagccttgg aattgaagaa tgaacaaaca ttgagagcag    240
atgagatact cccatcagaa tccaaacaaa aggactatga agaaagttct tgggattctg    300
agagtctctg tgagactgtt tcacagaagg atgtgtgttt acccaaggct gcgcatcaaa   360
aagaaataga taaataaat ggaaaattag aagagtctcc tgataatgat ggttttctga     420
aggctccctg cagaatgaaa gtttctattc caactaaagc cttagaattg atggacatgc    480
aaactttcaa agcagagcct cccgagaagc catctgcctt cgagcctgcc attgaaatgc   540
aaaagtctgt tccaaataaa gccttggaat tgaagaatga acaaacattg agagcagatc    600
agatgttccc ttcagaatca aacaaaaga aggttgaaga aaattcttgg gattctgaga    660
gtctccgtga gactgtttca cagaaggatg tgtgtgtacc caaggctaca catcaaaaag    720
aaatggataa aataagtgga aaattagaag attcaactag cctatcaaaa atcttggata   780
cagttcattc ttgtgaaaga gcaagggaac ttcaaaaga tcactgtgaa caacgtacag    840
```

| | |
|---|---|
| gaaaaatgga acaaatgaaa agaagttttt gtgtactgaa aaagaaactg tcagaagcaa | 900 |
| aagaaataaa atcacagtta gagaaccaaa aagttaaatg ggaacaagag ctctgcagtg | 960 |
| tgagattgac tttaaaccaa gaagaagaga agagaagaaa tgccgatata ttaaatgaaa | 1020 |
| aaattaggga agaattagga agaatcgaag agcagcatag gaaagagtta gaagtgaaac | 1080 |
| aacaacttga acaggctctc agaatacaag atatagaatt gaagagtgta gaaagtaatt | 1140 |
| tgaatcaggt ttctcacact catgaaaatg aaaattatct cttacatgaa aattgcatgt | 1200 |
| tgaaaagga aattgccatg ctaaaactgg aaatagccac actgaaacac caataccagg | 1260 |
| aaaaggaaaa taaatacttt gaggacatta agattttaaa agaaaagaat gctgaacttc | 1320 |
| agatgacccc tcgtgcc | 1337 |

<210> SEQ ID NO 468
<211> LENGTH: 2307
<212> TYPE: DNA
<213> ORGANISM: Homo sapiens

<400> SEQUENCE: 468

| | |
|---|---|
| attgagagca gatgagatac tcccatcaga atccaaacaa aaggactatg aagaaagttc | 60 |
| ttgggattct gagagtctct gtgagactgt ttcacagaag gatgtgtgtt tacccaaggc | 120 |
| tacacatcaa aaagaaatag ataaaataaa tggaaaatta gaagggtctc ctgttaaaga | 180 |
| tggtcttctg aaggctaact gcggaatgaa agtttctatt ccaactaaag ccttagaatt | 240 |
| gatggacatg caaactttca aagcagagcc tcccgagaag ccatctgcct tcgagcctgc | 300 |
| cattgaaatg caaaagtctg ttccaaataa agccttggaa ttgaagaatg aacaaacatt | 360 |
| gagagcagat gagatactcc catcagaatc caaacaaaag gactatgaag aaagttcttg | 420 |
| ggattctgag agtctctgtg agactgtttc acagaaggat gtgtgtttac ccaaggctac | 480 |
| acatcaaaaa gaaatagata aataaatgg aaaattagaa gagtctcctg ataatgatgg | 540 |
| ttttctgaag tctccctgca gaatgaaagt ttctattcca actaaagcct tagaattgat | 600 |
| ggacatgcaa actttcaaag cagagcctcc cgagaagcca tctgccttcg agcctgccat | 660 |
| tgaaatgcaa aagtctgttc caaataaagc cttggaattg aagaatgaac aaacattgag | 720 |
| agcagatcag atgttcccct tcagaatcaaa acaaagaac gttgaagaaa attcttggga | 780 |
| ttctgagagt ctccgtgaga ctgtttcaca gaaggatgtg tgtgtaccca aggctacaca | 840 |
| tcaaaaagaa atggataaaa taagtggaaa attagaagat tcaactagcc tatcaaaaat | 900 |
| cttggataca gttcattctt gtgaaagagc aagggaactt caaaaagatc actgtgaaca | 960 |
| acgtacagga aaaatggaac aaatgaaaaa gaagttttgt gtactgaaaa agaaactgtc | 1020 |
| agaagcaaaa gaaataaaat cacagttaga gaaccaaaaa gttaaatggg aacaagagct | 1080 |
| ctgcagtgtg aggtttctca cactcatgaa aatgaaaatt atctcttaca tgaaaattgc | 1140 |
| atgttgaaaa aggaaattgc catgctaaaa ctggaaatag ccacactgaa acaccaatac | 1200 |
| caggaaaagg aaaataaata ctttgaggac attaagattt taaagaaaaa gaatgctgaa | 1260 |
| cttcagatga cccctaaaact gaaagaggaa tcattaacta aaggggcatc tcaatatagt | 1320 |
| gggcagctta agttctgat agctgagaac acaatgctca cttctaaatt gaaggaaaaa | 1380 |
| caagacaaag aaatactaga ggcagaaatt gaatcacacc atcctagact ggcttctgct | 1440 |
| gtacaagacc atgatcaaat tgtgacatca agaaaagtc aagaacctgc tttccacatt | 1500 |
| gcaggagatg cttgtttgca aagaaaaatg aatgttgatg tgagtagtac gatatataac | 1560 |

-continued

```
aatgaggtgc tccatcaacc actttctgaa gctcaaagga atccaaaag cctaaaaatt   1620 aatctcaatt atgcaggaga tgctctaaga gaaaatacat tggtttcaga acatgcacaa   1680
agagaccaac gtgaaacaca gtgtcaaatg aaggaagctg aacacatgta tcaaaacgaa   1740
caagataatg tgaacaaaca cactgaacag caggagtctc tagatcagaa attatttcaa   1800
ctacaaagca aaatatgtg gcttcaacag caattagttc atgcacataa gaaagctgac   1860
aacaaaagca agataacaat tgatattcat tttcttgaga ggaaaatgca acatcatctc   1920
ctaaaagaga aaaatgagga gatatttaat tacaataacc atttaaaaaa ccgtatatat   1980
caatatgaaa aagagaaagc agaaacagaa aactcatgag agacaagcag taagaaactt   2040
cttttggaga acaacagac cagatctttta ctcacaactc atgctaggag gccagtccta   2100
gcatcacctt atgttgaaaa tcttaccaat agtctgtgtc aacagaatac ttattttaga   2160
agaaaaattc atgatttctt cctgaagcct acagacataa aataacagtg tgaagaatta   2220
cttgttcacg aattgcataa agctgcacag gattcccatc taccctgatg atgcagcaga   2280
catcattcaa tccaaccaga atctcgc                                       2307
```

<210> SEQ ID NO 469
<211> LENGTH: 650
<212> TYPE: PRT
<213> ORGANISM: Homo sapiens
<220> FEATURE:
<221> NAME/KEY: VARIANT
<222> LOCATION: (1)...(650)
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
              5                  10                  15

Gly Arg Pro Arg Lys Ile Ala Trp Glu Lys Lys Glu Thr Pro Val Lys
         20                  25                  30

Thr Gly Cys Val Ala Arg Val Thr Ser Asn Lys Thr Lys Val Leu Glu
     35                  40                  45

Lys Gly Arg Ser Lys Met Ile Ala Cys Pro Thr Lys Glu Ser Ser Thr
 50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Ser Pro Asn
        195                 200                 205

Lys Asp Gly Leu Leu Lys Ala Thr Cys Gly Met Lys Val Ser Ile Pro
    210                 215                 220
```

-continued

```
Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
            245                 250                 255

Val Pro Asn Lys Ala Leu Glu Leu Lys Asn Glu Gln Thr Leu Arg Ala
        260                 265                 270

Asp Glu Ile Leu Pro Ser Glu Ser Lys Gln Lys Asp Tyr Glu Glu Ser
    275                 280                 285

Ser Trp Asp Ser Glu Ser Leu Cys Glu Thr Val Ser Gln Lys Asp Val
290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
            325                 330                 335

Gly Met Lys Val Ser Ile Pro Thr Lys Ala Leu Glu Leu Met Asp Met
        340                 345                 350

Gln Thr Phe Lys Ala Glu Pro Pro Glu Lys Pro Ser Ala Phe Glu Pro
    355                 360                 365

Ala Ile Glu Met Gln Lys Ser Val Pro Asn Lys Ala Leu Glu Leu Lys
370                 375                 380

Asn Glu Gln Thr Leu Arg Ala Asp Glu Ile Leu Pro Ser Glu Ser Lys
385                 390                 395                 400

Gln Lys Asp Tyr Glu Ser Ser Trp Asp Ser Glu Ser Leu Cys Glu
                405                 410                 415

Thr Val Ser Gln Lys Asp Val Cys Leu Pro Lys Ala Xaa His Gln Lys
                420                 425                 430

Glu Ile Asp Lys Ile Asn Gly Lys Leu Glu Glu Ser Pro Asp Asn Asp
            435                 440                 445

Gly Phe Leu Lys Ala Pro Cys Arg Met Lys Val Ser Ile Pro Thr Lys
        450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
                500                 505                 510

Met Phe Pro Ser Glu Ser Lys Gln Lys Xaa Val Glu Glu Asn Ser Trp
            515                 520                 525

Asp Ser Glu Ser Leu Arg Glu Thr Val Ser Gln Lys Asp Val Cys Val
530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
            565                 570                 575

Glu Arg Ala Arg Glu Leu Gln Lys Asp His Cys Glu Gln Arg Thr Gly
        580                 585                 590

Lys Met Glu Gln Met Lys Lys Phe Cys Val Leu Lys Lys Lys Leu
    595                 600                 605

Ser Glu Ala Lys Glu Ile Lys Ser Gln Leu Glu Asn Gln Lys Val Lys
    610                 615                 620

Trp Glu Gln Glu Leu Cys Ser Val Arg Phe Leu Thr Leu Met Lys Met
625                 630                 635                 640
```

```
Lys Ile Ile Ser Tyr Met Lys Ile Ala Cys
                645                 650

<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
                 5                  10                  15

Gly Arg Pro Arg Lys Ile Ala Trp Glu Lys Glu Thr Pro Val Lys
             20                  25                  30

Thr Gly Cys Val Ala Arg Val Thr Ser Asn Lys Thr Lys Val Leu Glu
             35                  40                  45

Lys Gly Arg Ser Lys Met Ile Ala Cys Pro Thr Lys Glu Ser Ser Thr
     50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Pro Pro Lys Lys Pro Ser Ala Phe
            115                 120                 125

Lys Pro Ala Ile Glu Met Gln Asn Ser Val Pro Asn Lys Ala Phe Glu
130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Gly Lys Asn Arg
            195                 200                 205

Phe Leu Phe Lys Asn Gln Leu Thr Glu Tyr Phe Ser Lys Leu Met Arg
        210                 215                 220

Arg Asp Ile Leu
225

<210> SEQ ID NO 471
<211> LENGTH: 154
<212> TYPE: PRT
<213> ORGANISM: Homo sapiens
<220> FEATURE:
<221> NAME/KEY: VARIANT
<222> LOCATION: (1)...(154)
<223> OTHER INFORMATION: Xaa = Any Amino Acid

<400> SEQUENCE: 471

Met Arg Leu His Pro Trp Arg Lys Glu His Leu Thr Gln Leu Lys Ala
                 5                  10                  15

Trp Trp Lys Lys His Leu Met Arg Leu His Pro Trp Lys Glu His
             20                  25                  30

Leu Thr Arg Leu Lys Ala Trp Trp Lys Lys His Leu Met Arg Leu His
         35                  40                  45

Pro Trp Trp Arg Glu His Leu Thr Lys Phe Asn Val Trp Arg Lys Arg
     50                  55                  60
```

```
His Leu Glu Ser Ser Asn Ser Gln Gln Lys Lys His Leu Gly Lys Leu
 65                  70                  75                  80

Arg Val Leu Gln Lys Lys His Leu Arg Asn Leu Arg Gly Gln Gln Lys
                 85                  90                  95

Glu Asp Leu Gly Arg Ser His Gly Arg Lys Lys Met Thr Gln Leu Arg
            100                 105                 110

Gln Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys Lys
    130                 135                 140

Lys Lys Lys Xaa Lys Lys Lys Lys Lys
145                 150
```

<210> SEQ ID NO 472
<211> LENGTH: 466
<212> TYPE: PRT
<213> ORGANISM: Homo sapiens
<220> FEATURE:
<221> NAME/KEY: VARIANT
<222> LOCATION: (1)...(466)
<223> OTHER INFORMATION: Xaa = Any Amino Acid

<400> SEQUENCE: 472

```
Met Ser Pro Ala Lys Glu Thr Ser Glu Lys Phe Thr Trp Ala Ala Lys
                  5                  10                  15

Gly Arg Pro Arg Lys Ile Ala Trp Glu Lys Glu Thr Pro Val Lys
             20                  25                  30

Thr Gly Cys Val Ala Arg Val Thr Ser Asn Lys Thr Lys Val Leu Glu
         35                  40                  45

Lys Gly Arg Ser Lys Met Ile Ala Cys Pro Thr Lys Glu Ser Ser Thr
     50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255
```

-continued

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
            275                 280                 285

Ser Trp Asp Thr Glu Ser Leu Cys Glu Thr Val Ser Gln Lys Asp Val
            290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Glu Lys Pro Ser Ala Phe Glu Pro
            355                 360                 365

Ala Ile Glu Met Gln Lys Ser Val Pro Asn Lys Ala Leu Glu Leu Lys
            370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
            420                 425                 430

Glu Ile Asp Lys Ile Asn Gly Lys Leu Glu Gly Lys Asn Arg Phe Leu
            435                 440                 445

Phe Lys Asn His Leu Thr Lys Tyr Phe Ser Lys Leu Met Arg Lys Asp
            450                 455                 460

Ile Leu
465

<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
                5                   10                  15

Asp Gly Leu Leu Lys Ala Asn Cys Gly Met Lys Val Ser Ile Pro Thr
            20                  25                  30

Lys Ala Leu Glu Leu Met Asp Met Gln Thr Phe Lys Ala Glu Pro Pro
            35                  40                  45

Glu Lys Pro Ser Ala Phe Glu Pro Ala Ile Glu Met Gln Lys Ser Val
50                  55                  60

Pro Asn Lys Ala Leu Glu Leu Lys Asn Glu Gln Thr Leu Arg Ala Asp
65                  70                  75                  80

Glu Ile Leu Pro Ser Glu Ser Lys Gln Lys Asp Tyr Glu Glu Ser Ser
                85                  90                  95

Trp Asp Ser Glu Ser Leu Cys Glu Thr Val Ser Gln Lys Asp Val Cys
            100                 105                 110

Leu Pro Lys Ala Ala His Gln Lys Glu Ile Asp Lys Ile Asn Gly Lys
            115                 120                 125

Leu Glu Glu Ser Pro Asp Asn Asp Gly Phe Leu Lys Ala Pro Cys Arg
            130                 135                 140

Met Lys Val Ser Ile Pro Thr Lys Ala Leu Glu Leu Met Asp Met Gln
145                 150                 155                 160

```
Thr Phe Lys Ala Glu Pro Pro Glu Lys Pro Ser Ala Phe Glu Pro Ala
            165                 170                 175
Ile Glu Met Gln Lys Ser Val Pro Asn Lys Ala Leu Glu Leu Lys Asn
        180                 185                 190
Glu Gln Thr Leu Arg Ala Asp Gln Met Phe Pro Ser Glu Ser Lys Gln
            195                 200                 205
Lys Lys Val Glu Glu Asn Ser Trp Asp Ser Glu Ser Leu Arg Glu Thr
        210                 215                 220
Val Ser Gln Lys Asp Val Cys Val Pro Lys Ala Thr His Gln Lys Glu
225                 230                 235                 240
Met Asp Lys Ile Ser Gly Lys Leu Glu Asp Ser Thr Ser Leu Ser Lys
            245                 250                 255
Ile Leu Asp Thr Val His Ser Cys Glu Arg Ala Arg Glu Leu Gln Lys
            260                 265                 270
Asp His Cys Glu Gln Arg Thr Gly Lys Met Glu Gln Met Lys Lys Lys
        275                 280                 285
Phe Cys Val Leu Lys Lys Leu Ser Glu Ala Lys Glu Ile Lys Ser
        290                 295                 300
Gln Leu Glu Asn Gln Lys Val Lys Trp Glu Gln Glu Leu Cys Ser Val
305                 310                 315                 320
Arg Leu Thr Leu Asn Gln Glu Glu Lys Arg Arg Asn Ala Asp Ile
            325                 330                 335
Leu Asn Glu Lys Ile Arg Glu Glu Leu Gly Arg Ile Glu Glu Gln His
            340                 345                 350
Arg Lys Glu Leu Glu Val Lys Gln Gln Leu Glu Gln Ala Leu Arg Ile
            355                 360                 365
Gln Asp Ile Glu Leu Lys Ser Val Glu Ser Asn Leu Asn Gln Val Ser
            370                 375                 380
His Thr His Glu Asn Glu Asn Tyr Leu Leu His Glu Asn Cys Met Leu
385                 390                 395                 400
Lys Lys Glu Ile Ala Met Leu Lys Leu Glu Ile Ala Thr Leu Lys His
            405                 410                 415
Gln Tyr Gln Glu Lys Glu Asn Lys Tyr Phe Glu Asp Ile Lys Ile Leu
            420                 425                 430
Lys Glu Lys Asn Ala Glu Leu Gln Met Thr Pro Arg Ala
            435                 440                 445

<210> SEQ ID NO 474
<211> LENGTH: 3865
<212> TYPE: DNA
<213> ORGANISM: Homo sapien
<220> FEATURE:
<221> NAME/KEY: misc_feature
<222> LOCATION: (2448)...(2631)
<223> OTHER INFORMATION: 184 bp insert of B726P splice form

<400> SEQUENCE: 474
tccgagctga ttacagacac caaggaagat gctgtaaaga gtcagcagcc acagccctgg      60
ctagctggcc ctgtgggcat ttattagtaa agttttaatg acaaaagctt tgagtcaaca     120
cacccgtggg taattaacct ggtcatcccc accctggaga gccatcctgc ccatgggtga     180
tcaaagaagg aacatctgca ggaacacctg atgaggctgc acccttggcg aaagaacac      240 ctgacacagc tgaaagcttg gtggaaaaaa cacctgatga ggctgcaccc ttggtggaaa     300
gaacacctga cacggctgaa agcttggtgg aaaaaacacc tgatgaggct gcatccttgg     360
```

```
tggagggaac atctgacaaa attcaatgtt tggagaaagc gacatctgga aagttcgaac    420
agtcagcaga agaaacacct agggaaatta cgagtcctgc aaaagaaaca tctgagaaat    480
ttacgtggcc agcaaaagga agacctagga agatcgcatg ggagaaaaaa gaagacacac    540
ctagggaaat tatgagtccc gcaaaagaaa catctgagaa atttacgtgg gcagcaaaag    600
gaagacctag gaagatcgca tgggagaaaa aagaaacacc tgtaaagact ggatgcgtgg    660
caagagtaac atctaataaa actaaagttt tggaaaaagg aagatctaag atgattgcat    720
gtcctacaaa agaatcatct acaaaagcaa gtgccaatga tcagaggttc ccatcagaat    780
ccaaacaaga ggaagatgaa gaatattctt gtgattctcg gagtctcttt gagagttctg    840
caaagattca agtgtgtata cctgagtcta tatcaaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaagagtctc taataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga atgcaaaag tctgttccaa   2040 ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagcctat caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga actgtcagag agcaaaagaa ataaaatcac   2400
agttagagaa ccaaaaagtt aaatgggaac aagagctctg cagtgtgaga ttgactttaa   2460
accaagaaga agagaagaga agaaatgccg atatattaaa tgaaaaaatt agggaagaat   2520
taggaagaat cgaagagcag cataggaaag agttagaagt gaaacaacaa cttgaacagg   2580
ctctcagaat acaagatata gaattgaaga gtgtagaaag taatttgaat caggtttctc   2640
acactcatga aaatgaaaat tatctcttac atgaaaattg catgttgaaa aaggaaattg   2700
ccatgctaaa actggaaata gccacactga acaccaata ccaggaaaag gaaataaat   2760
```

-continued

```
actttgagga cattaagatt ttaaaagaaa agaatgctga acttcagatg accctaaaac   2820
tgaaagagga atcattaact aaaagggcat ctcaatatag tgggcagctt aaagttctga   2880
tagctgagaa cacaatgctc acttctaaat tgaaggaaaa acaagacaaa gaaatactag   2940
aggcagaaat tgaatcacac catcctagac tggcttctgc tgtacaagac catgatcaaa   3000
ttgtgacatc aagaaaaagt caagaacctg ctttccacat tgcaggagat gcttgtttgc   3060
aaagaaaaat gaatgttgat gtgagtagta cgatatataa caatgaggtg ctccatcaac   3120
cactttctga agctcaaagg aaatccaaaa gcctaaaaat taatctcaat tatgcmggag   3180
atgctctaag agaaaataca ttggtttcag aacatgcaca agagaccaa cgtgaaacac   3240
agtgtcaaat gaaggaagct gaacacatgt atcaaaacga acaagataat gtgaacaaac   3300
acactgaaca gcaggagtct ctagatcaga aattatttca actacaaagc aaaaatatgt   3360
ggcttcaaca gcaattagtt catgcacata agaaagctga caacaaaagc aagataacaa   3420
ttgatattca ttttcttgag aggaaaatgc aacatcatct cctaaaagag aaaaatgagg   3480
agatatttaa ttacaataac catttaaaaa accgtatata tcaatatgaa aaagagaaag   3540
cagaaacaga aaactcatga gagacaagca gtaagaaact tcttttggag aaacaacaga   3600
ccagatcttt actcacaact catgctagga ggccagtcct agcatcacct tatgttgaaa   3660
atcttaccaa tagtctgtgt caacagaata cttattttag aagaaaaatt catgatttct   3720
tcctgaagcc tacagacata aataacagt gtgaagaatt acttgttcac gaattgcata   3780
aagctgcaca ggattcccat ctaccctgat gatgcagcag acatcattca atccaaccag   3840
aatctcgctc tgtcactcag gctgg                                        3865
```

<210> SEQ ID NO 475
<211> LENGTH: 1002
<212> TYPE: PRT
<213> ORGANISM: Homo sapien
<220> FEATURE:
<221> NAME/KEY: VARIANT
<222> LOCATION: (1)...(1002)
<223> OTHER INFORMATION: Xaa = Any Amino Acid

<400> SEQUENCE: 475

```
Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
```

-continued

```
            145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575
```

```
Glu Arg Ala Arg Glu Leu Gln Lys Asp His Cys Glu Gln Arg Thr Gly
            580                 585                 590
Lys Met Glu Gln Met Lys Lys Lys Phe Cys Val Leu Lys Lys Lys Leu
            595                 600                 605
Ser Glu Ala Lys Glu Ile Lys Ser Gln Leu Glu Asn Gln Lys Val Lys
            610                 615                 620
Trp Glu Gln Glu Leu Cys Ser Val Arg Leu Thr Leu Asn Gln Glu Glu
625                 630                 635                 640
Glu Lys Arg Arg Asn Ala Asp Ile Leu Asn Glu Lys Ile Arg Glu Glu
            645                 650                 655
Leu Gly Arg Ile Glu Glu Gln His Arg Lys Glu Leu Glu Val Lys Gln
            660                 665                 670
Gln Leu Glu Gln Ala Leu Arg Ile Gln Asp Ile Glu Leu Lys Ser Val
            675                 680                 685
Glu Ser Asn Leu Asn Gln Val Ser His Thr His Glu Asn Glu Asn Tyr
            690                 695                 700
Leu Leu His Glu Asn Cys Met Leu Lys Lys Glu Ile Ala Met Leu Lys
705                 710                 715                 720
Leu Glu Ile Ala Thr Leu Lys His Gln Tyr Gln Glu Lys Glu Asn Lys
            725                 730                 735
Tyr Phe Glu Asp Ile Lys Ile Leu Lys Glu Lys Asn Ala Glu Leu Gln
            740                 745                 750
Met Thr Leu Lys Leu Lys Glu Glu Ser Leu Thr Lys Arg Ala Ser Gln
            755                 760                 765
Tyr Ser Gly Gln Leu Lys Val Leu Ile Ala Glu Asn Thr Met Leu Thr
            770                 775                 780
Ser Lys Leu Lys Glu Lys Gln Asp Lys Glu Ile Leu Glu Ala Glu Ile
785                 790                 795                 800
Glu Ser His His Pro Arg Leu Ala Ser Ala Val Gln Asp His Asp Gln
            805                 810                 815
Ile Val Thr Ser Arg Lys Ser Gln Glu Pro Ala Phe His Ile Ala Gly
            820                 825                 830
Asp Ala Cys Leu Gln Arg Lys Met Asn Val Asp Val Ser Ser Thr Ile
            835                 840                 845
Tyr Asn Asn Glu Val Leu His Gln Pro Leu Ser Glu Ala Gln Arg Lys
            850                 855                 860
Ser Lys Ser Leu Lys Ile Asn Leu Asn Tyr Ala Gly Asp Ala Leu Arg
865                 870                 875                 880
Glu Asn Thr Leu Val Ser Glu His Ala Gln Arg Asp Gln Arg Glu Thr
            885                 890                 895
Gln Cys Gln Met Lys Glu Ala Glu His Met Tyr Gln Asn Glu Gln Asp
            900                 905                 910
Asn Val Asn Lys His Thr Glu Gln Gln Glu Ser Leu Asp Gln Lys Leu
            915                 920                 925
Phe Gln Leu Gln Ser Lys Asn Met Trp Leu Gln Gln Leu Val His
            930                 935                 940
Ala His Lys Lys Ala Asp Asn Lys Ser Lys Ile Thr Ile Asp Ile His
945                 950                 955                 960
Phe Leu Glu Arg Lys Met Gln His His Leu Leu Lys Glu Lys Asn Glu
            965                 970                 975
Glu Ile Phe Asn Tyr Asn Asn His Leu Lys Asn Arg Ile Tyr Gln Tyr
            980                 985                 990
```

```
Glu Lys Glu Lys Ala Glu Thr Glu Asn Ser
        995                 1000

<210> SEQ ID NO 476
<211> LENGTH: 356
<212> TYPE: DNA
<213> ORGANISM: Homo sapien

<400> SEQUENCE: 476
aggtctgccg gaaatgttag gcaccccaac tcaagtccca ggccccaggc atctttcctg      60
ccctgccttg cttggcccat ccagtccagg cgcctggagc aagtgctcag ctacttctcc     120
tgcactttga agacccctc ccactcctgg cctcacattt ctctgtgtga tcccccactt     180
ctgggctctg ccaccccaca gtgggaaagg ccaccctaga aagaagtccg ctggcaccca     240
taggaagggg cctcaggagc aggaagggcc aggaccagaa ccttgcccac ggcaactgcc     300
ttcctgcctc tcccctttcct cctctgctct tgatctgtgt ttcaataaat taatgt       356

<210> SEQ ID NO 477
<211> LENGTH: 1876
<212> TYPE: DNA
<213> ORGANISM: Homo sapien

<400> SEQUENCE: 477
atgacctgcg gatcaggatt tggtgggcgc gccttcagct gcatctcggc ctgcgggccg      60
cgccccggcc gctgctgcat caccgccgcc ccctaccgtg gcatctcctg ctaccgcggc     120
ctcaccgggg gcttcggcag ccacagcgtg tgcggaggct ttcgggccgg ctcctgcgga     180
cgcagcttcg gctaccgctc cggggcgtg tgcgggccca gtcccccatg catcaccacc     240
gtgtcggtca acgagagcct cctcacgccc ctcaacctgg agatcgaccc caacgcgcag     300
tgcgtgaagc aggaggagaa ggagcagatc aagtccctca acagcaggtt cgcggccttc     360
atcgacaagg tgcgcttcct ggagcagcag aacaaactgc tggagacaaa gctgcagttc     420
taccagaacc gcgagtgttg ccagagcaac ctggagcccc tgtttgaggg ctacatcgag     480
actctgcggc gggaggccga gtgcgtggag ccgacagcg ggaggctggc ctcagagctt     540
aaccacgtgc aggaggtgct ggagggctac aagaagaagt atgaggagga ggtttctctg     600
agagcaacag ctgagaacga gtttgtggct ctgaagaagg atgtggactg cgcctacctc     660
cgcaagtcag acctggaggc caacgtggag gccctgatcc aggagatcga cttcctgagg     720
cggctgtatg aggaggagat ccgcattctc cagtcgcaca tctcagacac ctccgtggtt     780
gtcaagctgg acaacagccg ggacctgaac atggactgca tcattgccga gattaaggca     840
cagtatgacg acattgtcac ccgcagccgg gccgaggccg agtcctggta ccgcagcaag     900
tgtgaggaga tgaaggccac ggtgatcagg cacgggggaga ccctgcgccg caccaaggag     960
gagatcaatg agctgaaccg catgatccaa aggctgacgg ccgaggtgga aatgccaag    1020
tgccagaact ccaagctgga ggccgcggtg gctcagtctg agcagcaggg tgaggcagcc    1080
ctcagtgatg cccgctgcaa gctggccgag ctggagggcg ccctgcagaa ggccaagcag    1140
gacatggcct gcctgatcag ggagtaccag gaggtgatga actccaagct gggcctggac    1200
atcgagatcg ccacctacag gcgcctgctg gagggcgagg agcagaggct atgtgaaggc    1260
attggggctg tgaatgtctg tgtcagcagc tcccggggcg gggtcgtgtg cggggacctc    1320
tgcgtgtcag gctcccggcc agtgactggc agtgtctgca gcgctccgtg caacgggaac    1380
gtggcggtga gcaccggcct gtgtgcgccc tgcggccaat tgaacaccac ctgcggaggg    1440
```

-continued

```
ggttcctgcg gcgtgggctc ctgtggtatc agctccctgg gtgtgggagtc ttgcggcagc    1500
agctgccgga aatgttaggc accccaactc aagtcccagg ccccaggcat ctttcctgcc    1560
ctgccttgct tggcccatcc agtccaggcg cctggagcaa gtgctcagct acttctcctg    1620
cactttgaaa gaccccctccc actcctggcc tcacatttct ctgtgtgatc ccccacttct    1680
gggctctgcc accccacagt gggaaaggcc accctagaaa gaagtccgct ggcacccata    1740
ggaaggggcc tcaggagcag gaagggccag gaccagaacc ttgcccacgg caactgcctt    1800
cctgcctctc cccttcctcc tctgctcttg atctgtgttt caataaatta atgtagccaa    1860
aaaaaaaaaa aaaaaa                                                     1876
```

<210> SEQ ID NO 478
<211> LENGTH: 505
<212> TYPE: PRT
<213> ORGANISM: Homo sapien

<400> SEQUENCE: 478

```
Met Thr Cys Gly Ser Gly Phe Gly Gly Arg Ala Phe Ser Cys Ile Ser
 1               5                  10                  15

Ala Cys Gly Pro Arg Pro Gly Arg Cys Cys Ile Thr Ala Ala Pro Tyr
            20                  25                  30

Arg Gly Ile Ser Cys Tyr Arg Gly Leu Thr Gly Phe Gly Ser His
        35                  40                  45

Ser Val Cys Gly Gly Phe Arg Ala Gly Ser Cys Gly Arg Ser Phe Gly
    50                  55                  60

Tyr Arg Ser Gly Gly Val Cys Gly Pro Ser Pro Cys Ile Thr Thr
65                  70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
```

```
                290                 295                 300
Lys Ala Thr Val Ile Arg His Gly Glu Thr Leu Arg Arg Thr Lys Glu
305                 310                 315                 320
Glu Ile Asn Glu Leu Asn Arg Met Ile Gln Arg Leu Thr Ala Glu Val
                325                 330                 335
Glu Asn Ala Lys Cys Gln Asn Ser Lys Leu Glu Ala Ala Val Ala Gln
                340                 345                 350
Ser Glu Gln Gln Gly Glu Ala Ala Leu Ser Asp Ala Arg Cys Lys Leu
                355                 360                 365
Ala Glu Leu Glu Gly Ala Leu Gln Lys Ala Lys Gln Asp Met Ala Cys
370                 375                 380
Leu Ile Arg Glu Tyr Gln Glu Val Met Asn Ser Lys Leu Gly Leu Asp
385                 390                 395                 400
Ile Glu Ile Ala Thr Tyr Arg Arg Leu Leu Glu Gly Glu Glu Gln Arg
                405                 410                 415
Leu Cys Glu Gly Ile Gly Ala Val Asn Val Cys Val Ser Ser Ser Arg
                420                 425                 430
Gly Gly Val Val Cys Gly Asp Leu Cys Val Ser Gly Ser Arg Pro Val
                435                 440                 445
Thr Gly Ser Val Cys Ser Ala Pro Cys Asn Gly Asn Val Ala Val Ser
450                 455                 460
Thr Gly Leu Cys Ala Pro Cys Gly Gln Leu Asn Thr Thr Cys Gly Gly
465                 470                 475                 480
Gly Ser Cys Gly Val Gly Ser Cys Gly Ile Ser Ser Leu Gly Val Gly
                485                 490                 495
Ser Cys Gly Ser Ser Cys Arg Lys Cys
                500                 505

<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 479
ggtccattcc tttcctcgcg tngggttttc tctgtgtcag cgagcctcgg tacactgatt    60
tccgatcaaa agaatcatca tctttacctt gacttttcag ggaattactg aactttcttc   120
tcagaagata gggcacagcc attgccttgg cctcacttga aggtctgca  tttgggtcct   180 ctggtctctt gccaagtttc ccagccactc gagggagaaa t                       221

<210> SEQ ID NO 480
<211> LENGTH: 36
<212> TYPE: DNA
<213> ORGANISM: Artificial Sequence
<220> FEATURE:
<223> OTHER INFORMATION: PCR primer

<400> SEQUENCE: 480
cggcgaattc accatgggaa caagagctct gcagtg                              36

<210> SEQ ID NO 481
<211> LENGTH: 62
<212> TYPE: DNA
<213> ORGANISM: Artificial Sequence
<220> FEATURE:
```

<223> OTHER INFORMATION: PCR primer

<400> SEQUENCE: 481

| | | |
|---|---|---|
| cggcaagctt taatggtga tggtgatgat gtataacttc tgtttctgct ttctcttttt | 60 | |
| ca | 62 | |

<210> SEQ ID NO 482
<211> LENGTH: 972
<212> TYPE: DNA
<213> ORGANISM: Homo sapiens

<400> SEQUENCE: 482

| | |
|---|---|
| atgggaacaa gagctctgca gtgtgaggtt tctcacactc atgaaaatga aaattatctc | 60 |
| ttacatgaaa attgcatgtt gaaaaaggaa attgccatgc taaaactgga aatagccaca | 120 |
| ctgaaacacc aataccagga aaaggaaaat aaatactttg aggacattaa gattttaaaa | 180 |
| gaaaagaatg ctgaacttca gatgacccta aaactgaaag aggaatcatt aactaaaagg | 240 |
| gcatctcaat atagtgggca gcttaaagtt ctgatagctg agaacacaat gctcacttct | 300 |
| aaattgaagg aaaaacaaga caaagaaata ctagaggcag aaattgaatc acaccatcct | 360 |
| agactggctt ctgctgtaca agaccatgat caaattgtga catcaagaaa agtcaagaa | 420 |
| cctgctttcc acattgcagg agatgcttgt ttgcaaagaa aaatgaatgt tgatgtgagt | 480 |
| agtacgatat ataacaatga ggtgctccat caaccacttt ctgaagctca aggaaaatcc | 540 |
| aaaagcctaa aaattaatct caattatgcc ggagatgctc taagagaaaa tacattggtt | 600 |
| tcagaacatg cacaaagaga ccaacgtgaa cacagtgtc aaatgaagga agctgaacac | 660 |
| atgtatcaaa acgaacaaga taatgtgaac aaacacactg aacagcagga gtctctagat | 720 |
| cagaaattat ttcaactaca aagcaaaaat atgtggcttc aacagcaatt agttcatgca | 780 |
| cataagaaag ctgacaacaa agcaagata acaattgata ttcattttct tgagaggaaa | 840 |
| atgcaacatc atctcctaaa agagaaaaat gaggagatat ttaattacaa taaccatta | 900 |
| aaaaccgta tatatcaata tgaaaagag aaagcagaaa cagaagttat acatcatcac | 960 |
| catcaccatt aa | 972 |

<210> SEQ ID NO 483
<211> LENGTH: 323
<212> TYPE: PRT
<213> ORGANISM: Homo sapiens

<400> SEQUENCE: 483

```
Met Gly Thr Arg Ala Leu Gln Cys Glu Val Ser His Thr His Glu Asn
                5                  10                  15
Glu Asn Tyr Leu Leu His Glu Asn Cys Met Leu Lys Lys Glu Ile Ala
            20                  25                  30
Met Leu Lys Leu Glu Ile Ala Thr Leu Lys His Gln Tyr Gln Glu Lys
        35                  40                  45
Glu Asn Lys Tyr Phe Glu Asp Ile Lys Ile Leu Lys Glu Lys Asn Ala
    50                  55                  60
Glu Leu Gln Met Thr Leu Lys Leu Lys Glu Glu Ser Leu Thr Lys Arg
65                  70                  75                  80
Ala Ser Gln Tyr Ser Gly Gln Leu Lys Val Leu Ile Ala Glu Asn Thr
                85                  90                  95
Met Leu Thr Ser Lys Leu Lys Glu Lys Gln Asp Lys Glu Ile Leu Glu
            100                 105                 110
```

```
Ala Glu Ile Glu Ser His His Pro Arg Leu Ala Ser Ala Val Gln Asp
        115                 120                 125
His Asp Gln Ile Val Thr Ser Arg Lys Ser Gln Glu Pro Ala Phe His
130                 135                 140
Ile Ala Gly Asp Ala Cys Leu Gln Arg Lys Met Asn Val Asp Val Ser
145                 150                 155                 160
Ser Thr Ile Tyr Asn Asn Glu Val Leu His Gln Pro Leu Ser Glu Ala
                165                 170                 175
Gln Arg Lys Ser Lys Ser Leu Lys Ile Asn Leu Asn Tyr Ala Gly Asp
            180                 185                 190
Ala Leu Arg Glu Asn Thr Leu Val Ser Glu His Ala Gln Arg Asp Gln
            195                 200                 205
Arg Glu Thr Gln Cys Gln Met Lys Glu Ala Glu His Met Tyr Gln Asn
    210                 215                 220
Glu Gln Asp Asn Val Asn Lys His Thr Glu Gln Gln Glu Ser Leu Asp
225                 230                 235                 240
Gln Lys Leu Phe Gln Leu Gln Ser Lys Asn Met Trp Leu Gln Gln Gln
                245                 250                 255
Leu Val His Ala His Lys Lys Ala Asp Asn Lys Ser Lys Ile Thr Ile
            260                 265                 270
Asp Ile His Phe Leu Glu Arg Lys Met Gln His His Leu Leu Lys Glu
        275                 280                 285
Lys Asn Glu Glu Ile Phe Asn Tyr Asn Asn His Leu Lys Asn Arg Ile
    290                 295                 300
Tyr Gln Tyr Glu Lys Glu Lys Ala Glu Thr Glu Val Ile His His His
305                 310                 315                 320
His His His

<210> SEQ ID NO 484
<211> LENGTH: 1518
<212> TYPE: DNA
<213> ORGANISM: Homo sapiens

<400> SEQUENCE: 484
atgacctgcg gatcaggatt tggtgggcgc gccttccgct gcatctcggc ctgcgggccg      60
cggcccggcc gctgctgcat caccgccgcc ccctaccgtg gcatctcctg ctaccgcggc     120
ctcaccgggg gcttcggcag ccacagcgtg tgcggaggct ttcgggccgg ctcctgcgga     180
cgcagcttcg gctaccgctc cggggcgtg tgcgggccca gtcccccatg catcaccacc     240
gtgtcggtca cgagagcct cctcacgccc ctcaacctgg agatcgaccc caacgcgcag     300
tgcgtgaagc aggaggagaa ggagcagatc aagtccctca cagcaggtt cgcggccttc     360
atcgacaagg tgcgcttcct ggagcagcag aacaaactgc tggagacaaa gctgcagttc     420
taccagaacc gcgagtgttg ccagagcaac ctggagcccc tgtttgaggg ctacatcgag     480
actctgcggc gggaggccga gtgcgtggag ccgacagcg ggaggctggc ctcagagctt     540
aaccacgtgc aggaggtgct ggagggctac aagaagaagt atgaggagga ggtttctctg     600
agagcaacag ctgagaacga gtttgtggct ctgaagaagg atgtggactg cgcctacctc     660
cgcaagtcag acctggaggc caacgtggag gccctgatcc aggagatcga cttcctgagg     720
cggctgtatg aggaggagat ccgcattctc cagtcgcaca tctcagacac ctccgtggtt     780
gtcaagctgg acaacagccg ggacctgaac atggactgca tcattgccga gattaaggca     840
cagtatgacg acattgtcac ccgcagccgg gccgaggccg agtcctggta ccgcagcaag     900
```

-continued

```
tgtgaggaga tgaaggccac ggtgatcagg cacggggaga ccctgcgccg caccaaggag    960
gagatcaatg agctgaaccg catgatccaa aggctgacgg ccgaggtgga aatgccaag    1020 tgccagaact ccaagctgga ggccgcggtg gcccagtctg agcagcaggg tgaggcagcc   1080
ctcagtgatg cccgctgcaa gctggccgag ctggagggcg ccctgcagaa ggccaagcag   1140
gacatggcct gcctgatcag ggagtaccag gaggtgatga actccaagct gggcctggac   1200
atcgagatcg ccacctacag gcgcctgctg gagggcgagg agcagaggct atgtgaaggc   1260
attggggctg tgaatgtctg tgtcagcagc tcccggggcg gggtcgtgtg cggggacctc   1320
tgcgtgtcag gctcccggcc agtgactggc agtgtctgca gcgctccgtg caacgggaac   1380
gtggcggtga gcaccggcct gtgtgcgccc tgcggccaat tgaacaccac ctgcggaggg   1440
ggttcctgcg gcgtgggctc ctgtggtatc agctccctgg gtgtggggtc ttgcggcagc   1500
agctgccgga aatgttag                                                  1518
```

<210> SEQ ID NO 485
<211> LENGTH: 505
<212> TYPE: PRT
<213> ORGANISM: Homo sapiens

<400> SEQUENCE: 485

```
Met Thr Cys Gly Ser Gly Phe Gly Gly Arg Ala Phe Arg Cys Ile Ser
              5                  10                  15

Ala Cys Gly Pro Arg Pro Gly Arg Cys Cys Ile Thr Ala Ala Pro Tyr
         20                  25                  30

Arg Gly Ile Ser Cys Tyr Arg Gly Leu Thr Gly Gly Phe Gly Ser His
     35                  40                  45

Ser Val Cys Gly Gly Phe Arg Ala Gly Ser Cys Gly Arg Ser Phe Gly
 50                  55                  60

Tyr Arg Ser Gly Gly Val Cys Gly Pro Ser Pro Cys Ile Thr Thr
 65                  70                  75                  80

Val Ser Val Asn Glu Ser Leu Leu Thr Pro Leu Asn Leu Glu Ile Asp
                 85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
```

```
                260                 265                 270
Cys Ile Ile Ala Glu Ile Lys Ala Gln Tyr Asp Asp Ile Val Thr Arg
                275                 280                 285
Ser Arg Ala Glu Ala Glu Ser Trp Tyr Arg Ser Lys Cys Glu Glu Met
        290                 295                 300
Lys Ala Thr Val Ile Arg His Gly Glu Thr Leu Arg Arg Thr Lys Glu
305                 310                 315                 320
Glu Ile Asn Glu Leu Asn Arg Met Ile Gln Arg Leu Thr Ala Glu Val
                325                 330                 335
Glu Asn Ala Lys Cys Gln Asn Ser Lys Leu Glu Ala Ala Val Ala Gln
                340                 345                 350
Ser Glu Gln Gln Gly Glu Ala Ala Leu Ser Asp Ala Arg Cys Lys Leu
        355                 360                 365
Ala Glu Leu Glu Gly Ala Leu Gln Lys Ala Lys Gln Asp Met Ala Cys
        370                 375                 380
Leu Ile Arg Glu Tyr Gln Glu Val Met Asn Ser Lys Leu Gly Leu Asp
385                 390                 395                 400
Ile Glu Ile Ala Thr Tyr Arg Arg Leu Leu Glu Gly Glu Glu Gln Arg
                405                 410                 415
Leu Cys Glu Gly Ile Gly Ala Val Asn Val Cys Val Ser Ser Ser Arg
                420                 425                 430
Gly Gly Val Val Cys Gly Asp Leu Cys Val Ser Gly Ser Arg Pro Val
        435                 440                 445
Thr Gly Ser Val Cys Ser Ala Pro Cys Asn Gly Asn Val Ala Val Ser
        450                 455                 460
Thr Gly Leu Cys Ala Pro Cys Gly Gln Leu Asn Thr Thr Cys Gly Gly
465                 470                 475                 480
Gly Ser Cys Gly Val Gly Ser Cys Gly Ile Ser Ser Leu Gly Val Gly
                485                 490                 495
Ser Cys Gly Ser Ser Cys Arg Lys Cys
                500                 505

<210> SEQ ID NO 486
<211> LENGTH: 827
<212> TYPE: DNA
<213> ORGANISM: Homo sapiens

<400> SEQUENCE: 486
gcattctcca gtcgcacatc tcagacacct ccgtggttgt caagctggac aacagccggg     60
acctgaacat ggactgcatc attgccgaga ttaaggcaca gtatgacgac attgtcaccc    120
gcagccgggc cgaggccgag tcctggtacc gcagcaagtg tgaggagatg aaggccacgg    180
tgatcaggca cggggagacc ctgcgccgca ccaaggagga gatcaatgag ctgaaccgca    240
tgatccaaag gctgacggcc gaggtggaga atgccaagtg ccagaactcc aagctggagg    300
ccgcggtggc ccagtctgag cagcagggtg aggcagccct cagtgatgcc cgctgcaagc    360
tggccgagct ggagggcgcc ctgcagaagg ccaagcagga catggcctgc ctgatcaggg    420
agtaccagga ggtgatgaac tccaagctgg gcctggacat cgagatcgcc acctacaggc    480
gcctgctgga gggcgaggag cagaggctat gtgaaggcat tggggctgtg aatgtctgtg    540
tcagcagctc ccggggcggg gtcgtgtgcg ggacctctg cgtgtcaggc tcccggccag    600
tgactggcag tgtctgcagc gctccgtgca acgggaacgt ggcggtgagc accggcctgt    660
gtgcgccctg cggccaattg aacaccacct gcggagggg ttcctgcggc gtgggctcct    720
```

```
gtggtatcag ctccctgggt gtggggtctt gcggcagcag ctgccggaaa tgttaggcac      780
cccaactcaa gtcccaggcc ccaggcatct ttcctgccct gccttgc                   827
```

<210> SEQ ID NO 487
<211> LENGTH: 235
<212> TYPE: PRT
<213> ORGANISM: Homo sapiens

<400> SEQUENCE: 487

```
Met Asp Cys Ile Ile Ala Glu Ile Lys Ala Gln Tyr Asp Asp Ile Val
                5                  10                  15

Thr Arg Ser Arg Ala Glu Ala Glu Ser Trp Tyr Arg Ser Lys Cys Glu
             20                  25                  30

Glu Met Lys Ala Thr Val Ile Arg His Gly Glu Thr Leu Arg Arg Thr
         35                  40                  45

Lys Glu Glu Ile Asn Glu Leu Asn Arg Met Ile Gln Arg Leu Thr Ala
     50                  55                  60

Glu Val Glu Asn Ala Lys Cys Gln Asn Ser Lys Leu Glu Ala Ala Val
 65                  70                  75                  80

Ala Gln Ser Glu Gln Gln Gly Glu Ala Ala Leu Ser Asp Ala Arg Cys
                 85                  90                  95

Lys Leu Ala Glu Leu Glu Gly Ala Leu Gln Lys Ala Lys Gln Asp Met
            100                 105                 110

Ala Cys Leu Ile Arg Glu Tyr Gln Glu Val Met Asn Ser Lys Leu Gly
        115                 120                 125

Leu Asp Ile Glu Ile Ala Thr Tyr Arg Arg Leu Leu Glu Gly Glu Glu
    130                 135                 140

Gln Arg Leu Cys Glu Gly Ile Gly Ala Val Asn Val Cys Val Ser Ser
145                 150                 155                 160

Ser Arg Gly Gly Val Val Cys Gly Asp Leu Cys Val Ser Gly Ser Arg
                165                 170                 175

Pro Val Thr Gly Ser Val Cys Ser Ala Pro Cys Asn Gly Asn Val Ala
            180                 185                 190

Val Ser Thr Gly Leu Cys Ala Pro Cys Gly Gln Leu Asn Thr Thr Cys
        195                 200                 205

Gly Gly Gly Ser Cys Gly Val Gly Ser Cys Gly Ile Ser Ser Leu Gly
    210                 215                 220

Val Gly Ser Cys Gly Ser Ser Cys Arg Lys Cys
225                 230                 235
```

<210> SEQ ID NO 488
<211> LENGTH: 9
<212> TYPE: PRT
<213> ORGANISM: Homo sapiens

<400> SEQUENCE: 488

```
Ser Leu Thr Lys Arg Ala Ser Gln Tyr
                5
```

<210> SEQ ID NO 489
<211> LENGTH: 27
<212> TYPE: DNA
<213> ORGANISM: Homo sapiens

<400> SEQUENCE: 489

```
tcattaacta aagggcatc tcaatat                                           27
```

-continued

<210> SEQ ID NO 490
<211> LENGTH: 3288
<212> TYPE: DNA
<213> ORGANISM: Homo sapiens

<400> SEQUENCE: 490

| | | | | | |
|---|---|---|---|---|---|
| atgaagttgc | tgatggtcct | catgctggcg | gccctctccc | agcactgcta | cgcaggctct | 60 |
| ggctgcccct | tattggagaa | tgtgatttcc | aagacaatca | atccacaagt | gtctaagact | 120 |
| gaatacaaag | aacttcttca | agagttcata | gacgacaatg | ccactacaaa | tgccatagat | 180 |
| gaattgaagg | aatgttttct | taaccaaacg | gatgaaactc | tgagcaatgt | tgaggtgttt | 240 |
| atgcaattaa | tatatgacag | cagtctttgt | gatttattta | tgagtcccgc | aaaagaaaca | 300 |
| tctgagaaat | ttacgtgggc | agcaaaagga | agacctagga | gatcgcatg | ggagaaaaaa | 360 |
| gaaacacctg | taaagactgg | atgcgtggca | agagtaacat | ctaataaaac | taaagttttg | 420 |
| gaaaaaggaa | gatctaagat | gattgcatgt | cctacaaaag | aatcatctac | aaaagcaagt | 480 |
| gccaatgatc | agaggttccc | atcagaatcc | aaacaagagg | aagatgaaga | atattcttgt | 540 |
| gattctcgga | gtctctttga | gagttctgca | agattcaag | tgtgtatacc | tgagtctata | 600 |
| tatcaaaaag | taatggagat | aaatagagaa | gtagaagagc | ctcctaagaa | gccatctgcc | 660 |
| ttcaagcctg | ccattgaaat | gcaaaactct | gttccaaata | aagcctttga | attgaagaat | 720 |
| gaacaaacat | tgagagcaga | tccgatgttc | ccaccagaat | ccaaacaaaa | ggactatgaa | 780 |
| gaaaattctt | gggattctga | gagtctctgt | gagactgttt | cacagaagga | tgtgtgttta | 840 |
| cccaaggcta | cacatcaaaa | agaaatagat | aaaataaatg | gaaaattaga | agagtctcct | 900 |
| aataaagatg | tcttctgaa | ggctacctgc | ggaatgaaag | tttctattcc | aactaaagcc | 960 |
| ttagaattga | aggacatgca | aactttcaaa | gcagagcctc | cggggaagcc | atctgccttc | 1020 |
| gagcctgcca | ctgaaatgca | aaagtctgtc | ccaaataaag | ccttggaatt | gaaaaatgaa | 1080 |
| caaacattga | gagcagatga | gatactccca | tcagaatcca | acaaaagga | ctatgaagaa | 1140 |
| agttcttggg | attctgagag | tctctgtgag | actgtttcac | agaaggatgt | gtgtttaccc | 1200 |
| aaggctrcrc | atcaaaaaga | aatagataaa | ataaatggaa | aattagaagg | gtctcctgtt | 1260 |
| aaagatggtc | ttctgaaggc | taactgcgga | atgaaagttt | ctattccaac | taaagcctta | 1320 |
| gaattgatgg | acatgcaaac | tttcaaagca | gagcctcccg | agaagccatc | tgccttcgag | 1380 |
| cctgccattg | aaatgcaaaa | gtctgttcca | aataaagcct | tggaattgaa | gaatgaacaa | 1440 |
| acattgagag | cagatgagat | actcccatca | gaatccaaac | aaaaggacta | tgaagaaagt | 1500 |
| tcttgggatt | ctgagagtct | ctgtgagact | gtttcacaga | aggatgtgtg | tttacccaag | 1560 |
| gctrcrcatc | aaaaagaaat | agataaaata | aatggaaaat | tagaagagtc | tcctgataat | 1620 |
| gatggttttc | tgaaggctcc | ctgcagaatg | aaagtttcta | ttccaactaa | agccttagaa | 1680 |
| ttgatggaca | tgcaaacttt | caaagcagag | cctcccgaga | agccatctgc | cttcgagcct | 1740 |
| gccattgaaa | tgcaaaagtc | tgttccaaat | aaagccttgg | aattgaagaa | tgaacaaaca | 1800 |
| ttgagagcag | atcagatgtt | cccttcagaa | tcaaacaaa | agaasgttga | gaaaattct | 1860 |
| tgggattctg | agagtctccg | tgagactgtt | tcacagaagg | atgtgtgtgt | acccaaggct | 1920 |
| acacatcaaa | agaaatgga | taaaataagt | ggaaaattag | aagattcaac | tagcctatca | 1980 |
| aaaatcttgg | atacagttca | ttcttgtgaa | agagcaaggg | aacttcaaaa | agatcactgt | 2040 |
| gaacaacgta | caggaaaaat | ggaacaaatg | aaaaagaagt | tttgtgtact | gaaaagaaa | 2100 |
| ctgtcagaag | caaaagaaat | aaaatcacag | ttagagaacc | aaaaagttaa | atgggaacaa | 2160 |

```
gagctctgca gtgtgagatt gactttaaac caagaagaag agaagagaag aaatgccgat      2220
atattaaatg aaaaaattag ggaagaatta ggaagaatcg aagagcagca taggaaagag      2280
ttagaagtga acaacaact tgaacaggct ctcagaatac aagatataga attgaagagt      2340
gtagaaagta atttgaatca ggtttctcac actcatgaaa atgaaaatta tctcttacat      2400
gaaaattgca tgttgaaaaa ggaaattgcc atgctaaaac tggaaatagc cacactgaaa      2460
caccaatacc aggaaaagga aaataaatac tttgaggaca ttaagatttt aaaagaaaag      2520
aatgctgaac ttcagatgac cctaaaactg aaagaggaat cattaactaa aagggcatct      2580
caatatagtg ggcagcttaa agttctgata gctgagaaca caatgctcac ttctaaattg      2640
aaggaaaaac aagacaaaga aatactagag gcagaaattg aatcacacca tcctagactg      2700
gcttctgctg tacaagacca tgatcaaatt gtgacatcaa gaaaaagtca agaacctgct      2760
ttccacattg caggagatgc ttgtttgcaa agaaaaatga atgttgatgt gagtagtacg      2820
atatataaca atgaggtgct ccatcaacca ctttctgaag ctcaaaggaa atccaaaagc      2880
ctaaaaatta atctcaatta tgcmggagat gctctaagag aaaatacatt ggtttcagaa      2940
catgcacaaa gagaccaacg tgaaacacag tgtcaaatga aggaagctga acacatgtat      3000
caaaacgaac aagataatgt gaacaaacac actgaacagc aggagtctct agatcagaaa      3060
ttatttcaac tacaaagcaa aaatatgtgg cttcaacagc aattagttca tgcacataag      3120
aaagctgaca caaaagcaa gataacaatt gatattcatt tcttgagag gaaaatgcaa      3180 catcatctcc taaagagaa aaatgaggag atatttaatt acaataacca tttaaaaaac      3240
cgtatatatc aatatgaaaa agagaaagca gaaacagaaa actcatga               3288
```

<210> SEQ ID NO 491
<211> LENGTH: 2232
<212> TYPE: DNA
<213> ORGANISM: Homo sapiens

<400> SEQUENCE: 491

```
atgaagttgc tgatggtcct catgctggcg gccctctccc agcactgcta cgcaggctct        60
ggctgcccct tattggagaa tgtgatttcc aagacaatca atccacaagt gtctaagact       120
gaatacaaag aacttcttca agagttcata gacgacaatg ccactacaaa tgccatagat       180
gaattgaagg aatgttttct taaccaaacg gatgaaactc tgagcaatgt tgaggtgttt       240
atgcaattaa tatatgacag cagtctttgt gatttattta tgagtcccgc aaaagaaaca       300
tctgagaaat ttacgtgggc agcaaaagga agacctagga gatcgcatg ggagaaaaaa       360 gaaacacctg taaagactgg atgcgtggca agagtaacat ctaataaaac taaagttttg       420 gaaaaggaa gatctaagat gattgcatgt cctacaaaag aatcatctac aaaagcaagt       480
gccaatgatc agaggttccc atcagaatcc aaacaagagg aagatgaaga atattcttgt       540
gattctcgga gtctctttga gagttctgca agattcaag tgtgtatacc tgagtctata       600
tatcaaaaag taatggagat aaatagaaaa gtagaagagc tcctaagaa gccatctgcc       660 ttcaagcctg ccattgaaat gcaaaactct gttccaaata aagcctttga attgaagaat       720
gaacaaacat tgagagcaga tccgatgttc ccaccagaat ccaaacaaaa ggactatgaa       780
gaaaattctt gggattctga gagtctctgt gagactgttt cacagaagga tgtgtgttta       840
cccaaggcta cacatcaaaa agaaatagat aaaataaatg gaaaattaga agagtctcct       900
aataaagatg gtcttctgaa ggctacctgc ggaatgaaag tttctattcc aactaaagcc       960
ttagaattga aggacatgca aacttttcaaa gcagagcctc cggggaagcc atctgccttc      1020
```

```
gagcctgcca ctgaaatgca aaagtctgtc ccaaataaag ccttggaatt gaaaaatgaa    1080
caaacattga gagcagatga gatactccca tcagaatcca aacaaaagga ctatgaagaa    1140
agttcttggg attctgagag tctctgtgag actgtttcac agaaggatgt gtgtttaccc    1200
aaggctrcrc atcaaaaaga aatagataaa ataaatggaa aattagaagg gtctcctgtt    1260
aaagatggtc ttctgaaggc taactgcgga atgaaagttt ctattccaac taaagcctta    1320
gaattgatgg acatgcaaac tttcaaagca gagcctcccg agaagccatc tgccttcgag    1380
cctgccattg aaatgcaaaa gtctgttcca aataaagcct tggaattgaa gatgaacaaa    1440
acattgagag cagatgagat actcccatca gaatccaaac aaaaggacta tgaagaaagt    1500
tcttgggatt ctgagagtct ctgtgagact gtttcacaga aggatgtgtg tttacccaag    1560
gctrcrcatc aaaagaaat agataaaata aatggaaaat agaagagtc tcctgataat    1620 gatggttttc tgaaggctcc ctgcagaatg aaagtttcta ttccaactaa agccttagaa    1680
ttgatggaca tgcaaacttt caaagcagag cctcccgaga gccatctgc cttcgagcct    1740 gccattgaaa tgcaaaagtc tgttccaaat aaagccttgg aattgaagaa tgaacaaaca    1800
ttgagagcag atcagatgtt cccttcagaa tcaaaacaaa gaasgttga agaaaattct    1860 tgggattctg agagtctccg tgagactgtt tcacagaagg atgtgtgtgt acccaaggct    1920
acacatcaaa agaaatgga taaataagt ggaaaattag aagattcaac tagcctatca    1980
aaaatcttgg atacagttca ttcttgtgaa gagcaaggg aacttcaaaa agatcactgt    2040
gaacaacgta caggaaaaat ggaacaaatg aaaagaagt tttgtgtact gaaaaagaaa    2100
ctgtcagaag caaagaaat aaaatcacag ttagagaacc aaaaagttaa atgggaacaa    2160
gagctctgca gtgtgaggtt tctcacactc atgaaaatga aaattatctc ttacatgaaa    2220
attgcatgtt ga                                                         2232
```

<210> SEQ ID NO 492
<211> LENGTH: 1233
<212> TYPE: DNA
<213> ORGANISM: Homo sapiens

<400> SEQUENCE: 492

```
atgaagttgc tgatggtcct catgctggcg gccctctccc agcactgcta cgcaggctct      60
ggctgcccct tattggagaa tgtgatttcc aagacaatca atccacaagt gtctaagact    120
gaatacaaag aacttcttca agagttcata gacgacaatg ccactacaaa tgccatagat    180
gaattgaagg aatgttttct taaccaaacg gatgaaactc tgagcaatgt tgaggtgttt    240
atgcaattaa tatatgacag cagtctttgt gatttattta tgggaacaag agctctgcag    300
tgtgaggttt ctcacactca tgaaaatgaa aattatctct acatgaaaaa ttgcatgttg    360
aaaaaggaaa ttgccatgct aaaactggaa atagccacac tgaacaccaa ataccaggaa    420
aaggaaaata aatactttga ggacattaag attttaaaag aaaagaatgc tgaacttcag    480
atgaccctaa aactgaaaga ggaatcatta actaaagggg catctcaata tagtgggcag    540
cttaaagttc tgatagctga gaacacaatg ctcacttcta aattgaagga aaaacaagac    600
aaagaaatac tagaggcaga aattgaatca ccatcccta gactggcttc tgctgtacaa    660
gaccatgatc aaattgtgac atcaagaaaa agtcaagaac ctgctttcca cattgcagga    720
gatgcttgtt tgcaaagaaa aatgaatgtt gatgtgagta gtacgatata taacaatgag    780
gtgctccatc aaccactttc tgaagctcaa aggaaatcca aagcctaaa aattaatctc    840
```

-continued

```
aattatgccg agatgctct aagagaaaat acattggttt cagaacatgc acaaagagac      900
caacgtgaaa cacagtgtca atgaaggaa gctgaacaca tgtatcaaaa cgaacaagat      960
aatgtgaaca acacactga acagcaggag tctctagatc agaaattatt tcaactacaa     1020
agcaaaaata tgtggcttca acagcaatta gttcatgcac ataagaaagc tgacaacaaa     1080
agcaagataa caattgatat tcattttctt gagaggaaaa tgcaacatca tctcctaaaa     1140
gagaaaaatg aggagatatt taattacaat aaccatttaa aaaccgtat atatcaatat      1200 gaaaaagaga aagcagaaac agaagttata taa                                  1233
```

<210> SEQ ID NO 493
<211> LENGTH: 1095
<212> TYPE: PRT
<213> ORGANISM: Homo sapiens
<220> FEATURE:
<221> NAME/KEY: variant
<222> LOCATION: (1)...(1095)
<223> OTHER INFORMATION: Xaa = Any amino acid

<400> SEQUENCE: 493

```
Met Lys Leu Leu Met Val Leu Met Leu Ala Ala Leu Ser Gln His Cys
                 5                  10                  15

Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
         35                  40                  45

Phe Ile Asp Asp Asn Ala Thr Thr Asn Ala Ile Asp Glu Leu Lys Glu
     50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Ser Pro
                 85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Pro Glu Ser Lys Gln
                245                 250                 255

Lys Asp Tyr Glu Glu Asn Ser Trp Asp Ser Glu Ser Leu Cys Glu Thr
            260                 265                 270

Val Ser Gln Lys Asp Val Cys Leu Pro Lys Ala Thr His Gln Lys Glu
        275                 280                 285
```

-continued

```
Ile Asp Lys Ile Asn Gly Lys Leu Glu Glu Ser Pro Asn Lys Asp Gly
    290                 295                 300
Leu Leu Lys Ala Thr Cys Gly Met Lys Val Ser Ile Pro Thr Lys Ala
305                 310                 315                 320
Leu Glu Leu Lys Asp Met Gln Thr Phe Lys Ala Glu Pro Pro Gly Lys
                325                 330                 335
Pro Ser Ala Phe Glu Pro Ala Thr Glu Met Gln Lys Ser Val Pro Asn
                340                 345                 350
Lys Ala Leu Glu Leu Lys Asn Glu Gln Thr Leu Arg Ala Asp Glu Ile
                355                 360                 365
Leu Pro Ser Glu Ser Lys Gln Lys Asp Tyr Glu Glu Ser Ser Trp Asp
    370                 375                 380
Ser Glu Ser Leu Cys Glu Thr Val Ser Gln Lys Asp Val Cys Leu Pro
385                 390                 395                 400
Lys Ala Xaa His Gln Lys Glu Ile Asp Lys Ile Asn Gly Lys Leu Glu
                405                 410                 415
Gly Ser Pro Val Lys Asp Gly Leu Leu Lys Ala Asn Cys Gly Met Lys
                420                 425                 430
Val Ser Ile Pro Thr Lys Ala Leu Glu Leu Met Asp Met Gln Thr Phe
            435                 440                 445
Lys Ala Glu Pro Pro Glu Lys Pro Ser Ala Phe Glu Pro Ala Ile Glu
    450                 455                 460
Met Gln Lys Ser Val Pro Asn Lys Ala Leu Glu Leu Lys Asn Glu Gln
465                 470                 475                 480
Thr Leu Arg Ala Asp Glu Ile Leu Pro Ser Glu Ser Lys Gln Lys Asp
                485                 490                 495
Tyr Glu Glu Ser Ser Trp Asp Ser Glu Ser Leu Cys Glu Thr Val Ser
                500                 505                 510
Gln Lys Asp Val Cys Leu Pro Lys Ala Xaa His Gln Lys Glu Ile Asp
    515                 520                 525
Lys Ile Asn Gly Lys Leu Glu Glu Ser Pro Asp Asn Asp Gly Phe Leu
    530                 535                 540
Lys Ala Pro Cys Arg Met Lys Val Ser Ile Pro Thr Lys Ala Leu Glu
545                 550                 555                 560
Leu Met Asp Met Gln Thr Phe Lys Ala Glu Pro Pro Glu Lys Pro Ser
                565                 570                 575
Ala Phe Glu Pro Ala Ile Glu Met Gln Lys Ser Val Pro Asn Lys Ala
                580                 585                 590
Leu Glu Leu Lys Asn Glu Gln Thr Leu Arg Ala Asp Gln Met Phe Pro
    595                 600                 605
Ser Glu Ser Lys Gln Lys Xaa Val Glu Glu Asn Ser Trp Asp Ser Glu
    610                 615                 620
Ser Leu Arg Glu Thr Val Ser Gln Lys Asp Val Cys Val Pro Lys Ala
625                 630                 635                 640
Thr His Gln Lys Glu Met Asp Lys Ile Ser Gly Lys Leu Glu Asp Ser
                645                 650                 655
Thr Ser Leu Ser Lys Ile Leu Asp Thr Val His Ser Cys Glu Arg Ala
                660                 665                 670
Arg Glu Leu Gln Lys Asp His Cys Glu Gln Arg Thr Gly Lys Met Glu
                675                 680                 685
Gln Met Lys Lys Lys Phe Cys Val Leu Lys Lys Leu Ser Glu Ala
    690                 695                 700
```

```
Lys Glu Ile Lys Ser Gln Leu Glu Asn Gln Lys Val Lys Trp Glu Gln
705                 710                 715                 720

Glu Leu Cys Ser Val Arg Leu Thr Leu Asn Gln Glu Glu Lys Arg
            725                 730                 735

Arg Asn Ala Asp Ile Leu Asn Glu Lys Ile Arg Glu Glu Leu Gly Arg
            740                 745                 750

Ile Glu Glu Gln His Arg Lys Glu Leu Glu Val Lys Gln Gln Leu Glu
            755                 760                 765

Gln Ala Leu Arg Ile Gln Asp Ile Glu Leu Lys Ser Val Glu Ser Asn
770                 775                 780

Leu Asn Gln Val Ser His Thr His Glu Asn Glu Asn Tyr Leu Leu His
785                 790                 795                 800

Glu Asn Cys Met Leu Lys Lys Glu Ile Ala Met Leu Lys Leu Glu Ile
                805                 810                 815

Ala Thr Leu Lys His Gln Tyr Gln Glu Lys Glu Asn Lys Tyr Phe Glu
            820                 825                 830

Asp Ile Lys Ile Leu Lys Glu Lys Asn Ala Glu Leu Gln Met Thr Leu
            835                 840                 845

Lys Leu Lys Glu Glu Ser Leu Thr Lys Arg Ala Ser Gln Tyr Ser Gly
850                 855                 860

Gln Leu Lys Val Leu Ile Ala Glu Asn Thr Met Leu Thr Ser Lys Leu
865                 870                 875                 880

Lys Glu Lys Gln Asp Lys Glu Ile Leu Glu Ala Glu Ile Glu Ser His
                885                 890                 895

His Pro Arg Leu Ala Ser Ala Val Gln Asp His Asp Gln Ile Val Thr
            900                 905                 910

Ser Arg Lys Ser Gln Glu Pro Ala Phe His Ile Ala Gly Asp Ala Cys
            915                 920                 925

Leu Gln Arg Lys Met Asn Val Asp Val Ser Ser Thr Ile Tyr Asn Asn
930                 935                 940

Glu Val Leu His Gln Pro Leu Ser Glu Ala Gln Arg Lys Ser Lys Ser
945                 950                 955                 960

Leu Lys Ile Asn Leu Asn Tyr Ala Gly Asp Ala Leu Arg Glu Asn Thr
                965                 970                 975

Leu Val Ser Glu His Ala Gln Arg Asp Gln Arg Glu Thr Gln Cys Gln
            980                 985                 990

Met Lys Glu Ala Glu His Met Tyr Gln Asn Glu Gln Asp Asn Val Asn
            995                 1000                1005

Lys His Thr Glu Gln Gln Glu Ser Leu Asp Gln Lys Leu Phe Gln Leu
    1010                1015                1020

Gln Ser Lys Asn Met Trp Leu Gln Gln Gln Leu Val His Ala His Lys
1025                1030                1035                1040

Lys Ala Asp Asn Lys Ser Lys Ile Thr Ile Asp Ile His Phe Leu Glu
                1045                1050                1055

Arg Lys Met Gln His His Leu Leu Lys Glu Lys Asn Glu Glu Ile Phe
            1060                1065                1070

Asn Tyr Asn Asn His Leu Lys Asn Arg Ile Tyr Gln Tyr Glu Lys Glu
            1075                1080                1085

Lys Ala Glu Thr Glu Asn Ser
            1090                1095

<210> SEQ ID NO 494
<211> LENGTH: 743
<212> TYPE: PRT
```

-continued

```
<213> ORGANISM: Homo sapiens
<220> FEATURE:
<221> NAME/KEY: variant
<222> LOCATION: (1)...(743)
<223> OTHER INFORMATION: Xaa = Any amino acid

<400> SEQUENCE: 494
```

Met Lys Leu Leu Met Val Leu Met Leu Ala Ala Leu Ser Gln His Cys
              5                  10                  15

Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
             35                  40                  45

Phe Ile Asp Asp Asn Ala Thr Thr Asn Ala Ile Asp Glu Leu Lys Glu
 50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Ser Pro
                 85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
            115                 120                 125

Val Ala Arg Val Thr Ser Asn Lys Thr Lys Val Leu Glu Lys Gly Arg
130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
            195                 200                 205

Arg Glu Val Glu Glu Pro Pro Lys Lys Pro Ser Ala Phe Lys Pro Ala
            210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Glu Ser Lys Gln
                245                 250                 255

Lys Asp Tyr Glu Glu Asn Ser Trp Asp Ser Glu Ser Leu Cys Glu Thr
            260                 265                 270

Val Ser Gln Lys Asp Val Cys Leu Pro Lys Ala Thr His Gln Lys Glu
            275                 280                 285

Ile Asp Lys Ile Asn Gly Lys Leu Glu Glu Ser Pro Asn Lys Asp Gly
            290                 295                 300

Leu Leu Lys Ala Thr Cys Gly Met Lys Val Ser Ile Pro Thr Lys Ala
305                 310                 315                 320

Leu Glu Leu Lys Asp Met Gln Thr Phe Lys Ala Glu Pro Pro Gly Lys
                325                 330                 335

Pro Ser Ala Phe Glu Pro Ala Thr Glu Met Gln Lys Ser Val Pro Asn
            340                 345                 350

Lys Ala Leu Glu Leu Lys Asn Glu Gln Thr Leu Arg Ala Asp Glu Ile
            355                 360                 365

Leu Pro Ser Glu Ser Lys Gln Lys Asp Tyr Glu Glu Ser Ser Trp Asp
            370                 375                 380

```
Ser Glu Ser Leu Cys Glu Thr Val Ser Gln Lys Asp Val Cys Leu Pro
385                 390                 395                 400

Lys Ala Xaa His Gln Lys Glu Ile Asp Lys Ile Asn Gly Lys Leu Glu
            405                 410                 415

Gly Ser Pro Val Lys Asp Gly Leu Leu Lys Ala Asn Cys Gly Met Lys
            420                 425                 430

Val Ser Ile Pro Thr Lys Ala Leu Glu Leu Met Asp Met Gln Thr Phe
            435                 440                 445

Lys Ala Glu Pro Pro Glu Lys Pro Ser Ala Phe Glu Pro Ala Ile Glu
450                 455                 460

Met Gln Lys Ser Val Pro Asn Lys Ala Leu Glu Leu Lys Asn Glu Gln
465                 470                 475                 480

Thr Leu Arg Ala Asp Glu Ile Leu Pro Ser Glu Ser Lys Gln Lys Asp
                485                 490                 495

Tyr Glu Glu Ser Ser Trp Asp Ser Glu Ser Leu Cys Glu Thr Val Ser
                500                 505                 510

Gln Lys Asp Val Cys Leu Pro Lys Ala Xaa His Gln Lys Glu Ile Asp
            515                 520                 525

Lys Ile Asn Gly Lys Leu Glu Glu Ser Pro Asp Asn Asp Gly Phe Leu
            530                 535                 540

Lys Ala Pro Cys Arg Met Lys Val Ser Ile Pro Thr Lys Ala Leu Glu
545                 550                 555                 560

Leu Met Asp Met Gln Thr Phe Lys Ala Glu Pro Pro Glu Lys Pro Ser
                565                 570                 575

Ala Phe Glu Pro Ala Ile Glu Met Gln Lys Ser Val Pro Asn Lys Ala
                580                 585                 590

Leu Glu Leu Lys Asn Glu Gln Thr Leu Arg Ala Asp Gln Met Phe Pro
                595                 600                 605

Ser Glu Ser Lys Gln Lys Xaa Val Glu Glu Asn Ser Trp Asp Ser Glu
            610                 615                 620

Ser Leu Arg Glu Thr Val Ser Gln Lys Asp Val Cys Val Pro Lys Ala
625                 630                 635                 640

Thr His Gln Lys Glu Met Asp Lys Ile Ser Gly Lys Leu Glu Asp Ser
                645                 650                 655

Thr Ser Leu Ser Lys Ile Leu Asp Thr Val His Ser Cys Glu Arg Ala
            660                 665                 670

Arg Glu Leu Gln Lys Asp His Cys Glu Gln Arg Thr Gly Lys Met Glu
            675                 680                 685

Gln Met Lys Lys Lys Phe Cys Val Leu Lys Lys Leu Ser Glu Ala
            690                 695                 700

Lys Glu Ile Lys Ser Gln Leu Glu Asn Gln Lys Val Lys Trp Glu Gln
705                 710                 715                 720

Glu Leu Cys Ser Val Arg Phe Leu Thr Leu Met Lys Met Lys Ile Ile
                725                 730                 735

Ser Tyr Met Lys Ile Ala Cys
            740

<210> SEQ ID NO 495
<211> LENGTH: 410
<212> TYPE: PRT
<213> ORGANISM: Homo sapiens

<400> SEQUENCE: 495
```

```
Met Lys Leu Leu Met Val Leu Met Leu Ala Ala Leu Ser Gln His Cys
                  5                  10                  15

Tyr Ala Gly Ser Gly Cys Pro Leu Leu Glu Asn Val Ile Ser Lys Thr
              20                  25                  30

Ile Asn Pro Gln Val Ser Lys Thr Glu Tyr Lys Glu Leu Leu Gln Glu
              35                  40                  45

Phe Ile Asp Asp Asn Ala Thr Thr Asn Ala Ile Asp Glu Leu Lys Glu
     50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Gly Thr
                  85                  90                  95

Arg Ala Leu Gln Cys Glu Val Ser His Thr His Glu Asn Glu Asn Tyr
              100                 105                 110

Leu Leu His Glu Asn Cys Met Leu Lys Lys Glu Ile Ala Met Leu Lys
             115                 120                 125

Leu Glu Ile Ala Thr Leu Lys His Gln Tyr Gln Glu Lys Glu Asn Lys
             130                 135                 140

Tyr Phe Glu Asp Ile Lys Ile Leu Lys Glu Lys Asn Ala Glu Leu Gln
145                 150                 155                 160

Met Thr Leu Lys Leu Lys Glu Glu Ser Leu Thr Lys Arg Ala Ser Gln
                 165                 170                 175

Tyr Ser Gly Gln Leu Lys Val Leu Ile Ala Glu Asn Thr Met Leu Thr
             180                 185                 190

Ser Lys Leu Lys Glu Lys Gln Asp Lys Glu Ile Leu Glu Ala Glu Ile
             195                 200                 205

Glu Ser His His Pro Arg Leu Ala Ser Ala Val Gln Asp His Asp Gln
210                 215                 220

Ile Val Thr Ser Arg Lys Ser Gln Glu Pro Ala Phe His Ile Ala Gly
225                 230                 235                 240

Asp Ala Cys Leu Gln Arg Lys Met Asn Val Asp Val Ser Ser Thr Ile
                 245                 250                 255

Tyr Asn Asn Glu Val Leu His Gln Pro Leu Ser Glu Ala Gln Arg Lys
             260                 265                 270

Ser Lys Ser Leu Lys Ile Asn Leu Asn Tyr Ala Gly Asp Ala Leu Arg
275                 280                 285

Glu Asn Thr Leu Val Ser Glu His Ala Gln Arg Asp Gln Arg Glu Thr
             290                 295                 300

Gln Cys Gln Met Lys Glu Ala Glu His Met Tyr Gln Asn Glu Gln Asp
305                 310                 315                 320

Asn Val Asn Lys His Thr Glu Gln Gln Glu Ser Leu Asp Gln Lys Leu
                 325                 330                 335

Phe Gln Leu Gln Ser Lys Asn Met Trp Leu Gln Gln Leu Val His
             340                 345                 350

Ala His Lys Lys Ala Asp Asn Lys Ser Lys Ile Thr Ile Asp Ile His
             355                 360                 365

Phe Leu Glu Arg Lys Met Gln His Leu Leu Lys Glu Lys Asn Glu
     370                 375                 380

Glu Ile Phe Asn Tyr Asn Asn His Leu Lys Asn Arg Ile Tyr Gln Tyr
385                 390                 395                 400

Glu Lys Glu Lys Ala Glu Thr Glu Val Ile
                 405                 410
```

COMPOSITIONS AND METHODS FOR THE THERAPY AND DIAGNOSIS OF BREAST CANCER

CROSS-REFERENCE TO RELATED APPLICATIONS

This application is a continuation in part of U.S. patent application Ser. No. 09/604,287, filed Jun. 22, 2000, which is a continuation-in-part of U.S. patent application Ser. No. 09/590,751, filed Jun. 8, 2000, which is a continuation-in-part of U.S. patent application Ser. No. 09/551,621, filed Apr. 17, 2000, which is a continuation-in-part of U.S. patent application Ser. No. 09/433,826, filed on Nov. 3, 1999, which is a continuation-in-part of U.S. application Ser. No. 09/389,681, filed on Sep. 2, 1999, which is a continuation-in-part of U.S. application Ser. No. 09/339,338, filed on Jun. 23, 1999, which is a continuation-in-part of U.S. application Ser. No. 09/285,480, filed on Apr. 2, 1999, which is a continuation-in-part of U.S. application Ser. No. 09/222,575, filed Dec. 28, 1998.

TECHNICAL FIELD OF THE INVENTION

The present invention relates generally to therapy and diagnosis of cancer, such as breast cancer. The invention is more specifically related to polypeptides comprising at least a portion of a breast tumor protein, and to polynucleotides encoding such polypeptides. Such polypeptides and polynucleotides may be used in compositions for prevention and treatment of breast cancer, and for the diagnosis and monitoring of such cancers.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, Breast Cancer 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

Briefly stated, the present invention provides compositions and methods for the diagnosis and therapy of cancer, such as breast cancer. In one aspect, the present invention provides polypeptides comprising at least a portion of a breast tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in SEQ ID NO: 1–175, 178, 180, 182–468, 474, 476, 477 479, 484, 486 and 489; (b) variants of a sequence recited in SEQ ID NO: 1–175, 178, 180, 182–468, 474, 476, 477, 479, 484, 486 and 489; and (c) complements of a sequence of (a) or (b). In specific embodiments, the polypeptides of the present invention comprise at least a portion of a tumor protein that includes an amino acid sequence selected from the group consisting of sequences recited in SEQ ID NO: 176, 179, 181, 469–473, 475, 485, 487 and 488, and variants thereof.

The present invention further provides polynucleotides that encode a polypeptide as described above, or a portion thereof (such as a portion encoding at least 15 amino acid residues of a breast tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, immunogenic compositions, or vaccines for prophylactic or therapeutic use are provided. Such compositions comprise a polypeptide or polynucleotide as described above and an immunostimulant.

The present invention further provides pharmaceutical compositions that comprise: (a) an antibody or antigen-binding fragment thereof that specifically binds to a breast tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, immunogenic compositions, or vaccines, are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins. Exemplary fusion proteins according to the present invention comprise a first amino acid portion and a second amino acid portion wherein the first amino acid portion includes 9 or more contiguous amino acids from mammaglobin as depicted by amino acids 1–93 of SEQ ID NO: 493; wherein the second amino acid portion includes 9 or more contiguous amino acids from B726P as depicted by SEQ ID NO: 475, SEQ ID NO: 469, or SEQ ID NO: 176; and wherein the first amino acid portion is connected to either the amino terminal or carboxy-terminal end of the second amino acid portion.

Still further embodiments of the present invention provide fusion proteins wherein said first amino acid portion is selected from the group consisting of IDELKECFLNQT-DETLSNVE (amino acids 59–78 of SEQ ID NO: 493); TTNAIDELKECFLNQ (amino acids 55–69 of SEQ ID NO: 493); SQHCYAGSGCPLLENVISKTI (amino acids 13–33 of SEQ ID NO: 493); EYKELLQEFIDDNATTNAID (amino acids 41–60 of SEQ ID NO: 493); KLLMVLMLA (amino acids 2–10 of SEQ ID NO: 493); QEFIDDNATT-NAI (amino acids 47–59 of SEQ ID NO: 493); and LKEC-FLNQTDETL (amino acids 62–74 of SEQ ID NO: 493).

Alternative embodiments provide fusion proteins wherein the second amino acid portion includes 9 or more contiguous amino acids encoded by (1) the combined upstream and downstream open reading frame (ORF) of B726P as depicted in SEQ ID NO: 475; (2) the upstream ORF of B726P as depicted in from SEQ ID NO: 469; and (3) the downstream ORF of B726P as depicted in SEQ ID NO: 176. Fusion proteins according to the present invention may also comprise a second amino acid portion that includes 9 or more contiguous amino acids from the amino acid sequence depicted by amino acids 1–129 of SEQ ID NO: 475. Still additional exemplary fusion proteins are depicted herein by SEQ ID NO: 493; SEQ ID NO: 494; and SEQ ID NO: 495.

Fusion proteins are provided wherein the mammaglobin amino acid portion is connected to the amino-terminus of the B726P amino acid portion while other fusion proteins are provided wherein the mammaglobin amino acid portion is connected to the carboxy-terminus of the B726P amino acid portion. The connection between the mammaglobin amino acid portion and the B726P portion may be a covalent bond. Additionally, a stretch of amino acids either unrelated or related to either mammaglobin and/or B726P may be incorporated between or either amino- or carboxy-terminal to either the mammaglobin and/or B726P amino acid portion.

The present invention also provides isolated polynucleotides that encode any of the fusion proteins that are specifically disclosed herein as well as those fusion proteins that may be accomplished with routine experimentation by the ordinarily skilled artisan.

Within related aspects, pharmaceutical compositions comprising a fusion protein, or a polynucleotide encoding a fusion protein, in combination with a physiologically acceptable carrier are provided.

Compositions are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be breast cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a breast tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 10 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence of JBTT18.

SEQ ID NO: 24 is the determined cDNA sequence of JBTT19.

SEQ ID NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6 (also known as B709P).

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6-2.

SEQ ID NO: 46 is the determined cDNA sequence of SYN21B9.

SEQ ID NO: 47 is the determined cDNA sequence of SYN21B9-2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21G10-2.

SEQ ID NO: 51 is the determined cDNA sequence of SYN21G11.

SEQ ID NO: 52 is the determined cDNA sequence of SYN21G11-2.

SEQ ID NO: 53 is the determined cDNA sequence of SYN21H8.

SEQ ID NO: 54 is the determined cDNA sequence of SYN22A10. SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6 (also known as B709P).

SEQ ID NO: 63 is the determined cDNA sequence of B723P.

SEQ ID NO: 64 is the determined cDNA sequence for B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 111 is the determined cDNA sequence of 13140.

SEQ ID NO: 112 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051

SEQ ID NO: 118 is the determined cDNA sequence of 13052

SEQ ID NO: 119 is the determined cDNA sequence of 13055

SEQ ID NO: 120 is the determined cDNA sequence of 13058

SEQ ID NO: 121 is the determined cDNA sequence of 13062

SEQ ID NO: 122 is the determined cDNA sequence of 13064

SEQ ID NO: 123 is the determined cDNA sequence of 13080

SEQ ID NO: 124 is the determined cDNA sequence of 13093

SEQ ID NO: 125 is the determined cDNA sequence of 13094

SEQ ID NO: 126 is the determined cDNA sequence of 13095
SEQ ID NO: 127 is the determined cDNA sequence of 13096
SEQ ID NO: 128 is the determined cDNA sequence of 13099
SEQ ID NO: 129 is the determined cDNA sequence of 13100
SEQ ID NO: 130 is the determined cDNA sequence of 13103
SEQ ID NO: 131 is the determined cDNA sequence of 13106
SEQ ID NO: 132 is the determined cDNA sequence of 13107
SEQ ID NO: 133 is the determined cDNA sequence of 13108
SEQ ID NO: 134 is the determined cDNA sequence of 13121
SEQ ID NO: 135 is the determined cDNA sequence of 13126
SEQ ID NO: 136 is the determined cDNA sequence of 13129
SEQ ID NO: 137 is the determined cDNA sequence of 13130
SEQ ID NO: 138 is the determined cDNA sequence of 13134
SEQ ID NO: 139 is the determined cDNA sequence of 13141
SEQ ID NO: 140 is the determined cDNA sequence of 13142
SEQ ID NO: 141 is the determined cDNA sequence of 14376
SEQ ID NO: 142 is the determined cDNA sequence of 14377
SEQ ID NO: 143 is the determined cDNA sequence of 14383
SEQ ID NO: 144 is the determined cDNA sequence of 14384
SEQ ID NO: 145 is the determined cDNA sequence of 14387
SEQ ID NO: 146 is the determined cDNA sequence of 14392
SEQ ID NO: 147 is the determined cDNA sequence of 14394
SEQ ID NO: 148 is the determined cDNA sequence of 14398
SEQ ID NO: 149 is the determined cDNA sequence of 14401
SEQ ID NO: 150 is the determined cDNA sequence of 14402
SEQ ID NO: 151 is the determined cDNA sequence of 14405
SEQ ID NO: 152 is the determined cDNA sequence of 14409
SEQ ID NO: 153 is the determined cDNA sequence of 14412
SEQ ID NO: 154 is the determined cDNA sequence of 14414
SEQ ID NO: 155 is the determined cDNA sequence of 14415
SEQ ID NO: 156 is the determined cDNA sequence of 14416
SEQ ID NO: 157 is the determined cDNA sequence of 14419
SEQ ID NO: 158 is the determined cDNA sequence of 14426
SEQ ID NO: 159 is the determined cDNA sequence of 14427
SEQ ID NO: 160 is the determined cDNA sequence of 14375
SEQ ID NO: 161 is the determined cDNA sequence of 14378
SEQ ID NO: 162 is the determined cDNA sequence of 14379
SEQ ID NO: 163 is the determined cDNA sequence of 14380
SEQ ID NO: 164 is the determined cDNA sequence of 14381
SEQ ID NO: 165 is the determined cDNA sequence of 14382
SEQ ID NO: 166 is the determined cDNA sequence of 14388
SEQ ID NO: 167 is the determined cDNA sequence of 14399
SEQ ID NO: 168 is the determined cDNA sequence of 14406
SEQ ID NO: 169 is the determined cDNA sequence of 14407
SEQ ID NO: 170 is the determined cDNA sequence of 14408
SEQ ID NO: 171 is the determined cDNA sequence of 14417
SEQ ID NO: 172 is the determined cDNA sequence of 14418
SEQ ID NO: 173 is the determined cDNA sequence of 14423
SEQ ID NO: 174 is the determined cDNA sequence of 14424
SEQ ID NO: 175 is the determined cDNA sequence of B726P-20
SEQ ID NO: 176 is the predicted amino acid sequence of B726P-20
SEQ ID NO: 177 is a PCR primer
SEQ ID NO: 178 is the determined cDNA sequence of B726P-74
SEQ ID NO: 179 is the predicted amino acid sequence of B726P-74
SEQ ID NO: 180 is the determined cDNA sequence of B726P-79
SEQ ID NO: 181 is the predicted amino acid sequence of B726P-79
SEQ ID NO: 182 is the determined cDNA sequence of 19439.1, showing homology to the mammaglobin gene
SEQ ID NO: 183 is the determined cDNA sequence of 19407.1, showing homology to the human keratin gene
SEQ ID NO: 184 is the determined cDNA sequence of 19428.1, showing homology to human chromosome 17 clone
SEQ ID NO: 185 is the determined cDNA sequence of B808P (19408), showing no significant homology to any known gene
SEQ ID NO: 186 is the determined cDNA sequence of 19460.1, showing no significant homology to any known gene SEQ ID NO: 187 is the determined cDNA sequence of 19419.1, showing homology to Ig kappa light chain SEQ ID NO: 188 is the determined cDNA sequence of 19411.1, showing homology to human alpha-1 collagen SEQ ID NO: 189 is the determined cDNA sequence of 19420.1, showing homology to mus musculus proteinase-3

SEQ ID NO: 190 is the determined cDNA sequence of 19432.1, showing homology to human high motility group box SEQ ID NO: 191 is the determined cDNA sequence of 19412.1, showing homology to the human plasminogen activator gene SEQ ID NO: 192 is the determined cDNA sequence of 19415.1, showing homology to mitogen activated protein kinase SEQ ID NO: 193 is the determined cDNA sequence of 19409.1, showing homology to the chondroitin sulfate proteoglycan protein SEQ ID NO: 194 is the determined cDNA sequence of 19406.1, showing no significant homology to any known gene SEQ ID NO: 195 is the determined cDNA sequence of 19421.1, showing homology to human fibronectin SEQ ID NO: 196 is the determined cDNA sequence of 19426.1, showing homology to the retinoic acid receptor responder 3

SEQ ID NO: 197 is the determined cDNA sequence of 19425.1, showing homology to MyD88 mRNA SEQ ID NO: 198 is the determined cDNA sequence of 19424.1, showing homology to peptide transporter (TAP-1) mRNA SEQ ID NO: 199 is the determined cDNA sequence of 19429.1, showing no significant homology to any known gene SEQ ID NO: 200 is the determined cDNA sequence of 19435.1, showing homology to human polymorphic epithelial mucin SEQ ID NO: 201 is the determined cDNA sequence of B813P (19434.1), showing homology to human GATA-3 transcription factor SEQ ID NO: 202 is the determined cDNA sequence of 19461.1, showing homology to the human AP-2 gene SEQ ID NO: 203 is the determined cDNA sequence of 19450.1, showing homology to DNA binding regulatory factor SEQ ID NO: 204 is the determined cDNA sequence of 19451.1, showing homology to Na/H exchange regulatory co-factor SEQ ID NO: 205 is the determined cDNA sequence of 19462.1, showing no significant homology to any known gene SEQ ID NO: 206 is the determined cDNA sequence of 19455.1, showing homology to human mRNA for histone HAS.Z SEQ ID NO: 207 is the determined cDNA sequence of 19459.1, showing homology to PAC clone 179N16

SEQ ID NO: 208 is the determined cDNA sequence of 19464.1, showing no significant homology to any known gene SEQ ID NO: 209 is the determined cDNA sequence of 19414.1, showing homology to lipophilin B SEQ ID NO: 210 is the determined cDNA sequence of 19413.1, showing homology to chromosome 17 clone hRPK.209_J_20

SEQ ID NO: 211 is the determined cDNA sequence of 19416.1, showing no significant homology to any known gene SEQ ID NO: 212 is the determined cDNA sequence of 19437.1, showing homology to human clone 24976 mRNA SEQ ID NO: 213 is the determined cDNA sequence of 19449.1, showing homology to mouse DNA for PG-M core protein SEQ ID NO: 214 is the determined cDNA sequence of 19446.1, showing no significant homology to any known gene SEQ ID NO: 215 is the determined cDNA sequence of 19452.1, showing no significant homology to any known gene SEQ ID NO: 216 is the determined cDNA sequence of 19483.1, showing no significant homology to any known gene SEQ ID NO: 217 is the determined cDNA sequence of 19526.1, showing homology to human lipophilin C SEQ ID NO: 218 is the determined cDNA sequence of 19484.1, showing homology to the secreted cement gland protein XAG-2

SEQ ID NO: 219 is the determined cDNA sequence of 19470.1, showing no significant homology to any known gene SEQ ID NO: 220 is the determined cDNA sequence of 19469.1, showing homology to the human HLA-DM gene SEQ ID NO: 221 is the determined cDNA sequence of 19482.1, showing homology to the human pS2 protein gene SEQ ID NO: 222 is the determined cDNA sequence of B805P (19468.1), showing no significant homology to any known gene SEQ ID NO: 223 is the determined cDNA sequence of 19467.1, showing homology to human thrombospondin mRNA SEQ ID NO: 224 is the determined cDNA sequence of 19498.1, showing homology to the CDC2 gene involved in cell cycle control SEQ ID NO: 225 is the determined cDNA sequence of 19506.1, showing homology to human cDNA for TREB protein SEQ ID NO: 226 is the determined cDNA sequence of B806P (19505.1), showing no significant homology to any known gene SEQ ID NO: 227 is the determined cDNA sequence of 19486.1, showing homology to type I epidermal keratin SEQ ID NO: 228 is the determined cDNA sequence of 19510.1, showing homology to glucose transporter for glycoprotein SEQ ID NO: 229 is the determined cDNA sequence of 19512.1, showing homology to the human lysyl hydroxylase gene SEQ ID NO: 230 is the determined cDNA sequence of 19511.1, showing homology to human palimotoyl-protein thioesterase SEQ ID NO: 231 is the determined cDNA sequence of 19508.1, showing homology to human alpha enolase SEQ ID NO: 232 is the determined cDNA sequence of B807P (19509.1), showing no significant homology to any known gene SEQ ID NO: 233 is the determined cDNA sequence of B809P (19520.1), showing homology to clone 102D24 on chromosome 11q13.31

SEQ ID NO: 234 is the determined cDNA sequence of 19507.1, showing homology toprosome beta-subunit SEQ ID NO: 235 is the determined cDNA sequence of 19525.1, showing homology to human pro-urokinase precursor SEQ ID NO: 236 is the determined cDNA sequence of 19513.1, showing no significant homology to any known gene SEQ ID NO: 237 is the determined cDNA sequence of 19517.1, showing homology to human PAC 128M19 clone SEQ ID NO: 238 is the determined cDNA sequence of 19564.1, showing homology to human cytochrome P450-IIB SEQ ID NO: 239 is the determined cDNA sequence of 19553.1, showing homology to human GABA-A receptor pi subunit SEQ ID NO: 240 is the determined cDNA sequence of B811P (19575.1), showing no significant homology to any known gene SEQ ID NO: 241 is the determined cDNA sequence of B810P (19560.1), showing no significant homology to any known gene SEQ ID NO: 242 is the determined cDNA sequence of 19588.1, showing homology to aortic carboxypetidase-like protein SEQ ID NO: 243 is the determined cDNA sequence of 19551.1, showing homology to human BCL-1 gene SEQ ID NO: 244 is the determined cDNA sequence of 19567.1, showing homology to human proteasome-related mRNA SEQ ID NO: 245 is the determined cDNA sequence of B803P (19583.1), showing no significant homology to any known gene SEQ ID NO: 246 is the determined cDNA sequence of B812P (19587.1), showing no significant homology to any known gene SEQ ID NO: 247 is the determined cDNA sequence of B802P (19392.2), showing homology to human chromosome 17

SEQ ID NO: 248 is the determined cDNA sequence of 19393.2, showing homology to human nicein B2 chain SEQ ID NO: 249 is the determined cDNA sequence of 19398.2, human MHC class II DQ alpha mRNA SEQ ID NO: 250 is the determined cDNA sequence of B804P (19399.2), showing homology to human Xp22 BAC GSHB-184P14

SEQ ID NO: 251 is the determined cDNA sequence of 19401.2, showing homology to human ikB kinase-b gene SEQ ID NO: 252 is the determined cDNA sequence of 20266, showing no significant homology to any known gene SEQ ID NO: 253 is the determined cDNA sequence of B826P (20270), showing no significant homology to any known gene SEQ ID NO: 254 is the determined cDNA sequence of 20274, showing no significant homology to any known gene SEQ ID NO: 255 is the determined cDNA sequence of 20276, showing no significant homology to any known gene SEQ ID NO: 256 is the determined cDNA sequence of 20277, showing no significant homology to any known gene SEQ ID NO: 257 is the determined cDNA sequence of B823P (20280), showing no significant homology to any known gene SEQ ID NO: 258 is the determined cDNA sequence of B821P (20281), showing no significant homology to any known gene SEQ ID NO: 259 is the determined cDNA sequence of B824P (20294), showing no significant homology to any known gene SEQ ID NO: 260 is the determined cDNA sequence of 20303, showing no significant homology to any known gene SEQ ID NO: 261 is the determined cDNA sequence of B820P (20310), showing no significant homology to any known gene SEQ ID NO: 262 is the determined cDNA sequence of B825P (20336), showing no significant homology to any known gene SEQ ID NO: 263 is the determined cDNA sequence of B827P (20341), showing no significant homology to any known gene SEQ ID NO: 264 is the determined cDNA sequence of 20941, showing no significant homology to any known gene SEQ ID NO: 265 is the determined cDNA sequence of 20954, showing no significant homology to any known gene SEQ ID NO: 266 is the determined cDNA sequence of 20961, showing no significant homology to any known gene SEQ ID NO: 267 is the determined cDNA sequence of 20965, showing no significant homology to any known gene SEQ ID NO: 268 is the determined cDNA sequence of 20975, showing no significant homology to any known gene SEQ ID NO: 269 is the determined cDNA sequence of 20261, showing homology to Human p120 catenin SEQ ID NO: 270 is the determined cDNA sequence of B822P (20262), showing homology to Human membrane glycoprotein 4F2

SEQ ID NO: 271 is the determined cDNA sequence of 20265, showing homology to Human Na, K-ATPase Alpha 1

SEQ ID NO: 272 is the determined cDNA sequence of 20267, showing homology to Human heart HS 90, partial cds SEQ ID NO: 273 is the determined cDNA sequence of 20268, showing homology to Human mRNA GPI-anchored protein p137

SEQ ID NO: 274 is the determined cDNA sequence of 20271, showing homology to Human cleavage stimulation factor 77 kDa subunit SEQ ID NO: 275 is the determined cDNA sequence of 20272, showing homology to Human p190-B SEQ ID NO: 276 is the determined cDNA sequence of 20273, showing homology to Human ribophorin SEQ ID NO: 277 is the determined cDNA sequence of 20278, showing homology to Human ornithine amino transferase SEQ ID NO: 278 is the determined cDNA sequence of 20279, showing homology to Human S-adenosylmethionine synthetase SEQ ID NO: 279 is the determined cDNA sequence of 20293, showing homology to Human x inactivation transcript SEQ ID NO: 280 is the determined cDNA sequence of 20300, showing homology to Human cytochrome p450

SEQ ID NO: 281 is the determined cDNA sequence of 20305, showing homology to Human elongation factor-1 alpha SEQ ID NO: 282 is the determined cDNA sequence of 20306, showing homology to Human epithelial ets protein SEQ ID NO: 283 is the determined cDNA sequence of 20307, showing homology to Human signal transducer mRNA SEQ ID NO: 284 is the determined cDNA sequence of 20313, showing homology to Human GABA-A receptor pi subunit mRNA SEQ ID NO: 285 is the determined cDNA sequence of 20317, showing homology to Human tyrosine phosphatase SEQ ID NO: 286 is the determined cDNA sequence of 20318, showing homology to Human cathepsine B proteinase SEQ ID NO: 287 is the determined cDNA sequence of 20320, showing homology to Human 2-phosphopyruvate-hydratase-alpha-enolase SEQ ID NO: 288 is the determined cDNA sequence of 20321, showing homology to Human E-cadherin SEQ ID NO: 289 is the determined cDNA sequence of 20322, showing homology to Human hsp86

SEQ ID NO: 290 is the determined cDNA sequence of B828P (20326), showing homology to Human x inactivation transcript SEQ ID NO: 291 is the determined cDNA sequence of 20333, showing homology to Human chromatin regulator, SMARCA5

SEQ ID NO: 292 is the determined cDNA sequence of 20335, showing homology to Human sphingolipid activator protein 1

SEQ ID NO: 293 is the determined cDNA sequence of 20337, showing homology to Human hepatocyte growth factor activator inhibitor type 2

SEQ ID NO: 294 is the determined cDNA sequence of 20338, showing homology to Human cell adhesion molecule CD44

SEQ ID NO: 295 is the determined cDNA sequence of 20340, showing homology to Human nuclear factor (erythroid-derived)-like 1

SEQ ID NO: 296 is the determined cDNA sequence of 20938, showing homology to Human vinculin mRNA SEQ ID NO: 297 is the determined cDNA sequence of 20939, showing homology to Human elongation factor EF-1-alpha SEQ ID NO: 298 is the determined cDNA sequence of 20940, showing homology to Human nestin gene SEQ ID NO: 299 is the determined cDNA sequence of 20942, showing homology to Human pancreatic ribonuclease SEQ ID NO: 300 is the determined cDNA sequence of 20943, showing homology to Human transcobalamin I SEQ ID NO: 301 is the determined cDNA sequence of 20944, showing homology to Human beta-tubulin SEQ ID NO: 302 is the determined cDNA sequence of 20946, showing homology to Human HS1 protein SEQ ID NO: 303 is the determined cDNA sequence of 20947, showing homology to Human cathepsin B SEQ ID NO: 304 is the determined cDNA sequence of 20948, showing homology to Human testis enhanced gene transcript SEQ ID NO: 305 is the determined cDNA sequence of 20949, showing homology to Human elongation factor EF-1-alpha SEQ ID NO: 306 is the determined cDNA sequence of 20950, showing homology to Human ADP-ribosylation factor 3

SEQ ID NO: 307 is the determined cDNA sequence of 20951, showing homology to Human IFP53 or WRS for tryptophanyl-tRNA synthetase SEQ ID NO: 308 is the determined cDNA sequence of 20952, showing homology to Human cyclin-dependent protein kinase SEQ ID NO: 309 is the determined cDNA sequence of 20957, showing homology to Human alpha-tubulin isoform 1

SEQ ID NO: 310 is the determined cDNA sequence of 20959, showing homology to Human tyrosine phosphatase-61 bp deletion SEQ ID NO: 311 is the determined cDNA sequence of 20966, showing homology to Human tyrosine phosphatase SEQ ID NO: 312 is the determined cDNA sequence of B830P (20976), showing homology to Human nuclear factor NF 45

SEQ ID NO: 313 is the determined cDNA sequence of B829P (20977), showing homology to Human delta-6 fatty acid desaturase SEQ ID NO: 314 is the determined cDNA sequence of 20978, showing homology to Human nuclear aconitase SEQ ID NO: 315 is the determined cDNA sequence of clone 23176.

SEQ ID NO: 316 is the determined cDNA sequence of clone 23140.

SEQ ID NO: 317 is the determined cDNA sequence of clone 23166.

SEQ ID NO: 318 is the determined cDNA sequence of clone 23167.

SEQ ID NO: 319 is the determined cDNA sequence of clone 23177.

SEQ ID NO: 320 is the determined cDNA sequence of clone 23217.

SEQ ID NO: 321 is the determined cDNA sequence of clone 23169.

SEQ ID NO: 322 is the determined cDNA sequence of clone 23160.

SEQ ID NO: 323 is the determined cDNA sequence of clone 23182.

SEQ ID NO: 324 is the determined cDNA sequence of clone 23232.

SEQ ID NO: 325 is the determined cDNA sequence of clone 23203.

SEQ ID NO: 326 is the determined cDNA sequence of clone 23198.

SEQ ID NO: 327 is the determined cDNA sequence of clone 23224.

SEQ ID NO: 328 is the determined cDNA sequence of clone 23142.

SEQ ID NO: 329 is the determined cDNA sequence of clone 23138.

SEQ ID NO: 330 is the determined cDNA sequence of clone 23147.

SEQ ID NO: 331 is the determined cDNA sequence of clone 23148.

SEQ ID NO: 332 is the determined cDNA sequence of clone 23149.

SEQ ID NO: 333 is the determined cDNA sequence of clone 23172.

SEQ ID NO: 334 is the determined cDNA sequence of clone 23158.

SEQ ID NO: 335 is the determined cDNA sequence of clone 23156.

SEQ ID NO: 336 is the determined cDNA sequence of clone 23221.

SEQ ID NO: 337 is the determined cDNA sequence of clone 23223.
SEQ ID NO: 338 is the determined cDNA sequence of clone 23155.
SEQ ID NO: 339 is the determined cDNA sequence of clone 23225.
SEQ ID NO: 340 is the determined cDNA sequence of clone 23226.
SEQ ID NO: 341 is the determined cDNA sequence of clone 23228.
SEQ ID NO: 342 is the determined cDNA sequence of clone 23229.
SEQ ID NO: 343 is the determined cDNA sequence of clone 23231.
SEQ ID NO: 344 is the determined cDNA sequence of clone 23154.
SEQ ID NO: 345 is the determined cDNA sequence of clone 23157.
SEQ ID NO: 346 is the determined cDNA sequence of clone 23153.
SEQ ID NO: 347 is the determined cDNA sequence of clone 23159.
SEQ ID NO: 348 is the determined cDNA sequence of clone 23152.
SEQ ID NO: 349 is the determined cDNA sequence of clone 23161.
SEQ ID NO: 350 is the determined cDNA sequence of clone 23162.
SEQ ID NO: 351 is the determined cDNA sequence of clone 23163.
SEQ ID NO: 352 is the determined cDNA sequence of clone 23164.
SEQ ID NO: 353 is the determined cDNA sequence of clone 23165.
SEQ ID NO: 354 is the determined cDNA sequence of clone 23151.
SEQ ID NO: 355 is the determined cDNA sequence of clone 23150.
SEQ ID NO: 356 is the determined cDNA sequence of clone 23168.
SEQ ID NO: 357 is the determined cDNA sequence of clone 23146.
SEQ ID NO: 358 is the determined cDNA sequence of clone 23170.
SEQ ID NO: 359 is the determined cDNA sequence of clone 23171.
SEQ ID NO: 360 is the determined cDNA sequence of clone 23145.
SEQ ID NO: 361 is the determined cDNA sequence of clone 23174.
SEQ ID NO: 362 is the determined cDNA sequence of clone 23175.
SEQ ID NO: 363 is the determined cDNA sequence of clone 23144.
SEQ ID NO: 364 is the determined cDNA sequence of clone 23178.
SEQ ID NO: 365 is the determined cDNA sequence of clone 23179.
SEQ ID NO: 366 is the determined cDNA sequence of clone 23180.
SEQ ID NO: 367 is the determined cDNA sequence of clone 23181.
SEQ ID NO: 368 is the determined cDNA sequence of clone 23143
SEQ ID NO: 369 is the determined cDNA sequence of clone 23183.
SEQ ID NO: 370 is the determined cDNA sequence of clone 23184.
SEQ ID NO: 371 is the determined cDNA sequence of clone 23185.
SEQ ID NO: 372 is the determined cDNA sequence of clone 23186.
SEQ ID NO: 373 is the determined cDNA sequence of clone 23187.
SEQ ID NO: 374 is the determined cDNA sequence of clone 23190.
SEQ ID NO: 375 is the determined cDNA sequence of clone 23189.
SEQ ID NO: 376 is the determined cDNA sequence of clone 23202.
SEQ ID NO: 378 is the determined cDNA sequence of clone 23191.
SEQ ID NO: 379 is the determined cDNA sequence of clone 23188.
SEQ ID NO: 380 is the determined cDNA sequence of clone 23194.
SEQ ID NO: 381 is the determined cDNA sequence of clone 23196.
SEQ ID NO: 382 is the determined cDNA sequence of clone 23195.
SEQ ID NO: 383 is the determined cDNA sequence of clone 23193.
SEQ ID NO: 384 is the determined cDNA sequence of clone 23199.
SEQ ID NO: 385 is the determined cDNA sequence of clone 23200.
SEQ ID NO: 386 is the determined cDNA sequence of clone 23192.
SEQ ID NO: 387 is the determined cDNA sequence of clone 23201.
SEQ ID NO: 388 is the determined cDNA sequence of clone 23141.
SEQ ID NO: 389 is the determined cDNA sequence of clone 23139.
SEQ ID NO: 390 is the determined cDNA sequence of clone 23204.
SEQ ID NO: 391 is the determined cDNA sequence of clone 23205.
SEQ ID NO: 392 is the determined cDNA sequence of clone 23206.
SEQ ID NO: 393 is the determined cDNA sequence of clone 23207.
SEQ ID NO: 394 is the determined cDNA sequence of clone 23208.
SEQ ID NO: 395 is the determined cDNA sequence of clone 23209.
SEQ ID NO: 396 is the determined cDNA sequence of clone 23210.
SEQ ID NO: 397 is the determined cDNA sequence of clone 23212.
SEQ ID NO: 398 is the determined cDNA sequence of clone 23212.
SEQ ID NO: 399 is the determined cDNA sequence of clone 23214.

SEQ ID NO: 400 is the determined cDNA sequence of clone 23215.
SEQ ID NO: 401 is the determined cDNA sequence of clone 23216.
SEQ ID NO: 402 is the determined cDNA sequence of clone 23137.
SEQ ID NO: 403 is the determined cDNA sequence of clone 23218.
SEQ ID NO: 404 is the determined cDNA sequence of clone 23220.
SEQ ID NO: 405 is the determined cDNA sequence of clone 19462.
SEQ ID NO: 406 is the determined cDNA sequence of clone 19430.
SEQ ID NO: 407 is the determined cDNA sequence of clone 19407.
SEQ ID NO: 408 is the determined cDNA sequence of clone 19448.
SEQ ID NO: 410 is the determined cDNA sequence of clone 19447.
SEQ ID NO: 410 is the determined cDNA sequence of clone 19426.
SEQ ID NO: 411 is the determined cDNA sequence of clone 19441.
SEQ ID NO: 412 is the determined cDNA sequence of clone 19454.
SEQ ID NO: 413 is the determined cDNA sequence of clone 19463.
SEQ ID NO: 414 is the determined cDNA sequence of clone 19419.
SEQ ID NO: 415 is the determined cDNA sequence of clone 19434.
SEQ ID NO: 416 is the determined extended cDNA sequence of B1820P.
SEQ ID NO: 417 is the determined extended cDNA sequence of B821P.
SEQ ID NO: 418 is the determined extended cDNA sequence of B822P.
SEQ ID NO: 419 is the determined extended cDNA sequence of B823P.
SEQ ID NO: 420 is the determined extended cDNA sequence of B824P.
SEQ ID NO: 421 is the determined extended cDNA sequence of B825P.
SEQ ID NO: 422 is the determined extended cDNA sequence of B826P.
SEQ ID NO: 423 is the determined extended cDNA sequence of B827P.
SEQ ID NO: 424 is the determined extended cDNA sequence of B828P.
SEQ ID NO: 425 is the determined extended cDNA sequence of B829P.
SEQ ID NO: 426 is the determined extended cDNA sequence of B830P.
SEQ ID NO: 427 is the determined cDNA sequence of clone 266B4.
SEQ ID NO: 428 is the determined cDNA sequence of clone 22892.
SEQ ID NO: 429 is the determined cDNA sequence of clone 266G3.
SEQ ID NO: 430 is the determined cDNA sequence of clone 22890.
SEQ ID NO: 431 is the determined cDNA sequence of clone 264B4.
SEQ ID NO: 432 is the determined cDNA sequence of clone 22883.
SEQ ID NO: 433 is the determined cDNA sequence of clone 22882.
SEQ ID NO: 434 is the determined cDNA sequence of clone 22880.
SEQ ID NO: 435 is the determined cDNA sequence of clone 263G1.
SEQ ID NO: 436 is the determined cDNA sequence of clone 263G6.
SEQ ID NO: 437 is the determined cDNA sequence of clone 262B2.
SEQ ID NO: 438 is the determined cDNA sequence of clone 262B6.
SEQ ID NO: 439 is the determined cDNA sequence of clone 22869.
SEQ ID NO: 440 is the determined cDNA sequence of clone 21374.
SEQ ID NO: 441 is the determined cDNA sequence of clone 21362.
SEQ ID NO: 442 is the determined cDNA sequence of clone 21349.
SEQ ID NO: 443 is the determined cDNA sequence of clone 21309.
SEQ ID NO: 444 is the determined cDNA sequence of clone 21097.
SEQ ID NO: 445 is the determined cDNA sequence of clone 21096.
SEQ ID NO: 446 is the determined cDNA sequence of clone 21094.
SEQ ID NO: 447 is the determined cDNA sequence of clone 21093.
SEQ ID NO: 448 is the determined cDNA sequence of clone 21091.
SEQ ID NO: 449 is the determined cDNA sequence of clone 21089.
SEQ ID NO: 450 is the determined cDNA sequence of clone 21087.
SEQ ID NO: 451 is the determined cDNA sequence of clone 21085.
SEQ ID NO: 452 is the determined cDNA sequence of clone 21084.
SEQ ID NO: 453 is a first partial cDNA sequence of clone 2BT1-40.
SEQ ID NO: 454 is a second partial cDNA sequence of clone 2BT1-40.
SEQ ID NO: 455 is the determined cDNA sequences of clone 21063.
SEQ ID NO: 456 is the determined cDNA sequence of clone 21062.
SEQ ID NO: 457 is the determined cDNA sequence of clone 21060.
SEQ ID NO: 458 is the determined cDNA sequence of clone 21053.
SEQ ID NO: 459 is the determined cDNA sequence of clone 21050.
SEQ ID NO: 460 is the determined cDNA sequence of clone 21043.
SEQ ID NO: 461 is the determined cDNA sequence of clone 21037.

SEQ ID NO: 462 is the determined cDNA sequence of clone 21048.

SEQ ID NO: 463 is a consensus DNA sequence of B726P (referred to as B726P-spliced_seq_B726P).

SEQ ID NO: 464 is the determined cDNA sequence of a second splice form of B726P (referred to as 27490.seq_B726P).

SEQ ID NO: 465 is the determined cDNA sequence of a third splice form of B726P (referred to as 27068.seq_B726P).

SEQ ID NO: 466 is the determined cDNA sequence of a second splice form of B726P (referred to as 23113.seq_B726P).

SEQ ID NO: 467 is the determined cDNA sequence of a second splice form of B726P (referred to as 23103.seq_B726P).

SEQ ID NO: 468 is the determined cDNA sequence of a second splice form of B726P (referred to as 19310.seq_B726P).

SEQ ID NO: 469 is the predicted amino acid sequence encoded by the upstream ORF of SEQ ID NO: 463.

SEQ ID NO: 470 is the predicted amino acid sequence encoded by SEQ ID NO: 464.

SEQ ID NO: 471 is the predicted amino acid sequence encoded by SEQ ID NO: 465.

SEQ ID NO: 472 is the predicted amino acid sequence encoded by SEQ ID NO: 466.

SEQ ID NO: 473 is the predicted amino acid sequence encoded by SEQ ID NO: 467.

SEQ ID NO: 474 is the determined cDNA sequence for an alternative splice form of B726P.

SEQ ID NO: 475 is the amino acid sequence encoded by SEQ ID NO: 474.

SEQ ID NO: 476 is the isolated cDNA sequence of B720P.

SEQ ID NO: 477 is the cDNA sequence of a known keratin gene.

SEQ ID NO: 478 is the amino acid sequence encoded by SEQ ID NO: 477.

SEQ ID NO: 479 is the determined cDNA sequence for clone 19465.

SEQ ID NO: 480 and 481 are PCR primers.

SEQ ID NO: 482 is the cDNA sequence for the expressed downstream ORF of B726P.

SEQ ID NO: 483 is the amino acid sequence for the expressed recombinant downstream ORF of B726P.

SEQ ID NO: 484 is the determined full-length cDNA sequence for B720P.

SEQ ID NO: 485 is the amino acid sequence encoded by SEQ ID NO: 484.

SEQ ID NO: 486 is the determined cDNA sequence of a truncated form of B720P, referred to as B720P-tr.

SEQ ID NO: 487 is the amino acid sequence of B720P-tr.

SEQ ID NO: 488 is the amino acid sequence of a naturally processed epitope of B726P recognized by B726P-specific CTL.

SEQ ID NO: 489 is a DNA sequence encoding the B726P epitope set forth in SEQ ID NO: 488.

SEQ ID NO: 490 is a DNA sequence encoding a fusion protein wherein mammaglobin is fused to a B726P combined upstream and downstream open reading frame (ORF) (the amino acid sequence of the B726P combined ORF is disclosed herein by SEQ ID NO: 475 which is encoded by the DNA sequence of SEQ ID NO: 474).

SEQ ID NO: 491 is a DNA sequence encoding a fusion protein wherein mammaglobin is fused to a B726P upstream ORF (the amino acid sequence of the B726P upstream ORF is disclosed herein by SEQ ID NO: 469 which is encoded by the DNA sequence of SEQ ID NO: 463).

SEQ ID NO: 492 is a DNA sequence encoding a fusion protein wherein mammaglobin is fused to a B726P downstream ORF (the amino acid sequence of the B726P downstream ORF is disclosed herein by SEQ ID NO: 176 which is encoded by the DNA sequence of SEQ ID NO: 175).

SEQ ID NO: 493 is the amino acid sequence encoded by the DNA sequence of SEQ ID NO: 490.

SEQ ID NO: 494 is the amino acid sequence encoded by the DNA sequence of SEQ ID NO: 491.

SEQ ID NO: 495 is the amino acid sequence encoded by the DNA sequence of SEQ ID NO: 492.

DETAILED DESCRIPTION OF THE INVENTION

As noted above, the present invention is generally directed to compositions and methods for using the compositions, for example in the therapy and diagnosis of cancer, such as breast cancer. Certain illustrative compositions described herein include breast tumor polypeptides, polynucleotides encoding such polypeptides, binding agents such as antibodies, antigen presenting cells (APCs) and/or immune system cells (e.g., T cells). A "breast tumor protein," as the term is used herein, refers generally to a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer.

Therefore, in accordance with the above, and as described further below, the present invention provides illustrative polynucleotide compositions having sequences set forth in SEQ ID NO: 1–175, 178, 180, 182–468, 474, 476, 477, 479, 484, 486 and 489, illustrative polypeptide compositions having amino acid sequences set forth in SEQ ID NO: 176, 179, 181, 469–473, 475, 485, 487 and 488, antibody compositions capable of binding such polypeptides, and numerous additional embodiments employing such compositions, for example in the detection, diagnosis and/or therapy of human breast cancer.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like.

Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to fall length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO: 1–175, 178, 180, 182–468, 474, 476, 477 479, 484, 486 and 489, or to any continuous portion of the sequence, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g. one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a fall length gene from a suitable library (e.g., a breast tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A fill length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked inmunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Site-Specific Mutagensis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1–3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal GABA$_A$ receptor and human EGF (Jaskulski et al., 1988; Vasanthakumar and Ahmed, 1989; Peris et al., 1998; U.S. Pat. Nos. 5,801,154; 5,789,573; 5,718,709 and 5,610,288, each specifically incorporated herein by reference in its entirety). Antisense constructs have also been described that inhibit and can be used to treat a variety of abnormal cellular proliferations, e.g. cancer (U.S. Pat. Nos. 5,747,470; 5,591,317 and 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage.

Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis 6 virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g. multiple ribozymes targeted to different genes, ribozymes coupled with known small molecule inhibitors, or intermittent treatment with combinations of ribozymes and/or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11-13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

In the present invention, a polypeptide composition is also understood to comprise one or more polypeptides that are immunologically reactive with antibodies generated against a polypeptide of the invention, particularly a polypeptide having the amino acid sequence disclosed in SEQ ID NO: 176, 179, 181, 469–473, 475, 485, 487 and 488, or to active fragments, or to variants or biological functional equivalents thereof.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO: 1–175, 178, 180, 182–468, 474, 476, 477 479, 484, 486 and 489, or to active fragments, or to variants thereof, or to one or more nucleic acid sequences which hybridize to one or more of these sequences under conditions of moderate to high stringency. Particularly illustrative polypeptides include the amino acid sequence disclosed in SEQ ID NO: 176, 179, 181, 469–473, 475, 485, 487 and 488.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96% 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In order to improve the antigenicity and/or immunogenicity of breast tumor proteins according to the present invention, fusion proteins comprising antigenic and/or immunogenic portions of two or more breast tumor proteins may be prepared. Exemplary breast tumor fusion proteins may be prepared through conventional recombinant DNA methodology by combining a DNA sequence encoding mammaglobin with a DNA sequence encoding either (1) the combined B726P upstream and downstream ORFs (SEQ ID NO: 490), (2) the upstream B726P ORF (SEQ ID NO: 491), and/or (3) the downstream B726P ORF (SEQ ID NO: 492). See, e.g., Ausubel, F. M. et al., "Short Protocols in Molecular Biology" ($4^{nd}$ ed. 1999); incorporated herein by reference in its entirety). Exemplary fusion proteins are disclosed herein by SEQ ID NO: 493 (mammaglobin-combined B726P ORF), SEQ ID NO: 494 (mammaglobin-upstream B726P ORF), and SEQ ID NO: 495 (mammaglobin-downstream B726P ORF). The DNA sequence encoding mammaglobin is disclosed herein by nucleotides 1–279 of SEQ ID NOs: 490–492 and the corresponding mammaglobin amino acid sequence is disclosed herein as amino acids 1–93 of SEQ ID NOs: 493–495. See, also, U.S. Pat. Nos. 5,668,267; 5,922, 836; 5,855,889; 5,968,754; and 6,004,756, each of which U.S. Patent is incorporated by reference herein in its entirety.

In addition to the exemplary fusion proteins prepared by the fusion of a full-length mammaglobin coding region with various B726P coding regions, the present invention further provides fusion proteins comprising immunogenic portions of 9 or more contiguous amino acids from either or both of mammaglobin and B726P. More preferably, immunogenic portions may be 10, 11, 12, 13, 14, 15, 16, 17, 18, 19, 20 or more contiguous amino acids from either or both of mammaglobin and/or B726P. Alternatively, immunogenic portions may be at least 25, 30, 35, 40, 45, 50, 75, 100, 250, 500, or 1095 contiguous amino acids from either or both of mammaglobin and/or B726P and may also include any integral number of amino acids between 20 and 1095 contiguous amino acids from either or both of mammaglobin and/or B726P.

Representative immunogenic portions of mammaglobin are disclosed in co-pending U.S. patent application Ser. No. 60/136,528. Exemplary immunogenic portions include the following mammaglobin peptide sequences: IDELKECFLNQTDETLSNVE (amino acids 59–78 of SEQ ID NO: 493); TTNAIDELKECFLNQ (amino acids 55–69 of SEQ ID NO: 493); SQHCYAGSGCPLLENVISKTI (amino acids 13–33 of SEQ ID NO: 493); EYKELLQEFIDDNATTNAID (amino acids 41–60 of SEQ ID NO: 493), and/or KLLMVLMLA (amino acids 2–10 of SEQ ID NO: 493). Other preferred epitopes comprise a glycosylation site of mammaglobin. Such epitopes are particularly useful for the generation of antibodies that specifically bind to glycosylated mammaglobin. Two such sites are the N-linked glycosylation sites asparagine (Asp)-53 (QEFIDDNATTNAI; amino acids 47–59 of SEQ ID NO: 493) and Asp-68 (LKECFLNQTDETL; amino acids 62–74 of SEQ ID NO: 493).

The present invention also contemplates that a wide variety of immunogenic portions from the B726P combined, B726P upstream, and/or B726P downstream amino acid sequences may find use in mammaglobin-B726P fusion proteins. For example, a particularly suitable mammaglobin-B726P fusion protein may be prepared by fusing mammaglobin to a downstream B726P epitope recognized by B726P-specific CTL clones, described herein in Example 4, which epitope is included within the N-terminal end of the downstream region of B726P (i.e. amino acids 1–129 of SEQ ID NO: 176).

It will be apparent to those of skill in the art that the precise amino acid sequence and primary sequence arrangement of the mammaglobin and/or B726P portions of the fusion proteins may be varied without deviating from the scope of the present invention. For example, conservative amino acids substitutions within either or both of the mammaglobin or B726P portions may be made, for example, to achieve fusion proteins having improved properties such as increased protein stability and/or immunogenicity. In addition, the present invention contemplates that the mammaglobin portion may be fused to either the N-terminus or C-terminus of the B726P portion to achieve fusion proteins that have the desired antigenic and/or immunogenic properties.

Fusion proteins according to the present invention, as exemplified by the mammaglobin-B726P fusion proteins disclosed herein by this Example, will find use as cancer vaccines, reagents for antibody therapeutics, and/or in various diagnostic assays. It is expected that these fusion proteins will have improved antigenic and/or immunogenic properties as compared to either the mammaglobin and/or B726P proteins alone.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a breast tumor polypeptide (100 ng/ml–100 µg/ml, preferably 200 ng/ml–25 µg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a breast tumor polypeptide, polynucleotide or polypeptide-expressing APC may be CD4$^+$ and/or CD8$^+$. Breast tumor protein-specific T cells may be expanded using standard techniques. Within preferred embodiments, the T cells are derived from a patient, a related donor or an unrelated donor, and are administered to the patient following stimulation and expansion.

For therapeutic purposes, CD4$^+$ or CD8$^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable solutions for administration to a cell or an animal, either alone, or in combination with one or more other modalities of therapy.

It will also be understood that, if desired, the nucleic acid segment, RNA, DNA or PNA compositions that express a polypeptide as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., 1990; Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989; Fresta and Puglisi, 1996), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

Immunogenic Compositions

In certain preferred embodiments of the present invention, immunogenic compositions, or vaccines, are provided. The immunogenic compositions will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and immunogenic compositions within the scope of the present invention may also contain other compounds, which may be biologically active or inactive. For example, one or more immunogenic portions of other tumor antigens may be present, either incorporated into a fusion polypeptide or as a separate compound, within the composition.

Illustrative immunogenic compositions may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. It will be apparent that an immunogenic composition may comprise both a polynucleotide and a polypeptide component. Such immunogenic compositions may provide for an enhanced immune response.

It will be apparent that an immunogenic composition may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the immunogenic compositions of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the immunogenic compositions provided herein, the adjuvant composition is preferably designed to induce an immune response predominantly of the Th1 type. High levels of Th1-type cytokines (e.g., IFN-$\gamma$, TNF$\alpha$, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any immunogenic composition provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and immunogenic compositions to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g. CD40, CD80, CD86 and 4-1BB).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456–460, 1997. Antigen loading of dendritic cells may be achieved by incubating dendritic cells or progenitor cells with the breast tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Immunogenic compositions and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a immunogenic composition or pharmaceutical composition may be stored in a freeze-dried condition requiring only the addition of a sterile liquid carrier immediately prior to use.

Cancer Therapy

In further aspects of the present invention, the compositions described herein may be used for immunotherapy of cancer, such as breast cancer. Within such methods, pharmaceutical compositions and immunogenic compositions are typically administered to a patient. As used herein, a "patient" refers to any warm-blooded animal, preferably a human. A patient may or may not be afflicted with cancer. Accordingly, the above pharmaceutical compositions and immunogenic compositions may be used to prevent the development of a cancer or to treat a patient afflicted with a cancer. A cancer may be diagnosed using criteria generally accepted in the art, including the presence of a malignant tumor. Pharmaceutical compositions and immunogenic compositions may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and immunogenic compositions may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such immunogenic compositions should also be capable of causing an immune response that leads to an improved clinical outcome (e.g., more frequent remissions, complete or partial or longer disease-free survival) in treated patients as compared to non-treated patients. In general, for pharmaceutical compositions and immunogenic compositions comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnosis

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising $CD4^+$ and/or $CD8^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 µg/ml). It may be desirable to incubate another aliquot of a T cell sample in the absence of breast tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–175, 178, 180, 182–468, 474, 476, 477 479, 484, 486 and 489. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided in SEQ ID NO: 14, 21, 22, 27, 29, 30, 32, 38, 44, 45, 53, 72 and 73. The sequences of SEQ ID NO: 1, 3, 16, 17, 34, 48, 57, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO: 63–87. Comparison of the sequences of SEQ ID NO: 74–87 with those in the gene bank as described above, revealed homology to previously identified human genes. No significant homologies were found to the sequences of SEQ ID NO: 63–73.

Three DNA isoforms for the clone B726P (partial sequence provided in SEQ ID NO: 71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 181.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO: 464–468, with the predicted amino acid sequences encoded by SEQ ID NO: 464–467 being provided in SEQ ID NO: 470–473, respectively. Using standard computer techniques, a 3,681 bp consensus DNA sequence (SEQ ID NO: 463) was created that contains two large open reading frames. The downstream ORF encodes the amino acid sequence of SEQ ID NO:176. The predicted amino acid sequence encoded by the upstream ORF is provided in SEQ ID NO: 469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO: 474, with the corresponding amino acid sequence being provided in SEQ ID NO: 475.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO: 182–251 and 479 were 2 or more fold over-expressed in human breast tumor tissues over normal human tissues. No significant homologies were found for nineteen of these clones, including, SEQ ID NO: 185, 186, 194, 199, 205, 208, 211, 214–216, 219, 222, 226, 232, 236, 240, 241, 245, 246 and 479, with the exception of some previously identified expressed sequence tags (ESTs). The remaining clones share some homology to previously identified genes, specifically SEQ ID NO: 181–184, 187–193, 195–198, 200–204, 206, 207, 209, 210, 212, 213, 217, 218, 220, 221, 223–225, 227–231, 233–235, 237–239, 242–244 and 247–251.

One of the cDNA clones isolated by PCR subtraction as described above (SEQ ID NO: 476; referred to as B720P) which was shown by microarray to be over-expressed in breast tumor tissues, was found to be identical to a known keratin gene. The full-length cDNA sequence of the known keratin gene is provided in SEQ ID NO: 477, with the corresponding amino acid sequence being provided in SEQ ID NO: 478. Primers were generated based on the sequence of SEQ ID NO: 477 and used to clone full-length cDNA from mRNA which was obtained from total RNA showing high expression of B720P in real-time PCR analysis. Products were then cloned and sequenced. The determined full-length cDNA sequence for B720P is provided in SEQ ID NO: 484, with the corresponding amino acid sequence being provided in SEQ ID NO: 485.

In further studies, a truncated form of B720P (referred to as B720P-tr) was identified in breast carcinomas. This antigen was cloned from mRNA derived from total breast tumor RNA that showed high expression of B720P-tr in real-time PCR analysis. mRNA was used to generate a pool of cDNA which was then used as a template to amplify the cDNA corresponding to B720P-tr by PCR. The determined cDNA sequence for B720P-tr is provided in SEQ ID NO: 486. B720P-tr has an ORF of 708 base pairs which encodes a 236 amino acid protein (SEQ ID NO: 487). The size of the transcript was confirmed by northern analysis.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2); additionally, over-expression was found in a majority of normal breast tissues. Clone 19483.1 (SEQ ID NO: 216) was over-expressed in a few breast tumors, with no over-expression in any normal tissues tested. Clone 19470.1 (SEQ ID NO: 219) was found to be slightly over-expressed in some breast tumors. Clone 19468.1 (SEQ ID NO: 222) was found to be slightly over-expressed in the majority of breast tumors tested. Clone 19505.1 (SEQ ID NO: 226) was found to be slightly over-expressed in 50% of breast tumors, as well as in SCID tumor tissues, with some degree of over-expression in found in normal breast. Clone 1509.1 (SEQ ID NO: 232) was found to be over-expressed in very few breast tumors, but with a certain degree of over-expression in metastatic breast tumor tissues, as well as no significant over-expression found in normal tissues. Clone 19513.1 (SEQ ID NO: 236) was shown to be slightly over-expressed in few breast tumors, with no significant over-expression levels found in normal tissues. Clone 19575.1 (SEQ ID NO: 240) showed low level over-expression in some breast tumors and also in normal breast. Clone 19560.1 (SEQ ID NO: 241) was over-expressed in 50% of breast tumors tested, as well as in some normal breast tissues. Clone 19583.1 (SEQ ID NO: 245) was slightly over-expressed in some breast tumors, with very low levels of over-expression found in normal tissues. Clone 19587.1 (SEQ ID NO: 246) showed low level over-expression in some breast tumors and no significant over-expression in normal tissues.

Clone 19520.1 (SEQ ID NO: 233), showing homology to clone 102D24 on chromosome 11q13.31, was found to be over-expressed in breast tumors and in SCID tumors. Clone 19517.1 (SEQ ID NO: 237), showing homology to human PAC 128M19 clone, was found to be slightly over-expressed in the majority of breast tumors tested. Clone 19392.2 (SEQ ID NO: 247), showing homology to human chromosome 17, was shown to be over-expressed in 50% of breast tumors tested. Clone 19399.2 (SEQ ID NO: 250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO: 405–415. Comparison of these sequences to those in the public database, as outlined above, revealed homologies between the sequences of SEQ ID NO: 408, 411, 413 and 414 and previously isolated ESTs. The sequences of SEQ ID NO: 405–407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO: 316–404. Comparison of these sequences with those in the public database, as described above, revealed no significant homologies to the sequence of SEQ ID NO: 366. The sequences of SEQ ID NO: 321–325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO: 427–439. The determined cDNA sequences of 22 clones identified using the modified Gemtools analysis are provided in SEQ ID NO: 440–462, wherein SEQ ID NO: 453 and 454 represent two partial, non-overlapping, sequences of the same clone.

Comparison of the clone sequences of SEQ ID NO: 436 and 437 (referred to as 263G6 and 262B2) with those in the public databases, as described above, revealed no significant homologies to previously identified sequences. The sequences of SEQ ID NO: 427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2BT1-59, 2BT1-52 and 2BT1-40, respectively) showed some homology to previously isolated expressed sequences tags (ESTs). The sequences of SEQ ID NO: 428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

EXAMPLE 2

Isolation and Characterization of Breast Tumor Polypeptides Obtained by PCR-Based Subtraction using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO: 88–116, respectively. The isolated cDNA sequences of SEQ ID NO: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO: 252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO: 269–314, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO: 416–426, respectively.

EXAMPLE 3

Synthesis of Polypeptides

Polypeptides may be synthesized on an Perkin Elmer/ Applied Biosystems Division 430A peptide synthesizer using FMOC chemistry with HPTU (O-Benzotriazole-N,N, N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 4

Elicitation of Breast Antigen-Specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO:176) at an M.O.I. of 2.5 and matured for 8 hours by the addition of 2 micrograms/ml CD40 ligand. CD8 positive cells were enriched for by the depletion of CD4 and CD14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma Elispot assays (Lalvani et al., *J. Exp. Med.* 186:859–865, 1997) using IFN-gamma treated autologous fibroblasts transduced to express either B726P or an irrelevant, control, antigen as antigen presenting cells (APC). Of approximately 96 lines, one line (referred to as 6–2B) was identified that appeared to specifically recognize B7726P transduced APC but not control antigen-transduced APC. This microculture was cloned using standard protocols. B726P-specific CTL were identified by Elispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B*1501.

In order to define more accurately the location of the epitope recognized by the B726P-specific CTL clones, a deletion construct comprising only the N-terminal half of B726P (B726Pdelta3') was constructed (a.a. 1–129) into the pBIB retroviral expression plasmid. This plasmid as well as other plasmids containing B726P were transfected into COS-7 cells either alone or in combination with a plasmid expressing HLA-B*1501. Aproximately 48 hours after transfection, a B726P-specific CTL clone (1–9B) was added at approximately 10e4 cells per well. The wells were harvested the next day and the amount of IFN-gamma released was measured by ELISA. The CTL responded above background (EGFP) to COS-7 cells that had been transfected with both B726P and HLA-B*1501. There was no response above background to COS-7 cells that had been transfected with B726P or HLA-B*1501 only. Importantly, a higher response was seen with COS-7 cells that had been transfected with HLA-B*1501 and B726Pdelta3'. This result indicated that the epitope was likely to be located in the N-terminal region (a.a. 1–129) of B726P. This region was examined and amino acid sequences that corresponded to the HLA-B*1501 peptide binding motif (J. Immunol.1999, 162:7277–84) were identified and synthesized. These peptides were pulsed at 10 ug/ml onto autologous B-LCL overnight. The next day the cells were washed and the ability of the cells to stimulate the B726P-specific CTL clone 1–9B was assayed in a IFN-gamma ELISPOT assay. Of the eleven peptides tested, only one peptide, having the amino acid sequence SLTKRASQY (a.a. 76–84; SEQ ID NO: 488) was able to be recognized by the CTL. This result identifies this peptide as being a naturally-processed epitope recognized by this B726P-specific CTL clone.

EXAMPLE 5

Preparation and Characterization of Antibodies against Breast Tumor Polypeptides Polyclonal antibodies against the breast tumor antigen B726P were prepared as follows.

The downstream ORF of B726P (SEQ ID NO:176) expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the colorimetric reaction was stopped with 100 microliters of 1N $H_2SO_4$ and read immediately at 450 nm. The polyclonal antibodies showed immunoreactivity to B726P.

EXAMPLE 6

Protein Expression Breast Tumor Antigens

The downstream ORF of B726P (SEQ ID NO:176), together with a C-terminal 6× His Tag, was expressed in insect cells using the baculovirus expression system as follows.

The cDNA for the full-length downstream ORF of B726P was PCR amplified using the primers of SEQ ID NO: 480 and 481. The PCR product with the expected size was recovered from agarose gel, restriction digested with EcoRI and Hind II, and ligated into the transfer plasmid pFastBacl, which was digested with the same restriction enzymes. The sequence of the insert was confirmed by DNA sequencing. The recombinant transfer plasmid pFBB726P was used to make recombinant bacmid DNA and virus using the Bac-To-Bac Baculovirus expression system (BRL Life Technologies, Gaithersburg, Md.). High Five cells were infected with the recombinant virus BVB726P to produce protein. The cDNA and amino acid sequences of the expressed B726P recombinant protein are provided in SEQ ID NO: 482 and 483, respectively.

From the foregoing, it will be appreciated that, although specific embodiments of the invention have been described herein for the purposes of illustration, various modifications may be made without deviating from the spirit and scope of the invention.

What is claimed is:

1. An isolated antibody, or antigen-binding fragment thereof, that specifically binds to a breast tumor protein that comprises an amino acid sequence that is encoded by a polynucleotide sequence recited in SEQ ID NO:175.

2. A diagnostic kit, comprising:
   (a) one or more antibodies according to claim 1; and
   (b) a detection reagent comprising a reporter group.

3. A kit according to claim 2, wherein the antibodies are immobilized on a solid support.

4. A kit according to claim 2, wherein the detection reagent comprises an anti-immunoglobulin, protein G, protein A or lectin.

5. A kit according to claim 2, wherein the reporter group is selected from the group consisting of radioisotopes, fluorescent groups, luminescent groups, enzymes, biotin and dye particles.

* * * * *